United States Patent
Von Nussbaum et al.

(10) Patent No.: US 7,368,424 B2
(45) Date of Patent: *May 6, 2008

(54) ACYLATED NONADEPSIPEPTIDES

(75) Inventors: Franz Von Nussbaum, Duesseldorf (DE); Nina Brunner, Essen (DE); Sonja Anlauf, Wuppertal (DE); Rainer Endermann, Wuppertal (DE); Chantal Fürstner, Müheim (DE); Elke Hartmann, Wuppertal (DE); Johannes Köbberling, Grevenbroich (DE); Jacques Ragot, Duesseldorf (DE); Guido Schiffer, Wuppertal (DE); Joachim Schuhmacher, Wuppertal (DE); Niels Svenstrup, Velbert (DE); Joachim Telser, Wuppertal (DE); Michael-Alexander Bruening, Berlin (DE)

(73) Assignee: AiCuris GmbH & Co. KG, Wuppertal (DE)

( * ) Notice: Subject to any disclaimer, the term of this patent is extended or adjusted under 35 U.S.C. 154(b) by 133 days.

This patent is subject to a terminal disclaimer.

(21) Appl. No.: 10/840,749

(22) Filed: May 6, 2004

(65) Prior Publication Data
US 2005/0075281 A1 Apr. 7, 2005

(30) Foreign Application Priority Data
May 9, 2003 (DE) ................. 103 20 781

(51) Int. Cl.
*A61K 38/00* (2006.01)
*A61K 38/12* (2006.01)
*C07K 5/00* (2006.01)
*C07K 7/00* (2006.01)
*C07K 16/00* (2006.01)
*C07K 17/00* (2006.01)

(52) U.S. Cl. .......................... 514/9; 530/317
(58) Field of Classification Search .............. None
See application file for complete search history.

(56) References Cited

U.S. PATENT DOCUMENTS

| 4,754,018 A | 6/1988 | Tymiak et al. .............. 530/317 |
| 2005/0075281 A1* | 4/2005 | Von Nussbaum et al. |

FOREIGN PATENT DOCUMENTS

| EP | 0196042 | 1/1986 |
| JP | 01132600 | 5/1989 |
| WO | WO2004099239 | * 11/2004 |

OTHER PUBLICATIONS

Tenover. Mechanisms of antimicrobial resistance in bacteria. Am Infect Control 2006. vol. 34, pp. S3-S10.*

Maki et al. Katanosin B and Plusbacin A3, Inhibitors of Peptidoglycan Synthesis in Methicillin-Resistant Staphylococcus aureus. Antimicrobial Agents and Chemotherapy, Jun. 2001, pp. 1823-1827.*

(Continued)

*Primary Examiner*—Cecilia J. Tsang
*Assistant Examiner*—Marcela M Cordero Garcia
(74) *Attorney, Agent, or Firm*—Morrison & Foerster LLP

(57) ABSTRACT

The invention relates to nonadepsipeptides and process for their preparation, and to their use for producing medicaments for the treatment and/or prophylaxis of diseases, in particular bacterial infectious diseases.

15 Claims, 16 Drawing Sheets

OTHER PUBLICATIONS

Palomo, C., Oiarbide, M., Ganboa, I., Miranda, J., "A concise synthesis of α-amino acid N-carboxy anhydrides of (2S, 3S)-β-substituted serines", Tetrahedron Letts., 42: 8955-8957 (2001).

Harada, K., Suzuki, M., Kato, A., Fujii, K., Oka, H., Ito, Y., "Separation of WAP-8294A components, a novel anti-methicillin-resistant *Staphylococcus aureus* antibiotic, using high-speed counter-current chromatography", J. of Chrom. A., 932 75-81 (2001).

Egner, B., Bradley, M., "Monitoring the solid phase synthesis of analogues of lysobactin and the katanosins using *in situ* MALDI-TOF MS", Tetrahedron, 53(41): 14021-14030 (1997).

Tymiak, A., McCormick, T., Unger, S., "Structure determination of lysobactin, a macrocyclic peptide lactone antibiotic", J. Org. Chem., 54: 1149-1157 (1989).

Green, D., "The bacterial cell wall as a source of antibacterial targets", Expert Opin. Ther. Targets, 6:1-19 (2002).

Baquero, F., "Gram-positive resistance: challenge for the development of new antibiotics", J. Antimicrob. Chemo., 39(Supp. A): 1-6 (1997).

Johnson, A., Livemore, D., Tillotson, G., "Antimicrobial susceptibility of Gram-posititve bacteria: what's current, what's anticipated?", J. Hosp. Infect., 49(Supp. A): S3-S11 (2001).

Goldrick, B., "First reported care of VRSA in the United States", Am. J. Nurs., 102:17 (2002).

O'Sullivan, J., McCullough J., Tymiak, A., Kirsch, D., Trejo, W., Principe, P., "Lysobactin, a novel antibacterial agent produced by *lysobacter sp.*", J. Antibiot., 41: 1740-1744 (1988).

Bonner, D., O'Sullivan, J., Tanaka, S.K., Clark, J., Whitney, R., "Lysobactin, a novel antibacterial agent produced by *lysobacter sp.*", J. Antibiot., 41: 1745-1751 (1988).

Shoji, J., Hinoo, H., Matsumoto, K., Hattori T., Yoshida, T., Matsurra, S., Kondo, E., "Isolaton and characterization of Katanosins A and B", J.. Antibiot., 41(6): 713-718 (1988).

\* cited by examiner

NUF1020-1-1

| Current Data Parameters | | | D1 | 1.00000000 sec |
|---|---|---|---|---|
| NAME | 143665.10.fid.j | | NUC1 | 1H |
| EXPNO | 1 | | P1 | 9.00 usec |
| PROCNO | 1 | | PL1 | 3.00 dB |
| | | | SFO1 | 200.1315010 MHz |
| F2 - Acquisition Parameters | | | | |
| Date_ | 20030117 | | F2 - Processing parameters | |
| Time | 11.55 | | SI | 32768 |
| INSTRUM | spect | | SF | 200.1300029 MHz |
| PROBHD | 5 mm 1H | | WDW | EM |
| | | | SSB | 0 |
| PULPROG | zg45 | | LB | 0.20 Hz |
| TD | 32768 | | GB | 0 |
| SOLVENT | DMSO | | PC | 1.00 |
| NS | 512 | | | |
| DS | 2 | | 1D NMR plot parameters | |
| SWH | 4139.073 Hz | | CX | 37.50 cm |
| FIDRES | 0.126314 Hz | | F1P | 9.000 ppm |
| AQ | 3.9584243 sec | | F1 | 1801.17 Hz |
| RG | 322.5 | | F2P | -0.375 ppm |
| DW | 120.800 usec | | F2 | -75.05 Hz |
| DE | 6.00 usec | | PPMCM | 0.25000 ppm/cm |
| TE | 300.0 K | | HZCM | 50.03250 Hz/cm |

Fig. 9

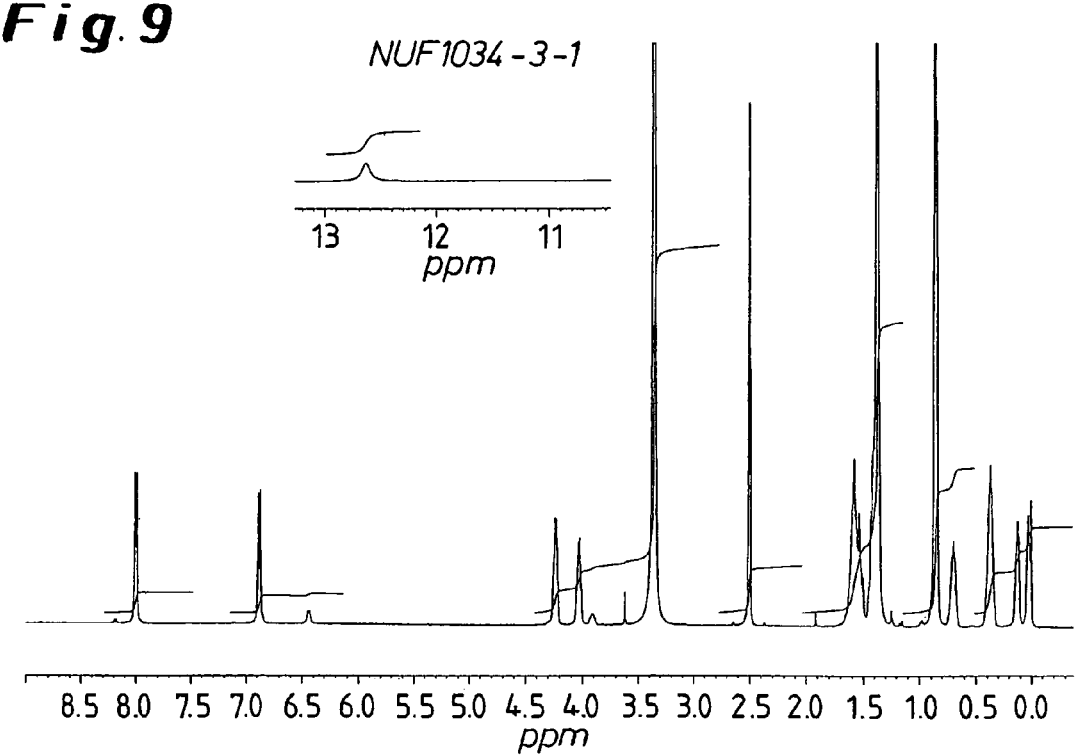

| Current Data Parameters | | ============ CHANNEL f1 ====== | |
|---|---|---|---|
| NAME | 143651 | NUC1 | 1H |
| EXPNO | 100 | P1 | 13.50 usec |
| PROCNO | 1 | PL1 | -3.00 dB |
| | | SF01 | 500.2340018 MHz |
| F2 - Acquisition Parameters | | | |
| Date_ | 20030225 | F2 - Processing parameters | |
| Time | 9.56 | SI | 32768 |
| INSTRUM | spect | SF | 500.2300055 MHz |
| PROBHD | 5 mm CP DUL | WDW | EM |
| PULPROG | zg30 | SSB | 0 |
| TD | 32768 | LB | 0.30 Hz |
| SOLVENT | DMSO | GB | 0 |
| NS | 16 | PC | 1.00 |
| DS | 2 | | |
| SWH | 10330.578 Hz | 1D NMR plot parameters | |
| FIDRES | 0.315264 Hz | CX | 37.50 cm |
| AQ | 1.5860212 sec | F1P | 13.000 ppm |
| RG | 16 | F1 | 6502.99 Hz |
| DW | 48.400 usec | F2P | -0.375 ppm |
| DE | 6.50 usec | F2 | -187.59 Hz |
| TE | 300.0 K | PPMCM | 0.35667 ppm/cm |
| D1 | 1.00000000 sec | HZCM | 178.41537 Hz/cm |

Fig. 10

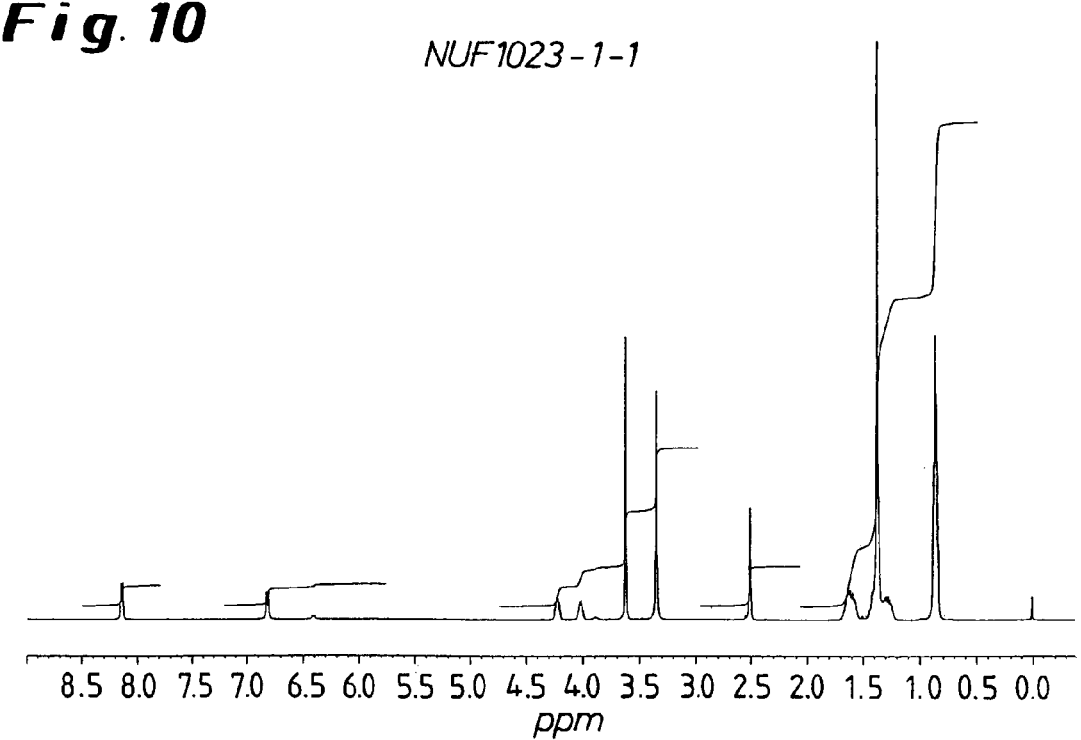

| Current Data Parameters | | | ============ CHANNEL f1 ====== | |
|---|---|---|---|---|
| NAME | 143682 | | NUC1 | 1H |
| EXPNO | 100 | | P1 | 13.50 usec |
| PROCNO | 1 | | PL1 | -3.00 dB |
| | | | SFO1 | 500.2340018 MHz |
| F2 - Acquisition Parameters | | | | |
| Date_ | 20030331 | | F2 - Processing parameters | |
| Time | 15.25 | | SI | 32768 |
| INSTRUM | spect | | SF | 500.2300029 MHz |
| PROBHD | 5 mm CP DUL | | WDW | EM |
| PULPROG | zg30 | | SSB | 0 |
| TD | 32768 | | LB | 0.30 Hz |
| SOLVENT | DMSO | | GB | 0 |
| NS | 16 | | PC | 1.00 |
| DS | 2 | | | |
| SWH | 10330.578 Hz | | 1D NMR plot parameters | |
| FIDRES | 0.315264 Hz | | CX | 37.50 cm |
| AQ | 1.5860212 sec | | F1P | 9.000 ppm |
| RG | 16 | | F1 | 4502.07 Hz |
| DW | 48.400 usec | | F2P | -0.375 ppm |
| DE | 6.50 usec | | F2 | -187.59 Hz |
| TE | 300.0 K | | PPMCM | 0.25000 ppm/cm |
| D1 | 1.00000000 sec | | HZCM | 125.05750 Hz/cm |

Fig. 12

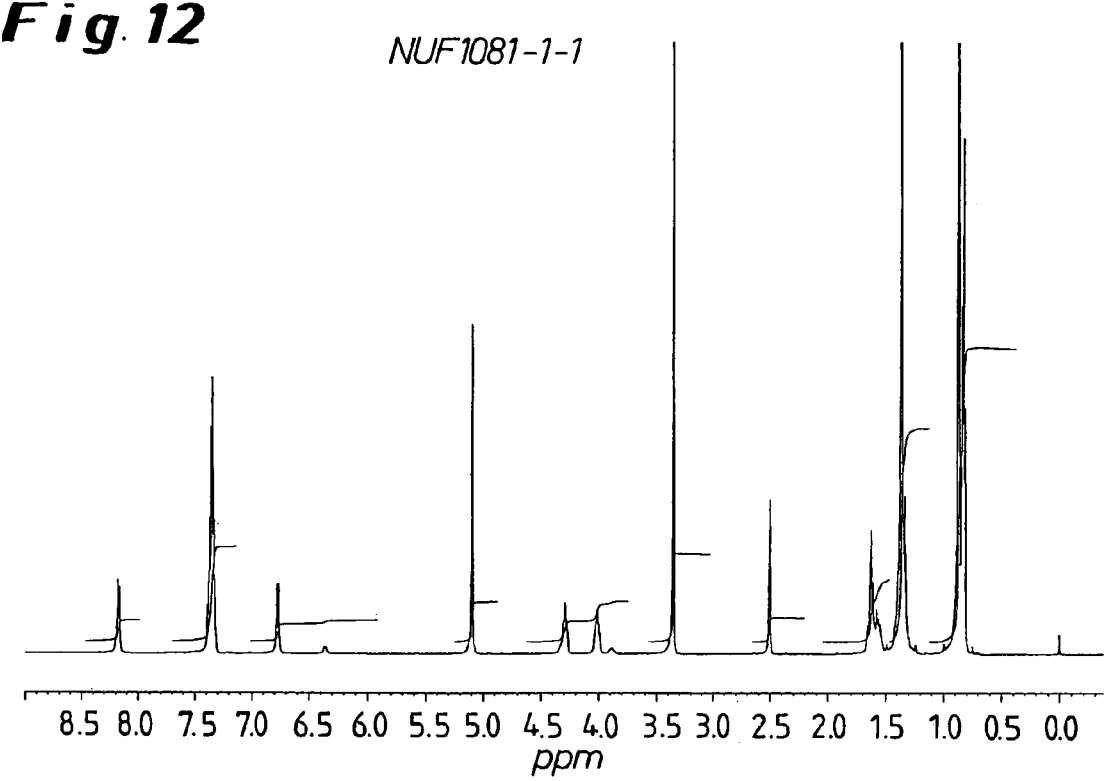

NUF1081-1-1

| Current Data Parameters | | ============ CHANNEL f1 ====== | |
|---|---|---|---|
| NAME | 143655 | NUC1 | 1H |
| EXPNO | 100 | P1 | 13.50 usec |
| PROCNO | 1 | PL1 | -3.00 dB |
| | | SFO1 | 500.2340018 MHz |
| F2 - Acquisition Parameters | | | |
| Date_ | 20030226 | F2 - Processing parameters | |
| Time | 9.56 | SI | 32768 |
| INSTRUM | spect | SF | 500.2300056 MHz |
| PROBHD | 5 mm CP DUL | WDW | EM |
| PULPROG | zg30 | SSB | 0 |
| TD | 32768 | LB | 0.30 Hz |
| SOLVENT | DMSO | GB | 0 |
| NS | 16 | PC | 1.00 |
| DS | 2 | | |
| SWH | 10330.578 Hz | 1D NMR plot parameters | |
| FIDRES | 0.315264 Hz | CX | 37.50 cm |
| AQ | 1.5860212 sec | F1P | 9.000 ppm |
| RG | 35.9 | F1 | 4502.07 Hz |
| DW | 48.400 usec | F2P | -0.375 ppm |
| DE | 6.50 usec | F2 | -187.59 Hz |
| TE | 300.0 K | PPMCM | 0.25000 ppm/cm |
| D1 | 1.00000000 sec | HZCM | 125.05750 Hz/cm |

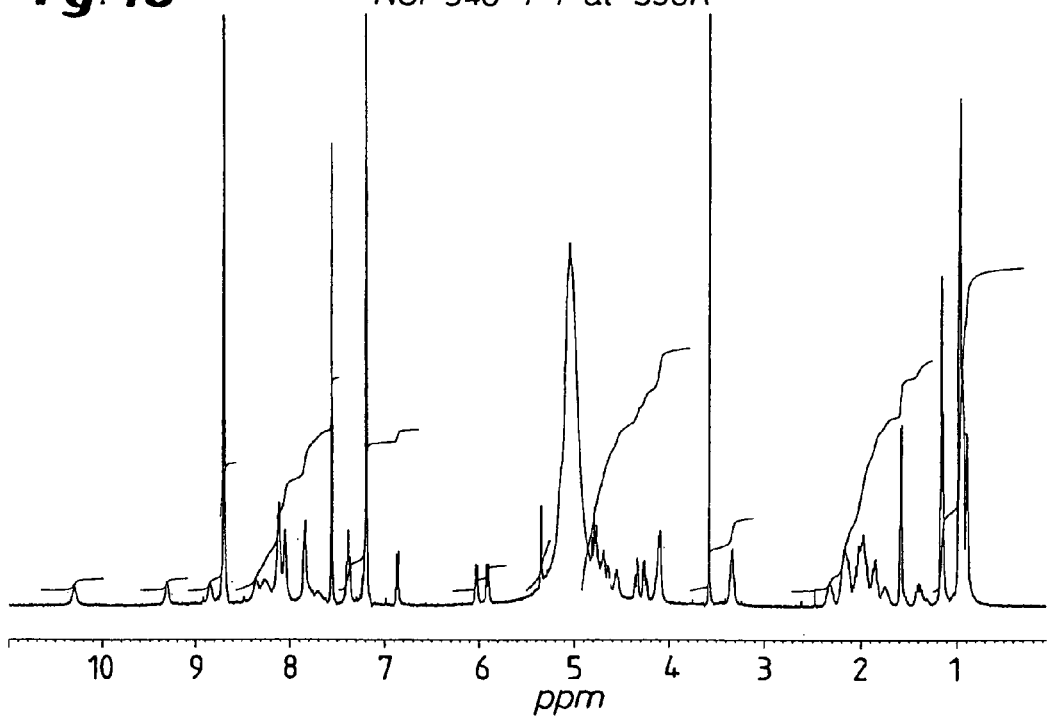

Fig.13　NUF946-1-1 at 338K

```
Current Data Parameters                    ============ CHANNEL f1 ======
NAME              122405          NUC1                1H
EXPNO                 70          P1              8.70 usec
PROCNO                 1          PL1            -6.00 dB
                                  SFO1     400.1322007 MHz
F2 - Acquisition Parameters
Date_           20030127          F2 - Processing parameters
Time               14.32          SI                65536
INSTRUM            spect          SF       400.1300022 MHz
PROBHD       5 mm TXI 1H-         WDW                  EM
PULPROG             zg30          SSB                   0
TD                 32768          LB               0.20 Hz
SOLVENT              Pyr          GB                    0
NS                     4          PC                 1.00
DS                     2
SWH            4807.692 Hz        1D NMR plot parameters
FIDRES         0.146719 Hz        CX              37.50 cm
AQ            3.4079220 sec       F1P             9.000 ppm
RG                  35.9          F1            3601.17 Hz
DW              104.000 usec      F2P            -0.375 ppm
DE                6.00 usec       F2            -150.05 Hz
TE                 300.0 K        PPMCM         0.25000 ppm/cm
D1           0.50000000 sec       HZCM        100.03250 Hz/cm
```

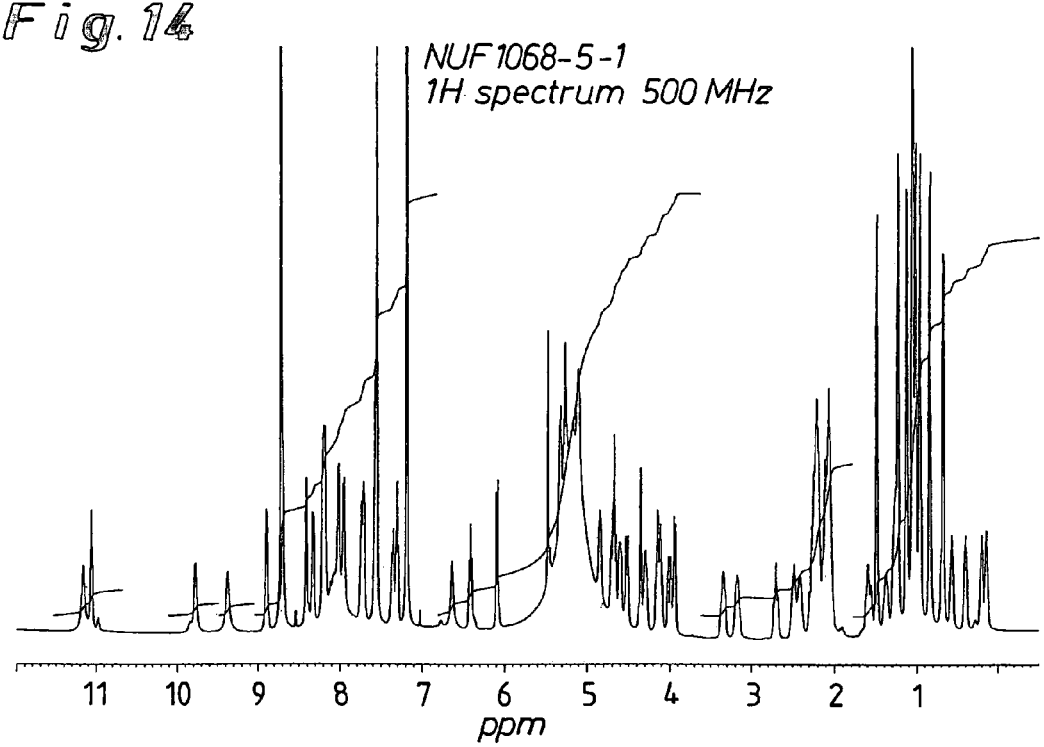

Fig. 14

```
Current Data Parameters              ============ CHANNEL f1 ======
NAME                 143691          NUC1                    1H
EXPNO                   101          P1                13.50 usec
PROCNO                    1          PL1               -3.00 dB
                                     SFO1       500.2340018 MHz
F2 - Acquisition Parameters
Date_              20030414          F2 - Processing parameters
Time                  14.23          SI                    32768
INSTRUM                spect         SF         500.2305738 MHz
PROBHD         5 mm CP DUL           WDW                      EM
PULPROG                 zg30         SSB                       0
TD                    65536          LB                 0.30 Hz
SOLVENT                DMSO          GB                        0
NS                      512          PC                     1.00
DS                        2
SWH              10330.578 Hz        1D NMR plot parameters
FIDRES            0.157632 Hz        CX                37.50 cm
AQ               3.1719923 sec       F1P              18.375 ppm
RG                      128          F1              9191.74 Hz
DW                  48.400 usec      F2P               9.000 ppm
DE                   6.50 usec       F2              4502.08 Hz
TE                   300.0 K         PPMCM           0.25000 ppm/cm
D1              1.00000000 sec       HZCM          125.05764 Hz/cm
```

NUF1068-3-1
13C NMR spectrum

ACYLATED NONADEPSIPEPTIDES

The invention relates to nonadepsipeptides and processes for their preparation, and to their use for producing medicaments for the treatment and/or prophylaxis of diseases, in particular bacterial infectious diseases.

The bacterial cell wall is synthesized by a number of enzymes (cell wall biosynthesis) and is essential for the survival and reproduction of microorganisms. The structure of this macromolecule, as well as the proteins involved in the synthesis thereof, are highly conserved within the bacteria. Owing to its essential nature and uniformity, cell wall biosynthesis is an ideal point of attack for novel antibiotics (D. W. Green, The bacterial cell wall as a source of antibacterial targets, *Expert Opin. Ther. Targets*, 2002, 6, 1-19).

Vancomycin and penicillins are inhibitors of bacterial cell wall biosynthesis and are successful examples of the antibiotic potency of this principle of action. They have been employed for several decades clinically for the treatment of bacterial infections, especially with Gram-positive pathogens. The growing occurrence of resistant microbes, e.g. methicillin-resistant staphylococci, penicillin-resistant pneumococci and vancomycin-resistant enterococci (F. Baquero, Gram-positive resistance: challenge for the development of new antibiotics, *J. Antimicrob. Chemother.*, 1997, 39, Suppl A:1-6; A. P. Johnson, D. M. Livermore, G. S. Tillotson, Antimicrobial susceptibility of Gram-positive bacteria: what's current, what's anticipated?, *J. Hosp. Infect.*, 2001, (49), Suppl A: 3-11) and recently also for the first time vancomycin-resistant staphylococci (B. Goldrick, First reported case of VRSA in the United States, *Am. J. Nurs.*, 2002, 102, 17) means that these substances are increasingly losing their therapeutic efficacy.

The present invention describes a novel class of cell wall biosynthesis inhibitors without cross resistance with known antibiotic classes.

The natural product lysobactin and some derivatives are described as having antibacterial activity in U.S. Pat. No. 4,754,018. The isolation and antibacterial activity of lysobactin is also described in EP-A-196 042 and JP 01132600.

The antibacterial effect of lysobactin and katanosin A is furthermore described in O'Sullivan, J. et al., *J. Antibiot.* 1988, 41, 1740-1744, Bonner, D. P. et al., *J. Antibiot.* 1988, 41, 1745-1751, Shoji, J. et al., *J. Antibiot.* 1988, 41, 713-718 and Tymiak, A. A. et al., *J. Org. Chem.* 1989, 54, 1149-1157.

One object of the present invention is to provide alternative compounds with comparable or improved antibacterial effect and better tolerability, e.g. less nephrotoxicity, for the treatment of bacterial diseases in humans and animals.

The invention relates to compounds of the formula

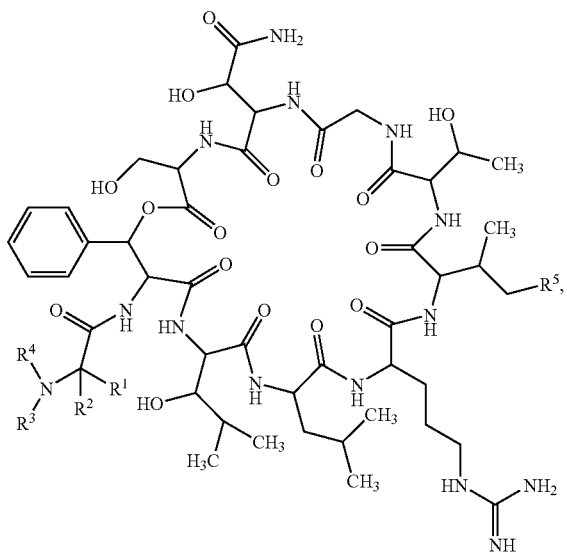

(I)

in which

R[1] is hydrogen, $C_3$-$C_6$-cycloalkyl, $C_5$-$C_6$-cycloalkenyl, $C_3$-$C_6$-cycloalkylmethyl, 5- to 7-membered heterocyclylmethyl, methyl, ethyl, n-propyl, isopropyl, 1-methylprop-1-yl, 2-methylprop-1-yl, 2,2-dimethylprop-1-yl, 1,1-dimethylprop-1-yl, 1-ethyl-prop-1-yl, 1-ethyl-1-methylprop-1-yl, n-butyl, 2-methylbut-1-yl, 3-methylbut-1-yl, 1-ethylbut-1-yl, tert-butyl, 4-methylpent-1-yl, n-hexyl, alkenyl or aryl, where R[1] may be substituted by 0, 1, 2 or 3 substituents independently of one another selected from the group consisting of halogen, hydroxy, amino, cyano, trimethylsilyl, alkyl, alkoxy, benzyloxy, $C_3$-$C_6$-cycloalkyl, aryl, 5- to 10-membered heteroaryl, alkylamino, aryl-amino, alkylcarbonylamino, arylcarbonylamino, alkylcarbonyl, alkoxycarbonyl, arylcarbonyl and benzyloxycarbonylamino, in which aryl and heteroaryl in turn may be substituted by 0, 1, 2 or 3 substituents independently of one another selected from the group consisting of halogen, hydroxy, amino, cyano, nitro, alkyl, alkoxy and phenyl, R[2] is hydrogen or $C_1$-$C_4$-alkyl, or R[1] and R[2] together with the carbon atom to which they are bonded form a $C_3$-$C_6$-cycloalkyl ring or a 5- to 7-membered heterocyclyl ring, where the cycloalkyl ring and the heterocyclyl ring may be substituted by 0, 1, 2 or 3 substituents independently of one another selected from the group consisting of trifluoromethyl, alkyl, alkoxy and alkylcarbonyl, $R^3$ is alkyl, $C_3$-$C_6$-cycloalkyl, 5- to 7-membered heterocyclyl, aryl, 5- or 6-membered heteroaryl, alkylcarbonyl, alkoxycarbonyl, $C_3$-$C_6$-cycloalkylcarbonyl, 5- to 7-membered heterocyclylcarbonyl, arylcarbonyl, 5- or 6-membered heteroarylcarbonyl or alkylaminocarbonyl, where alkyl, cycloalkyl, heterocyclyl, aryl, heteroaryl, alkoxycarbonyl, cycloalkylcarbonyl, heterocyclylcarbonyl, arylcarbonyl, heteroarylcarbonyl and alkylaminocarbonyl may be substituted by 0, 1, 2 or 3 substituents independently of one another selected from the group consisting of halogen, hydroxy, amino, alkylamino and phenyl, and where alkylcarbonyl is substituted by one amino or alkylamino substituent, and where alkylcarbonyl may be substituted by a further 0, 1 or 2 substituents independently of one another selected from the group consisting of halogen, hydroxy, trimethylsilyl, alkoxy, alkylthio, benzyloxy, $C_3$-$C_6$-cycloalkyl, phenyl, naphthyl, 5- to 10-membered heteroaryl, alkylcarbonylamino, alkoxycarbonylamino, arylcarbonylamino, arylcarbonyloxy, benzyloxycarbonyl and benzyloxycarbonylamino, in which phenyl and heteroaryl in turn may be substituted by 0, 1, 2 or 3 substituents independently of one another selected from the group consisting of halogen, hydroxy, nitro, alkyl, alkoxy and phenyl, or two substituents on the same carbon atom in the alkylcarbonyl form together with the carbon atom to which they are bonded a $C_3$-$C_6$-cycloalkyl ring or a 5- to 7-membered heterocyclyl ring, where the cycloalkyl ring and the heterocyclyl ring may be substituted by 0, 1, 2 or 3 substituents independently of one another selected from the group consisting of trifluoromethyl, alkyl and alkoxy, or where the cycloalkyl ring may be benzo-fused, $R^4$ is hydrogen, $C_1$-$C_4$-alkyl, cyclopropyl or cyclopropylmethyl, or $R^3$ and $R^4$ together with the nitrogen atom to which they are bonded form a 5- to 7-membered heterocyclyl ring, where the heterocyclyl ring may be substituted by 0, 1, 2 or 3 substituents independently of one another selected from the group consisting of halogen, hydroxy, amino, cyano, alkyl, alkoxy and alkylamino, and $R^5$ is hydrogen or methyl, and their salts, their solvates and the solvates of their salts, with the proviso that in the case where $R^1$ is hydrogen, $R^2$ is 2-methylprop-1-yl, $R^4$ is hydrogen and $R^5$ is methyl, and the carbon atom to which $R^1$ and $R^2$ are bonded has the (S) configuration, or where $R^1$ is 2-methylprop-1-yl, $R^2$ is hydrogen, $R^4$ is hydrogen and $R^5$ is methyl, and the carbon atom to which $R^1$ and $R^2$ are bonded has the (S) configuration, $R^3$ is not glycyl, D-alanyl, L-alanyl or D-leucyl, and with the proviso that in the case where $R^1$ is hydrogen, $R^2$ is 2-methylprop-1-yl, $R^4$ is hydrogen and $R^5$ is hydrogen, and the carbon atom to which $R^1$ and $R^2$ are bonded has the (S) configuration, or where $R^1$ is 2-methylprop-1-yl, $R^2$ is hydrogen, $R^4$ is hydrogen and $R^5$ is hydrogen, and the carbon atom to which $R^1$ and $R^2$ are bonded has the (S) configuration, $R^3$ is not D-leucyl.

Compounds of the invention are compounds of the formulae (I), (Ia), (Ib) and (Ic) and the salts, solvates, solvates of the salts and prodrugs thereof, the compounds which are emcompassed by formulae (I), (Ia), (Ib) and (Ic) and are of the formulae mentioned below, and the salts, solvates, solvates of the salts and prodrugs thereof, and the compounds which are encompassed by formulae (I), (Ia), (Ib) and (Ic) and are mentioned below as exemplary embodiments, and the salts, solvates, solvates of the salts and prodrugs thereof, where the compounds which are encompassed by formulae (I), (Ia), (Ib) and (Ic) and are mentioned below are not already salts, solvates, solvates of the salts and prodrugs.

The compounds of the invention may, depending on their structure, exist in stereoisomeric forms (enantiomer, diastereomers). The invention therefore relates to the enantiomers or diastereomers and respective mixtures thereof. The stereoisomerically pure constituents can be isolated from such mixtures of enantiomers and/or diastereomers in a known manner.

Where the compounds of the invention can exist in tautomeric forms, the present invention encompasses all tautomeric forms.

Salts preferred for the purposes of the present invention are physiologically acceptable salts of the compounds of the invention. However, also included are salts which are not themselves suitable for pharmaceutical applications but can be used for example for the isolation or purification of the compounds of the invention.

Physiologically acceptable salts of the compounds of the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of conventional bases such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds of the invention which form a complex in the solid or liquid state through coordination with solvent molecules. Hydrates are a special form of solvates in which the coordination takes place with water.

For the purposes of the present invention, the substituents have the following meaning, unless otherwise specified:

Alkyl per se and "alk" and "alkyl" in alkoxy, alkylamino, alkylcarbonyl, alkoxycarbonyl alkylaminocarbonyl alkylcarbonylamino and alkoxycarbonylamino is a linear or branched alkyl radical having as a rule 1 to 6, preferably 1 to 4, particularly preferably 1 to 3, carbon atoms, by way of example and preferably methyl, ethyl, n-propyl, isopropyl, tert-butyl, 2,2-dimethylprop-1-yl, n-pentyl and n-hexyl.

Alkoxy is by way of example and preferably methoxy, ethoxy, n-propoxy, isopropoxy, tert-butoxy, n-pentoxy and n-hexoxy.

Alkenyl is a straight-chain or branched alkenyl radical having 2 to 6 carbon atoms. Preference is given to a straight-chain or branched alkenyl radical having 2 to 4, particularly preferably having 2 to 3, carbon atoms. The following may be mentioned by way of example and preferably: vinyl, allyl, n-prop-1-en-1-yl, n-but-2-en-1-yl, 2-methylprop-1-en-1-yl and 2-methylprop-2-en-1-yl.

Alkylamino is an alkylamino radical having one or two alkyl substituents (chosen independently of one another), by way of example and preferably methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino. $C_1$-$C_3$-alkylamino is, for example, a monoalkylamino radical having 1 to 3 carbon atoms or a dialkylamino radical having 1 to 3 carbon atoms in each alkyl substituent.

Arylamino is an aryl substituent linked via an amino group, where a further substituent such as, for example, aryl or alkyl is bonded where appropriate to the amino group, by way of example and preferably phenylamino, naphthylamino, phenylmethylamino or diphenylamino.

Alkylcarbonyl is by way of example and preferably methylcarbonyl, ethylcarbonyl, n-propylcarbonyl, isopropylcarbonyl, tert-butylcarbonyl, n-pentylcarbonyl and n-hexylcarbonyl.

Alkoxycarbonyl is by way of example and preferably methoxycarbonyl, ethoxycarbonyl, n-propoxycarbonyl, isopropoxycarbonyl, tert-butoxycarbonyl, n-pentoxycarbonyl and n-hexoxycarbonyl.

Alkoxycarbonylamino is by way of example and preferably methoxycarbonylamino, ethoxycarbonylamino, n-propoxy-carbonylamino, isopropoxycarbonylamino, tert-butoxycarbonylamino, n-pentoxycarbonylamino and n-hexoxycarbonylamino.

Cycloalkylcarbonyl is a cycloalkyl substituent linked via a carbonyl group, by way of example and preferably cyclopropylcarbonyl, cyclobutylcarbonyl, cyclopentylcarbonyl and cyclohexylcarbonyl.

Heterocyclylcarbonyl is a heterocyclyl substituent linked via a carbonyl group, by way of example and preferably tetrahydrofuran-2-ylcarbonyl, pyrrolidin-2-ylcarbonyl, pyrrolidin-3-ylcarbonyl, pyrrolinylcarbonyl, piperidinylcarbonyl, morpholinylcarbonyl and perhydroazepinylcarbonyl.

Arylcarbonyl is an aryl substituent linked via a carbonyl group, by way of example and preferably phenylcarbonyl, naphthylcarbonyl and phenanthrenylcarbonyl.

Heteroarylcarbonyl is a heteroaryl substituent linked via a carbonyl group, by way of example and preferably thienylcarbonyl, furylcarbonyl, pyrrolylcarbonyl, thiazolylcarbonyl, oxazolylcarbonyl, imidazolylcarbonyl, pyridylcarbonyl, pyrimidylcarbonyl, pyridazinylcarbonyl, indolylcarbonyl, indazolylcarbonyl, benzofuranylcarbonyl, benzothiophenylcarbonyl, quinolinylcarbonyl and isoquinolinylcarbonyl.

Alkylcarbonylamino is by way of example and preferably methylcarbonylamino, ethylcarbonylamino, n-propylcarbonylamino, isopropylcarbonylamino, tert-butylcarbonylamino, n-pentylcarbonylamino and n-hexylcarbonylamino.

Arylcarbonylamino is by way of example and preferably phenylcarbonylamino, naphthylcarbonylamino and phenanthrenylcarbonylamino.

Alkylaminocarbonyl is an alkylaminocarbonyl radical having one or two alkyl substituents (chosen independently of one another), by way of example and preferably methylaminocarbonyl, ethylaminocarbonyl, n-propylaminocarbonyl, isopropylaminocarbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-tert-butyl-N-methylaminocarbonyl, ethyl-N-n-pentylamino-carbonyl and N-n-hexyl-N-methylaminocarbonyl. $C_1$-$C_3$-alkylaminocarbonyl is for example a monoalkylaminocarbonyl radical having 1 to 3 carbon atoms or a dialkylaminocarbonyl radical having 1 to 3 carbon atoms in each alkyl substituent.

Cycloalkyl is a cycloalkyl group having, as a rule, 3 to 6 carbon atoms, by way of example and preferably cyclopropyl, cyclobutyl, cyclopentyl and cyclohexyl.

Cycloalkenyl is a cycloalkenyl group having, as a rule, 5 to 6 carbon atoms and one or two double bonds, by way of example and preferably cyclopent-1-en-1-yl, cyclopent-2-en-1-yl, cyclopent-3-en-1-yl, cyclohex-1-en-1-yl, cyclohex-2-en-1-yl and cyclohex-3-en-1-yl.

Aryl is a mono- to tricyclic aromatic, carbocyclic radical having, as a rule, 6 to 14 carbon atoms; by way of example and preferably phenyl, naphthyl and phenanthrenyl.

Heterocyclyl is a mono- or polycyclic, preferably mono- or bicyclic, heterocyclic radical having, as a rule, 5 to 7 ring atoms and up to 3, preferably up to 2, heteroatoms and/or heterogroups from the series N, O, S, SO, $SO_2$. The heterocyclyl radicals may be saturated or partially unsaturated. Preference is given to 5- to 7-membered, monocyclic saturated heterocyclyl radicals having up to two heteroatoms from the series O, N and S, such as by way of example and preferably tetrahydrofuran-2-yl, pyrrolidin-2-yl, pyrrolidin-3-yl, pyrrolinyl, piperidinyl, morpholinyl and perhydroazepinyl.

Heteroaryl is an aromatic, mono- or bicyclic radical having, as a rule, 5 to 10, preferably 5 to 6, ring atoms and up to 5, preferably up to 4, heteroatoms from the series S, O and N, by way of example and preferably thienyl, furyl, pyrrolyl, thiazolyl, oxazolyl, imidazolyl, pyridyl, pyrimidyl, pyridazinyl, indolyl, indazolyl, benzofuranyl, benzothiophenyl, quinolinyl and isoquinolinyl.

Carbonyl-linked amino acid is an amino acid which is linked via the carbonyl group of the acid function of the amino acid. Preference is given in this connection to α-amino acids in the L or the D configuration, especially naturally occurring α-amino acids such as, for example, glycine, L-alanine, L-valine, L-leucine, L-isoleucine, L-proline, L-phenylalanine, L-tryptophan or naturally occurring α-amino acids in the unnatural D configuration, such as, for example, D-alanine, D-valine, D-leucine, D-isoleucine, D-proline, D-phenylalanine, D-tryptophan or unnatural amino acids having a side group linked to the α carbon atom of the amino acid, such as, for example, $C_3$-$C_6$-cycloalkylmethyl, $C_3$-$C_6$-cycloalkyl, ethyl, n-propyl, 2,2-dimethylpropyl, tert-butyl, 3-methylbutyl, n-hexyl or allyl, or the side chain forms with the α carbon atom of the amino acid a ring such as, for example, cyclopropyl (amino acid: 1-amino-1-cyclopropanecarboxylic acid), cyclobutyl, cyclopentyl, cyclohexyl or a 5- to 7-membered heterocycle, where the ring may be benzo-fused, or β-amino acids (for the nomenclature, cf.: D. Seebach, M. Overhand, F. N. M. Kühnle, B. Martinoni, L. Oberer, U. Hommel, H. Widmer, *Helv. Chim. Acta* 1996, 79, 913-941), such as, for example, β-alanine, β-phenylalanine, β-Aib or derivatives of 2,3-diaminopropionic acid (e.g. 2,3-diamino-3-phenylpropionic acid).

Halogen is fluorine, chlorine, bromine and iodine, preferably fluorine and chlorine.

DESCRIPTION OF THE FIGURES

FIG. 9: $^1$H NMR (500 MHz, $d_6$-DMSO) of N-(tert-butoxycarbonyl)-D-leucyl-3-cyclopropyl-L-alanine (Example 5A).

FIG. 10: $^1$H NMR (500 MHz, $d_6$-DMSO) of methyl-N-(tert-butoxycarbonyl)-D-leucyl-L-norvalinate (Example 6A).

FIG. 12: $^1$H NMR (500 MHz, $d_6$-DMSO) of benzyl N-(tert-butoxycarbonyl)-D-leucyl-3-tert-butyl-L-alaninate (Example 8A).

FIG. 13: $^1$H NMR (400 MHz, 338 K, $d_5$-pyridine) of deleucyllysobactin bistrifluoroacetate (Example 11A).

FIG. 14: $^1$H NMR (500 MHz, $d_5$-pyridine) of D-leucyl-$N^1$-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-3-cyclopropyl-L-alaninamide bistrifluoroacetate (Example 1).

Figure 1:
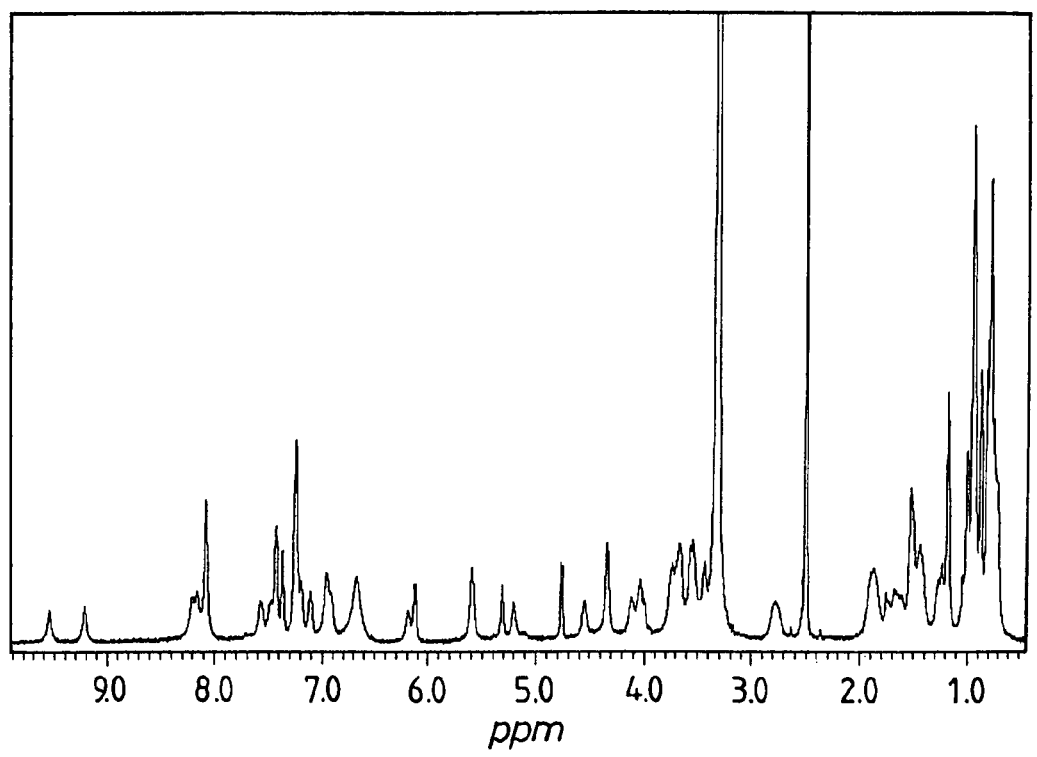
FIG. 1: $^1$H NMR (500 MHz, $d_6$-DMSO, 302 K) of Example 1A.
Figure 2:
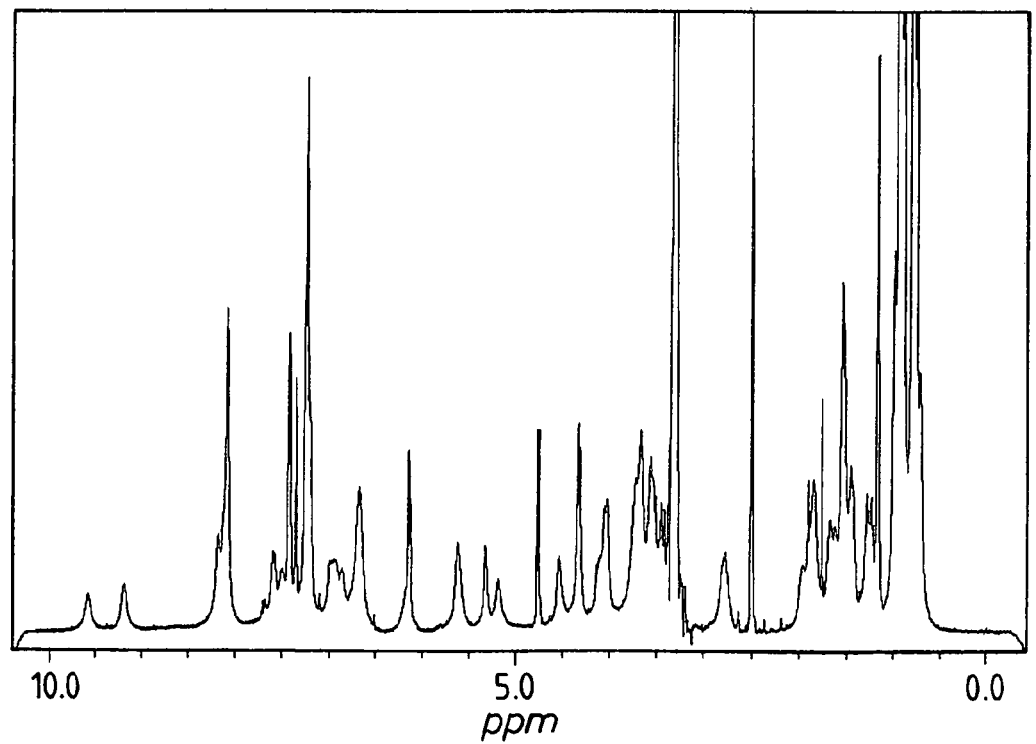
FIG. 2: $^1$H NMR (500 MHz, $d_6$-DMSO, 302 K) of Example 2A.
Figure 3:
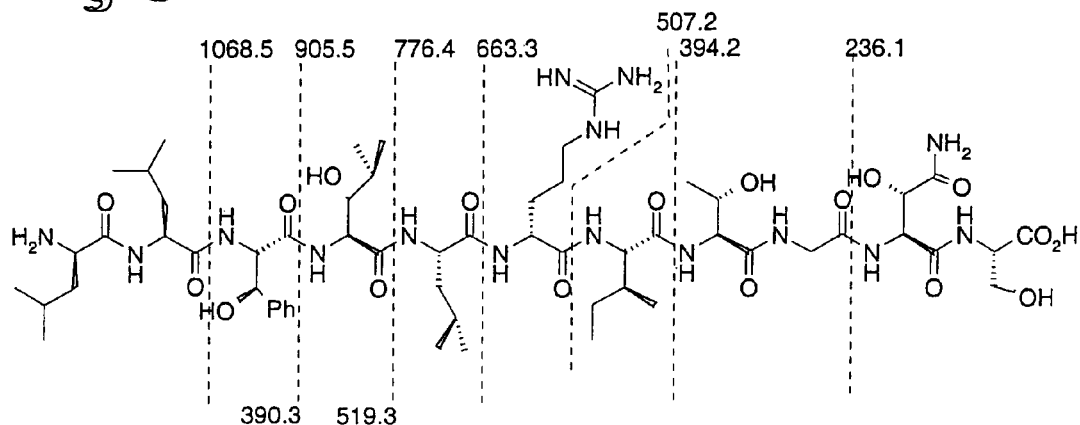
FIG. 3: MALDI-MS sequencing of hydrolytically ring-opened lysobactin.
Figure 4:
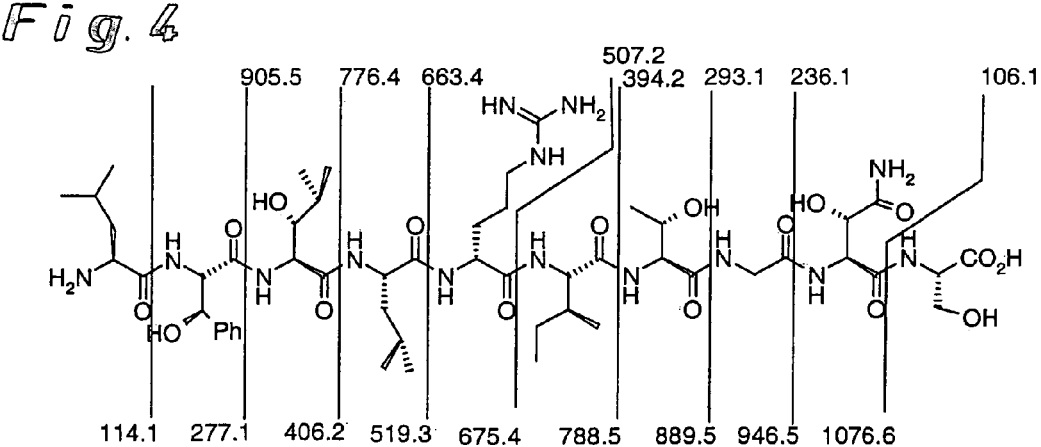
FIG. 4: MALDI-MS sequencing of hydrolytically ring-opened decadepsipeptide (Example 11A).
Figure 5:
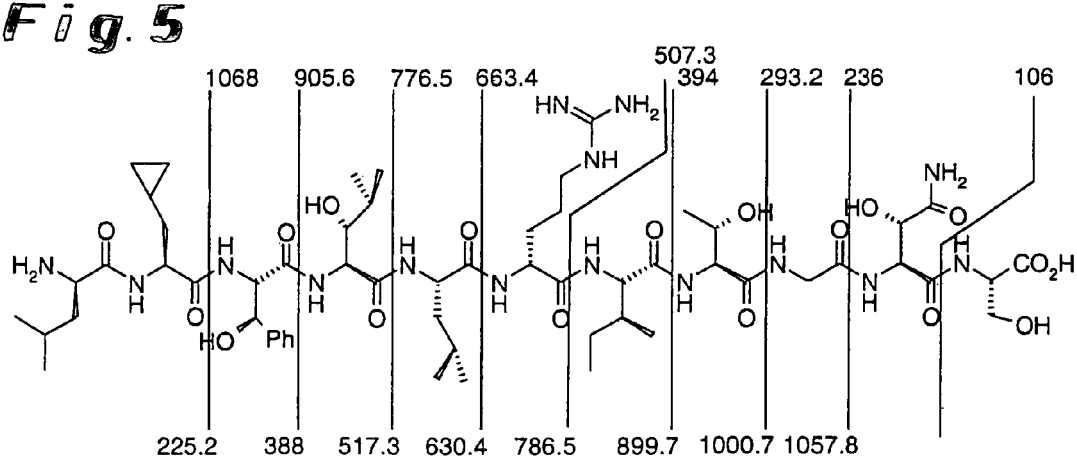
FIG. 5: MALDI-MS sequencing of hydrolytically ring-opened undecadepsipeptide (Example 1).
Figure 6:
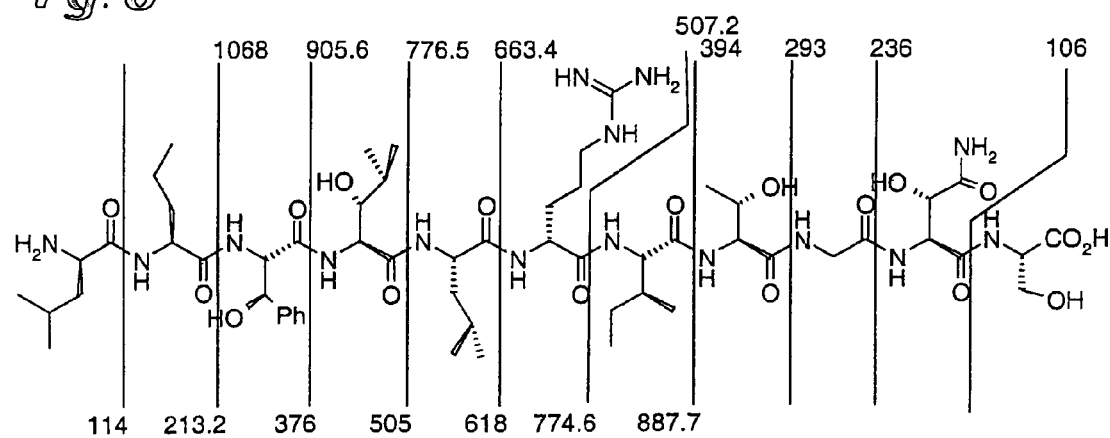
FIG. 6: MALDI-MS sequencing of hydrolytically ring-opened undecadepsipeptide (Example 2).
Figure 7:
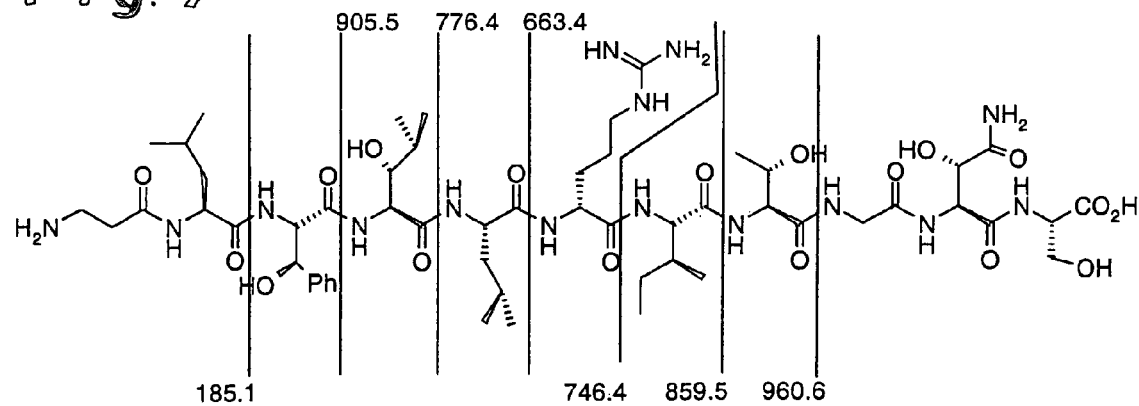
FIG. 7: MALDI-MS sequencing of hydrolytically ring-opened undecadepsipeptide (Example 8).
Figure 8:
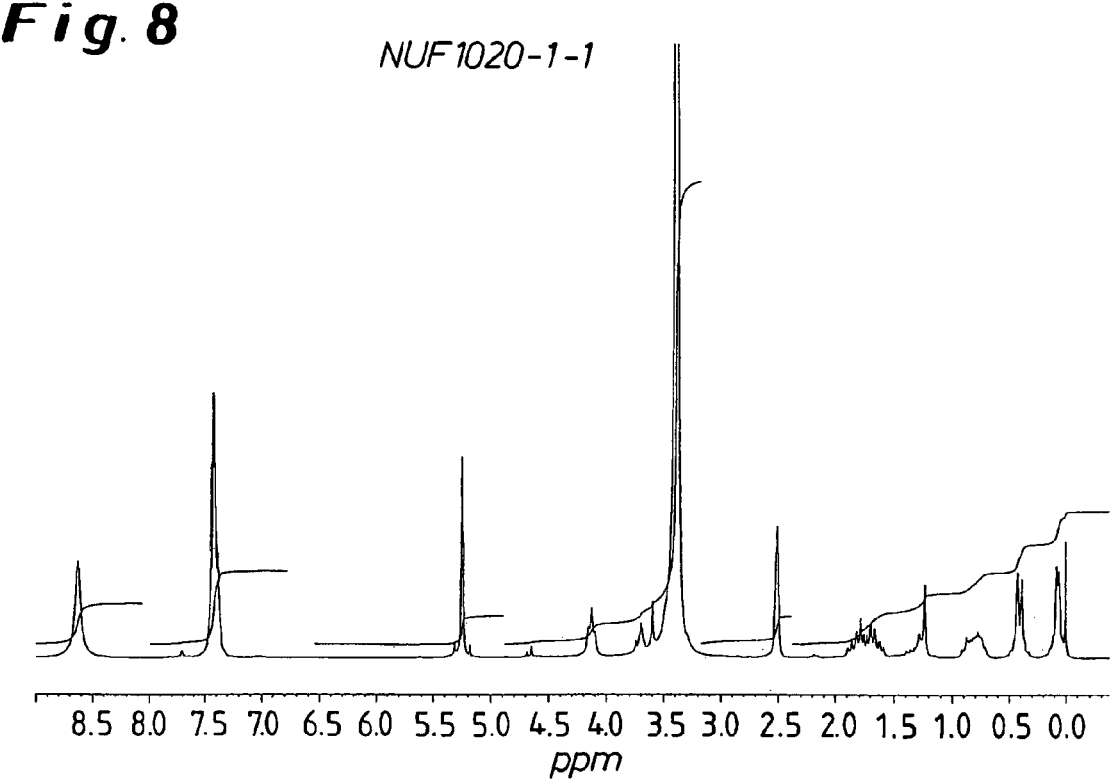
FIG. 8: $^1$H NMR (200 MHz, $d_6$-DMSO) of benzyl 3-cyclopropyl-L-alaninate hydrochloride (Example 3A).
Figure 11:
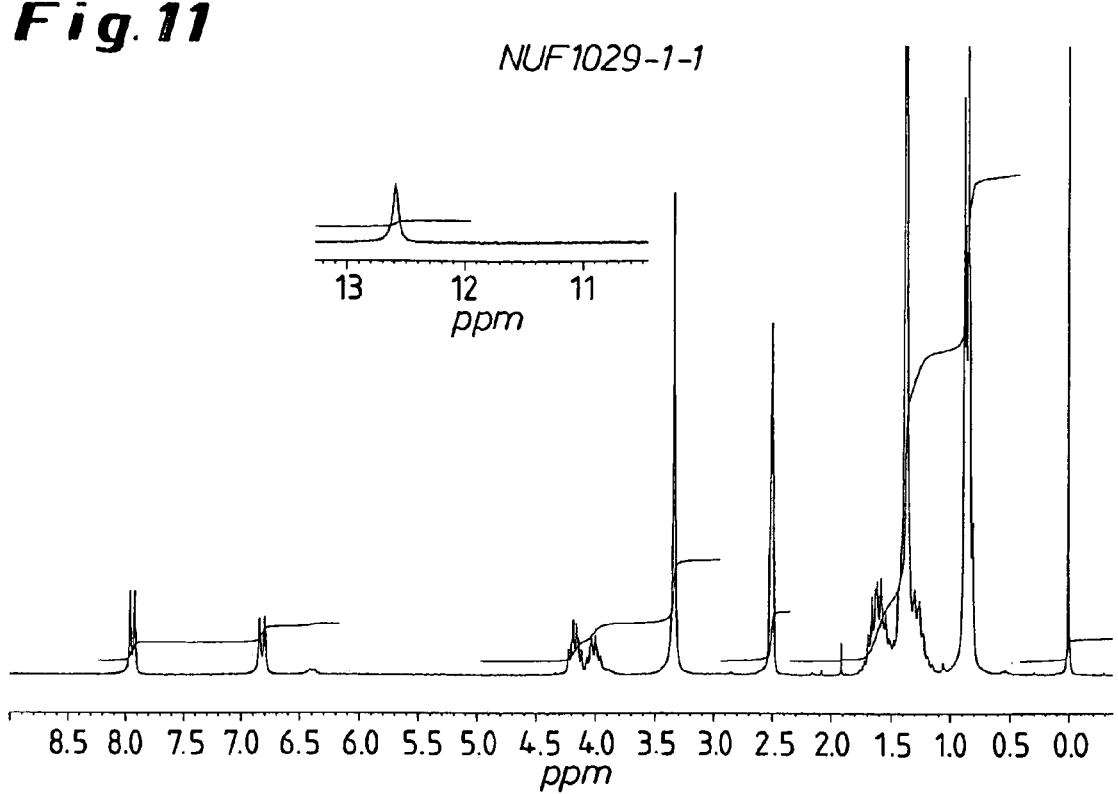
FIG. 11: $^1$H NMR (200 MHz, $d_6$-DMSO) of N-(tert-Butoxycarbonyl)-D-leucyl-L-norvaline (Example 7A).
Figure 15:
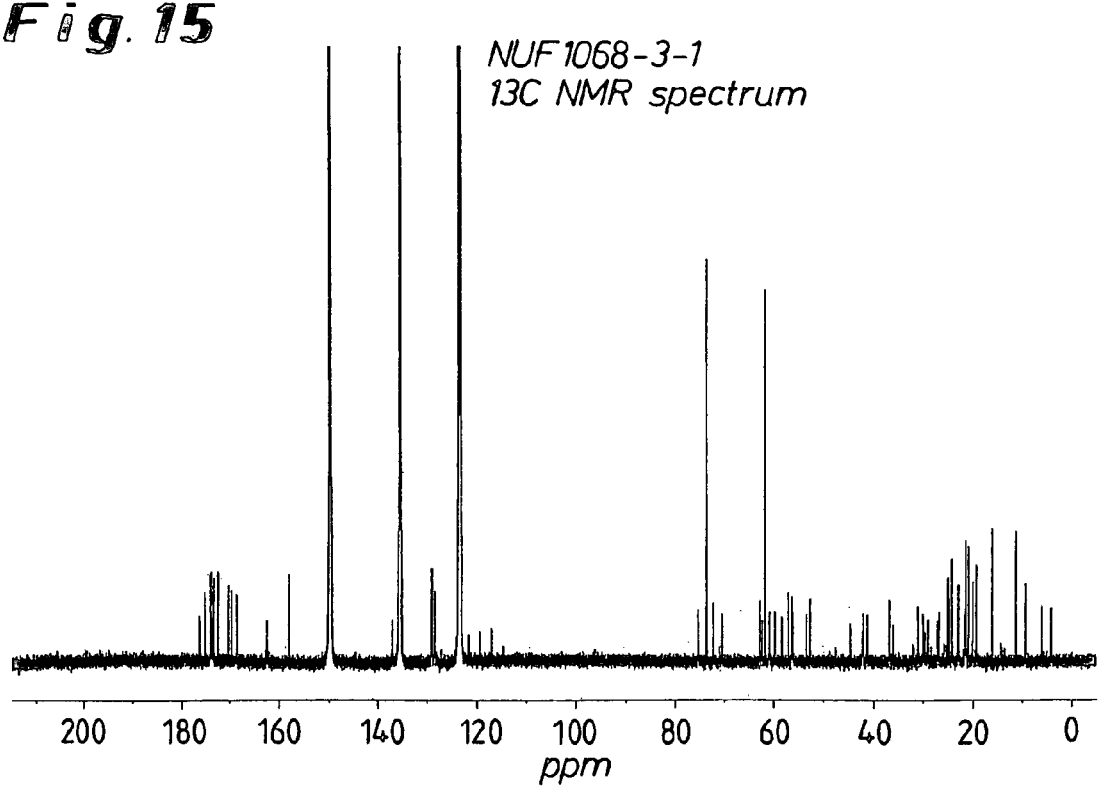
FIG. 15: $^{13}$C NMR (126 MHz, $d_5$-pyridine) of D-leucyl-$N^1$-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-3-cyclopropyl-L-alaninamide bistrifluoroacetate (Example 1).
Figure 16:
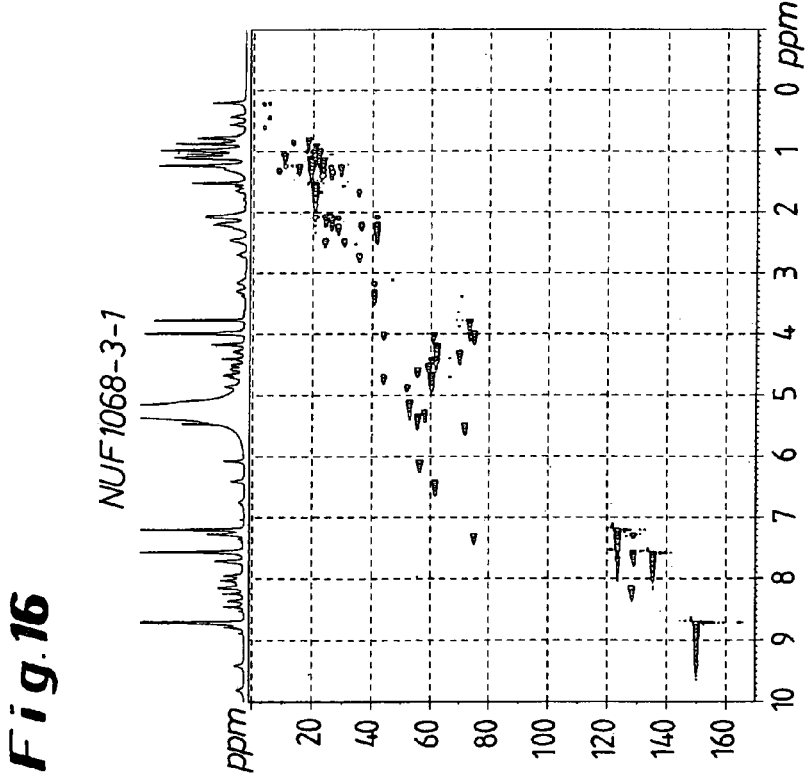
FIG. 16: HSQC NMR (500 MHz, $d_5$-pyridine) of D-leucyl-$N^1$-{(3S,6S,12S,15S,18R,21S,24S,27S,-28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-3-cyclopropyl-L-alaninamide bistrifluoroacetate (Example 1).
Figure 17:
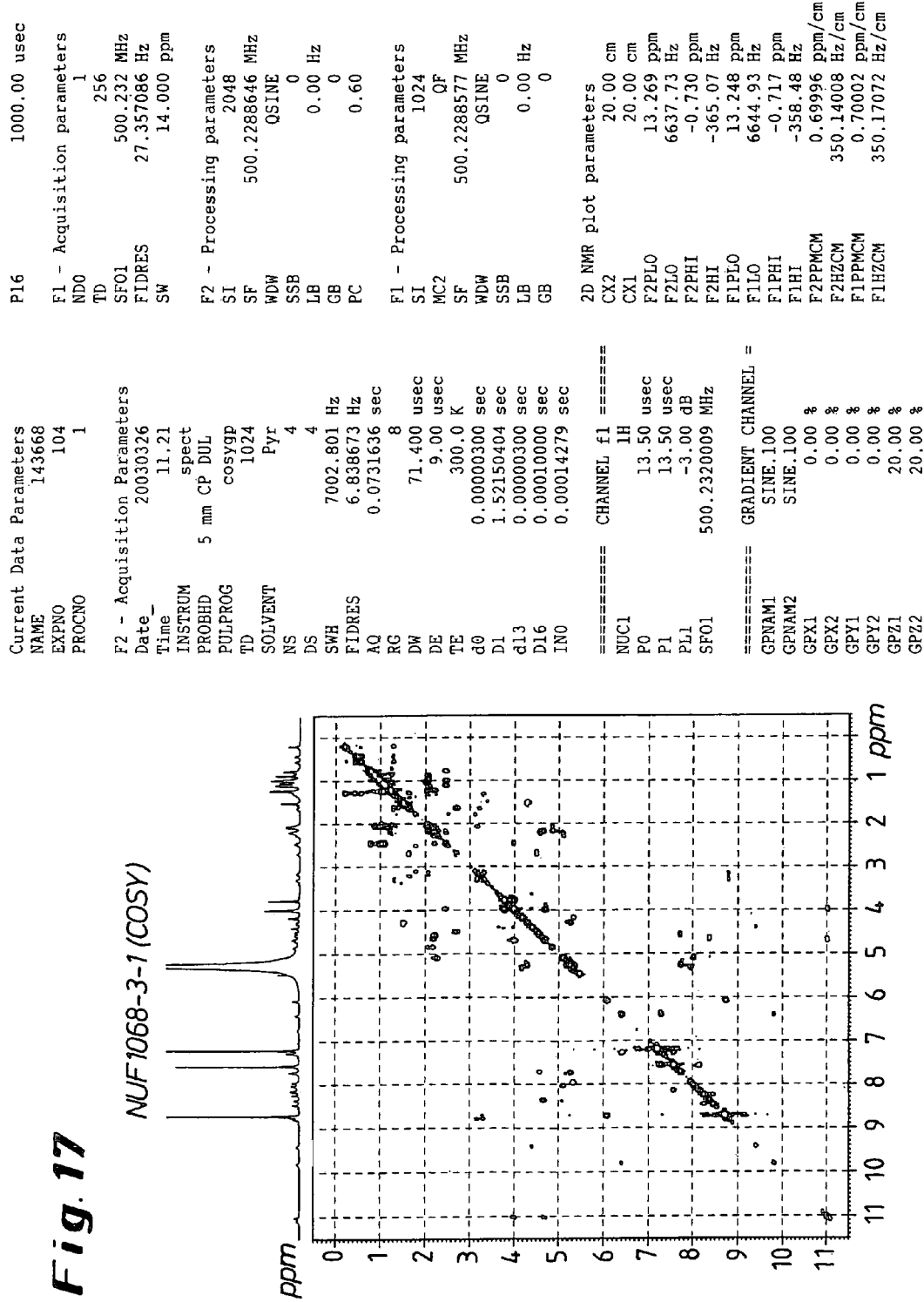
FIG. 17: COSY NMR (500 MHz, $d_5$-pyridine) of D-leucyl-$N^1$-{(3S,6S,12S,15S,18R,21S,24S,27S,-28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-3-cyclopropyl-L-alaninamide bistrifluoroacetate (Example 1).
Figure 18:
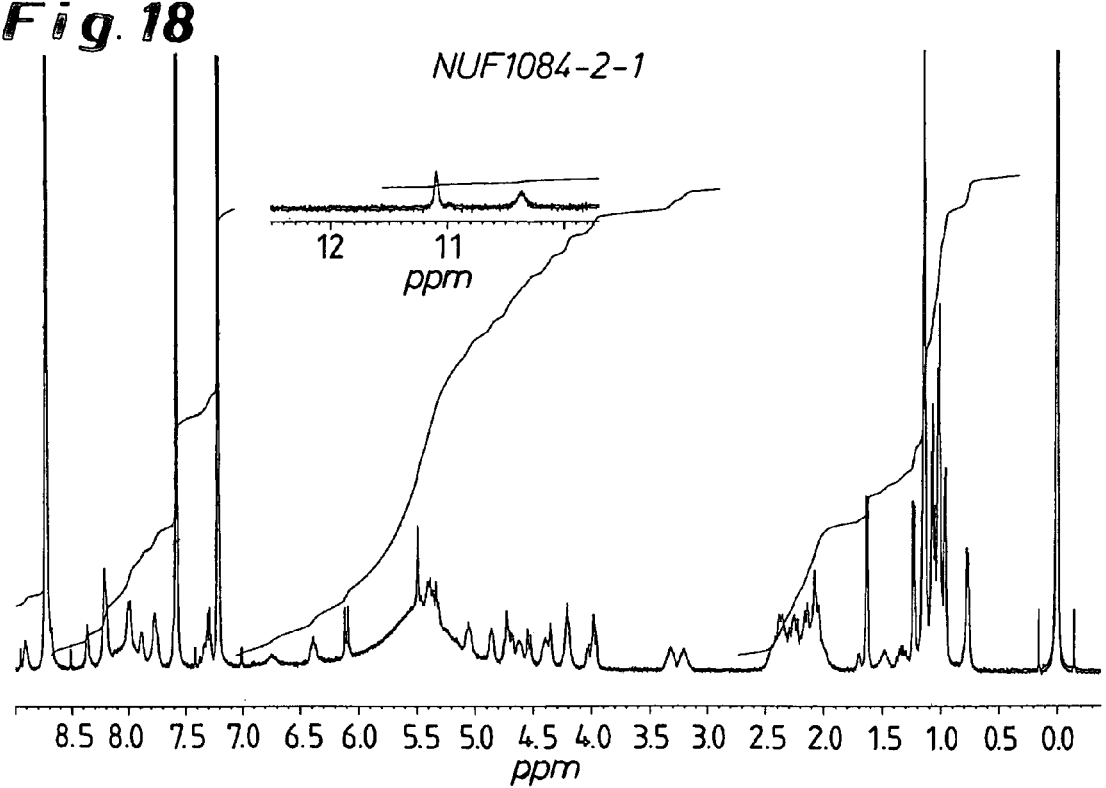
FIG. 18: $^1$H NMR (400 MHz, $d_5$-pyridine) of undecadepsipeptide bistrifluoroacetate (Example 3).
Figure 19:
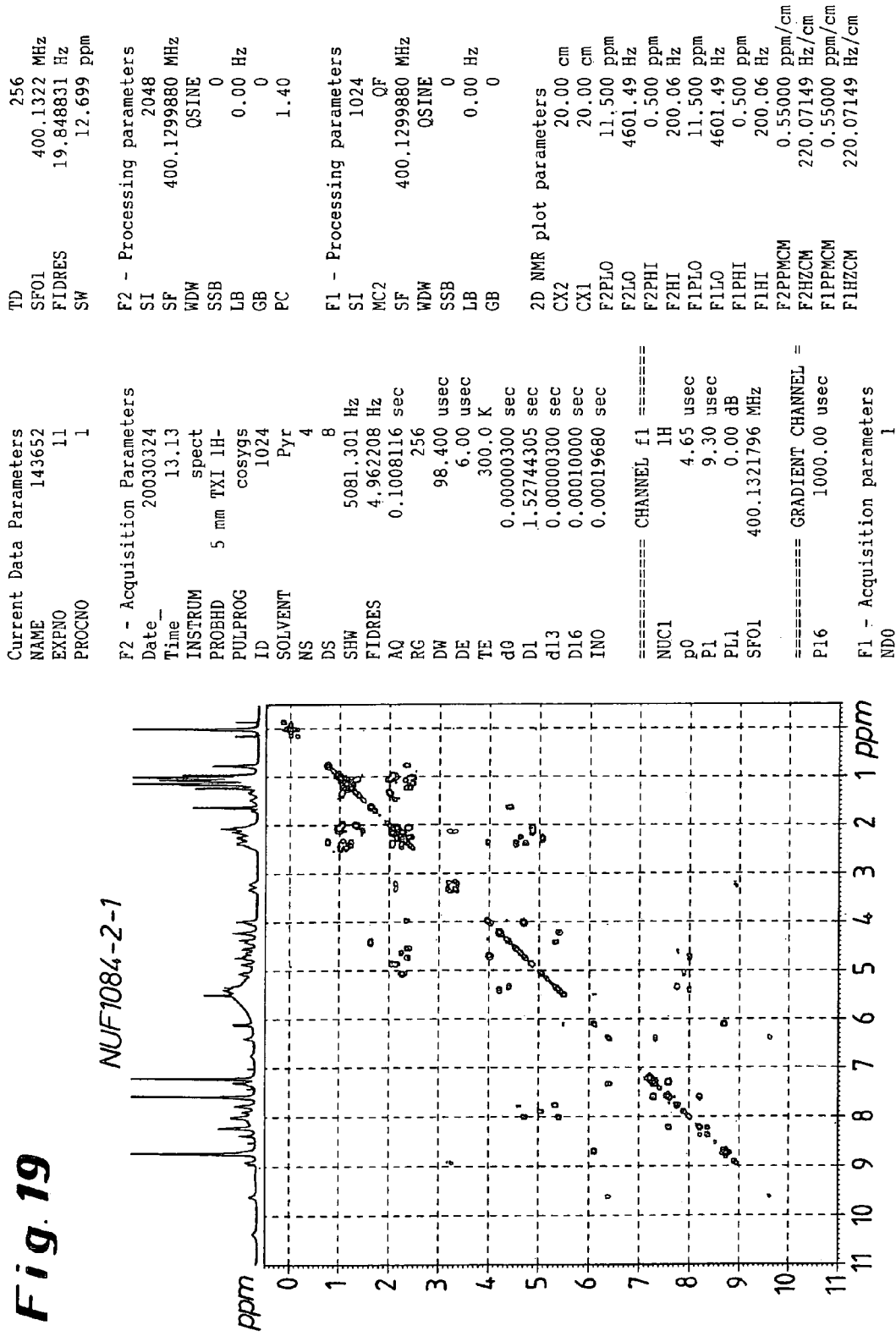
FIG. 19: $^1$H,$^1$H—COSY (400 MHz, $d_5$-pyridine) of undecadepsipeptide bistrifluoroacetate (Example 3).
Figure 20:
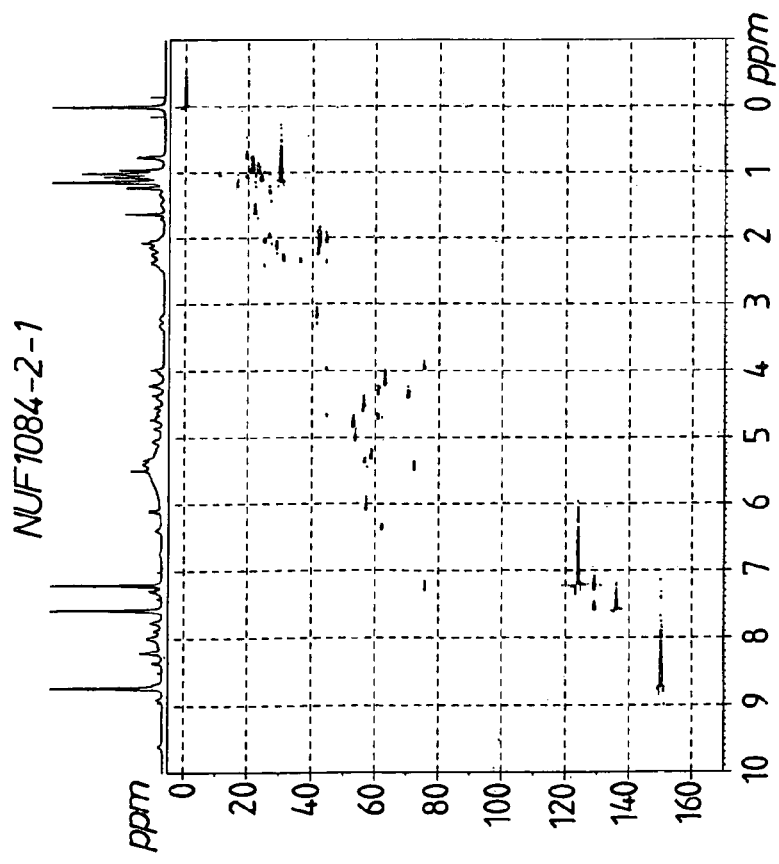
FIG. 20: HSQC NMR (500 MHz, $d_5$-pyridine) of D-leucyl-$N^1$-{(3S,6S,12S,15S,18R,21S,24S,27S,-28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-3-tert-butyl-L-alaninamide bistrifluoroacetate (Example 3).

The invention also relates to compounds of the formula (I) which correspond to the formula

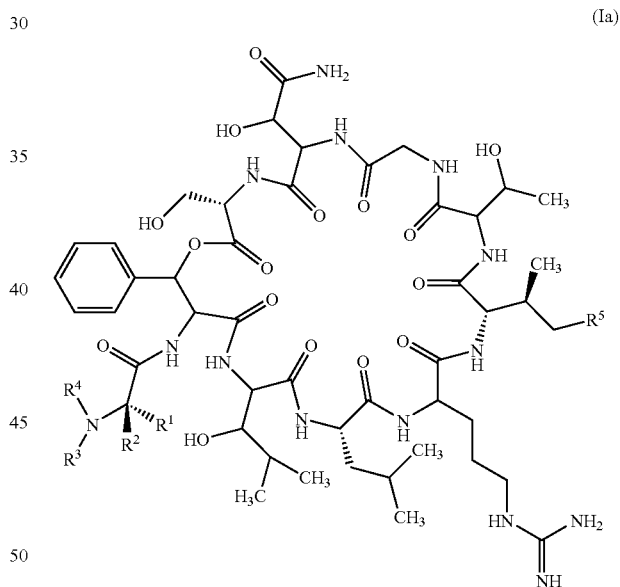

(Ia)

in which $R^1$, $R^2$, $R^3$, $R^4$ and $R^5$ have the meaning indicated above, and their salts, their solvates and the solvates of their salts, with the proviso that in the case where $R^1$ is 2-methylprop-1-yl, $R^2$ is hydrogen, $R^4$ is hydrogen and $R^5$ is methyl, $R^3$ is not glycyl, D-alanyl, L-alanyl or D-leucyl, and with the proviso that in the case where $R^1$ is 2-methylprop-1-yl, $R^2$ is hydrogen, $R^4$ is hydrogen and $R^5$ is hydrogen, $R^3$ is not D-leucyl.

The invention also relates to compounds of the formula (I) which correspond to the formula

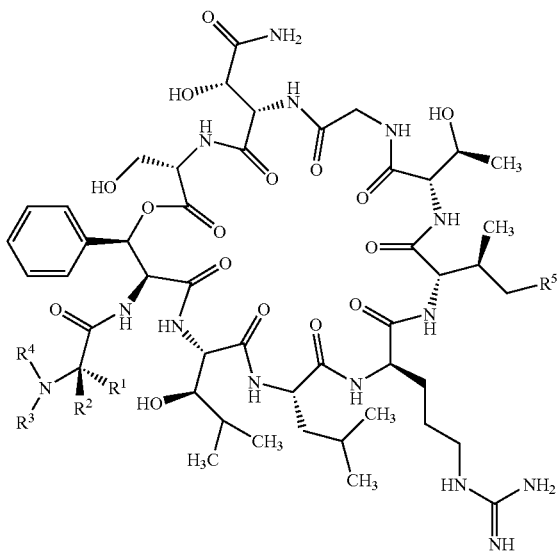

(Ib)

in which $R^1$, $R^2$, $R^3$, $R^4$ and $R^5$ have the meaning indicated above, and their salts, their solvants and the solvates of their salts, with the proviso that in the case where $R^1$ is 2-methylprop-1-yl, $R^2$ is hydrogen, $R^4$ is hydrogen and $R^5$ is methyl, $R^3$ is not glycyl, D-alanyl, L-alanyl or D-leucyl, and with the proviso that in the case where $R^1$ is 2-methylprop-1-yl, $R^2$ is hydrogen, $R^4$ is hydrogen and $R^5$ is hydrogen, $R^3$ is not D-leucyl.

Preference is given to compounds of the formulae (Ia) and (Ib) in which $R^1$ is 2-methylprop-1-yl, $R^2$ is hydrogen or $C_1$-$C_4$-alkyl, $R^3$ is alkyl, $C_3$-$C_6$-cycloalkyl, 5- to 7-membered heterocyclyl, aryl, 5- or 6-membered heteroaryl, alkylcarbonyl, alkoxycarbonyl, $C_3$-$C_6$-cycloalkylcarbonyl, 5- to 7-membered heterocyclylcarbonyl, arylcarbonyl, 5- or 6-membered heteroarylcarbonyl or alkylaminocarbonyl, where alkyl, cycloalkyl, heterocyclyl, aryl, heteroaryl, alkoxycarbonyl, cycloalkylcarbonyl, heterocyclylcarbonyl, arylcarbonyl, heteroarylcarbonyl and alkylaminocarbonyl may be substituted by 0, 1, 2 or 3 substituents independently of one another selected from the group consisting of halogen, hydroxy, amino, alkylamino and phenyl, and where alkycarbonyl is substituted by one amino or alkylamino substituent, and where alkylcarbonyl may be substituted by a further 0, 1 or 2 substituents independently of one another selected from the group consisting of halogen, hydroxy, trimethylsilyl, alkoxy, alkylthio, benzyloxy, $C_3$-$C_6$-cycloalkyl, phenyl, naphthyl, 5- to 10-membered heteroaryl, alkylcarbonylamino, alkoxycarbonylamino, arylcarbonylamino, arylcarbonyloxy, benzyloxycarbonyl and benzyloxycarbonylamino, in which phenyl and heteroaryl in turn may be substituted by 0, 1, 2 or 3 substituents independently of one another selected from the group consisting of halogen, hydroxy, nitro, alkyl, alkoxy and phenyl, or two substituents on the same carbon atom in the alkylcarbonyl form together with the carbon atom to which they are bonded a $C_3$-$C_6$-cycloalkyl ring or a 5- to 7-membered heterocyclyl ring, where the cycloalkyl ring and the heterocyclyl ring may be substituted by 0, 1, 2 or 3 substituents independently of one another selected from the group consisting of trifluoromethyl, alkyl and alkoxy, or where the cycloalkyl ring may be benzo-fused, $R^4$ is hydrogen, $C_1$-$C_4$-alkyl, cyclopropyl or cyclopropylmethyl, or $R^3$ and $R^4$ together with the nitrogen atom to which they are bonded form a 5- to 7-membered heterocyclyl ring, where the heterocyclyl ring may be substituted by 0, 1, 2 or 3 substituents independently of one another selected from the group consisting of halogen, hydroxy, amino, cyano, alkyl, alkoxy and alkylamino, and $R^5$ is hydrogen or methyl, and their salts, their solvates and the solvates of their salts, with the proviso that in the case where $R^2$ is hydrogen, $R^4$ is hydrogen and $R^5$ is methyl, $R^3$ is not glycyl, D-alanyl, L-alanyl or D-leucyl, and with the proviso that in the case where $R^2$ is hydrogen, $R^4$ is hydrogen and $R^5$ is hydrogen, $R^3$ is not D-leucyl.

Preference is also given to compounds of the formulae (Ia) and (Ib) in which $R^1$ is 2-methylprop-1-yl, $R^2$ is hydrogen or $C_1$-$C_4$-alkyl, $R^3$ is $C_1$-$C_6$-alkylcarbonyl or 5- to 7-membered heterocyclylcarbonyl, where alkylcarbonyl is substituted by one amino substituent, and where alkylcarbonyl may be substituted a further 0, 1 or 2 substituents independently of one another selected from the group consisting of halogen, hydroxy, trimethylsilyl, alkoxy, alkylthio, benzyloxy, $C_3$-$C_6$-cycloalkyl, phenyl, naphthyl, 5- to 10-membered heteroaryl, alkylcarbonylamino, alkoxycarbonylamino, arylcarbonylamino, arylcarbonyloxy, benzyloxycarbonyl and benzyloxycarbonylamino, in which phenyl in turn may be substituted by 0, 1, 2 or 3 substituents independently of one another selected from the group consisting of halogen, hydroxy, alkyl, alkoxy and phenyl, or two substituents on the same carbon atom in the alkylcarbonyl form together with the carbon atom to which they are bonded a $C_3$-$C_6$-cycloalkyl ring or a 5- to 7-membered heterocyclyl ring, where the cycloalkyl ring and the heterocyclyl ring may be substituted by 0, 1, 2 or 3 substituents independently of one another selected from the group consisting of trifluoromethyl, alkyl and alkoxy, or where the cycloalkyl ring may be benzo-fused, $R^4$ is hydrogen or $C_1$-$C_4$-alkyl, and $R^5$ is methyl, and their salts, their solvates and the solvates of their salts, with the proviso that in the case where $R^2$ is hydrogen and $R^4$ is hydrogen, $R^3$ is not glycyl, D-alanyl, L-alanyl or D-leucyl.

Preference is also given to compounds of the formulae (Ia) and (Ib) in which $R^1$ is 2-methylprop-1-yl, $R^2$ is hydrogen, $R^3$ is $C_1$-$C_6$-alkylcarbonyl, where alkylcarbonyl is substituted by one amino substituent, and where alkylcarbonyl may be substituted by a further 0, 1 or 2 substituents independently of one another selected from the group consisting of trimethylsilyl, $C_1$-$C_4$-alkoxy, methylthio, benzyloxy, $C_3$-$C_6$-cycloalkyl, phenyl, naphthyl, thienyl, pyridyl, indolyl, $C_1$-$C_4$-alkoxycarbonylamino, benzyloxycarbonyl and benzyloxycarbonylamino, in which phenyl in turn may be substituted by 0, 1, 2 or 3 substituents independently of one another selected from the group consisting of halogen, $C_1$-$C_4$-alkyl, $C_1$-$C_4$-alkoxy and phenyl, or two substituents on the same carbon atom in the alkylcarbonyl form together with the carbon atom to which they are bonded a $C_3$-$C_6$-cycloalkyl ring, where the cycloalkyl ring may be benzo-fused, $R^4$ is hydrogen, and $R^5$ is methyl, and their salts, their solvates and the solvates of their salts, with the proviso that $R^3$ is not glycyl, D-alanyl, L-alanyl or D-leucyl.

Preference is also given to compounds of the formula (I) which correspond to the formula

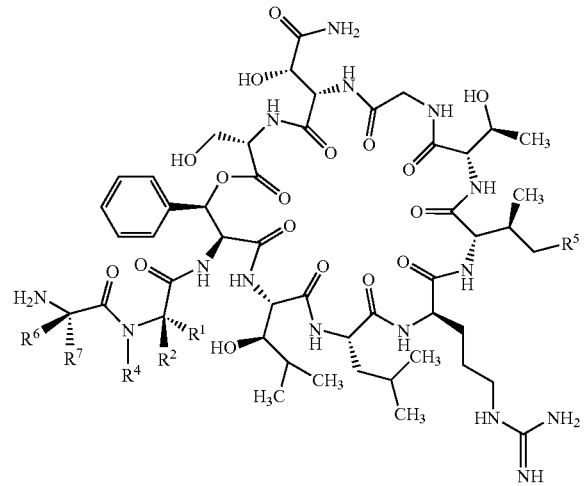

(Ic)

in which $R^1$ is 2-methylprop-1-yl, $R^2$ is hydrogen, $R^4$ is hydrogen, $R^5$ is methyl, $R^6$ is methyl, isopropyl, 1-methylprop-1-yl, 2,2-dimethylprop-1-yl, $C_3$-$C_6$-cycloalkyl, phenyl, thienyl, tert-butoxycarbonylaminopropyl, tert-butoxycarbonylaminobutyl, benzyloxycarbonylaminopropyl or benzyloxycarbonylaminobutyl, where phenyl may be substituted by 0, 1 or 2 substituents independently of one another selected from the group consisting of halogen, methoxy and phenyl, and where methyl is substituted by a substituent selected from the group consisting of trimethylsilyl, tert-butoxy, benzyloxy, $C_3$-$C_6$-cycloalkyl, phenyl, naphthyl, pyridyl, indolyl and benzyloxycarbonyl, in which phenyl in turn may be substituted by 0, 1 or 2 substituents independently of one another selected from the group consisting of halogen, methoxy and phenyl, and $R^7$ is hydrogen, or $R^6$ and $R^7$ together with the carbon atom to which they are bonded form a $C_3$-$C_6$-cycloalkyl ring, and their salts, their solvates and the solvates of their salts.

Preference is also given to compounds of the formulae (Ia) and (Ib), in which $R^1$ is hydrogen, $C_3$-$C_6$-cycloalkyl, $C_5$-$C_6$-cycloalkenyl, $C_3$-$C_6$-Cycloalkylmethyl, 5- to 7-membered heterocyclylmethyl, methyl, ethyl, n-propyl, isopropyl, 1-methylprop-1-yl, 2,2-dimethylprop-1-yl, 1,1-dimethylprop-1-yl, 1-ethyl-prop-1-yl, 1-ethyl-1-methylprop-1-yl, n-butyl, 2-methylbut-1-yl, 3-methylbut-1-yl, 1-ethylbut-1-yl, tert-butyl, 4-methylpent-1-yl, n-hexyl, alkenyl or aryl, where $R^1$ may be substituted by 0, 1, 2 or 3 substituents independently of one another selected from the group consisting of halogen, hydroxy, amino, cyano, trimethylsilyl, alkyl, alkoxy, benzyloxy, $C_3$-$C_6$-cycloalkyl, aryl, 5- to 10-membered heteroaryl, alkylamino, arylamino, alkylcarbonylamino, arylcarbonylamino, alkylcarbonyl, alkoxycarbonyl, arylcarbonyl and benzyloxycarbonylamino, in which aryl and heteroaryl in turn may be substituted by 0, 1, 2 or 3 substituents independently of one another selected from the group consisting of halogen, hydroxy, amino, cyano, nitro, alkyl, alkoxy and phenyl, $R^2$ is hydrogen or $C_1$-$C_4$-alkyl, or $R^1$ and $R^2$ together with the carbon atom to which they are bonded form a $C_3$-$C_6$-cycloalkyl ring or a 5- to 7-membered heterocyclyl ring, where the cycloalkyl ring and the heterocyclyl ring may be substituted by 0, 1, 2 or 3 substituents independently of one another selected from the group consisting of trifluoromethyl, alkyl, alkoxy and alkylcarbonyl, $R^3$ is alkyl, $C_3$-$C_6$-cycloalkyl, 5- to 7-membered heterocyclyl, aryl, 5- or 6-membered heteroaryl, alkylcarbonyl, alkoxycarbonyl, $C_3$-$C_6$-Cycloalkylcarbonyl, 5- to 7-membered heterocyclylcarbonyl, arylcarbonyl, 5- or 6-membered heteroarylcarbonyl or alkylaminocarbonyl, where alkyl, cycloalkyl, heterocyclyl, aryl, heteroaryl, alkoxycarbonyl, cycloalkylcarbonyl, heterocyclylcarbonyl, arylcarbonyl, heteroarylcarbonyl and alkylaminocarbonyl may be substituted by 0, 1, 2 or 3 substituents independently of one another selected from the group consisting of halogen, hydroxy, amino, alkylamino and phenyl, and where alkylcarbonyl is substituted by one amino or alkylamino substituent, and where alkylcarbonyl may be substituted by a further 0, 1 or 2 substituents independently of one another selected from the group consisting of halogen, hydroxy, trimethylsilyl, alkoxy, alkylthio, benzyloxy, $C_3$-$C_6$-cycloalkyl, phenyl, naphthyl, 5- to 10-membered heteroaryl, alkylcarbonylamino, alkoxycarbonylamino, arylcarbonylamino, arylcarbonyloxy, benzyloxycarbonyl and benzyloxycarbonylamino, in which phenyl and heteroaryl in turn may be substituted by 0, 1, 2 or 3 substituents independently of one another selected from the group consisting of halogen, hydroxy, nitro, alkyl, alkoxy and phenyl, or two substituents on the same carbon atom the alkyl carbonyl form together with the carbon atom to which they are bonded a $C_3$-$C_6$-cycloalkyl ring or a 5- to 7-membered heterocyclyl ring, where the cycloalkyl ring and the heterocyclyl ring may be substituted by 0, 1, 2 or 3 substituents independently of one another selected from the group consisting of trifluoromethyl, alkyl and alkoxy, or where the cycloalkyl ring may be benzo-fused, $R^4$ is hydrogen, $C_1$-$C_4$-alkyl, cyclopropyl or cyclopropylmethyl, or $R^3$ and $R^4$ together with the nitrogen atom to which they are bonded form a 5- to 7-membered heterocyclyl ring, where the heterocyclyl ring may be substituted by 0, 1, 2 or 3 substituents independently of one another selected from the group consisting of halogen, hydroxy, amino, cyano, alkyl, alkoxy and alkylamino, and $R^5$ is hydrogen or methyl, and their salts, their solvates and the solvates of their salts.

Preference is also given to compounds of the formulae (Ia) and (Ib), in which $R^1$ is 5- to 7-membered heterocyclylmethyl, methyl, ethyl, n-propyl, isopropyl, 1-methylprop-1-yl, 2,2-dimethylprop-1-yl, 1,1-dimethylprop-1-yl, 1-ethylprop-1-yl, 1-ethyl-1-methylprop-1-yl, n-butyl, 2-methylbut-1-yl, 3-methylbut-1-yl, 1-ethylbut-1-yl, tert-butyl, 4-methylpent-1-yl or n-hexyl, where $R^1$ may be substituted by 0, 1, 2 or 3 substituents independently of one another selected from the group consisting of trimethylsilyl, alkoxy, benzyloxy, $C_3$-$C_6$-cycloalkyl, aryl, 5- to 10-membered heteroaryl, alkylamino, alkylcarbonylamino, alkylcarbonyl, alkoxycarbonyl, arylcarbonyl and benzyloxycarbonylamino, in which aryl and heteroaryl in turn may be substituted by 0, 1, 2 or 3 substituents independently of one another selected from the group consisting of halogen, hydroxy, nitro, alkyl, alkoxy and phenyl, $R^2$ is hydrogen or $C_1$-$C_4$-alkyl, or $R^1$ and $R^2$ together with the carbon atom to which they are bonded form a $C_3$-$C_6$-cycloalkyl ring or a 5- to 7-membered heterocyclyl ring, where the cycloalkyl ring and the heterocyclyl ring may be substituted by 0, 1, 2 or 3 substituents independently of one another selected from the group consisting of trifluoromethyl, alkyl, alkoxy and alkylcarbonyl, $R^3$ is alkylcarbonyl or 5- to 7-membered heterocyclylcarbonyl, where alkylcarbonyl is substituted by one amino substituent, and where alkylcarbonyl may be substituted by a further 0, 1 or 2 substituents independently of one another selected from the group consisting of halogen, hydroxy, trimethylsilyl, alkoxy, alkylthio, benzyloxy, $C_3$-$C_6$-cycloalkyl, phenyl, naphthyl, 5- to 10-membered heteroaryl, alkylcarbonylamino, alkoxycarbonylamino, arylcarbonylamino, arylcarbonyloxy, benzyloxycarbonyl and benzyloxycarbonylamino, in which phenyl in turn may be substituted by 0, 1, 2 or 3 substituents independently of one another selected from the group consisting of halogen, hydroxy, alkyl, alkoxy and phenyl, or two substituents on the same carbon atom in the alkylcarbonyl form together with the carbon atom to which they are bonded a $C_3$-$C_6$-cycloalkyl ring or a 5- to 7-membered heterocyclyl ring,
  where the cycloalkyl ring and the heterocyclyl ring may be substituted by 0, 1, 2 or 3 substituents independently of one another selected from the group consisting of trifluoromethyl, alkyl and alkoxy, or
  where the cycloalkyl ring may be benzo-fused,
$R^4$ is hydrogen or $C_1$-$C_4$-alkyl, and
  $R^5$ is methyl,
  and their salts, their solvates and the solvates of their salts.

Preference is also given to compounds of the formulae (Ia) and (Ib) in which
  $R^1$ is methyl, ethyl, n-propyl, isopropyl, 1-methylprop-1-yl, 2,2-dimethylprop-1-yl, 1,1-dimethylprop-1-yl, 1-ethyl-prop-1-yl, 1-ethyl-1-methylprop-1-yl, n-butyl, 2-methylbut-1-yl, 3-methylbut-1-yl, 1-ethylbut-1-yl, tert-butyl, 4-methylpent-1-yl or n-hexyl,
    where $R^1$ may be substituted by 0 or 1 substituent selected from the group consisting of trimethylsilyl, $C_1$-$C_4$-alkoxy, benzyloxy, $C_3$-$C_6$-cycloalkyl, phenyl, naphthyl, pyridyl, indolyl, $C_1$-$C_4$-alkoxycarbonyl and benzyloxycarbonylamino,
    in which phenyl and pyridyl in turn may be substituted by 0, 1, 2 or 3 substituents independently of one another selected from the group consisting of halogen, hydroxy, nitro, $C_1$-$C_4$-alkyl, $C_1$-$C_4$-alkoxy and phenyl,
  $R^2$ is hydrogen, or
  $R^1$ and $R^2$ together with the carbon atom to which they are bonded form a $C_3$-$C_6$-cycloalkyl ring, where the cycloalkyl ring may be substituted by 0 or 1 substituent selected from the group consisting of trifluoromethyl and $C^1$-$C_4$-alkoxy,
$R^3$ is $C_1$-$C_6$-alkylcarbonyl,
  where alkylcarbonyl is substituted by one amino substituent, and
  where alkylcarbonyl may be substituted by a further 0, 1 or 2 substituents independently of one another selected from the group consisting of trimethylsilyl, $C_1$-$C_4$-alkoxy, methylthio, benzyloxy, $C_3$-$C_6$-cycloalkyl, phenyl, naphthyl, thienyl, pyridyl, indolyl, $C_1$-$C_4$-alkoxycarbonylamino, benzyloxycarbonyl and benzyloxycarbonylamino,
    in which phenyl in turn may be substituted by 0, 1, 2 or 3 substituents independently of one another selected from the group consisting of halogen, $C_1$-$C_4$-alkyl, $C_1$-$C_4$-alkoxy and phenyl,
  or two substituents on the same carbon atom in the alkylcarbonyl form together with the carbon atom to which they are bonded a $C_3$-$C_6$-cycloalkyl ring,
    where the cycloalkyl ring may be benzo-fused,
$R^4$ is hydrogen, and
  $R^5$ is methyl,
  and their salts, their solvates and the solvates of their salts.

Preference is also given to compounds of the formula (Ic), in which
  $R^1$ is methyl, phenylethyl, n-propyl, 1-methylprop-1-yl, 2,2-dimethylprop-1-yl, benzyloxycarbonylaminopropyl or benzyloxycarbonylaminobutyl,
    where methyl is substituted by one substituent selected from the group consisting of tert-butoxy, benzyloxy, $C_3$-$C_6$-cycloalkyl, phenyl, naphthyl, pyridyl, indolyl and tert-butoxycarbonyl,
    in which phenyl in turn may be substituted by 0, 1 or 2 substituents independently of one another selected from the group consisting of halogen, nitro, methoxy and phenyl,
  $R^2$ is hydrogen, or
  $R^1$ and $R^2$ together with the carbon atom to which they are bonded form a $C_3$-$C_6$-cycloalkyl ring,
  $R^4$ is hydrogen,
  $R^5$ is methyl,
  $R^6$ is methyl, isopropyl, 1-methylprop-1-yl, 2-methylprop-1-yl, 2,2-dimethylprop-1-yl, $C_3$-$C_6$-cycloalkyl, phenyl, thienyl, tert-butoxycarbonylaminopropyl, tert-butoxycarbonylaminobutyl, benzyloxycarbonylaminopropyl or benzyloxycarbonylaminobutyl,
    where phenyl may be substituted by 0, 1 or 2 substituents independently of one another selected from the group consisting of halogen, methoxy and phenyl, and
  where methyl is substituted by one substituent selected from the group consisting of trimethylsilyl, tert-butoxy, benzyloxy, $C_3$-$C_6$-cycloalkyl, phenyl, naphthyl, pyridyl, indolyl and benzyloxycarbonyl,
    in which phenyl in turn may be substituted by 0, 1 or 2 substituents independently of one another selected from the group consisting of halogen, methoxy and phenyl, and
  $R^7$ is hydrogen, or
  $R^6$ and $R^7$ together with the carbon atom to which they are bonded form a $C_3$-$C_6$-cycloalkyl ring,
  and their salts, their solvates and the solvates of their salts.

The invention also relates to those compounds of the formulae (I), (Ia) and (Ib), in which
  $R^1$ is hydrogen, $C_3$-$C_6$-cycloalkyl, $C_5$-$C_6$-cycloalkenyl, $C_3$-$C_6$-cycloalkylmethyl, 5- to 7-membered heterocyclylmethyl, methyl, ethyl, n-propyl, isopropyl, 1-methylprop-1-yl, 2,2-dimethylprop-1-yl, 1,1-dimethylprop-1-yl, 1-ethyl-prop-1-yl, 1-ethyl-1-methylprop-1-yl, 2-methylbut-1-yl, 3-methylbut-1-yl, 1-ethylbut-1-yl, tert-butyl, 4-methylpent-1-yl, n-hexyl, alkenyl or aryl,
    where $R^1$ may be substituted by 0, 1, 2 or 3 substituents independently of one another selected from the group consisting of halogen, hydroxy, amino, cyano, alkyl, alkoxy, $C_3$-$C_6$-cycloalkyl, aryl, alkylamino, arylamino, alkylcarbonylamino, arylcarbonylamino, alkylcarbonyl and arylcarbonyl,
  $R^2$ is hydrogen or $C_1$-$C_4$-alkyl, or
  $R^1$ and $R^2$ form together with the carbon atom to which they are bonded a $C_3$-$C_6$-cycloalkyl ring or a $C_5$-$C_7$ heterocyclyl ring, where the cycloalkyl ring and the heterocyclyl ring may be substituted by 0, 1, 2 or 3 substituents independently of one another selected from the group consisting of alkyl and alkylcarbonyl, $R^3$ is a carbonyl-linked amino acid, where the amino function of the amino acid may be substituted by 0, 1 or 2 $C_1$-$C_4$-alkyl substituents, or $R^3$ is alkyl, $C_3$-$C_6$-cycloalkyl, 5- to 7-membered heterocyclyl, aryl, 5- or 6-membered heteroaryl, alkylcarbonyl, alkoxycarbonyl, $C_3$-$C_6$-cycloalkylcarbonyl, 5- to 7-membered heterocyclylcarbonyl, arylcarbonyl, 5- or 6-membered heteroarylcarbonyl or alkylaminocarbonyl, where alkyl, $C_3$-$C_6$-cycloalkyl, 5- to 7-membered heterocyclyl, aryl, 5- or 6-membered heteroaryl, alkylcarbonyl, alkoxycarbonyl, $C_3$-$C_6$-cycloalkylcarbonyl, 5- to 7-membered heterocyclylcarbonyl, arylcarbonyl, 5- or 6-membered heteroarylcarbonyl and alkylaminocarbonyl may be substituted by 0, 1, 2 or 3 substituents independently of one another selected from the group consisting of halogen, hydroxy, amino and alkylamino, $R^4$ is hydrogen, $C_1$-$C_4$-alkyl, cyclopropyl or cyclopropylmethyl, or $R^3$ and $R^4$ together with the nitrogen atom to which they are bonded form a $C_5$-$C_7$-heterocyclyl ring, where the heterocyclyl ring may be substituted by 0, 1, 2 or 3 substituents independently of one another selected from the group consisting of halogen, hydroxy, amino, cyano, alkyl, alkoxy and alkylamino, and $R^5$ is hydrogen or methyl.

Preference is also given to those compounds of the formulae (I), (Ia) and (Ib) in which $R^1$ is cyclopropylmethyl, cyclopentylmethyl, cyclohexylmethyl, ethyl, n-propyl, isopropyl, 2,2-dimethylprop-1-yl or 2-methylbut-1-yl, $R^2$ is hydrogen, $R^3$ is a carbonyl-linked amino acid, $R^4$ is hydrogen, and $R^5$ is hydrogen or methyl.

Preference is also given to those compounds of the formulae (I), (Ia) and (Ib) in which $R^1$ is cyclopropylmethyl or n-propyl, $R^2$ is hydrogen, $R^3$ is a carbonyl-linked amino acid, $R^4$ is hydrogen, and $R^5$ is methyl.

Preference is also given to those compounds of the formulae (I), (Ia) and (Ib) in which $R^1$ is cyclopropylmethyl.

Preference is also given to those compounds of the formulae (I), (Ia) and (Ib) in which $R^2$ is hydrogen.

Preference is also given to those compounds of the formulae (I), (Ia) and (Ib) in which $R^3$ is carbonyl-linked amino acid.

Preference is also given to those compounds of the formulae (I), (Ia) and (Ib) in which $R^4$ is hydrogen.

Preference is also given to those compounds of the formulae (I), (Ia) and (Ib) in which $R^5$ is methyl.

The definitions of radicals indicated specifically in the respective combinations or preferred combinations of radicals are replaced irrespective of the particular combinations indicated for the radicals as desired also by the definitions of radicals of another combination.

Combinations of two or more of the abovementioned preferred ranges are very particularly preferred.

The invention further relates to a process for preparing the compounds of the formula (I), where compounds of the formula

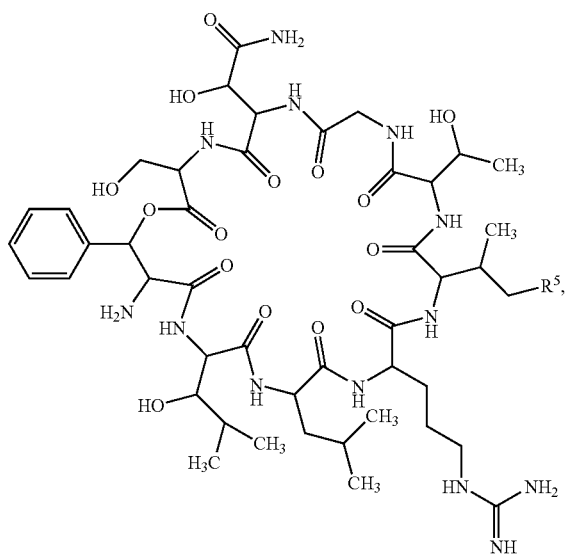

in which $R^5$ has the meaning indicated above, are reacted with compounds of the formula

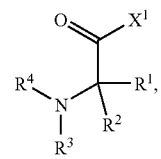

in which $R^1$, $R^2$, $R^3$ and $R^4$ have the meaning indicated above, and $X^1$ is halogen, preferably bromine, chlorine or fluorine, or hydroxy.

If $X^1$ is halogen, the reaction generally takes place in inert solvents, where appropriate in the presence of a base, preferably in a temperature range from −30° C. to 50° C. under atmospheric pressure.

Examples of inert solvents are tetrahydrofuran, methylene chloride, pyridine, dioxane or dimethylformamide, with preference for pyridine or dimethylformamide.

Preferred inert solvents are tetrahydrofuran or methylene chloride.-

Examples of bases are triethylamine, diisopropylethylamine or N-methylmorpholine, with preference for diisopropylethylamine.

If $X^1$ is hydroxy, the reaction generally takes place in inert solvents in the presence of a dehydrating reagent, where appropriate in the presence of a base, preferably in a temperature range from −30° C. to 50° C. under atmospheric pressure.

Examples of inert solvents are halohydrocarbons such as dichloromethane or trichloromethane, hydrocarbon such as benzene, nitromethane, dioxane, dimethylformamide or acetonitrile. It is likewise possible to employ mixtures of these solvents. Dichloromethane or dimethylformamide is particularly preferred.

Examples of dehydrating reagents suitable in this connection are carbodiimides such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium-3'-sulphonate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxy-tri(dimethylamino)phosphonium hexafluorophosphat,e or O-(benzotriazol-1-yl)-N,N,N'N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyl-uronium hexafluorophosphate (HATU), or 1-hydroxybenzotriazole (HOBt), or benzotriazol-1-yloxytris(dimethylamino)phosphonium hexafluorophosphate (BOP), or N-hydroxysuccinimide, or mixtures thereof, with bases.

Examples of bases are alkali metal carbonates such as, for example, sodium or potassium carbonate, or bicarbonate, or organic bases such as trialkylamines, e.g. triethylamine, N-methylmorpholine, N-methylpiperidine, 4-dimethylaminopyridine or diisopropylethylamine.

The condensation is preferably carried out with HATU or with EDC in the presence of HOBt.

The compounds of the formula (III) carry protective groups where appropriate, so that in these cases the reaction of compounds of the formula (II) with compounds of the formula (III) is followed by elimination of the protective groups with trifluoroacetic acid by methods known to the skilled person.

The compounds of the formula (II) can be synthesized by double Edmann degradation from lysobactin (Example 1A) or katanosin (Example 2A), as described in Example 10A to 13A in the experimental section.

The compounds of the formula (III) are known or can be synthesized by known processes from the appropriate precursors.

The preparation of the compounds of the invention can be illustrated by the following synthesis scheme.

Synthesis scheme:

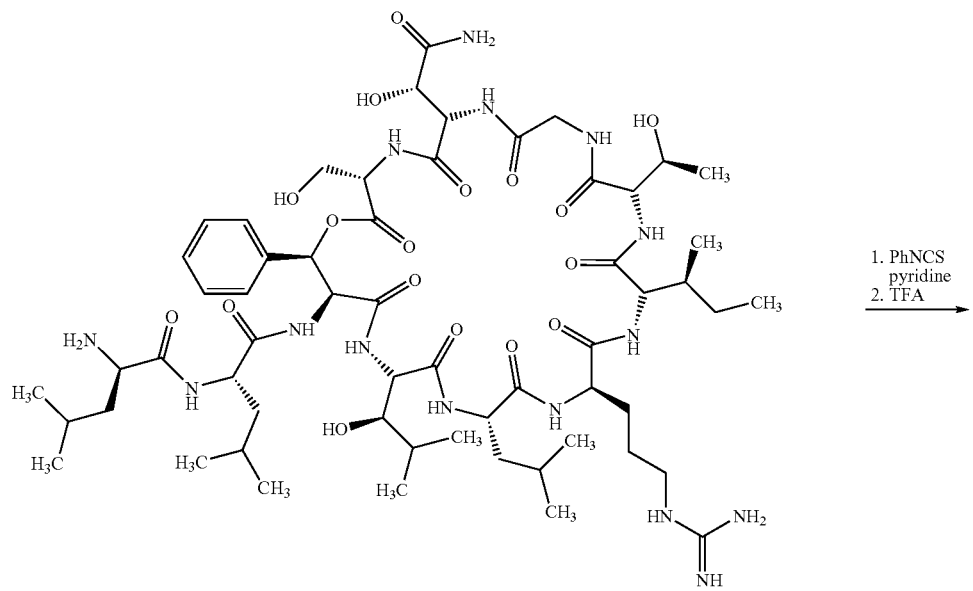

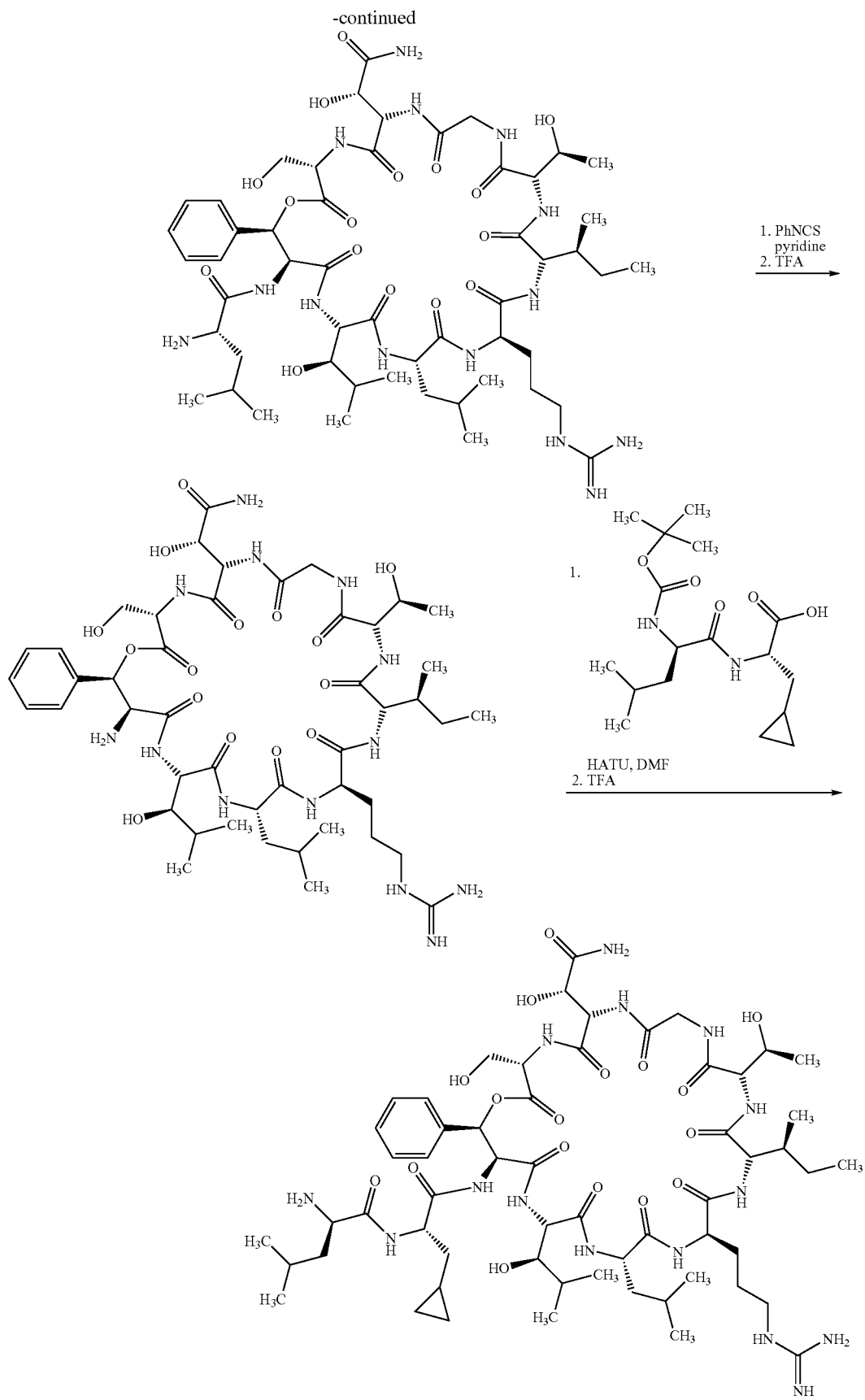

The compounds of the invention show a valuable range of pharmacological effects which could not have been predicted. They show an antibacterial effect.

They are therefore suitable for use as medicaments for the treatment and/or prophylaxis of diseases in humans and animals.

The compounds of the invention are distinguished by low nephrotoxicity compared with lysobactin.

The described nonadepsipeptides act as inhibitors of bacterial cell wall biosynthesis.

The preparations of the invention are particularly effective for bacteria and bacteroid microorganisms. They are therefore particularly suitable for the prophylaxis and chemotherapy of local and systemic infections caused by these pathogens in human and veterinary medicine.

The preparations of the invention can in principle be used against all bacteria and bacteroid microorganisms possessing a bacterial cell wall (murein sacculus) and the relevant enzyme systems, for example the following pathogens or mixtures of the following pathogens:

Gram-negative cocci (*Neisseria gonorrhoeae*) and Gram-negative rods such as enterobacteriaceae, e.g. *Escherichia coli, Haemophilus influenzae, Pseudomonas, Klebsiella,* Citrobacter (*C. freundii, C. diversus*), *Salmonella* and *Shigella*; also Enterobacter (*E. aerogenes, E. agglomerans*), *Hafilia, Serratia* (*S. marcescens*), *Providencia, Yersinia,* and the genus *Acinetobacter, Branhamella* and *Chlamydia.* The antibacterial range additionally includes strictly anaerobic bacteria such as, for example, *Bacteroides fragilis,* representatives of the genus *Peptococcus, Peptostreptococcus,* and the genus *Clostridium;* in addition mycobacteria, e.g. *M. tuberculosis.* The compounds of the invention show a particularly pronounced effect on Gram-positive cocci, e.g. staphylococci (*S aureus, S. epidermidis, S. haemolyticus, S. carnosus*), enterococci (*E. faecalis, E. faecium*) and streptococci (*S. agalactiae, S. pneumoniae, S. pyogenes*).

The above list of pathogens is mainly by way of example and is by no means to be interpreted restrictively. Examples which may be mentioned of diseases which are caused by the pathogens mentioned or mixed infections and can be prevented, improved or healed by the preparations of the invention are:

Infectious diseases in humans such as, for example, uncomplicated and complicated urinary tract infections, uncomplicated cutaneous and superficial infections, complicated cutaneous and soft tissue infections, community-acquired pneumonia, nosocomial pneumonias, acute exacerbations and secondary bacterial infections of chronic bronchitis, acute otitis media, acute sinusitis, streptococcal pharyngitis, bacterial meningitis, uncomplicated gonococcal and non-gonococcal urethritis/cervicitis, acute prostatitis, endocarditis, uncomplicated and complicated intra-abdominal infections, gynaecological infections, pelvic inflammatory disease, bacterial vaginosis, acute and chronic osteomyelitis, acute bacterial arthritis, empirical therapy in febrile neutropenic patients, also bacteraemias, MRSA infections, acute infectious diarrhoea, *Helicobacter pylori* infections, odontogenic infections, ophthalmological infections, postoperative infections (including periproctal abscess, wound infections, biliary infections, mastitis and acute appendicitis), cystic fibrosis and bronchiectasis.

Apart from humans, bacterial infections can also be treated in other species. Examples which may be mentioned are:

Pigs: diarrhoea, enterotoxaemia, sepsis, dysentery, salmonellosis, mastitis-metritis-agalactia syndrome, mastitis;

Ruminants (cattle, sheep, goats): diarrhoea, sepsis, bronchopneumonia, salmonellosis, pasteurellosis, genital infections;

Horses: bronchopneumonias, joint ill, puerperal and post-puerperal infections, salmonellosis;

Dogs and cats: bronchopneumonia, diarrhoea, dermatitis, otitis, urinary tract infections, prostatitis;

Poultry (hens, turkeys, quail, pigeons, ornamental birds and others): *E. coli* infections, chronic airway disorders, salmonellosis, pasteurellosis, psittacosis.

It is likewise possible to treat bacterial diseases in the rearing and management of productive and ornamental fish, in which case the antibacterial spectrum is extended beyond the pathogens mentioned above to further pathogens such as, for example, *Pasteurella, Brucella, Campylobacter, Listeria, Erysipelothrix,* corynebacteria, *Borellia, Treponema, Nocardia, Rickettsia, Yersinia.*

The present invention further relates to the use of the compounds of the invention for the treatment and/or prophylaxis of diseases, in particular of bacterial infectious diseases.

The present invention further relates to the use of the compounds of the invention for the treatment and/or prophylaxis of diseases, especially of the aforementioned diseases.

The present invention further relates to the use of the compounds of the invention for producing a medicament for the treatment and/or prophylaxis of diseases, especially of the aforementioned diseases.

The compounds of the invention are preferably used to produce medicaments suitable for the prophylaxis and/or treatment of bacterial diseases.

The present invention further relates to a method for the treatment and/or prophylaxis of diseases, especially of the aforementioned diseases, by using an antibacterially effective amount of the compounds of the invention.

The present invention further relates to medicaments comprising at least one compound of the invention and at least one or more further active ingredients, in particular for the treatment and/or prophylaxis of the aforementioned diseases. Preferred active ingredients for combination are compounds having antibacterial activity and having a different range of effects, in particular a supplementary range of effects, and/or being synergistic to the compounds of the invention.

The compounds of the invention can act systemically and/or locally. For this purpose, they can be administered in a suitable way such as, for example, by the oral, parenteral, pulmonary, nasal, sublingual, lingual, buccal, rectal, dermal, transdermal, conjunctival or otic route, or as implant or stent.

The compounds of the invention can be administered in administration forms suitable for these administration routes.

Suitable for oral administration are administration forms which function according to the prior art and deliver the compounds of the invention rapidly and/or in modified fashion, and which contain the compounds of the invention in crystalline and/or amorphized and/or dissolved form, such as, for example, tablets (uncoated or coated tablets, for example having enteric coatings or coatings which are insoluble or dissolve with a delay and control the release of the compound of the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Suitable for the other administration routes are, for example, pharmaceutical forms for inhalation (inter alia powder inhalers, nebulizers), nasal drops, solutions, sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (such as, for example, patches), milk, pastes, foams, dusting powders, implants or stents.

The compounds of the invention can be converted into the stated administration forms. This can take place in a manner known per se by mixing with inert, nontoxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as, for example, ascorbic acid), colours (e.g. inorganic pigments such as, for example, iron oxides) and masking flavours and/or odours.

The present invention further relates to medicaments which comprise at least one compound of the invention, normally together with one or more inert, nontoxic, pharmaceutically suitable excipients, and to the use thereof for the aforementioned purposes.

It has generally proved advantageous to administer on intravenous administration amounts of about 0.001 to 100 mg/kg, preferably about 0.1 to 10 mg/kg, of bodyweight to achieve effective results, and on oral administration the dosage is about 0.01 to 50 mg/kg, preferably 0.5 to 10 mg/kg, of bodyweight.

It may nevertheless be necessary where appropriate to deviate from the stated amounts, in particular as a function of the bodyweight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The per centage data in the following tests and examples are, unless indicated otherwise, per centages by weight; parts are parts by weight. Solvent ratios, dilution ratios and concentration data for the liquid/liquid solutions are in each case based on volume.

A. EXAMPLES

Abbreviations
Area (peak) area
BHI brain heart infusion
Boc tert-butyloxycarbonyl
br. broad signal (in NMR spectra)
Calc. calculated
conc. concentrated
D doublet (in NMR spectra)
DCI direct chemical ionization (in MS)
DCM dichloromethane
DIEA N,N-diisopropylethylamine
DMSO dimethyl sulphoxide
DMF N,N-dimethylformamide
EA ethyl acetate (acetic acid ethyl ester)
EDC 1-ethyl-3-(3-dimethylaminopropyl)carbodiimide (also EDCI)
EDCxHCl 1-ethyl-3-(3-dimethylaminopropyl)carbodiimide hydrochloride
EI electron impact ionization (in MS)
ESI electrospray ionization (in MS)
Ex. Example
h Hour
HATU O-(7-azabenzotriazol-1-yl)-N,N,N',N'-tetramethyluronium hexafluorophosphate
HOBt 1-hydroxybenzotriazole
HPLC high pressure, high performance liquid chromatography
HR high resolution
i. v. in vacuo
LC-MS coupled liquid chromatography-mass spectroscopy
LDA lithium diisopropylamide
m medium (in UV and IR spectra)
m multiplet (in NMR spectra)
MALDI matrix-assisted laser desorption/ionization
MIC minimum inhibitory concentration
min minute(s)
m.p. melting point
MRSA methicillin-resistance to *Staphylococcus aureus*
MS mass spectroscopy
NCCLS National Committee for Clinical Laboratory Standards
neg. negative
NMM N-methylmorpholine
NMR nuclear magnetic resonance spectroscopy
p.a. pro analysi
Pd—C palladium on carbon
pos. positive
quant. quantitative
RP-HPLC reverse phase HPLC
RT room temperature
$R_t$ retention time (in HPLC)
s strong (in UV and IR spectra)
s singlet (in NMR spectra)
sat. saturated
TBTU O-(benzotriazol-1-yl)-N,N,N',N'-tetramethyluronium tetrafluoroborate
TCTU O-(1H-6-chlorobenzotriazol-1-yl)-1,1,3,3-tetramethyluronium tetrafluoroborate
TFA trifluoroacetic acid
TFE 2,2,2-trifluoroethanol
THF tetrahydrofuran
TLC thin-layer chromatography
TOF time of flight
UV ultraviollett
Vis visible
VRSA vancomycin-resistance to *Stapylococcus aureus*
w weak (in UV and IR spectra)
Z, Cbz benzyloxycarbonyl References
Concerning the nomenclature of peptides and cyclodepsipeptides, compare:

1. A Guide to IUPAC Nomenclature of Organic Compounds (Recommendations 1993), 1993, Blackwell Scientific publications.
2. Nomenclature and symbolism for amino acids and peptides. Recommendations 1983. IUPAC-IUB Joint Commission on Biochemical Nomenclature, UK. *Biochemical Journal* 1984, 219, 345-373, and cited literature.

General LC-MS, HR-MS, HPLC and Gel Chromatography Methods

Method 1 (HPLC): instrument: HP1100 with DAD (G1315A) and autosampler (G1329A), auto-sampler thermostat (G1330A, 5° C.), degasser (G1322A) and binary pump (G1312A); precolumn: Waters Symmetry C-18, 10×2.1 mm, 3.5 µm; analytical column: Waters Symmetry C-18, 50×2.1 mm, 3.5 µm; column oven: 45° C.; eluent A: water/0.05% trifluoroacetic acid; eluent B: acetonitrile/0.05% trifluoroacetic acid; flow rate: 0.4 ml/min; gradient 0-100% B in 9 min, then 3 min at 100% B, then regeneration of the column.

Method 2 (LC-MS): instrument: Micromass LCT; ionization: ESI positive/negative; HP1100 with DAD and autosampler; oven 40° C.; column: Waters Symmetry C-18, 50×2.1 mm, 3.5 µm; eluent A: 0.1% formic acid/acetonitrile, eluent B: 0.1% formic acid/water; flow rate: 0.5 ml/min; gradient: 0-1 min 0% A, 1-6 min 90% A, 6-8 min 100% A, 8-10 min 100% A, 10-15 min 0% A.

Method 3 (HPLC): instrument: Gilson Abimed HPLC; UV detector 254 nm; binary pump system; column: Nucleosil RP-18, 7 µm; 250×50 mm; flow rate: 30 ml/min; eluent A: water/0.1% trifluoroacetic acid, eluent B: acetonitrile/0.1% trifluoroacetic acid; gradient: 0-40 min 20-25% B, 40-60 min 25% B, 60-110 min 25-50% B, 110-120 min 50% B, 120-130 min 50-100% B, 130-160 min 100% B, then regeneration of the chromatography column.

Method 4 (HPLC): instrument: Gilson Abimed HPLC; UV detector 254 nm; binary pump system; column: Nucleosil RP-18, 7 µm; 250×50 mm; flow rate 40 ml/min; eluent A: water/0.05% trifluoroacetic acid, eluent B: acetonitrile/0.05% trifluoroacetic acid; gradient: 0-105 min 20-25% B, 105-111 min 25% B, 111-131 min 25-27% B, 131-157 min 27-35% B, 157-192 min 35-40% B, 192-207 min 40-45% B, then regeneration of the chromatography column.

Method 5 (HPLC): instrument: Gilson Abimed HPLC; UV detector 254 nm; binary pump system; column: Nucleosil RP-18, 7 µm; 250×50 mm; flow rate: 40 ml/min; eluent A: water/0.05% trifluoroacetic acid, eluent B: acetonitrile/0.05% trifluoroacetic acid; gradient: 0-40 min 20-25% B, 40-105 min 25% B, 105-130 min 25-27% B, 130-170 min 27-40% B, 170-190 min 40% B, 190-210 min 40-45% B, then regeneration of the chromatography column.

Method 6 (gel chromatography on Sephadex LH-20): gel chromatography is carried out on Sephadex LH-20 (Pharmacia) without pressure. Fractions are taken according to UV activity (UV detector for 254 nm, Knauer) (ISCO Foxy 200 fraction collector). Column dimensions: 32×7 cm (1000-100 µmol scale); 30×4 cm (100-10 µmol scale); 25×2 cm (10-1 µmol scale).

Method 7 (preparative HPLC; Symmetry; acetic acid): instrument: Gilson Abimed HPLC; UV detector 210 nm; binary pump system; column: SymmetryPrep™C$_{18}$, Waters, 7 µm; 300×19 mm; flow rate: 7 ml/min; eluent A: water/0.5-0.25% acetic acid, eluent B: acetonitrile; gradient: 0-2 min 5% B, 2-60 min 5-90% B, 60-80 min 100% B, then regeneration of the chromatography column.

Method 8 (preparative HPLC; Symmetry; TFA): instrument: Gilson Abimed HPLC; UV detector 210 nm; binary pump system; column: SymmetryPrep™C$_{18}$, Waters, 7 µm; 300×19 mm; flow rate: 7 ml/min; eluent A: water/0.1-0.25% trifluoroacetic acid, eluent B: acetonitrile; gradient: 0-8 min 5% B, 8-40 min 5-60% B, 40-60 min 60% B, 60-75 min 60-100% B, 75-80 min 100% B, then regeneration of the chromatography column.

Method 9 (preparative HPLC; Kromasil, acetic acid): instrument: Gilson Abimed HPLC; UV detector 210 nm; binary pump system; column: Kromasil-100A C$_{18}$, 5 µm; 250×20 mm; flow rate: 25 ml/min; eluent A: water/0.25-0.5% acetic acid, eluent B: acetonitrile; gradient: 0-3 min 5% B, 3-30 min 5-100% B, 30-38 min 100% B, then regeneration of the chromatography column.

Method 10 (preparative HPLC; Kromasil, TFA): instrument: Gilson Abimed HPLC; UV detector 210 nm; binary pump system; column: Kromasil-100A C$_{18}$, 5 µm; 250×20 mm; flow rate: 25 ml/min; eluent A: water/0.1-0.25% trifluoroacetic acid, eluent B: acetonitrile; gradient: 0-3 min 5% B, 3-30 min 5-100% B, 30-38 min 100% B, then regeneration of the chromatography column.

Method 11 (LC-MS): MS instrument type: Micromass ZQ; HPLC instrument type: HP 1100 series; UV DAD; column: Grom-Sil 120 ODS-4 HE 50×2 mm, 3.0 µm; eluent A: water/0.025% formic acid, eluent B: acetonitrile/0.025% formic acid; gradient: 0-2.9 min 0-70% B, 2.9-3.1 min 70-90% B, 3.1-4.5 min 70-90% B; oven: 50° C, flow rate: 0.8 mi/min, UV detection: 210 nm.

Method 12 (LC-MS): MS instrument type: MS: Micromass LCT (ESI pos./neg.); HPLC instrument type: HP 1100 series; UV DAD 1100 series; column: SymmetryPrep™C$_{18}$, Waters, 50×2.1 mm, 3.5 µm; eluent A: water/0.1% formic acid, eluent B: acetonitrile/0.1% formic acid; gradient: 0-1 min 0% B, 1-5.5 min 0-95% B, 5.5-8 min 95% B, 8-8.1 min 95-0% B, 8.1-10 min 0% B, then regeneration of the chromatography column. Oven: 40° C., flow rate: 0.5 ml/min (briefly at 1 ml/min for 8.1-10 min), UV detection: 210 nm.

Method 13 (HPLC): HPLC instrument type: HP 1050 series; UV DAD 1100 series; column: SymmetryPrep™C$_{18}$, Waters, 50×2.1 mm, 3.5 µm; eluent A: water/0.05% trifluoroacetic acid, eluent B: acetonitrile; gradient: 0-9 min 0-100% B, 9-11 min 100% B, 11-12 min 100-0% B, then regeneration of the chromatography column. Oven: 40° C., flow rate: 0.4 ml/min, UV detection: 210 nm.

Method 14 (preparative HPLC; Nucleodur C$_{18}$, acetic acid): instrument: Gilson Abimed HPLC; UV detector 210 nm; binary pump system; column: Nucleodur C$_{18}$ gravity, Macherey-Nagel, 5 µm; 250×21 mm; flow rate: 20 ml/min; eluent A: water/0.25-0.5% acetic acid, eluent B: acetonitrile; gradient: 0-3 min 5% B, 3-30 min 5-100% B, 30-38 min 100% B, then regeneration of the chromatography column.

Method 15 (preparative HPLC; Nucleodur C$_{18}$, TFA): instrument: Gilson Abimed HPLC; UV detector 210 nm; binary pump system; column: Nucleodur C$_{18}$ gravity, Macherey-Nagel, 5 µm; 250×21 mm; flow rate: 7 ml/min; eluent A: water/0.1-0.25% trifluoroacetic acid, eluent B: acetonitrile; gradient: 0-8 min 5% B, 8-40 min 5-60% B. 40-60 min 60% B, 60-75 min 60-100% B, 75-80 min 100% B, then regeneration of the chromatography column.

Method 16 (preparative HPLC; YMC gel ODS-AQ5-5; acetic acid): instrument: Gilson Abimed HPLC; UV detector 254 nm; binary pump system; column: YMC Gel ODS-AQ5-5, 15 µm; 250×50 mm; flow rate: 25 ml/min; eluent A: water/0.5% acetic acid, eluent B: acetonitrile; gradient: 0-3 min 20% B, 3-25 min 20-95% B, then regeneration of the chromatography column.

Method 17 (LC-MS): instrument: Micromass Quattro LCZ, with HPLC Agilent series 1100; column: Grom-SIL120 ODS4 HE, 50×2.0 mm, 3 µm; eluent A: water/ 0.05% formic acid, eluent B: acetonitrile/0.05% formic acid; gradient: 0.0-0.2 min 100% A, 0.2-2.9 min 100-30% A, 2.9-3.1 min 30-10% A, 3.1-4.5 min 10% A; oven: 55° C., flow rate: 0.8 ml/min, UV detection: 208-400 nm.

Method 18 (HPLC): HPLC instrument type: HP 1050 series; UV DAD 1100 series; column: Kromasil $C_{18}$, 60×2 mm, 3.5 µm; eluent A: water/0.5% $HClO_4$, eluent B: acetonitrile; gradient: 0-0.5 min 2% B, 0.5-4.5 min 2-90% B, 4.5-6.5 min 90% B, 6.5-6.7 min 90-2% B, 6.7-7.5 min 2% B; flow rate: 0.75 ml/min, oven: 30° C., UV detection 210 nm.

Method 19 (LC-MS): MS instrument type: Micromass ZQ; HPLC instrument type: Waters Alliance 2790; column: Grom-Sil 120 ODS-4 HE 50×2 mm, 3.0 µm; eluent B: acetonitrile/0.05% formic acid, eluent A: water/0.05% formic acid; gradient: 0.0-2.0 min 5%-40% B, 2.0-4.5 min 40-90% B, 4.5-5.5 min 90% B; flow rate: 0.0 min 0.75 ml/min, 4.5 min 0.75 ml/min, 5.5 min 1.25 ml/min; oven: 45° C.; UV detection: 210 nm.

Method 20 MALDI-MS): The MALDI-MS/MS investigations are carried out on a 4700 Proteomics analyzer (Applied Biosystems, Framingham, Mass., USA) which is equipped with TOF/TOF ion optics and 200 Hz Nd:YAG laser (355 nm). The quasimolecular ions are accelerated in the ion source with 8 kV, selected with an electrical deflector (MS1), and undergo impacts with argon atoms in an impact cell disposed between MS1 and MS2. The resulting fragment ions are reaccelerated with 15 kV and characterized with the second time of flight mass analyser (MS2).

Method 21 (TOF-HR-MS): TOF-HR-MS-ESI+ spectra are recorded using a Micromass LCT instrument (capillary voltage: 3.2 KV, cone voltage: 42 V, source temperature: 120° C., desolvation temperature: 280° C.). A syringe pump (Harvard Apparatus) is used to supply the samples for this purpose. Leucin-encephalin (Tyr-Gly-Gly-Phe-Leu) is used as standard.

Method 22 (LC-MS): MS instrument type: Micromass ZQ; HPLC instrument type: Waters Alliance 2795; column: Phenomenex Synergi 2 µm Hydro-RP Mercury 20×4 mm; eluent A: water/0.25% formic acid, eluent B: acetonitrile/ 0.25% formic acid; gradient: 0.0-2.5 min, 90-30% A, flow rate 1-2 ml/min, 2.5-3.0 min, 30-5% A, flow rate 2.0 min, 3.0-4.5 min, 5% A; oven: 50° C.; UV detection: 210 nm.

Method 23 (FT-ICR-HR-MS): The precision measurements of mass are carried out in a high resolution Apex II Fourier-Transform ion cyclotron resonance mass spectrometer (Bruker Daltonik GmbH, Bremen) which is equipped with a 7 Tesla magnet, an external electrospray ion source and a Unix-based XMASS data system. The mass resolution is about 40 000 (50% valley definition).

Method 24 (preparative HPLC; Nucleodur $C_{18}$, acetic acid): instrument: Gilson Abimed HPLC; UV detector 210 nm; binary pump system; column: Nucleodur $C_{18}$ Gravity, Macherey-Nagel, 5 µm; 250×40 mm; flow rate: 15-45 ml/min; eluent A: water/0.2% acetic acid, eluent B: acetonitrile/0.2% acetic acid; gradient: 0-10 min 10% B, 10-24 min 10-30% B, 24-28 min 30-50% B, 28-35 min 50% B, 35-45 min 50-60% B, 45-53 min 60-70% B, 53-60 min 60-90% B, 60-70 min 100% B, then regeneration of the chromatography column.

Method 25 (preparative HPLC; Nucleodur $C_{18}$, trifluoroacetic acid): instrument: Gilson Abimed HPLC; UV detector 210 nm; binary pump system; column: Nucleodur $C_{18}$ Gravity, Macherey-Nagel, 5 µm; 250×40 mm; flow rate: 15-45 ml/min; eluent A: water/0.1% trifluoroacetic acid, eluent B: acetonitrile; gradient: 0-12 min 10% B, 12-20 min 10-35% B, 20-25 min 35-40% B, 25-35 min 40% B, 35-45 min 40-50% B, 45-50 min 50-60% B 100% B, 50-60 min 60-100% B, 60-75 min 100% B, then regeneration of the chromatography column.

Method 26 (LC-MS): MS instrument type: Micromass ZQ; HPLC instrument type: HP 1100 series; UV DAD; column: Phenomenex Synergi 2 µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5%A; flow rate: 0.0 min 1 ml/min, 2.5 min/3.0 min/4.5 min. 2 ml/min; oven: 50° C.; UV detection: 210 nm.

Method 27 (LC-MS): instrument: Micromass Platform LCZ with HPLC Agilent series 1100; column: Phenomenex Synergi 2 µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 28 (analytical HPLC): HPLC instrument type: HP 1050 series; UV DAD 1100 series; column: Kromasil $C_{18}$, 60×2 mm, 3.5 µm; eluent A: water/0.5% perchloric acid, eluent B: acetonitrile; gradient: 0-0.5 min 2% B, 0.5-4.5 min 2-90% B, 4.5-9.0 min 90% B, 9.0-9.2 min 90-2% B, 9.2-10.0 min 2% B; flow rate: 0.75 ml/min, oven: 30° C., UV detection: 210 nm.

Method 29 (LC-MS): MS instrument type: Micromass LCT (ESI pos./neg.); HPLC instrument type: HP 1100 series; UV DAD 1100 series; column: SymmetryPrep™$C_{18}$, Waters, 50×2.1 mm, 3.5 µm; eluent A: water/0.1% formic acid, eluent B: acetonitrile/0.1% formic acid; gradient: 0-1 mm 0% B, 1-6 min 0-90% B, 6-8 min 90-100% B, 8-10 min 100% B, 10-10.1 min 100-0% B, 10.1-12 min 0% B, then regeneration of the chromatography column. Oven: 40° C., flow rate: 0.5 ml/min (briefly at 1 ml/min at 10.1 min), UV detection: 210 nm.

Method 30 (LC-MS): MS instrument type: Micromass LCT (ESI pos./neg.); HPLC instrument type: HP 1100 series; UV DAD 1100 series; column: SymmetryPrep™$C_{18}$, Waters, 50×2.1 mm, 3.5 µm; eluent A: water/0.1% formic acid, eluent B: acetonitrile/0.1% formic acid; gradient: 0-1 min 0% B, 1-5.5 min 0-95% B, 5.5-8 min 95% B, 8-8.1 min 95-0% B, 8.1-10 min 0% B, then regeneration of the chromatography column. Oven: 40° C., flow rate: 0.5 ml/min (briefly at 1 ml/min at 8.1 min), UV detection: 210 nm.

Method 31 (preparative HPLC): instrument: Gilson Abimed HPLC; UV detector 210 nm; binary pump system; column: Reprosil ODS-A, 5 µm, 250×20 mm; eluent A: 0.2% trifluoroacetic acid in water, eluent B: acetonitrile; flow rate: 25 ml/min; column temperature 40° C.; 0-10 min 20% B, 10-15 min 80% B.

Method 32 (preparative HPLC): instrument: Gilson Abimed HPLC; UV detector 210 nm; binary pump system; column: Kromasil $C_{18}$, 5 µm, 100 E, 250×20 mm; eluent A: 0.05% trifluoroacetic acid in water, eluent B: 0.05% trifluoroacetic acid in acetonitrile: flow rate: 20 ml/min; 0-3 min 10% B, ramp, 30-38 min 90% B, 38-45 min 10% B. For N-butoxycarbonyl-protected substances, the trifluoroacetic acid in the mobile phase is always replaced by 0.05% acetic acid.

Method 33 (preparative HPLC): instrument: Gilson Abimed HPLC; UV detector 210 nm; binary pump system; column: Waters Symmetry-Prep™ $C_{18}$, 7 μm, 300×19 mm; eluent A: 0.05% trifluoroacetic acid in water, eluent B: 0.05% trifluoroacetic acid in acetonitrile: flow rate: 20 ml/min; 0-3 min 10% B, ramp, 30-38 min 90% B, 38-45 min 10% B. For N-butoxycarbonyl-protected substances, the trifluoroacetic acid in the mobile phase is always replaced by 0.05% acetic acid.

Method 34 (gel chromatography, Sephadex LH-20): the sample is chromatographed on Sephadex LH-20 under atmospheric pressure with a mobile phase composed of methanol+acetone 9+1+0.5% acetic acid. UV detection at 210 nm.

Method 35 (LC-MS): instrument: Micromass Quattro LCZ with HPLC Agilent series 1100; column: Phenomenex Synergi 2 μm Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 36 (analytical HPLC): instrument: Agilent 1100 with DAD (G1315B), binary pump (G1312A), autosampler (G1313A), solvent degasser (G1379A) and column thermostat (G1316A); column: Agilent Zorbax Eclipse XDB-C8 4.6×150×5 mm; column temperature: 30° C.; eluent A: 0.05% 70% perchloric acid in water; eluent B: acetonitrile; flow rate: 2.00 ml/min; gradient: 0-1 min 10% B, ramp, 4-5 min 90% B, ramp, 5.5 min 10% B.

Method 37 (LC-MS): instrument: Micromass Quattro LCZ with HPLC Agilent series 1100; column: Phenomenex Synergi 2 μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

General Procedures

General Procedure 1 (Edman$^{0.5\ and\ 1.5}$)

Phenyl isothiocyanate (50 mmol) is added dropwise under a protective argon gas atmosphere to a solution of the N-terminally free peptide (0.3 mmol) in dry pyridine (30 ml). The reaction mixture is stirred at 37° C. until (approx. 1 h) an analytical HPLC check (method 13) indicates sufficient conversion (>95%). The reaction mixture is concentrated in vacuo, controlling the temperature (<40° C.) and then lyophilized.

General Procedure 2 (Edman$^{1.0\ and\ 2.0}$)

Dry trifluoroacetic acid is added to the peptide-thiourea (0.2 mmol) as solid with vigorous stirring under a protective argon gas atmosphere, and the mixture is stirred at 40° C. until (approx. 20 min) an analytical HPLC check indicates sufficient conversion (>95%). The reaction mixture is rapidly concentrated in vacuo at room temperature (controlling the temperature). In order to remove further trifluoroactic acid from the crude product, the crude product is taken up in dichloromethane and again freed of solution in vacuo. This procedure is repeated with toluene (twice) and with dichloromethane (twice). Finally, the crude product is lyophilized.

General Procedure 3 (Acylation Edman$^{1.0\ and\ 2.0}$)

Initially N-methylmorpholine (0.3 equivalent, 1.3 μmol) is added to a solution of the N-terminally free depsipeptide (amine component, 1.0 equivalent, 4 μmol), of the free carboxylic acid (carboxylic acid component, 5-20 equivalents, 20-80 μmol), HOBt (10-40 equivalents, 40-160 μmol) and EDC×HCl (10-25 equivalents, 40-100 μmol) in dry DMF (1.0 ml) at 0° C. The reaction mixture is stirred (approx. 15 min) and further N-methylmorpholine (0.7 equivalent, 2.7 μmol) is added. The reaction mixture slowly (3-18 h) warms to room temperature, with virtually complete conversion of the amine component being observed by HPLC (for example method 13). The reaction mixture is evaporated under high vacuum and purified by chromatography.

General Procedure 4 (Acylation Edman$^{1.0\ and\ 2.0}$)

Initially HATU (4.1 equivalents, 360 μmol) is added to a solution of the N-terminally free depsipeptide (amine component, 1.0 equivalent, 88 μmol), of the free carboxylic acid (carboxylic acid component, 4.0 equivalents, 350 μmol) and N-methylmorpholine (4.0 equivalents, 350 μmol) in dry DMF (2.0 ml) at 0° C. The reaction mixture is stirred (approx. 15 min) and further N-methylmorpholine (5.0 equivalents, 438 μmol) is added. The reaction mixture slowly (approx. 1 h) warms to room temperature and is then stirred until conversion of amine component is complete (HPLC check, for example method 13) (approx. 3 h). The reaction mixture is evaporated under high vacuum and purified by chromatography.

General Procedure 5 (Elimination of the tert-butoxycarbonyl Protective Group)

The N-(tert-butoxycarbonyl)-peptide (30 μmol) is suspended in a little dichloromethane (5 ml), mixed with trifluoroacetic acid/dichloromethane (1/3, 30 ml) and stirred at RT (approx. 40 min) until analytical HPLC indicates complete conversion (for example method 13). In order to remove further trifluoroacetic acid from the crude product, the crude product is taken up in dichloromethane and again free of solvent in vacuo. This procedure is repeated with toluene (twice) and with dichloromethane (twice). Finally, the crude product is lyophilized.

General Procedure 6 (Peptide Coupling)

N-Methylmorpholine (3 equivalents, 6 mmol) is slowly added to a solution of the amine component (1.0 equivalent, 2 mmol), of the free carboxylic acid (carboxylic acid component, 1.2 equivalents, 2.4 mmol), HOBt (4 equivalents, 8 mmol) and EDC (2 equivalents, 4 mmol) in dry methylene chloride (75 ml) at −10° C. The reaction mixture slowly (approx. 12 h) warms to room temperature, with complete conversion of the amine component being observed by HPLC (for example method 13). The reaction mixture is evaporated in vacuo.

Workup method 1: for an aqueous workup, the crude product is taken up in ethyl acetate (200 ml). This is followed by washing three times with sat. aqueous sodium bicarbonate solution, once with 2N aqueous citric acid, once again with sat. aqueous sodium bicarbonate solution and once with sat. sodium chloride. The solution is dried over sodium sulphate and filtered. It is evaporated to dryness in vacuo and subsequently dried under high vacuum.

Workup method 2: The crude product is taken up in acetonitrile (2 ml) and then purified directly by chromatography.

General Procedure 7 (Hydrolytic Ester Cleavage, Saponification)

The carboxylic ester (3 mmol) is introduced into THF/water/DMF 200/100/2.5 (20 ml) under a protective argon gas atmosphere. At 0° C. with strict temperature control, powdered lithium hydroxide (3.6 mmol, 1.2 equivalents) is added in portions to the vigorously stirred solution. If conversion is observed to be incomplete by analytical HPLC (method 13) after 2 h, further solid lithium hydroxide is added (3.3 mmol, 1.1 equivalents). This procedure is repeated until conversion is complete, after which the reaction mixture is adjusted to pH 3-4 at 0° C. with 0.1N aqueous hydrochloric acid, concentrated in vacuo and then freeze dried. The crude product can then be gel-chromatographed (method 6; methanol/0.25% acetic acid) and/or purified by preparative HPLC (method 9 or method 14).

General Procedure 8 (Hydrogenolytic Ester Cleavage)

The benzyl ester of the peptide (1.2 mmol) is dissolved in methanol (60 ml) and, under a protective argon gas atmosphere, 10 per cent palladium/carbon (100 mg) is added. Hydrogenation is carried out at RT under atmospheric pressure until the analytical HPLC (method 13) indicates complete conversion. The reaction mixture is filtered (e.g. through kieselguhr, Celite®), concentrated in vacuo and dried under high vacuum.

General Procedure 9 (Elimination of the N-tert-butoxycarbonyl Protective Group, Dioxane, Hydrogen Chloride)

The N-(tert-butoxycarbonyl)-protected compound (1 mmol) is introduced into dioxane (2-3 ml). 4N hydrochloric acid in dioxane (30 ml) is added dropwise at RT with vigorous stirring. Stirring is continued until the analytical HPLC (method 13) indicates complete conversion (approx. 2 h). The reaction mixture is evaporated in vacuo at RT. The crude product is taken up in a little dichloromethane and again freed of solvent in vacuo. This procedure is repeated with toluene (twice) and with dichloromethane (twice). Finally, the crude product is lyophilized or directly reacted further.

General Procedure 10 (Hydrolytic Sample Preparation for MALDI-MS)

The depsipeptide (e.g. lysobactin, 0.05 µmol) to be opened is initially mixed in a microvial with a borate/hydrochloric acid buffer (Merck) of pH 8 (250 µl). The sample is left to stand overnight, mixed with acetic acid (100 µl) and freeze dried. The crude product is investigated without further purification steps by MALDI-MS sequencing.

General Procedure 11 (Peptide Coupling with Potassium Dihydrogenphosphate Quench)

Initially HATU (4.1 equivalents, 360 µmol) is added to a solution of the N-terminally free depsipeptide (amine component, 1.0 equivalent, 88 µmol), of the free carboxylic acid (carboxylic acid component, 4.0 equivalents, 350 µmol) and N-methylmorpholine (4.0 equivalents, 350 µmol) in dry dimethylformamide (2.0 ml) at 0° C. The reaction mixture is stirred (approx. 15 min) and further N-methylmorpholine (5.0 equivalents, 438 µmol) is added. The reaction mixture slowly (approx. 1 h) warms to room temperature and is then stirred until conversion of the amine component is complete (HPLC check, method 13) (approx. 3 h). The reaction mixture is mixed with solid potassium dihydrogenphosphate (10 equivalents, 500 µmol) and then evaporated under high vacuum and purified by chromatography.

General Procedure 12 (Solid-phase Synthesis of Dipeptides)

Introduce 1.0 g of trityl resin (equivalent to 1 mmol) into dichloromethane, add 5 equivalents of N-Fmoc-protected amino acid and 10 equivalents of ethyldiisopropylamine, shake at room temperature for 20 h, filter with suction, wash three times with dichloromethane/methanol/ethyldiisopropylamine (17/2/1), three times dichloromethane, twice dimethylformamide, three times dichloromethane. Dry under high vacuum over potassium hydroxide. Deprotect with piperidine/dimethylformamide 1/4 (twice 15 min), wash eight times with dimethylformamide. Coupling of 5 equivalents of N-Boc-protected amino acid with 5 equivalents of TBTU and 10 equivalents of ethyldiisopropylamine in dimethylformamide, room temperature overnight. Wash three times with dichloromethane/methanol/ethyldiisopropylamine (17/2/1), three times dichloromethane, three times dimethylformamide, twice dichloromethane, once diethyl ether.

Elimination with in each case 2.5 ml of acetic acid/trifluoroethanol/dichloromethane (1/1/3) room temperature, 2 h, then filter with suction, wash three times with 500 µl of cleavage solution each time, add 2.5 ml of cyclohexane, concentrate, concentrate repeatedly with addition of 5 ml of cyclohexane.

General Procedure 13 (Reductive N-alkylation)

Alternatively the appropriate aldehyde (0.10 mmol, 10 equivalents) or else the appropriate ketone (0.10 mmol, 10 equivalents) is added to a mixture from Example 1A (15 mg, 10 µmol) and activated molecular sieves (3 Å, 400 mg) in dry methanol (2 ml) under a protective argon gas atmosphere. The reaction mixture is stirred at room temperature for 30 min and then sodium cyanoborohydride (6 mg, 0.1 mmol, 10 equivalents) is added. After a further 18 h, the reaction mixture is quenched by adding 4N hydrochloric acid (500 µl) and then freeze dried, resulting in a solid crude product which is purified by preparative HPLC/UV-Vis (for example method 15). The product fractions are again freeze dried, resulting in solid foams as products.

General Procedure 14 (Coupling to Give the Dipeptide, EDC)

An N-protected amino acid and the ester (for example methyl or benzyl ester) of an amino acid are introduced in the equimolar ratio under argon into dichloromethane (40 ml/mmol of the amino acid) and cooled to −8° C. 1-Hydroxybenzotriazole (3 equivalents), N-methylmorpholine (3 equivalents), EDC (2 equivalents) are added dropwise in this sequence. Then a further 2 equivalents of N-methylmorpholine are added. The mixture is allowed to warm to room temperature and is stirred for 12 h. The dichloromethane is distilled off in a rotary evaporator, and the residue is taken up in ethyl acetate and washed with saturated sodium bicarbonate solution. The aqueous phase is washed once more with ethyl acetate, and the combined organic extracts are washed with aqueous 5% strength citric acid and subsequently again with saturated sodium bicarbonate solution. The organic phase is then dried over sodium sulphate, filtered and concentrated in vacuo.

General Procedure 15

A 1M solution of N-methylmorpholine in dimethylformamide is prepared. An N-protected amino acid and the ester (methyl or benzyl) of an amino acid are dissolved in the equimolar ratio under argon in dimethylformamide (14 ml/mmol) and cooled to 0° C. Then firstly 1 equivalent of the N-methylmorpholine solution, then TCTU (1.5 equivalents) and, after 15 min, N-methylmorpholine solution (1 equivalent) is added. Stirring is then continued at room temperature overnight. The mixture is loaded directly onto a reversed phase flash cartridge (Biotage 40M $C_{18}$) and purified with water-acetonitrile gradients (10-90% acetonitrile in 15 min, then holding for 5 min). The product is subsequently chromatographed (method 31).

General Procedure 16

A 1M solution of N-methylmorpholine in dimethylformamide is prepared.

An N-protected amino acid and the ester (methyl or benzyl) of an amino acid are dissolved in the equimolar ratio under argon in dimethylformamide (14 ml/mmol) and cooled to 0° C. Then firstly the N-methylmorpholine solution (1 equivalent), then HATU (1.5 equivalents) and, after 15 min, N-methylmorpholine solution (1 equivalent) is added. Stirring is then continued at room temperature overnight. The mixture is loaded directly onto a reversed phase flash cartridge (Biotage 40M $C_{18}$) and purified with water-acetonitrile gradients (10-90% acetonitrile in 15 min, then holding for 5 min).

General Procedure 17

The ester is dissolved in tetrahydrofuran/water 2/1 (15 ml/mmol), and the solution is cooled to 0° C. Solid lithium hydroxide monohydrate (2 equivalents) is added. The reaction mixture is stirred at 0° C. for about 1 h. If the reaction is complete (reaction check with HPLC, method 36), glacial acetic acid is used to acidify. The tetrahydrofuran is distilled off in vacuo, the residue is extracted with ethyl acetate, and the combined organic phases are dried over sodium sulphate and concentrated. The residue is purified by reversed phase flash chromatography (Biotage $C_{18}$ 40M, water+0.05% trifluoroacetic acid-acetonitrile+0.05% trifluoroacetic acid gradient 10-90% in 15 min, holding for 10 min). Product-containing fractions are concentrated in a rotary evaporator or lyophilized.

General Procedure 18

The benzyl ester is dissolved in methanol (36 ml/mmol). Then, under argon, 10% palladium on activated carbon (228 mg/mmol) is added, and hydrogenation is carried out under hydrostatic pressure for 1 h. The catalyst is filtered off, and the filtrate is concentrated and purified by flash chromatography (silica gel, cyclohexane/ethyl acetate 3/1 with 0.05% acetic acid).

General Procedure 19 (HATU Method)

A 1M solution of N-methylmorpholine in dimethylformamide is prepared. Example 11A (1 equivalent) and protected amino acid (4 equivalents) are introduced into dimethylformamide (10 ml/mmol of Example 11A) and cooled to 0° C. Then firstly 2 equivalents of the N-methylmorpholine solution, then HATU (4.1 equivalents), then after 15 min again 2 equivalents of the N-methylmorpholine solution and after 15 min the remaining 5 equivalents of the N-methylmorpholine solution are added. Stirring is then continued at room temperature overnight. The mixture is subsequently separated by chromatography (method 34) on Sephadex LH-20. Product-containing fractions are combined and concentrated in a rotary evaporator at a bath temperature not exceeding 30° C.

General Procedure 20

The N-(tert-butoxycarbonyl)-protected compound is suspended in dichloromethane (approx. 1.6 ml/10 mg of precursor). A solution of 30% strength trifluoroacetic acid in dichloromethane is added (approx. 0.32 ml/10 mg of precursor) and the mixture is stirred at room temperature for 30 min. The solvent is then distilled off in vacuo, during which the bath temperature should not exceed 30° C. The residue is purified by chromatography (method 33).

General Procedure 21

The N-(tert-butoxycarbonyl)-protected compound is dissolved in 30% strength trifluoroacetic acid in dichloromethane (approx. 1 ml/10 mg of precursor) and stirred at room temperature for 30 min. The solvent is then distilled off in vacuo, during which the bath temperature should not exceed 30° C. The residue is purified by chromatography (method 33).

General Procedure 22

The precursor is taken up in glacial acetic acid/water (1/2), 10% palladium on activated carbon (approx. 30 per cent of the weight of the precursor) is added, and hydrogenation is carried out under atmospheric pressure and at room temperature for 1 h. When the reaction check by analytical HPLC indicates complete reaction, the catalyst is filtered off, and the solvent is distilled off in vacuo, during which the bath temperature should not exceed 30° C. The residue is purified by chromatography (method 33).

General Procedure 23

Preparation of the buffer solution: a 0.1M sodium acetate solution is adjusted to pH 5 by adding glacial acetic acid.

The precursor is dissolved in a buffer/methanol (2/3) mixture, 10% palladium on activated carbon (approx. 20 per cent of the weight of the precursor) is added, and hydrogenation is carried out under atmospheric pressure and at room temperature until the reaction is complete (approx. 1 h, check by analytical HPLC). The catalyst is then filtered off, and the solvent is distilled off in vacuo, during which the bath temperature should not exceed 30° C. The residue is purified by chromatography (method 33).

Starting Compounds

Example 1A

D-Leucyl-N[1]-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide bistrifluoro-acetate

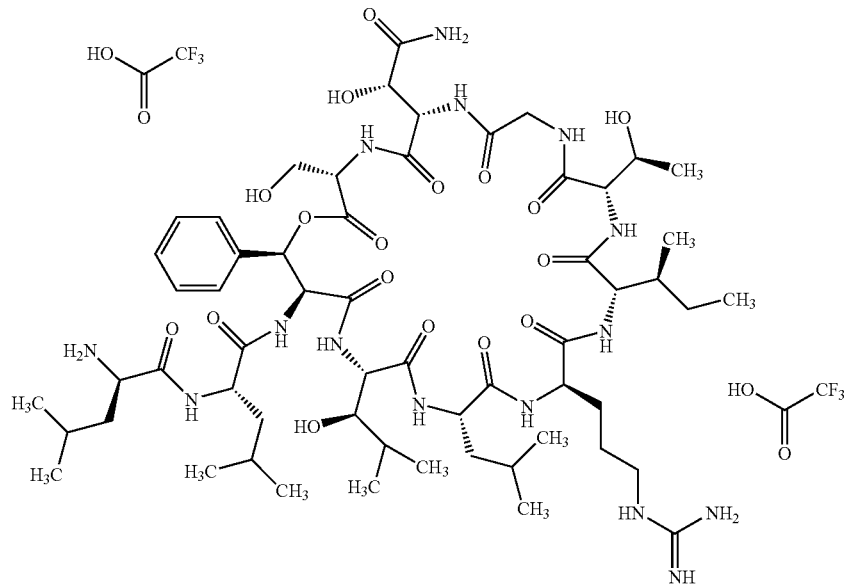

Example 2A

D-Leucyl-N[1]-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-isopropyl-2,5,8,11,14,17,20,23,26-nonaoxo-28-phenyl-1-oxa-4,7,10,13,16,19,22,25-octaazacyclooctacosan-27-yl}-L-leucinamide bistrifluoroacetate

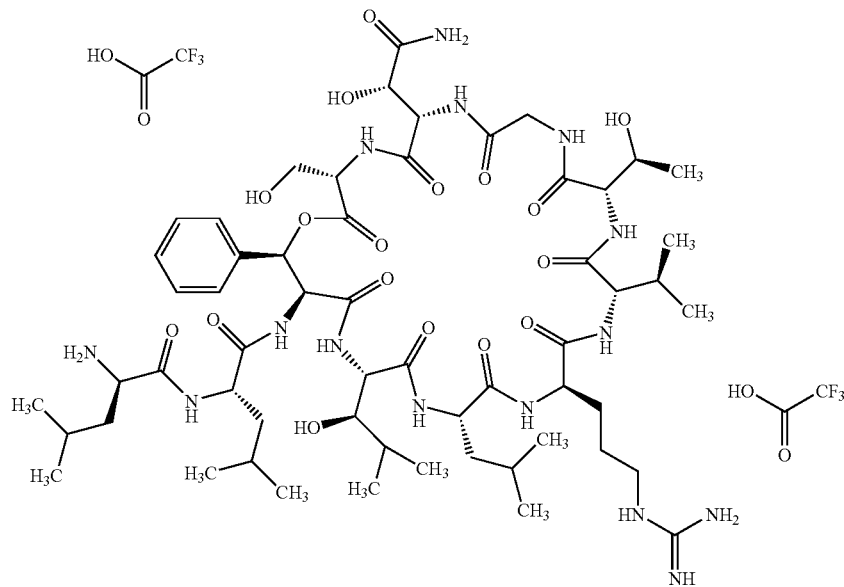

Fermentation of Example 1A and Example 2A

Culture Medium:

YM: yeast-malt agar: D-glucose (4 g/l), yeast extract (4 g/l), malt extract (10 g/l), 1 liter of Lewatit water. The pH is adjusted to 7.2 before the sterilization (20 minutes at 121° C.).

HPM: mannitol (5.4 g/l), yeast extract (5 g/l), meat peptone (3 g/l).

Working cell bank: the lyophilized strain (ATCC 53042) is grown in 50 ml of YM medium.

Flask fermentation: 150 ml of YM medium or 100 ml of HPM medium in a 1 l Erlenmeyer flask are inoculated with 2 ml of the working cell bank and left to grow at 28° C. on a shaker at 240 rpm for 30-48 hours.

30 l Fermentation: 300 ml of the flask fermentation (HPM medium) are used to inoculate a sterile 30 l nutrient medium solution (1 ml of antifoam SAG 5693/1). This culture is left to grow at 28° C., 300 rpm aerating with sterile air at 0.3 vvm for 21 hours. The pH is kept constant at pH=7.2 with 1M hydrochloric acid. In total, 880 ml of 1M hydrochloric acid are added during the culturing time.

Main culture (200 l): 15×150 ml YM medium in 1 l Erlenmeyer flask are inoculated with 2 ml of the working cell bank and left to grow at 28° C. and 240 rpm on a shaker for 48 hours. 2250 ml of this culture are used to inoculate a sterile 200 l nutrient medium solution (YM) (1 ml of antifoam SAG 5693/1) and left to grow at 28° C., 150 rpm aerating with sterile air at 0.3 vvm for 18.5 hours.

Samples (50 ml) are taken each hour to check the progress of the fermentation. 2 ml of this culture broth are mixed with 1 ml of methanol (0.5% trifluoroacetic acid) and filtered through a 0.45 µM filter. 30 µl of this suspension are analysed by HPLC (method 1 and method 2).

After 18.5 hours, the culture broth of the main culture is separated into supernatant and sediment at 17 000 rpm.

Isolation of Example 1A and Example 2A

The supernatant (183 l) is adjusted to pH 6.5-7 with concentrated trifluoroacetic acid or sodium hydroxide solution and loaded onto a Lewapol column (OC 1064, 60 l contents). Elution is then carried out with pure water, water/methanol 1:1 and then with pure methanol (with 0.1% trifluoroacetic acid). This organic phase is concentrated in vacuo to a remaining aqueous residue of 11.5 l.

The remaining aqueous phase is bound to silica gel $C_{18}$ and fractionated (MPLC, Biotage Flash 75, 75×30 cm, KP-C18-WP, 15-20 µm, flow rate: 30 ml/min; eluent: acetonitrile/water with 0.1% trifluoroacetic acid; gradient: 10%, 15% and 40% acetonitrile). The 40% acetonitrile phase, which contains the major amount of Example 1A and Example 2A, is concentrated in vacuo and then lyophilized (~13 g). This mixture of solids is separated in 1.2 g portions initially on a preparative HPLC (method 3), then by gel filtration on Sephadex LH-20 (5×70 cm, acetonitrile/water 1:1, in each case with 0.05% trifluoroacetic acid) and a further preparative HPLC (method 4).

This process affords 2250 mg if Example 1A and 33 mg of Example 2A.

The sediment is taken up in 4 l of 4:1 acetone/water, mixed with 2 kg of Celite, adjusted to pH=6 with trifluoroacetic acid, thoroughly stirred and centrifuged. The solvent is evaporated in vacuo, and the residue is freeze dried. The resulting lyophilizate (89.9 g) is taken up in methanol, filtered, concentrated and fractionated on silica gel (method 5) into Example 1A and Example 2. Example 1A is then purified by gel filtration (Sephadex LH-20, 5×68 cm, water/acetonitrile 9:1 (with 0.05% trifluoroacetic acid), flow rate: 2.7 ml/min, fraction size 13.5 ml) to give the pure substance.

This process affords 447 mg of Example 1A.

Example 1A

HPLC (method 1): $R_t$=6.19 min.

MS (ESIpos): m/z=1277 (M+H)$^+$ $^1$H NMR (500.13 MHz, d$_6$-DMSO): δ=0.75 (d, 3H), 0.78 (d, 6H), 0.80 (t, 3H), 0.82 (d, 3H), 0.90 (d, 3H), 0.91 (d, 3H), 0.92 (d, 3H), 0.95 (d, 3H), 0.96 (d, 3H), 1.05 (m, 1H), 1.19 (d, 3H), 1.25 (m, 2H), 1.50 (m, 4H), 1.51 (m, 2H), 1.55 (m, 1H), 1.61 (m, 1H), 1.65 (m, 1H), 1.84 (m, 1H), 1.85 (m, 1H), 1.86 (m, 1H), 1.89 (m, 1H), 1.95 (m, 1H), 2.75 (m, 2H), 3.40 (m, 1H), 3.52 (m, 2H), 3.53 (dd, 1H), 3.64 (m, 2H), 3.66 (m, 1H), 3.68 (dd, 1H), 3.73 (m, 2H), 4.00 (dd, 1H), 4.02 (br., 1H), 4.13 (br., 1H), 4.32 (dd, 1H), 4.39 (t, 1H), 4.55 (m, 1H), 4.75 (dd, 1H), 5.19 (t, 1H), 5.29 (d, 1H), 5.30 (br., 1H), 5.58 (m, 2H), 6.68 (m, 3H), 6.89 (d, 1H), 6.93 (m, 3H), 6.94 (br., 1H), 6.98 (d, 1H), 7.12 (br., 1H), 7.20 (br., 2H), 7.23 (m, 2H), 7.42 (m, 2H), 7.54 (d, 1H), 7.58 (d, 1H), 8.32 (br., 1H), 9.18 (br., 1H), 9.20 (m, 2H), 9.50 (br., 1H).

$^{13}$C-NMR (125.77 MHz, d$_6$-DMSO): δ=10.3, 15.3, 19.0, 19.2, 19.6, 20.0, 20.9, 22.0, 22.4, 23.0, 23.2, 24.3, 24.4, 25.0, 25.4, 26.0, 27.8, 30.9, 35.4, 39.5, 40.8, 40.9, 41.6, 44.1, 51.5, 52.7, 55.9, 56.2, 56.4, 57.9, 58.8, 60.2, 61.1, 62.6, 70.1, 71.6, 71.7, 75.5, 128.1, 128.6, 136.7, 156.8, 168.2, 170.1, 170.4, 171.2, 171.5, 171.9, 172.2, 172.4, 173.7.

The assignment of the signals took place in accordance with the assignment described in the literature (T. Kato, H. Hinoo, Y. Terui, *J. Antibiot.*, 1988, 41, 719-725).

$^1$H NMR (500 MHz, d$_6$-DMSO, 302 K) and $^{13}$C-NMR (d$_6$-DMSO) data:

| Residue | NH | CO | CH-α | CH-β | CH-χ | Further radicals |
|---|---|---|---|---|---|---|
| Leu 1 | 8.32 | 171.5 | 4.13 (51.5) | ~1.51 (41.6) | ~1.65 (25.0) | CH$_3$: 0.95 (22.0) |
|  |  |  |  |  |  | CH$_3$: 0.92 (22.4) |
| Leu 2 | 9.50 | 172.4 | 3.73 (56.2) | 1.86 (39.5) | 1.89 (24.4) | CH$_3$: 0.91 (23.0) |
|  |  |  |  | 1.25 (39.5) |  | CH$_3$: 0.75 (19.6) |
| Ph-Ser | 9.18 | 171.5 | 5.58 (61.1) | 6.89 (71.7) | — | Ph-o: 7.42 (128.1) |
|  |  |  |  |  |  | Ph-m: 7.23 (128.6) |
|  |  |  |  |  |  | Ph-p: 7.20 (128.6) |
|  |  |  |  |  |  | Ph-i: 136.7 |
| Hy-Leu | 9.20 | 171.2 | 3.66 (59.8) | 3.40 (75.5) | 1.84 (30.9) | CH$_3$: 0.96 (19.0) |
|  |  |  |  | —OH: 5.30 |  | CH$_3$: 0.78 (19.2) |
| Leu 3 | 7.12 | 171.5 | 4.02 (52.7) | 1.62 (40.9) | 1.95 (24.3) | CH$_3$: 0.82 (20.0) |
|  |  |  |  |  |  | CH$_3$: 0.78 (23.2) |

-continued

| Residue | NH | CO | CH-α | CH-β | CH-χ | Further radicals |
|---|---|---|---|---|---|---|
| Arg | 6.94 | 171.9 | 3.73 (56.4) | ~1.50 (27.8) | ~1.50 (26.0)<br>~1.25 (26.0) | CH$_2$-δ: 2.75 (40.8)<br>NH-δ: 7.20<br>[NH—C—NH$_3^+$]:<br>6.68 (156.8) |
| Ile | 7.58 | 170.4 | 3.68 (60.2) | ~1.85 (35.4)<br>CH$_3$: 0.90<br>(15.3) | ~1.05 (21.4)<br>~1.55 (25.4) | CH$_3$: 0.80 (10.3) |
| Thr | 6.98 | 171.5 | 4.39 (57.2) | 3.52 (70.1)<br>—OH: 5.29 | — | CH$_3$: 1.19 (20.9) |
| Gly | 9.20 | 172.2 | 4.00 (44.1)<br>3.53 (44.1) | — | — | — |
| Hy-Asn | 7.54 | 170.8 | 4.75 (56.2) | 4.32 (71.6)<br>—OH: 5.58 | — | CO—NH$_2$: 6.93<br>(173.7) |
| Ser | 6.93 | 168.2 | 4.55 (55.9) | 3.64 (62.6)<br>—OH: 5.19 | — | — |

Example 2A

HPLC (method 1): R$_t$=6.01 min.

MS (ESIpos): m/z=1263 (M+H)$^+$ $^1$H NMR (500.13 MHz, d$_6$-DMSO): δ=0.75 (d, 3H), 0.78 (d, 9H), 0.79 (d, 3H), 0.90 (d, 3H), 0.92 (d, 3H), 0.96 (d, 3H), 0.97 (d, 3H), 0.98 (d, 3H), 1.16 (d, 3H), 1.25 (m, 1H), 1.50 (m, 1H), 1.55 (m, 4H), 1.65 (m, 1H), 1.33 (m, 1H), 1.62 (m, 2H), 1.84 (m, 1H), 1.85 (m, 2H), 1.90 (m, 1H), 1.95 (m, 1H), 2.78 (m, 2H), 3.43 (m, 1H), 3.52 (m, 2H), 3.63 (m, 1H), 3.65 (m, 2H), 3.67 (dd, 1H), 3.70 (m, 1H), 3.71 (br., 1H), 4.01 (dd, 1H), 4.04 (br., 2H), 4.29 (t, 1H), 4.30 (dd, 1H), 4.54 (m, 1H), 4.73 (dd, 1H), 5.19 (t, 1H), 5.23 (d, 1H), 5.31 (br., 1H), 5.57 (br., 1H), 5.63 (d, 1H), 6.68 (m, 3H), 6.90 (m, 3H), 6.98 (d, 1H), 7.01 (br., 1H), 7.20 (br., 2H), 7.21 (br., 1H), 7.23 (m, 3H), 7.24 (br., 1H), 7.42 (m, 2H), 7.50 (br., 1H), 7.57 (d, 1H), 8.16 (br., 1H), 9.18 (br., 1H), 9.19 (d, 1H), 9.20 (br., 1H), 9.57 (br., 1H).

$^{13}$C-NMR (125.77 MHz, d$_6$-DMSO): δ=19.0, 19.2, 19.3, 19.4, 19.6, 20.9, 21.9, 22.0, 22.4, 23.0, 23.2, 23.7, 24.3, 24.5, 26.8, 27.8, 30.4, 35.4, 31.5, 39.0, 40.3, 40.9, 41.8, 44.3, 52.2, 52.4, 55.2, 55.4, 55.9, 56.5, 57.9, 60.0, 60.8, 61.1, 62.6, 71.1, 71.9, 74.8, 75.1, 127.9, 129.1, 136.1, 156.2, 167.4, 168.1, 171.0, 172.0, 172.2, 172.4, 172.5, 172.9, 173.3.

The assignment of the signals took place in accordance with the assignment described in the literature (T. Kato, H. Hinoo, Y. Terui, *J. Antibiot.*, 1988, 41, 719-725).

$^1$H NMR (500 MHz, d$_6$-DMSO, 302 K) and $^{13}$C-NMR (d$_6$-DMSO) data:

| Residue | NH | CO | CH-α | CH-β | CH-χ | Further radicals |
|---|---|---|---|---|---|---|
| Leu 1 | 8.16 | 173.3 | 4.04 (52.4) | ~1.55 (41.8) | ~1.65 (24.5) | CH$_3$: 0.98 (22.0)<br>CH$_3$: 0.92 (22.4) |
| Leu 2 | 9.57 | 172.4 | 3.71 (55.2) | 1.84 (39.0)<br>1.33 (39.0) | 1.90 (23.7) | CH$_3$: 0.90 (23.0)<br>CH$_3$: 0.75 (19.4) |
| Ph-Ser | 9.18 | 172.9 | 5.57 (61.1) | 6.90 (71.7) | — | Ph-o: 7.42 (127.9)<br>Ph-m: 7.23 (129.1)<br>Ph-p: 7.23 (129.1)<br>Ph-i: 136.1 |
| Hy-Leu | 9.20 | 173.3 | 3.63 (60.0) | 3.43 (74.8)<br>—OH: 5.31 | 1.85 (31.5) | CH$_3$: 0.96 (19.0)<br>CH$_3$: 0.78 (19.2) |
| Leu 3 | 7.21 | 172.5 | 4.04 (52.2) | 1.62 (40.9) | 1.85 (24.3) | CH$_3$: 0.79 (20.9)<br>CH$_3$: 0.78 (23.2) |
| Arg | 6.90 | 172.5 | 3.70 (55.4) | ~1.55 (27.8) | ~1.50 (26.8)<br>~1.25 (26.8) | CH$_2$-δ: 2.78 (40.3)<br>NH-δ: 7.24<br>[NH—C—NH$_3^+$]:<br>6.68 (156.2) |
| Val | 7.50 | 171.0 | 3.67 (60.8) | 1.95 (30.4) | — | CH$_3$: 0.97 (19.3)<br>CH$_3$: 0.78 (19.6) |
| Thr | 6.98 | 172.0 | 4.29 (57.9) | 3.52 (71.1)<br>—OH: 5.23 | — | CH$_3$: 1.16 (21.9) |
| Gly | 9.19 | 172.2 | 4.01 (44.3)<br>3.52 (44.3) | — | — | — |
| Hy-Asn | 7.57 | 168.1 | 4.73 (56.5) | 4.30 (71.9)<br>—OH: 5.63 | — | CO—NH$_2$: 7.20<br>(172.0) |
| Ser | 7.01 | 167.4 | 4.54 (55.9) | 3.65 (62.6)<br>—OH: 5.19 | — | — |

Determination of the Stereochemistry of Example 1A

The relative stereochemistry of Example 1A is identified by hydrolysing the depsipeptide with hydrochloric acid. For this purpose, 100 μg of Example 1A are mixed with 200 μl 6M hydrochloric acid, and the sample tube is sealed under vacuum and heated at 166° C. for 1 hour. After the hydrolysis, the sample is concentrated under high vacuum. The remaining residue is adjusted to pH=2.2 with 400 μl of sodium citrate buffer. Internal standard: homoarginine.

After the derivatization, the hydrolysate is analysed on a Permabond L-Chirasil-Val and FS-LipodexE column. The retention time of the individual amino acid derivatives from Example 1A is compared with D- and L-amino acids (after derivatization). All natural amino acids have the L configuration.

On the basis of the great agreement of Example 1A with the literature data, it is assumed that Example 1A corresponds in its stereochemistry to the stereochemistry described in the literature (T. Kato, H. Hinoo, Y. Terui, *J. Antibiot.*, 1988, 41 (6), 719-725).

Compound 1A resulting from the fermentation is employed in further reactions (see Example 10A). If the assignment of the stereochemistry in compound 1A is in fact different, the stereochemistry of the following products will also be correspondingly different.

Preparation of the Dipeptides

Example 3A

Benzyl 3-cyclopropyl-L-alaninate hydrochloride

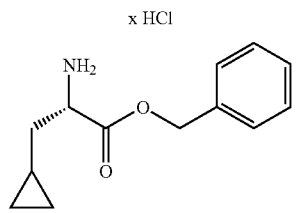

Benzyl N-(tert-butoxycarbonyl)-3-cyclopropyl-L-alaninate (260 mg, 0.81 mmol) (Neil W. Boaz, Sheryl D. Debenham, Elaine B. Mackenzie, Shannon E. Large, *Org. Lett.*, 2002, 14, 2421-2424) is reacted by general procedure 9. The product is obtained in quantitative yield.

HPLC/UV-Vis (method 13): $R_t$=5.13 min,
$\lambda_{max}$ (qualitative)=220 nm (s), 250-275 (w).
LC-MS (method 12): $R_t$=3.93 min;
MS (ESIpos.): m/z (%)=220 (100) [M+H]$^+$.

Example 4A

Benzyl N-(tert-butoxycarbonyl)-D-leucyl-3-cyclopropyl-L-alaninate

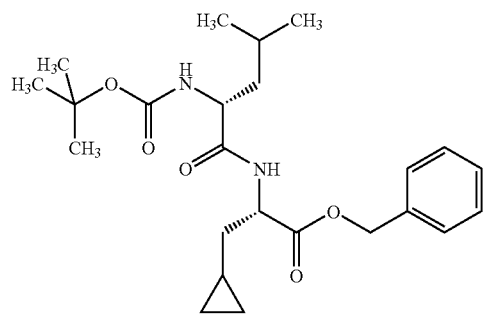

N-(tert-Butoxycarbonyl)-D-leucine (540 mg, 2.32 mmol) and benzyl 3-cyclopropyl-L-alaninate hydrochloride (Example 3A, 490 mg, 1.93 mmol) are reacted by general procedure 6. The crude product is purified by preparative HPLC, (method 16), resulting in a quantitive yield of the product.

$[\alpha]^{20}_{Na}$=+30° (c=0.1 in methylene chloride).
HPLC/UV-Vis (method 13): $R_t$=9.00 min,
$\lambda_{max}$ (qualitative)=220 nm (s), 250-275 (w).
LC-MS (method 17): $R_t$=3.40 min;
MS (ESIpos.): m/z (%)=333 (100) [M−Boc+H]$^+$, 433 (15) [M+H]$^+$.

Example 5A

N-(tert-Butoxycarbonyl)-D-leucyl-3-cyclopropyl-L-alanine

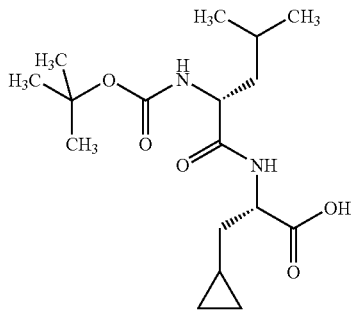

Benzyl N-(tert-butoxycarbonyl)-D-leucyl-3-cyclopropyl-L-alaninate (Example 4A, 500 mg, 1.16 mmol) is reacted by general procedure 8. 366 mg (92% of theory) of product are obtained.

$[\alpha]^{20}_{Na}$=+15° (c=0.1 in methylene chloride).
HPLC/UV-Vis (method 13): $R_t$=7.16 min.
LC-MS (method 12): $R_t$=5.28 min;
MS (ESIpos.): m/z (%)=343 (30) [M+H]$^+$.

Example 6A

Methyl N-(tert-butoxycarbonyl)-D-leucyl-L-norvalinate

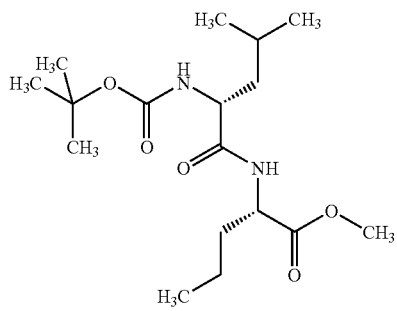

N-(tert-Butoxycarbonyl)-D-leucine (1000 mg, 4.32 mmol) and methyl L-norvalinate hydrochloride (1090 mg, 6.49 mmol) are reacted by general procedure 6. The crude product is purified by workup method 1. The product is obtained in quantitative yield.

HR-TOF-MS (method 21): $C_{17}H_{33}N_2O_5$ calc. 345.2389, found 345.2406; $C_{17}H_{32}N_2O_5Na$ calc. 367.2209, found 367.2207.

LC-MS (method 11): $R_t$=3.62 min;

MS (ESIpos.): m/z (%)=245 (30) [M−Boc+H]$^+$;

MS (ESIneg.): m/z (%)=389 [M+HCO$_2$H−H]$^−$, 343 (20) [M−H]$^−$.

Example 7A

N-(tert-Butoxycarbonyl)-D-leucyl-L-norvaline

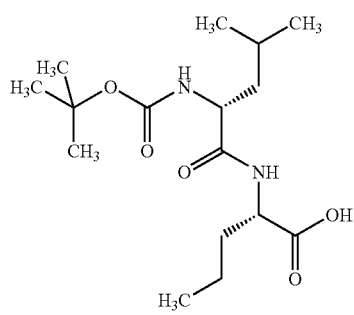

Methyl N-(tert-butoxycarbonyl)-D-leucyl-L-norvalinate (Example 6A, 1000 mg, 2.9 mmol) is reacted by general procedure 7. 808 mg (84% of theory) of product are obtained.

$[\alpha]^{20}_{Na}$=+24° (c=0.1 in methanol).

HPLC/UV-Vis (method 13): $R_t$=6.97 min.

LC-MS (method 12): $R_t$=5.33 min;

MS (ESIpos.): m/z (%)=331 (20) [M+H]$^+$;

MS (ESIneg.): m/z (%)=329 (20) [M−H]$^−$.

HR-TOF-MS (method 21): $C_{16}H_{31}N_2O_5$ calc. 331.2233, found 331.221.

Example 8A

Benzyl N-(tert-butoxycarbonyl)-D-leucyl-3-tert-butyl-L-alaninate

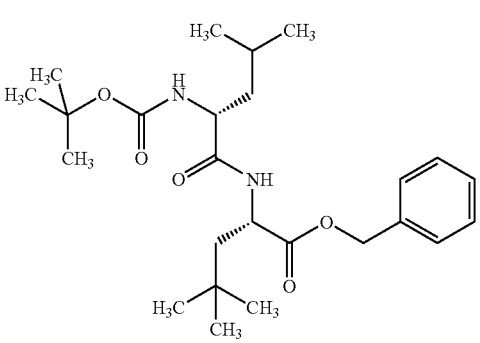

N-(tert-Butoxycarbonyl)-D-leucine (230 mg, 1.0 mmol) and benzyl-3-tert-butyl-L-alaninate hydrochloride (300 mg, 1.10 mmol) (John X. He, Wayne L. Cody, Annette M. Doherty, *J. Org. Chem.*, 1995, 60, 8262-8266) are reacted by general procedure 6. The crude product is purified (workup method 2) by preparative HPLC (method 16), resulting in 362 mg (80% of theory) of product.

$[\alpha]^{20}_{Na}$=+19° (c=0.1 in methylene chloride).

HPLC/UV-Vis (method 18): $R_t$=5.3 min.

LC-MS (method 22): $R_t$=2.83 min;

MS (ESIpos.): m/z (%)=349 (100) [M−Boc+H]$^+$, 449 (85) [M+H]$^+$.

Example 9A

N-(tert-Butoxycarbonyl)-D-leucyl-3-tert-butyl-L-alanine

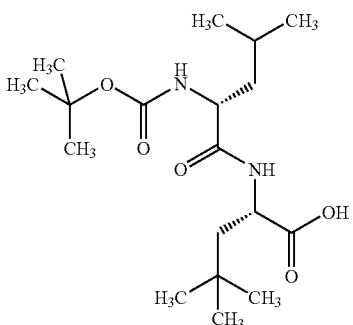

Benzyl N-(tert-butoxycarbonyl)-D-leucyl-3-tert-butyl-L-alaninate (Example 8A, 308 mg, 0.69 mmol) is reacted by general procedure 8. 245 mg (99% of theory) of product are obtained.

$[\alpha]^{20}_{Na}$=−2° (c=0.1 in methylene chloride).

HPLC/UV-Vis (method 13): $R_t$=7.70 min.

HR-TOF-MS (method 21): $C_{18}H_{35}N_2O_5$ calc. 359.2546, found 359.2535.

Example 10A

N-(Anilinocarbonothioyl)-D-leucyl-N¹-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide monotrifluoroacetate {N-(Anilinocarbonothioyl)lysobactin monotrifluoroacetate}

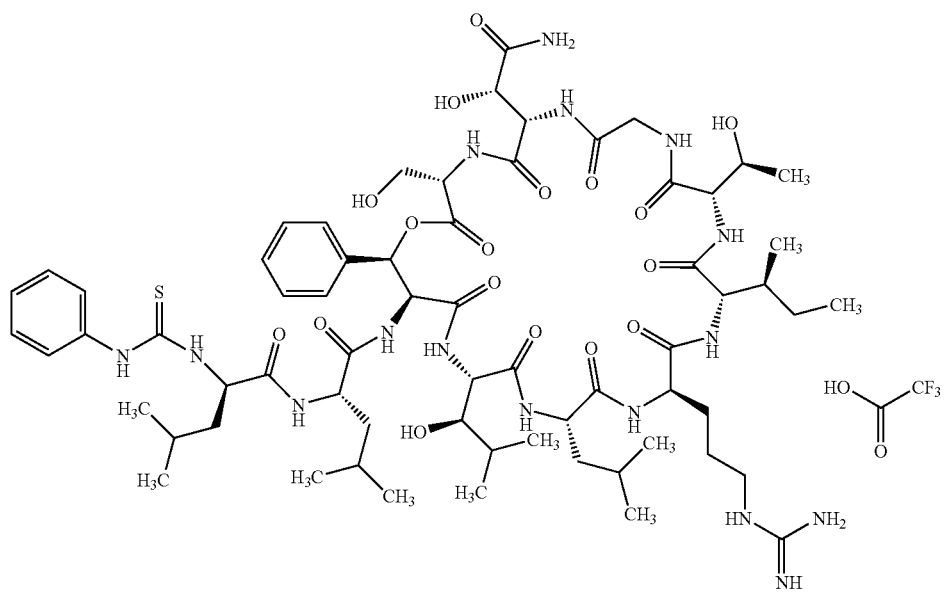

Lysobactin bistrifluoroacetate (500 mg, 0.33 mmol) (Example 1A) is reacted by general procedure 1. 600 mg (quant.) of product are obtained, which can be reacted further unpurified.

For further purification, the crude product can be gel chromatographed (method 6; methanol/0.1% acetic acid). The product-containing fractions are concentrated in vacuo at room temperature and then lyophilized. The product is obtained in 80% yield.

HPLC/UV-Vis (method 13): $R_t$=6.84 min, $\lambda_{max}$ (qualitative)=220 nm (s), 248 (m), 269 (m).

LC-MS (method 11): $R_t$=2.64 min;

MS (ESIpos.): m/z (%)=706.5 (50) [M+2H]$^{2+}$, 1412 (20) [M+H]$^+$;

LC-MS (method 12): $R_t$=4.95 min;

MS (ESIpos.): m/z (%)=1412 (100) [M+H]$^+$.

Example 11A

N¹-{(3S,6S,12S,15S,18R,21S,24S,27S,28R)-6-[(1S)-2-Amino-1-hydroxy-2-oxoethyl]-18-(3-{[amino(imino)methyl]amino}propyl)-12-[(1S)-1-hydroxyethyl]-3-(hydroxy-methyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide bistrifluoro-acetate {De-D-leucyllysobactin bistrifluoroacetate}

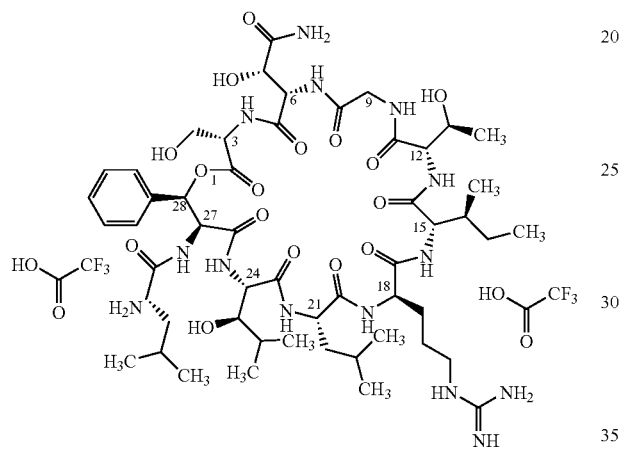

Thiourea (Example 10A) (300 mg, 0.2 mmol) is reacted by general procedure 2. The crude product is gel chromatographed (method 6; methanol/0.25% acetic acid) and then finally purified by preparative HPLC (method 8). 147 mg (65% of theory) of product are obtained.

HPLC/UV-Vis (method 13): $R_t$=4.96 min, $\lambda_{max}$ (qualitative)=220 nm (s), 255-270 (w).

LC-MS (method 12): $R_t$=3.84 min;

MS (ESIpos.): m/z (%)=582.4 (100) $[M+2H]^{2+}$, 1164 (20) $[M+H]^+$.

FT-ICR-HR-MS (method 23):

$C_{52}H_{88}N_{14}O_{16}$ $[M+2H]^{2+}$ calc. 582.32459, found 582.32460;

$C_{52}H_{87}N_{14}NaO_{16}$ $[M+H+Na]^{2+}$ calc. 593.31556, found 593.31564.

To determine the amino acid sequence, an analytical sample of the product is hydrolysed by general procedure 10.

MALDI-MS (method 20): m/z (%)=1181.7 (100) $[M+H]^+$.

Alternative Process for Preparation on a Larger Scale:

Example 2A (6.47 g, 4.30 mmol) is dissolved in pyridine (90 ml) under an argon atmosphere. Then phenyl isothiocyanate (1.16 g, 8.60 mmol, 2 equivalents) is added, and the reaction mixture is stirred at 37° C. for 1 h. The solvent is then distilled off in a rotary evaporator, and the residue is dried under oil pump vacuum overnight. The intermediate Example 10A is obtained in a crude yield of 6.60 g. The intermediate is reacted further without purification. For this purpose, Example 10A (6.60 g) is dissolved in trifluoroacetic acid (107 ml) under an argon atmosphere and stirred at room temperature for 30 min. The solution is then concentrated in vacuo in a rotary evaporator, briefly dried under oil pump vacuum, taken up in methyl tert-butyl ether (250 ml) and vigorously stirred until an amorphous powdery solid results. This is filtered off under reduced pressure and washed with methyl tert-butyl ether (200 ml) and then washed again with dichloromethane (twice 100 ml). The solid is transferred into a flask and dried under oil pump vacuum. Example 11A is obtained in a crude yield of 6.0 g (quant.). The product can be reacted without further purification.

Example 12A

N²-(Anilinocarbonothioyl)-N¹-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide monotrifluoroacetate

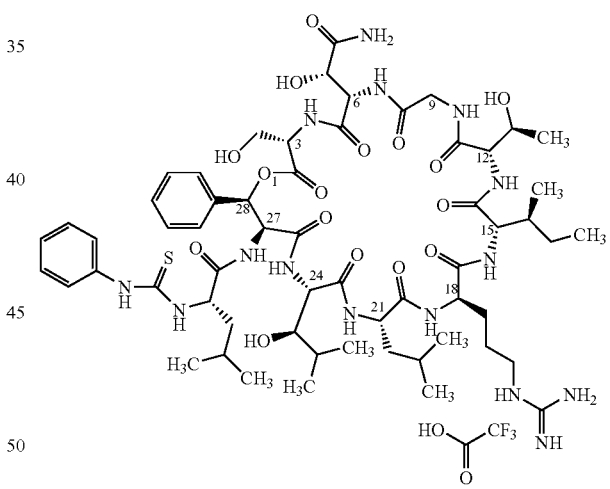

De-D-leucyllysobactin bistrifluoroacetate (Example 11A, 255 mg, 0.18 mmol) is reacted by general procedure 1. 322 mg (quant.) of product are obtained, which can be reacted further unpurified.

For further purification, the crude product can be gel chromatographed (method 6; methanol/0.1% acetic acid). The product-containing fractions are concentrated in vacuo at room temperature and then lyophilized.

HPLC/UV-Vis (method 13): $R_t$=6.56 min, $\lambda_{max}$ (qualitative)=220 nm (s), 245 (m), 268 (m).

LC-MS (method 12): $R_t$=4.85 min;

MS (ESIpos.): m/z (%)=1299 (100) $[M+H]^+$.

Example 13A (2S)-2-{(3S,6S,12S,15S,18R,21S,24S,27S,28R)-27-Amino-18-(3-{[amino(imino)methyl]amino}-propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-6-yl}-2-hydroxyethanamide bistrifluoroacetate {De(1-D-leucyl-2-L-leucyl)lysobactin bistrifluoroacetate}

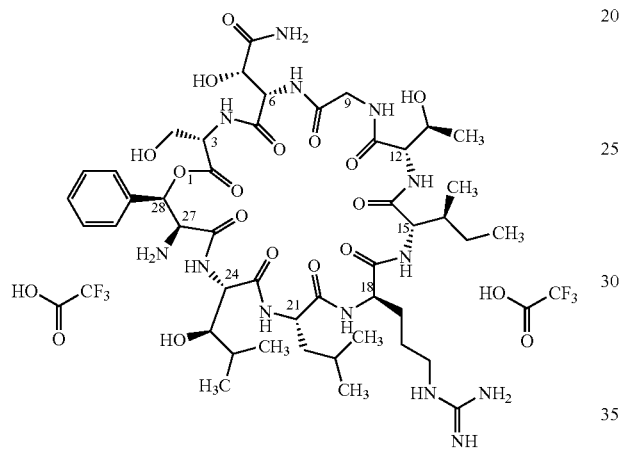

The thiourea (Example 12A, 66 mg, 34 μmol) is reacted by general procedure 2. The crude product can be prepurified by rapid gel chromatography (method 6; methanol/0.25% acetic acid). Preparative HPLC (method 8 or method 9 followed by subsequent metathesis of the chromatography product by adding TFA (100 μmol)) affords 45 mg (75% of theory) of product.

HPLC/UV-Vis (method 13): $R_t$=4.71 min,
$\lambda_{max}$ (qualitative)=220 nm (s), 255-270 (w).
LC-MS (method 11): $R_t$=1.65 min;
MS (ESIpos.): m/z (%)=526 (100) $[M+2H]^{2+}$, 1051 (15) $[M+H]^+$.

Alternative Process for Preparation on a Larger Scale:

The compound of example 11A (6.47 g, 4.30 mmol) is dissolved in pyridine (92 ml) under an argon atmosphere. Then phenyl isothiocyanate (8.75 g, 64.68 mmol, 15 equivalents) is added, and the reaction mixture is stirred at 37° C. for 1 hour. The solvent is then distilled off in a rotary evaporator, and the residue is dried under oil pump vacuum overnight. Example 12A is obtained in a crude yield of 6.0 g. The intermediate is reacted further without purification. For this purpose, crude Example 12A is dissolved in trifluoroacetic acid (82 ml) under an argon atmosphere and stirred at room temperature for 30 min. The solution is then concentrated in vacuo in a rotary evaporator, briefly dried under oil pump vacuum, taken up in methyl tert-butyl ether (250 ml) and stirred vigorously until an amorphous powdery solid results. This is filtered off under reduced pressure and washed with further methyl tert-butyl ether (200 ml) and then washed further with two portions each of 100 ml of dichloromethane. The solid is transferred into a flask and dried under oil pump vacuum. The title compound is obtained in a crude yield of 5.4 g (quant.). The product is purified further by preparative HPLC (method 31). 1.79 g of the title compound (32% of theory) are obtained.

Example 14A

N-(tert-Butoxycarbonyl)-D-leucyl-$N^1$-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-3-cyclopropyl-L-alaninamide monotrifluoroacetate

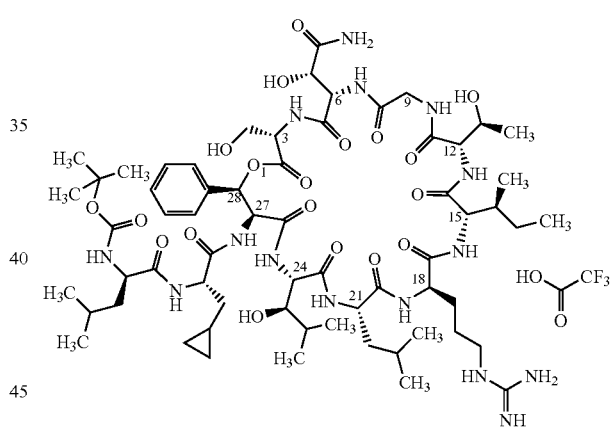

De(1-D-leucyl-2-L-leucyl)lysobactin bistrifluoroacetate (Example 13A, 112 mg, 88 μmol) and N-(tert-butoxycarbonyl)-D-leucyl-3-cyclopropyl-L-alanine (Example 5A, 120 mg, 350 μmol) are reacted by general procedure 4. The crude product is finally purified by preparative HPLC (method 8; or method 7 followed by subsequent methathesis of the chromatography product by adding TFA (200 μmol)). 87 mg (63% of theory) of product are obtained.

HPLC/UV-Vis (method 13): $R_t$=7.04 min,
$\lambda_{max}$ (qualitative)=220 nm (s), 255-270 (w).
LC-MS (method 11): $R_t$=2.61 min;
MS (ESIpos.): m/z (%)=638 (100) $[M-Boc+2H]^{2+}$, 1375 (15) $[M+H]^+$.
LC-MS (method 12): $R_t$=5.27 min;
MS (ESIpos.): m/z (%)=638 (30) $[M-Boc+2H]^{2+}$, 1375 (100) $[M+H]^+$.

Example 15A

N-(tert-Butoxycarbonyl)-D-leucyl-N$^1$-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-norvalinamide monotrifluoroacetate

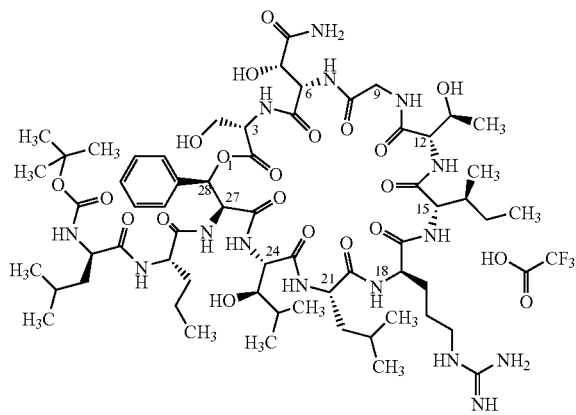

De(1-D-leucyl-2-L-leucyl)lysobactin bistrifluoroacetate (Example 13A, 5 mg, 4 µmol) and N-(tert-butoxycarbonyl)-D-leucyl-L-norvaline (Example 7A, 5 mg, 16 µmol) are reacted by general procedure 4. The crude product is finally purified by preparative HPLC (method 10; or method 9 followed by subsequent methathesis of the chromatography product by adding TFA (10 µmol)). 2.7 mg (51% of theory) of product are obtained.

HPLC/UV-Vis (method 13): R$_t$=6.97 min.

$\lambda_{max}$ (qualitative)=220 nm (s), 255-270 (w).

LC-MS (method 11): R$_t$=2.49 min;

MS (ESIpos.): m/z (%)=632 (100) [M−Boc+2H]$^{2+}$, 1363 (10) [M+H]$^+$.

Example 16A

N-(tert-Butoxycarbonyl)-D-leucyl-N$^1$-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-3-tert-butyl-L-alaninamide monotrifluoroacetate

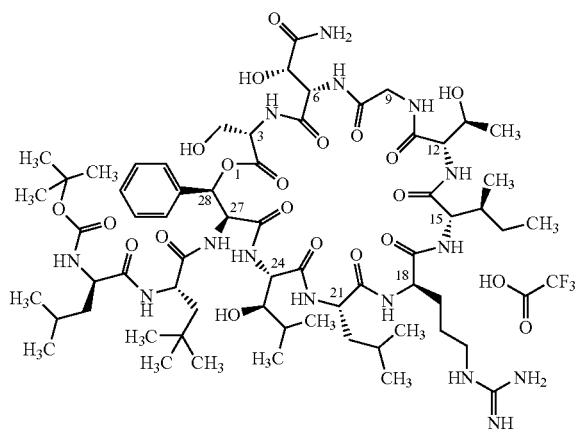

De(1-D-leucyl-2-L-leucyl)lysobactin bistrifluoroacetate (Example 13A, 21 mg, 14 µmol) and N-(tert-butoxycarbonyl)-D-leucyl-3-tert-butyl-L-alanine (Example 9A, 24 mg, 66 µmol) are reacted by general procedure 4. The crude product is finally purified by preparative HPLC (method 15; or method 14 followed by subsequent methathesis of the chromatography product by adding TFA (30 µmol)). 19 mg (75% of theory) of product are obtained.

HPLC/UV-Vis (method 13): R$_t$=7.31 min.

$\lambda_{max}$ (qualitative)=220 nm (s), 255-270 (w).

LC-MS (method 11): R$_t$=2.59 min;

MS (ESIpos.): m/z (%)=646 (100) [M−Boc+2H]$^{2+}$, 1391 (20) [M+H]$^+$.

Example 17A

N-(tert-Butoxycarbonyl)-L-leucyl-N$^1$-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide monotrifluoroacetate {N-(tert-Butoxycarbonyl)-epi-lysobactin monotrifluoroacetate}

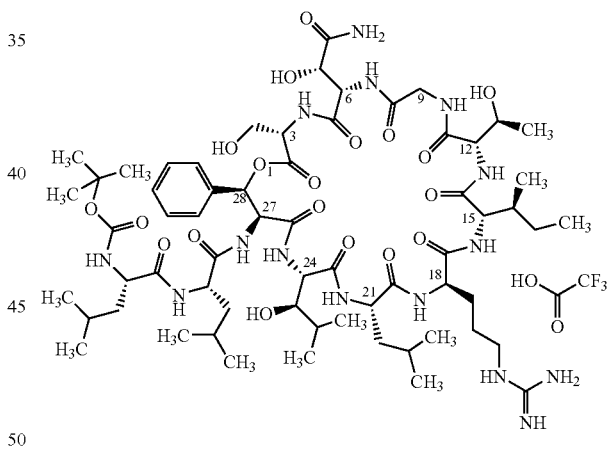

De-D-leucyllysobactin bistrifluoroacetate (Example 11A, 2.2 mg, 2 µmol) is reacted with N-(tert-butoxycarbonyl)leucine (7.9 mg, 32 µmol) in analogy to general procedure 3. The crude product is gel chromatographed (method 6; methanol/0.25% acetic acid) and then finally purified by preparative HPLC (method 14 followed by subsequent methathesis of the chromatography product by adding TFA (10 µmol)). Freeze drying of the product fractions results in 1.5 mg (64% of theory) of product.

HPLC/UV-Vis (method 13): R$_t$=6.97 min, $\lambda_{max}$ (qualitative)=220 nm (s), 255-270 (w).

LC-MS (method 12): R$_t$=4.76 min;

MS (ESIpos.): m/z (%)=1377 (100) [M+H]$^+$;

MS (ESIneg.): m/z (%)=1375 (100) [M−H]$^-$.

Example 18A

N²-{4-[(tert-Butoxycarbonyl)amino]butanoyl}-N¹-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide monotrifluoroacetate

[{4-[(tert-Butoxycarbonyl)amino]butanoyl}-de(leucyl)lysobactin monotrifluoroacetate]

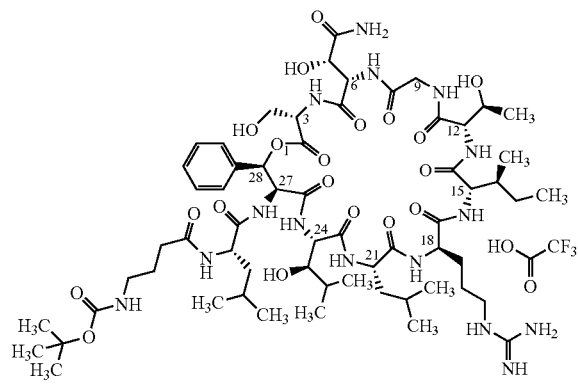

De-D-leucyllysobactin bistrifluoroacetate (Example 11A, 4.0 mg, 3 µmol) is reacted with 4-[(tert-butoxycarbonyl)amino]butanoic acid (11.7 mg, 57 µmol) in analogy to general procedure 3. The crude product is gel chromatographed (method 6; methanol/0.25% acetic acid) and then finally purified by preparative HPLC (method 14 followed by subsequent metathesis of the chromatography product by adding TFA (10 µmol)). Freeze drying of the product fractions results in 2.3 mg (59% of theory) of product.

HPLC/UV-Vis (method 13): $R_t$=6.67 min,
$\lambda_{max}$ (qualitative)=220 nm (s), 255-270 (w).
LC-MS (method 12): $R_t$=4.76 min;
MS (ESIpos.): m/z (%)=1349 (100) [M+H]⁺;
MS (ESIneg.): m/z (%)=1346 (100) [M−H]⁻.

Example 19A

N-(tert-Butoxycarbonyl)-N-methyl-D-leucyl-N¹-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide monotrifluoroacetate {N-(tert-Butoxycarbonyl)-N-methyl-lysobactin monotrifluoroacetate}

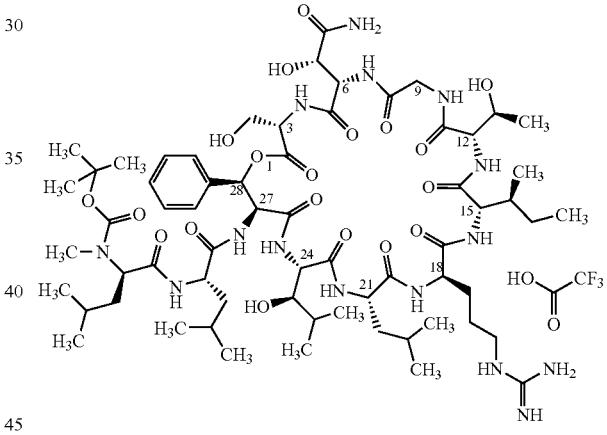

De-D-leucyllysobactin bistrifluoroacetate (Example 11A, 5.0 mg, 4 µmol) is reacted with N-(tert-butoxycarbonyl)-N-methyl-D-leucine hydrate (17.6 mg, 72 µmol) in analogy to general procedure 3. The crude product is gel chromatographed (method 6; methanol/0.25% acetic acid) and then finally purified by preparative HPLC (method 14 followed by subsequent metathesis of the chromatography product by adding TFA (10 µmol)). Freeze drying of the product fractions results in 2.0 mg (40% of theory) of product.

HPLC/UV-Vis (method 13): $R_t$=7.41 min,
$\lambda_{max}$ (qualitative)=220 nm (s), 255-270 (w).
LC-MS (method 12): $R_t$=5.11 min;
MS (ESIpos.): m/z (%)=1391 (100) [M+H]⁺;
MS (ESIneg.): m/z (%)=1389 (100) [M−H]⁻.

Example 20A

N²-{6-[(tert-Butoxycarbonyl)amino]hexanoyl}-N¹-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide monotrifluoroacetate

[N-{6-[(tert-Butoxycarbonyl)amino]hexanoyl}-de(leucyl)lysobactin monotrifluoroacetate]

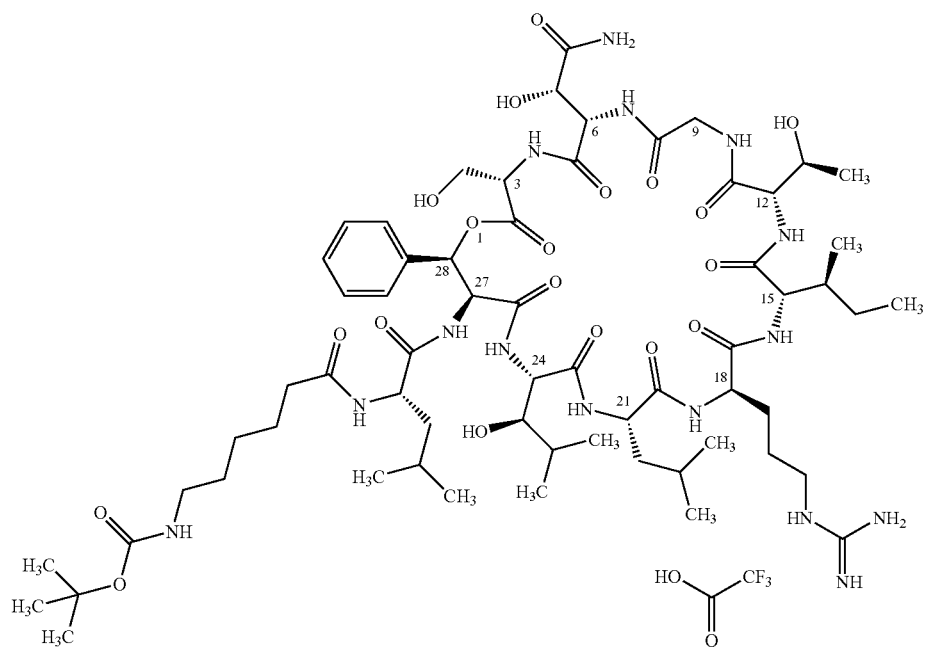

De-D-leucyllysobactin bistrifluoroacetate (Example 11A, 5.0 mg, 4 μmol) is reacted with 6-[(tert-butoxycarbonyl)amino]hexanoic acid (4.2 mg, 18 μmol) in analogy to general procedure 3. The crude product is gel chromatographed (method 6; methanol/0.25% acetic acid) and then finally purified by preparative HPLC (method 14 followed by subsequent metathesis of the chromatography product by adding TFA (10 μmol)). Freeze drying of the product fractions results in 900 μg (18% of theory) of product.

LC-MS (method 11): $R_f$=2.57 min;

MS (ESIpos.): m/z (%)=639 (100) [M−Boc+2H]²⁺, 1377 (10) [M+H]⁺;

MS (ESIneg.): m/z (%)=1375 (100) [M−H]⁻.

Example 21A

N²-{3-[(tert-Butoxycarbonyl)amino]propionyl}-N¹-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide monotrifluoroacetate

[N-{3-[(tert-Butoxycarbonyl)amino]propionyl}-de(leucyl)lysobactin monotrifluoroacetate]

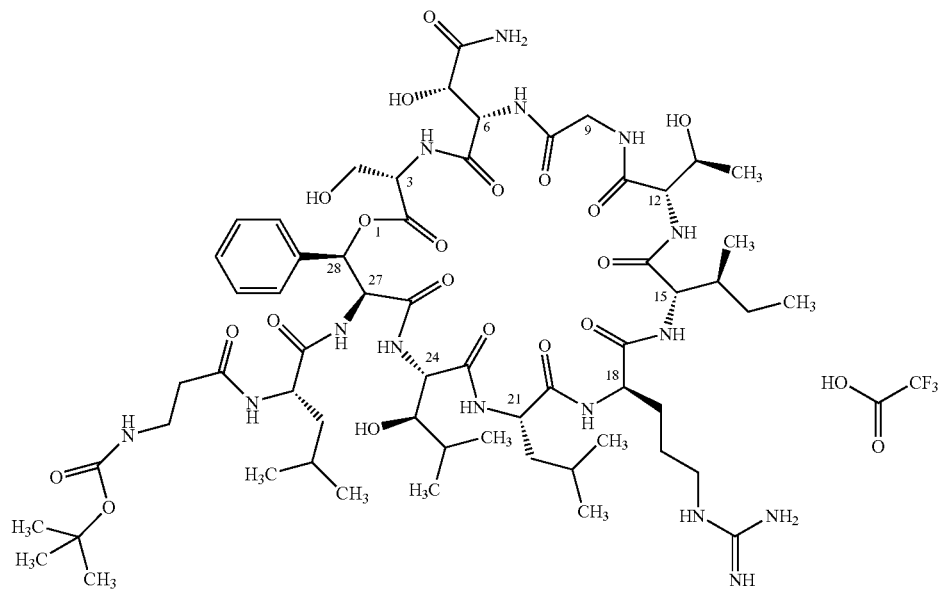

De-D-leucyllysobactin bistrifluoroacetate (Example 11A, 4.4 mg, 4 µmol) is reacted with 3-[(tert-butoxycarbonyl)amino]propionic acid (700 µg, 20 µmol) in analogy to general procedure 3. The crude product is gel chromatographed (method 6; methanol/0.25% acetic acid) and then finally purified by preparative HPLC (method 14 followed by subsequent metathesis of the chromatography product by adding TFA (10 µmol)). Freeze drying of the product fractions results in 2.0 mg (40% of theory) of product.

HPLC/UV-Vis (method 13): $R_t$=6.45 min,
$\lambda_{max}$ (qualitative)=220 nm (s), 255-270 (w).
LC-MS (method 12): $R_t$=4.73 min;
MS (ESIpos.): m/z (%)=1335.6 (100) [M+H]⁺;
MS (ESIneg.): m/z (%)=1333 (100) [M−H]⁻.

Example 22A

N²-({1-[(tert-Butoxycarbonyl)amino]cyclopropyl}carbonyl)-N¹-{(3S,6S,12S,15S,18R,21S,24S,-27S,28R)-6-[(1S)-2-amino-1-hydroxy-2-oxoethyl]-18-(3-{[amino-(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide monotrifluoroacetate

[N-({1-[(tert-Butoxycarbonyl)amino]cyclopropyl}carbonyl)-de(leucyl)lysobactin monotrifluoroacetate]

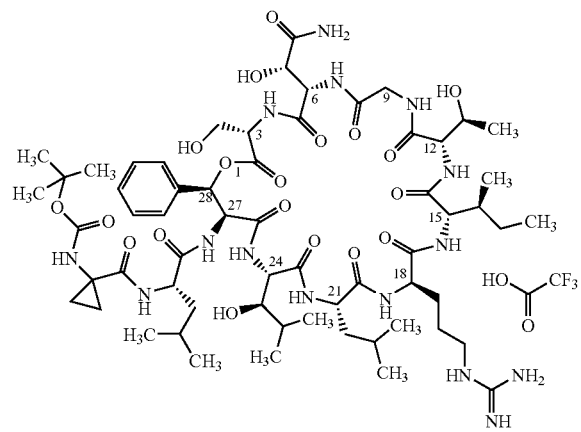

De-D-leucyllysobactin bistrifluoroacetate (Example 11A, 5.0 mg, 4 µmol) is reacted with 1-[(tert-butoxycarbonyl)amino]cyclopropanecarboxylic acid (3.6 mg, 18 µmol) in analogy to general procedure 3. The crude product is gel chromatographed (method 6; methanol/0.25% acetic acid) and then finally purified by preparative HPLC (method 14 followed by subsequent metathesis of the chromatography product by adding TFA (10 µmol)). Freeze drying of the product fractions results in 650 µg (13% of theory) of product.

LC-MS (method 11): $R_t$=2.54 min;
MS (ESIpos.): m/z (%)=624 (100) $[M-Boc+2H]^{2+}$, 1346 (20) $[M+H]^+$;
MS (ESIneg.): m/z (%)=1345 (100) $[M-H]^-$.

Example 23A

N-[(Benzyloxy)carbonyl]-3-[(tert-butoxycarbonyl)amino]-L-alanyl-N¹-{(3S,6S,12S,15S,18R,-21S,24S,27S,28R)-6-[(1S)-2-amino-1-hydroxy-2-oxoethyl]-18-(3-{[amino(imino)methyl]amino}-propyl)-12-[(1S)-1-hydroxyethyl)-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide monotrifluoroacetate

[N-[(Benzyloxy)carbonyl]-3-[(tert-butoxycarbonyl)amino]-L-alanyl}-de(leucyl)lysobactin monotrifluoroacetate]

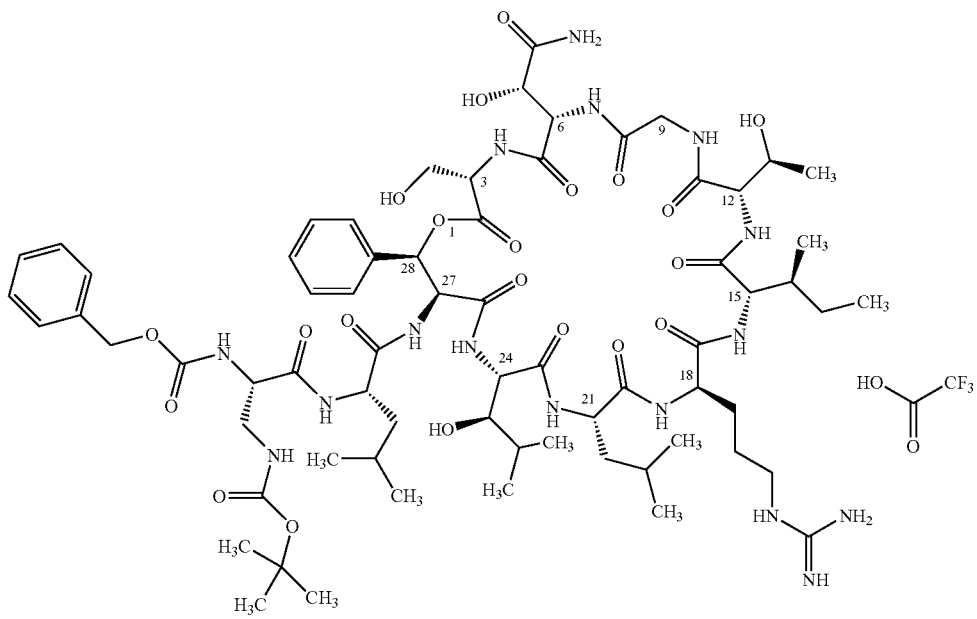

De-D-leucyllysobactin bistrifluoroacetate (Example 11A, 1.9 mg, 1.3 μmol) is reacted with N-[(benzyloxy)carbonyl]-3-[(tert-butoxycarbonyl)amino]-L-alanine (2.3 mg, 6.7 μmol) in analogy to general procedure 3. The crude product is gel chromatographed (method 6; methanol/0.25% acetic acid) and then finally purified by preparative HPLC (method 14 followed by subsequent metathesis of the chromatography product by adding TFA (10 μmol)). Freeze drying of the product fractions results in 900 μg (46% of theory) of product.

LC-MS (method 19): $R_t$=2.79 min;

MS (ESIpos.): m/z (%)=693 (100) [M–Boc+2H]$^{2+}$, 1484 (5) [M+H]$^+$;

MS (ESIneg.): m/z (%)=628 (100), 1482 (60) [M–H]$^-$.

Example 24A

N-(tert-Butoxycarbonyl)-D-leucyl-N$^1$-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide monotrifluoroacetate {N-(tert-Butoxycarbonyl)lysobactin monotrifluoroacetate}

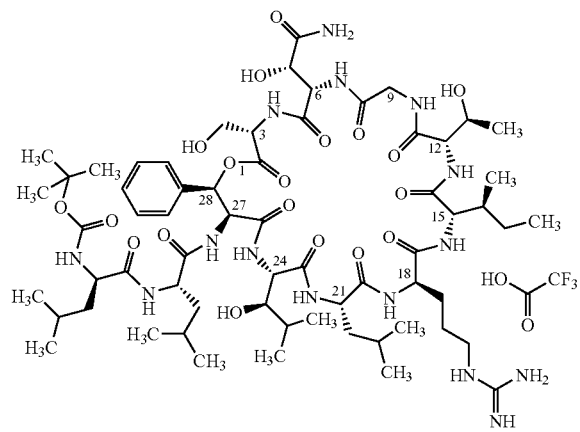

De-D-leucyllysobactin bistrifluoroacetate (Example 11A, 4.4 mg, 4 μmol) is reacted with N-(tert-butoxycarbonyl)-D-leucine hydrate (16 mg, 64 μmol) in analogy to general procedure 3. The crude product is gel chromatographed (method 6; methanol/0.25% acetic acid) and then finally purified by preparative HPLC (method 14 followed by subsequent metathesis of the chromatography product by adding TFA (20 μmol)). Freeze drying of the product fractions results in 1.3 mg (27% of theory) of product.

HPLC/UV-Vis (method 13): $R_t$=7.07 min, $\lambda_{max}$ (qualitative)=220 nm (s), 255-270 (w).

LC-MS (method 12): $R_t$=5.01 min;

MS (ESIpos.): m/z (%)=1377 (100) [M+H]$^+$;

MS (ESIneg.): m/z (%)=1375 (100) [M–H]$^-$.

Amino Acids and Derivatives

Example 25A and Example 26A (2R)-N-(tert-Butoxycarbonyl)-3-(trimethylsilyl)alanine and (2S)-N-(tert-butoxycarbonyl)-3-(trimethylsilyl)alanine Synthesis takes place as described by M. Merget, K. Günther, M. Bernd, E. Günther, R. Tacke, *J. Organomet. Chem.* 2001 628, 183-194. The enantiomers are separated by preparative HPLC on a chiral phase:

Gilson Abimed HPLC, UV detector 212 nm, column: Daicel Chiralpak AD-H 5 μm; 250×20 mm; flow rate: 15 ml/min; eluent A: iso-hexane, eluent B: 0.2% acetic acid/1% water/2-propanol; isocratic.

Example 25A

2R Compound

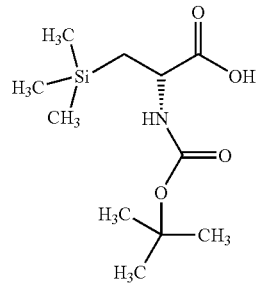

Preparative HPLC: $R_t$=4.16 min $[\alpha]_D^{20}$=+1.1 (c=0.83, methanol)

Example 26A

2S Compound

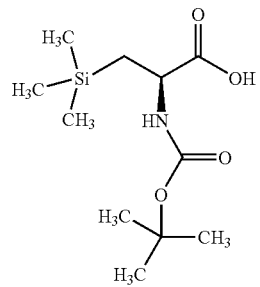

Preparative HPLC: $R_t$=9.27 min $[\alpha]_D^{20}$=–1.6 (c=0.66, methanol)

Example 27A

Methyl (2Z)-2-{[(benzyloxy)carbonyl]amino}-3-(1-methylcyclohexyl)acrylate

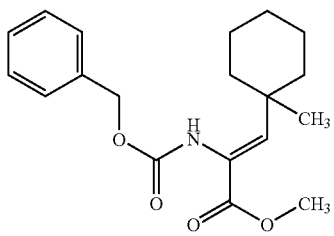

1-Methylcyclohexanecarbaldehyde (2.66 g, 21.08 mmol) and methyl {[(benzyloxy)carbonyl]amino}(dimethoxyphosphoryl)acetate (6.63 g, 20.02 mmol, 0.95 equivalent) are dissolved in 75 ml of tetrahydrofuran and cooled to −78° C. At −78° C., N,N,N',N'-tetramethylguanidine (27.92 g, 0.24 mol, 11.5 equivalents) is added dropwise and then stirred at −78° C. for 15 min and subsequently at room temperature for 4 days. The mixture is then extracted by shaking with ethyl acetate (twice 100 ml) and water, and the combined organic phases are washed with saturated sodium chloride solution and dried over sodium sulphate. After concentration, the crude product is chromatographed (Biotage 40M, cyclohexane/ethyl acetate 6/1, 27.5 ml/min). 0.91 g (13% of theory) of the title compound is obtained.

LC-MS (method 26): $R_t$=2.74 min,
MS (ESIpos.): m/z (%)=332.3 (70) [M+H]$^+$.

Example 28A

N-[(Benzyloxy)carbonyl]-3-(1-methylcyclohexyl)-D-alanine methyl ester

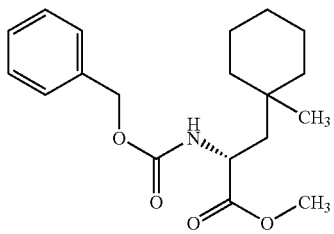

The compound of Example 27A (310 mg, 0.94 mmol) is dissolved in ethanol p.a. (60 ml). Argon is passed through using a needle for about 5 min, and then (−)-1,2-bis[(2R, 5R)diethylphospholano]benzene(cyclooctadiene)rhodium (I) triflate (2.7 mg, 4 μmol, 0.004 equivalent) is added and dissolved in an ultrasonic bath. Hydrogenation is carried out under a hydrogen pressure of 3 bar and at room temperature for 3 days. A further portion (2.7 mg, 4 μmol, 0.004 equivalent) of the catalyst is added to the mixture, and hydrogenation is continued under a pressure of 3 bar of hydrogen for one day. Addition of catalyst is repeated at 24 h intervals until the reaction is complete. The reaction is checked by LC-MS (method 35). The mixture is then filtered through silica gel (ethyl acetate) and the eluate is concentrated. Yield: 181 mg (58% of theory) of the title compound.

$^1$H NMR (300 MHz, CDCl$_3$): δ=0.94 (s, 3H), 1.23-1.55 (m, 11H), 1.78 (dd, 1H), 3.71 (s, 3H), 4.42 (m, 1H), 5.02 (m, 1H), 5.11 (s, 1H), 7.36 (m, 5H).
LC-MS (method 35): $R_t$=2.85 min,
MS (ESIpos.): m/z (%)=334 (25) [M+H]$^+$.
MS (DCI): m/z (%)=351 (100) [M+NH$_4$]$^+$.

Example 29A

N-[(Benzyloxy)carbonyl]-3-(1-methylcyclohexyl)-D-alanine

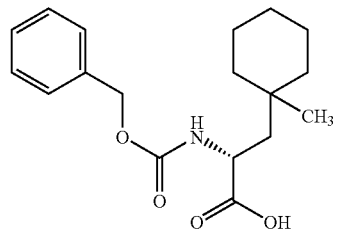

The compound of Example 28A (180 mg, 0.54 mmol) is dissolved in THF (3 ml). At 0° C., lithium hydroxide (2M in water, 0.59 ml, 1.19 mmol, 2.2 equivalents) is added dropwise and then stirred at 0° C. for 4 h. The mixture is left to stand at 7° C. overnight. Trifluoroacetic acid (0.12 ml, 1.62 mmol, 3 equivalents) is added to the mixture while cooling in ice, and, after extraction with ethyl acetate, the organic extract is dried over sodium sulphate. The crude product is purified by preparative HPLC (method 31). Yield: 135 mg (78% of theory) of the title compound.

$^1$H NMR (300 MHz, CDCl$_3$): δ=0.95 (s, 3H), 1.20-1.54 (m, 11H), 1.90 (m, 1H), 4.43 (m, 1H), 5.01 (d, 1H), 5.13 (s, 2H), 7.28-7.40 (m, 5H).
HPLC (method 18): $R_t$=4.8 min.
MS (method ESI): m/z (%)=318.1 (4), [M−H]$^-$.

Example 30A

Methyl (2Z)-2-{[(benzyloxy)carbonyl]amino}-3-(4-isopropylphenyl)acrylate

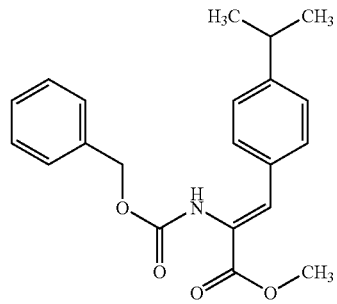

4-Isopropylbenzaldehyde (2.00 g, 13.50 mmol) and methyl{[(benzyloxy)carbonyl]amino}-(dimethoxyphosphoryl)acetate (3.58 g, 10.80 mmol, 0.8 equivalent) are dissolved in tetrahydrofuran (20 ml) and cooled to −78° C. At −78° C., N,N,N',N'-tetramethylguanidine (27.92 g, 0.24 mol, 11.5 equivalents) is added dropwise and then stirred at −78° C. for 3 h and subsequently at room temperature 3 days. The mixture is then extracted by shaking with ethyl acetate (twice 100 ml) and water, and the combined organic phases are washed with saturated sodium chloride solution and dried over sodium sulphate. After concentration, the crude product is chromatographed (Biotage 40M, cyclohexane/ethyl acetate 5/1). 3.47 g (73% of theory) of the title compound are obtained.

$^1$H NMR (300 MHz, CDCl$_3$): δ=(1.25 (d, 6H), 2.90 (sept, 1H), 3.80 (s, 3H), 5.13 (s, 2H), 6.22 (br s, 1H), 7.20 (d, 2H), 7.37 (m, 5H), 7.46 (d, 2H).

HPLC (method 28): R$_t$=5.10 min.

MS (DCI): m/z (%)=371.1 (100) [M+NH$_4$]$^+$.

Example 31A (N-Benzyloxycarbonyl)-4-isopropyl-D-phenylalanine methyl ester

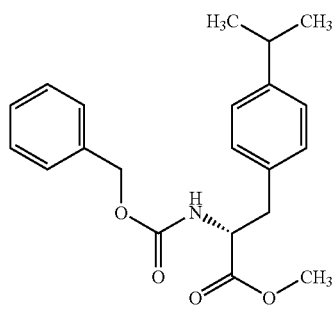

The exemplary compound of Example 30A (3.47 g, 9.82 mmol) is dissolved in ethanol p.a. (60 ml). Argon is passed through using a needle for about 10 min and then (−)-1,2-bis((2R,5R)diethylphospholano)benzene(cyclooctadiene)rhodium(I) triflate (28 mg, 39 μmol, 0.004 equivalent) is added and dissolved in an ultrasonic bath. Hydrogenation is carried out under a hydrogen pressure of 3 bar and at room temperature for 3 days. A further portion (28 mg, 39 μmol, 0.004 equivalent) of the catalyst is added to the mixture, and hydrogenation is continued under 3 bar for one day. Addition of catalyst is repeated at 24 h intervals until the reaction is complete. The reaction is checked by LC-MS (method 26). The mixture is then filtered through silica gel (ethyl acetate) and the eluate is concentrated. Yield: 3.27 g (89% of theory) of the title compound.

$^1$H NMR (300 MHz, CDCl$_3$): δ=1.21 (d, 6H), 2.87 (sept, 1H), 3.08 (d, 1H), 3.68 (s, 3H), 4.63 (m, 1H), 5.10 (s, 2H), 5.20 (m, 1H), 7.01 (d, 2H), 7.13 (d, 2H), 7.42 (m, 5H).

HPLC (method 36): R$_t$=3.88 min.

LC-MS (method 26): R$_t$=2.84 min,

MS (ESIpos.): m/z (%)=356 (15) [M+H]$^+$.

MS (DCI): m/z (%)=373 (100) [M+NH$_4$]$^+$.

Example 32A (N-Benzyloxycarbonyl)-4-isopropyl-D-phenylalanine

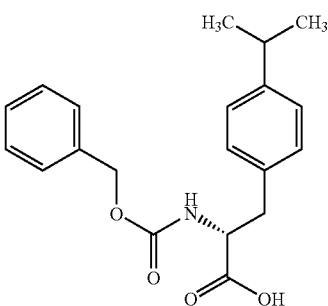

The compound of Example 31A (240 mg, 0.68 mmol) is dissolved in tetrahydrofuran (3 ml). At 0° C., lithium hydroxide (2M in water, 0.74 ml, 1.49 mmol, 2.2 equivalents) is added dropwise and then stirred at 0° C. for 1 h. Trifluoroacetic acid (0.16 ml, 2.03 mmol, 3 equivalents) is added to the mixture and, after extraction with ethyl acetate, the organic extract is dried over sodium sulphate. The crude product is purified by preparative HPLC (method 31). Yield: 86% of theory.

$^1$H NMR (200 MHz, CDCl$_3$): δ=1.22 (d, 6H), 2.87 (sept, 1H), 3.13 (m, 2H), 4.69 (m, 1H), 5.10 (s, 2H), 5.18 (s, 1H), 7.05 (d, 2H), 7.15 (d, 2H), 7.36 (m, 5H).

HPLC (method 36): R$_t$=3.64 min.

MS (DCI): m/z (%)=359.1 (100), [M+NH$_4$]$^+$.

Dipeptide Esters

Example 33A

N-(tert-Butoxycarbonyl)-3-tert-butyl-D-alanyl-3-tert-butyl-L-alanine benzyl ester

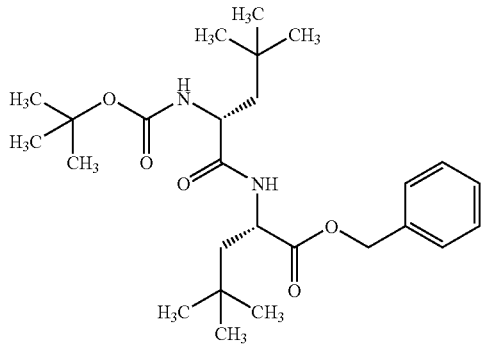

N-(tert-Butoxycarbonyl)-3-tert-butyl-D-alanine (3.28 g, 13.4 mmol) and benzyl 3-tert-butyl-L-alaninate hydrochloride (4.0 g, 14.7 mmol; J. X. He, W. L. Cody, A. M. Doherty, J. Org. Chem. 1995, 60, 8262-8266) are reacted by general procedure 6 (in this case 5 equivalents of N-methylmorpholine). Aqueous workup results in 6.0 g of product (97% of theory). The product can be finally purified by preparative HPLC (method 16).

$^1$H NMR (400 MHz, d$_6$-DMSO): δ=0.85 (s, 9H, tBu), 0.86 (s, 9H, tBu), 1.31 (s, 9H, OtBu), 1.35 (m, 2H, β-CH$_2$), 1.55 (m, 2H, β-CH$_2$), 3.98 (m, 1H, α-CH), 4.22 (m, 1H, α-CH), 5.04 (d, J=1.8 Hz, 2H, CH$_2$Ph), 6.72 (d, J=9.2 Hz, 1H, NH), 7.25-7.35 (m, 5H, Ph), 7.94 (d, J=7.8 Hz, 1H, NH).
[α]$^{20}_{Na}$=+17° (c=0.1 in methylene chloride).
HPLC/UV-Vis (method 13): R$_t$=9.6 min,
λ$_{max}$ (qualitative)=220 nm (s), 250-275 (w).
LC-MS (method 26): R$_t$=3.09 min;
MS (ESIpos.): m/z (%)=363 (30) [M–Boc+H]$^+$, 463 (100) [M+H]$^+$, 926 (50) [2M+H]$^+$.
HR-TOF-MS (method 21): C$_{26}$H$_{43}$N$_2$O$_5$ calc. 463.3172, found 463.3185 [M+H]$^+$.

Example 34A

N-(tert-Butoxycarbonyl)-3-(tert-butyl)-D-alanyl-3-(3-pyridyl)-L-alanine methyl ester

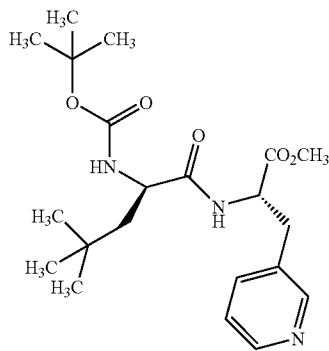

N-methylmorpholine (5 equivalents, 6.0 mmol), EDC (2.5 equivalents, 3.0 mmol) and HOBt (2.5 equivalents, 3.0 mmol) are added slowly to a solution of N-(tert-butoxycarbonyl)-3-tert-butyl-D-alanine (1.0 equivalent, 1.2 mmol) and 3-(3-pyridyl)-L-alanine methyl ester (1.0 equivalent, 1.2 mmol) in dry dichloromethane (3 ml) at –30° C. The reaction mixture slowly (approx. 12 h) warms to room temperature, with complete conversion being observed by means of HPLC (method 36). The reaction mixture is worked up by diluting with dichloromethane (20 ml) and washing with saturated sodium bicarbonate solution (10 ml). The organic phase is dried with magnesium sulphate, filtered and concentrated. The crude product is purified by flash chromatography (silica gel, gradient dichloromethane 100% to dichloromethane/methanol: 4/1), resulting in 466 mg (96% of theory) of product.

$^1$H NMR (400 MHz, d$_6$-DMSO): δ=0.78 (s, 9H, tBu), 1.17 (m, 2H, β-CH$_2$), 1.36 (s, 9H, OtBu), 3.00 (m, 2H, β-CH$_2$), 3.64 (s, 3H, OMe), 3.98 (m, 1H, α-CH), 4.49 (m, 1H, α-CH), 6.80 (d, J=7.0 Hz, 1H, NH), 7.26 (dd, J=4.0, 6.5 Hz, 1H, PyrH), 7.63 (d, J=6.5 Hz, 1H, PyrH), 8.27 (d, J=6.5 Hz, 1H, NH), 8.40 (d, J=4.0 Hz, 1H, PyrH), 8.42 (s, 1H, PyrH).

[α]$^{20}_{Na}$=+5° (c=0.19 in methanol).
HPLC/UV-Vis (method 28): R$_t$=4.0 min.
HPLC/UV-Vis (method 36): R$_t$=3.80 min.
$^{13}$C NMR (500 MHz, d$_6$-DMSO): δ=172.9, 171.6, 154.7, 150.2, 147.7, 136.6, 132.6, 123.1, 77.8, 52.6, 51.9, 51.4, 44.9, 33.6, 30.0, 29.2, 28.1.
LC-MS (method 26): R$_t$=1.75 min;
MS (ESIpos.): m/z (%)=308 (60), 352 (100), 408 (100) [M+H]$^+$;
MS (ESIneg.): m/z (%)=332 (100), 406 (5) [M–H]$^-$.
HR-TOF-MS (method 21): C$_{21}$H$_{34}$N$_3$O$_5$ [M+H]$^+$calc. 408.2498, found 408.2458.

TABLE 1

Dipeptide esters

| Ex. No. | Structure Name | Analytical data Preparation method |
|---|---|---|
| 35A | ![structure] N-tert-Butoxycarbonyl-3-tert-butyl-L-alanyl-3-tert-butyl-L-alanine benzyl ester | [α]$^{20}_{Na}$ = –44° (c = 0.1 in methylene chloride). HPLC/UV-Vis (method 13): R$_t$ = 9.5 min. $^1$H NMR (400 MHz, d$_6$-DMSO): δ = 0.81 (s, 9H, tBu), 0.83 (s, 9H, tBu), 1.31 (s, 9H, OtBu), 1.36 (m, 2H, β-CH$_2$), 1.57 (m, 2H, β-CH$_2$), 3.99 (m, 1H, α-CH), 4.22 (m, 1H, α-CH), 5.04 (d, J=1.8 Hz, 2H, CH$_2$Ph), 6.72 (d, J=9.2 Hz, 1H, NH), 7.29 (m, 5H, Ph), 7.95 (d, J=7.8 Hz, 1H, NH). HR-TOF-MS (method 21): C$_{26}$H$_{43}$N$_2$O$_5$ [M + H]$^+$ calc. 463.3172, found 463.3196. General procedure 6 (here 5 equivalents of N-methylmorpholine) from N-tert-butoxycarbonyl-3-tert-butyl-L-alanine (0.8 mmol) and 3-tert-butyl-L-alanine benzyl ester hydrochloride. Yield: 95% of theory |

TABLE 1-continued

Dipeptide esters

| Ex. No. | Structure Name | Analytical data Preparation method |
|---|---|---|
| 36A | 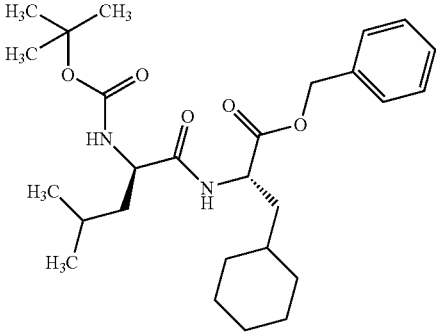<br>N-tert-Butoxycarbonyl-D-leucyl-3-cyclohexyl-L-alanine benzyl ester | $[\alpha]^{20}_{Na} = +16°$ (c = 0.1 in methylene chloride).<br>HPLC/UV-Vis (method 13): $R_t$ = 9.9 min.<br>HR-TOF-MS (method 21): $C_{27}H_{43}N_2O_5$ [M + H]$^+$ calc. 475.3172, found 475.3162.<br>General procedure 6 (here 5 equivalents of N-methylmorpholine) from N-tert-butoxycarbonyl-D-leucine (0.97 mmol) and 3-cyclohexyl-L-alanine benzyl ester hydrochloride.<br>Yield: 90% of theory |
| 37A | 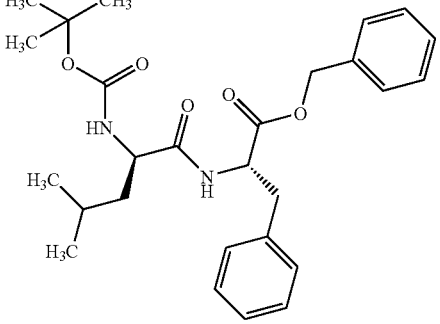<br>N-tert-Butoxycarbonyl-D-leucyl-L-phenylalanine benzyl ester | HPLC/UV-Vis (method 13): $R_t$ = 9.07 min.<br>LC-MS (method 26): $R_t$ = 2.94 min;<br>MS (ESIpos.): m/z (%) = 369 (50) [M − Boc + H]$^+$, 469 (100) [M + H]$^+$.<br>General procedure 6 (here 5 equivalents of N-methylmorpholine) from N-tert-butoxycarbonyl-D-leucine (3.12 mmol) and L-phenylalanine benzyl ester hydrochloride (3.43 mmol).<br>Yield: 98% of theory |
| 38A | 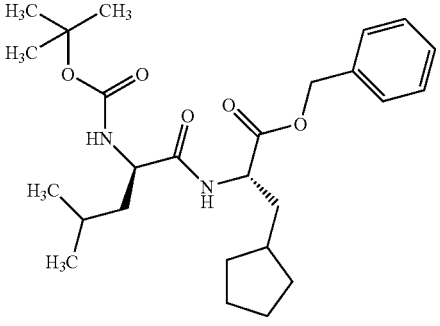<br>N-tert-Butoxycarbonyl-D-leucyl-3-cyclopentyl-L-alanine benzyl ester | HPLC/UV-Vis (method 13): $R_t$ = 9.47 min.<br>HPLC/UV-Vis (method 28): $R_t$ = 5.3 min.<br>LC-MS (method 29): $R_t$ = 7.1 min;<br>MS (ESIpos.): m/z (%) = 361 (80) [M − Boc + H]$^+$, 461 (100) [M + H]$^+$.<br>General procedure 6 (here 5 equivalents of N-methylmorpholine) from N-tert-butoxycarbonyl-D-leucune (0.34 mmol) and 3-cyclopentyl-L-alanine benzyl ester hydrochloride (0.37 mmol).<br>Yield: 94% of theory |
| 39A | 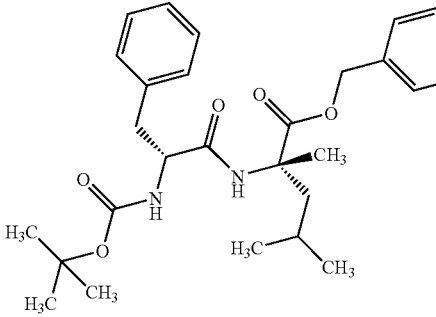<br>N-tert-Butoxycarbonyl-D-phenylalanyl-2-methyl-L-leucine benzyl ester | HPLC/UV-Vis (method 13): $R_t$ = 9.48 min.<br>LC-MS (method 26): $R_t$ = 3.09 min;<br>MS (ESIpos.): m/z (%) = 383 (100) [M − Boc + H]$^+$, 483 (90) [M + H]$^+$.<br>General procedure 6 (here 5 equivalents of N-methylmorpholine) from N-tert-butoxycarbonyl-D-phenylalanine (0.17 mmol) and 2-methyl-L-leucine benzyl ester hydrochloride.<br>Yield: 81% of theory |

TABLE 1-continued

Dipeptide esters

| Ex. No. | Structure Name | Analytical data Preparation method |
|---|---|---|
| 40A | N-tert-Butoxycarbonyl-3-cyclohexyl-D-alanyl-3-cyclohexyl-L-alanine benzyl ester | $[\alpha]^{20}_{Na}$ = +13° (c = 0.5 in methylene chloride).<br>HR-TOF-MS (method 21): $C_{30}H_{47}N_2O_5$ [M + H]$^+$ calc. 515.3485, found 515.3494.<br>General procedure 6 (here 5 equivalents of N-methylmorpholine) from N-tert-butoxycarbonyl-3-cyclohexyl-D-alanine (1.22 mmol) and 3-cyclohexyl-L-alanine benzyl ester hydrochloride (1.34 mmol).<br>Yield: 85% of theory (ee > 99%) |
| 41A | N-tert-Butoxycarbonyl-D-phenylalanyl-L-phenylalanine benzyl ester | HPLC/UV-Vis (method 13): $R_t$ = 9.16 min.<br>HPLC/UV-Vis (method 18): $R_t$ = 5.1 min.<br>HR-TOF-MS (method 21): $C_{30}H_{35}N_2O_5$ [M + H]$^+$ calc. 503.2546, found 503.2566.<br>General procedure 6 (here 5 equivalents of N-methylmorpholine) from N-tert-butoxycarbonyl-D-phenylalanine (3.77 mmol) and L-phenylalanine benzyl ester hydrochloride (4.15 mmol).<br>Yield: 96% of theory |
| 42A | N-tert-Butoxycarbonyl-3-(2-naphthyl)-D-alanyl-3-(1-naphthyl)-L-alanine methyl ester | HPLC/UV-Vis (method 13): $R_t$ = 9.24 min.<br>HPLC/UV-Vis (method 28): $R_t$ = 5.3 min; $\lambda_{max}$ (qualitative) = 222 nm (s), 282 (m).<br>LC-MS (method 22): $R_t$ = 2.78 min;<br>MS (ESIpos.): m/z (%) = 427 (80) [M − Boc + H]$^+$, 527 (100) [M + H]$^+$.<br>HR-TOF-MS (method 21): $C_{32}H_{35}N_2O_5$ [M + H]$^+$ calc. 527.2546, found 527.2552.<br>General procedure 6 (here 5 equivalents of N-methylmorpholine) from N-tert-butoxycarbonyl-3-(2-naphthyl)-D-alanine (0.75 mmol) and 3-(1-naphthyl)-L-alanine benzyl ester hydrochloride.<br>Yield: 92% of theory |

TABLE 1-continued

Dipeptide esters

| Ex. No. | Structure Name | Analytical data Preparation method |
|---|---|---|
| 43A | N-tert-Butoxycarbonyl-3-tert-butyl-D-alanyl-3-(3,4-dimethoxyphenyl)-L-alanine benzyl ester | HPLC/UV-Vis (method 13): $R_t$ = 8.89 min. LC-MS (method 26): $R_t$ = 2.87 min; MS (ESIpos.): m/z (%) = 443 (80) [M − Boc + H]$^+$, 543 (100) [M + H]$^+$. HR-TOF-MS (method 21): $C_{30}H_{43}N_2O_7$ [M + H]$^+$ calc. 543.3070, found 5473.3066. General procedure 6 (here 5 equivalents of N-methylmorpholine) from N-tert-butoxycarbonyl-3-tert-butyl-D-alanine (6.35 mmol) and 3-(3,4-dimethoxyphenyl)-L-alanine benzyl ester hydrochloride. Yield: 77% of theory |
| 44A | N-tert-Butoxycarbonyl-4-phenyl-D-phenylalanyl-4-phenyl-L-phenylalanine benzyl ester | $[\alpha]^{20}_{Na}$ = +16.7° (c = 0.6 in methylene chloride). HPLC/UV-Vis (method 13): $R_t$ = 10.31 min. HPLC/UV-Vis (method 18): $R_t$ = 5.7 min. HR-TOF-MS (method 21): $C_{42}H_{42}N_2O_5Na$ [M + Na]$^+$ calc. 677.2991, found 677.3014. General procedure 6 (here 5 equivalents of N-methylmorpholine) from N-tert-butoxycarbonyl-4-phenyl-D-phenylalanine (0.62 mmol) and 4-phenyl-L-phenylalanine benzyl ester hydrochloride (0.68 mmol). Yield: quant. |
| 45A | N-tert-Butoxycarbonyl-3-tert-butyl-D-alanyl-(1-amino-4-methoxy-cyclohexanecarboxylic acid) methyl ester | Diastereomer 1: LC-MS (method 26): $R_t$ = 2.39 min; MS (ESIpos.): m/z (%) = 315 (100) [M − Boc + H]$^+$, 415 (90) [M + H]$^+$. Diastereomer 2: LC-MS (method 26): $R_t$ = 2.44 min; MS (ESIpos.): m/z (%) = 315 (100) [M − Boc + H]$^+$, 415 (70) [M + H]$^+$. General procedure 6 from N-tert-butoxycarbonyl-3-tert-butyl-D-alanine (2.04 mmol) and methyl 1-amino-4-methoxycyclohexanecarboxylic acid methyl ester (2.24 mmol). Yield: 8% of theory (mixture of diastereomers). |

TABLE 1-continued

Dipeptide esters

| Ex. No. | Structure Name | Analytical data Preparation method |
|---|---|---|
| 46A | 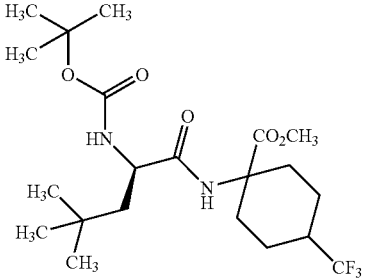<br>N-tert-Butoxycarbonyl-3-tert-butyl-D-alanyl-(1-amino-4-(trifluoromethyl)cyclohexanecarboxylic acid) methyl ester | HPLC/UV-Vis (method 13): $R_t$ = 8.74 min.<br>HPLC/UV-Vis (method 18): $R_t$ = 5.13 min.<br>LC-MS (method 26): $R_t$ = 2.76 min;<br>MS (ESIpos.): m/z (%) = 353 (50) [M − Boc + H]$^+$, 397 (60), 453 (100) [M + H]$^+$.<br>HR-TOF-MS (method 21): $C_{21}H_{36}N_2O_5F_3$ [M + H]$^+$ calc. 453.2576, found 453.2581.<br>General procedure 6 from N-tert-butoxycarbonyl-3-tert-butyl-D-alanine (2.04 mmol) and 1-amino-4-(trifluoromethyl)cyclohexanecarboxylic acid methyl ester (2.24 mmol).<br>Yield: 63% of theory (mixture of diastereomers). |
| 47A | 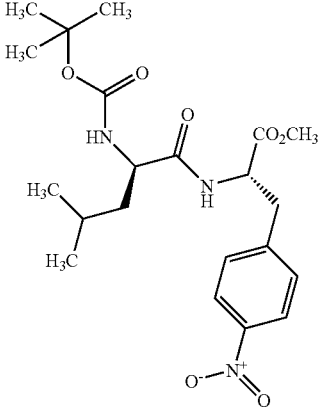<br>N-tert-Butoxycarbonyl-D-leucyl-4-nitro-L-phenylalanine methyl ester | HPLC/UV-Vis (method 13): $R_t$ = 8.03 min.<br>LC-MS (method 37): $R_t$ = 2.52 min:<br>MS (ESIpos.): m/z (%) = 338 (20) [M − Boc + H]$^+$, 379 (30), 382 (100), 438 (30) [M + H]$^+$.<br>General procedure 6 (here 2.5 equivalents of triethylamine as base) from N-tert-butoxycarbonyl-D-leucine (4.40 mmol) and 4-nitro-L-phenylalanine methyl ester hydrochloride (4.0 mmol).<br>Yield: 95% of theory |
| 48A | 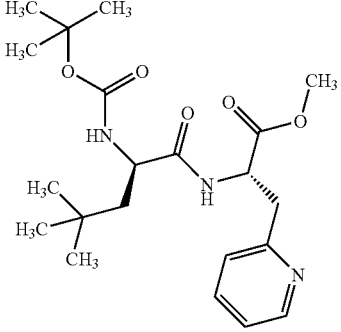<br>N-ter-Butoxycarbonyl-3-tert-butyl-D-alanyl-3-(2-pyridyl)-L-alanine methyl ester | HPLC/UV-Vis (method 28): $R_t$ = 4.1 min.<br>HPLC/UV-Vis (method 36): $R_t$ = 3.82 min.<br>LC-MS (method 26): $R_t$ = 2.07 min;<br>MS (ESIpos.): m/z (%) = 352 (100), 408 (95) [M + H]$^+$;<br>MS (ESIneg.): m/z (%) = 332 (100), 406 (5) [M − H]$^-$.<br>IR $\nu_{max}$ (NaCl, cm$^{-1}$): 3414, 1639, 1617, 1542, 1438, 1385, 1175, 620.<br>$^1$H NMR (400 MHz, d$_6$-DMSO): δ = 0.93 (s, 9H, tBu), 1.31-1.36 (m, 1H, β-CH), 1.41 (s, 9H, OtBu), 1.88 (m, 1H, β-CH), 3.31 (m, 2H, β-CH$_2$), 3.68 (s, 3H, OMe), 4.18 (m, 1H, α-CH), 4.79 (d, J=8.0 Hz, 1H), 4.92 (m, 1H, α-CH), 7.12-7.16 (m, 2H), 7.60 (dt, J=2.0, 8.0 Hz, 1H), 7.76 (d, J=6.5 Hz, 1H), 8.50 (d, J=4.0 Hz, 1H, NH).<br>$^{13}$C NMR (500 MHz, CDCl$_3$): δ = 172.7, 171.8, 157.1, 155.2, 149.1, 136.7, 123.8, 121.9, 79.9, 52.4, 52.3, 51.6, 46.0, 38.3, 30.4, 29.6, 28.3.<br>HR-TOF-MS (method 21): $C_{21}H_{34}N_3O_5$ [M + H]$^+$ calc. 408.2498, found 408.2494.<br>From N-tert-butoxycarbonyl-3-tert-butyl-D-alanine (2.0 mmol) and 2-pyridyl-L-alanine methyl ester dihydrochloride (2.0 mmol).<br>Yield: 41% of theory |

TABLE 1-continued

Dipeptide esters

| Ex. No. | Structure Name | Analytical data Preparation method |
|---|---|---|
| 49A | 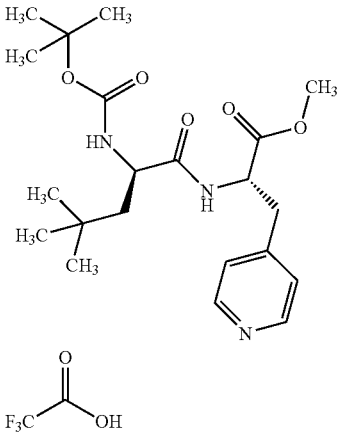<br>N-tert-Butoxycarbonyl-3-tert-butyl-D-alanyl-3-(4-pyridyl)-L-alanine methyl ester trifluoroacetate | $[\alpha]^{20}_{Na}$ = −18° (c = 0.28 in MeOH).<br>HPLC/UV-Vis (method 28): $R_t$ = 4.0 min.<br>HPLC/UV-Vis (method 36): $R_t$ = 3.80 min.<br>LC-MS (method 26): $R_t$ = 1.61 min;<br>MS (ESIpos.): m/z (%) = 352 (100), 408 (20) [M + H]$^+$;<br>MS (ESIneg.): m/z (%) = 332 (100), 406 (20) [M − H]$^−$.<br>IR $\nu_{max}$ (NaCl, cm$^{-1}$) 3414, 2959, 1680, 1509, 1203.<br>$^1$H NMR (500 MHz, d$_6$-DMSO): δ = 0.77 (s, 9H, tBu), 1.19-1.36 (m, 1H, β-CH), 1.36 (s, 9H, OtBu), 3.18 (m, 1H, β-CH), 3.36 (m, 2H, β-CH), 3.66 (s, 3H, OMe), 3.88 (m, 1H, α-CH), 4.70 (m, 1H, α-CH), 6.85 (d, J=8.5, 1H), 7.83 (d, J=6.0 Hz, 2H), 8.36 (d, J=8.0 Hz, 1H), 8.76 (m, 2H).<br>$^{13}$C NMR (500 MHz, d$_6$-DMSO): δ 173.1, 171.1, 158.4, 158.1, 154.9, 142.7, 127.4, 78.0, 52.2, 51.6, 44.8, 36.1, 30.7, 30.1, 29.4, 29.0, 28.2.<br>HR-TOF-MS (method 21): C$_{21}$H$_{34}$N$_3$O$_5$ [M + H]$^+$ calc. 408.2498, found 408.2525.<br>From N-tert-butoxycarbonyl-3-tert-butyl-D-alanine (1.26 mmol) and 4-pyridyl-L-alanine methyl ester dihydrochloride (1.26 mmol).<br>Yield: 75% of theory |
| 50A | 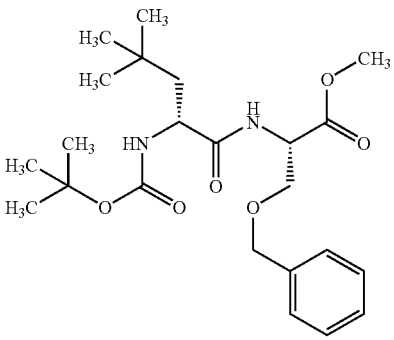<br>N-tert-Butoxycarbonyl)-3-tert-butyl-D-alanyl-O-benzyl-L-serine methyl ester | HPLC/UV-Vis (method 36): $R_t$ = 5.01 min.<br>LC-MS (method 26): $R_t$ = 2.73 min, MS (ESIpos.): m/z (%) = 437.3 (50) [M + H]$^+$.<br>$^1$H NMR (300 MHz, d$_6$-DMSO): δ = 0.89 (s, 9H), 1.38 (s, 9H), 1.42-1.60 (m, 2 H), 3.60 (dd, 1H), 3.61 (s, 3H), 3.75 (dd, 1H), 4.07 (m, 1H), 4.46-4.51 (m, 3H), 6.96 (d, 1H), 7.25-7.40 (m, 5H), 7.95 (d, 1H).<br>General procedure 14 from O-benzyl-L-serine methyl ester and N-(tert-butoxycarbonyl)-3-tert-butyl-D-alanine. Batch size: 0.96 mmol.<br>Yield: 64% of theory |
| 51A | 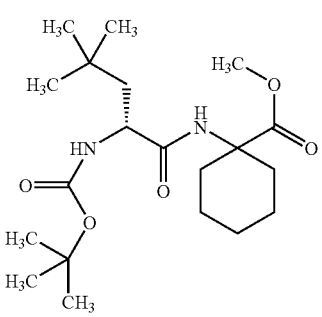<br>Methyl-1-{[N-tert-butoxycarbonyl)-3-tert-butyl-D-alanyl]amino}cyclohexanecarboxylate | HPLC/UV-Vis (method 36): $R_t$ = 4.99 min.<br>$^1$H NMR (300 MHz, d$_6$-DMSO): δ = 0.89 (s, 9H), 1.39 (s, 9H), 1.40-2.00 (m, 12H), 3.52 (s, 3H), 4.00 (m, 1H), 6.88 (d, 1H), 7.57 (s, 1H).<br>MS (DCI): m/z (%) = 402.2 [M + NH$_4$]$^+$.<br>General procedure 15 from methyl 1-aminocyclohexanecarboxylate and N-(tert-butoxycarbonyl)-3-tert-butyl-D-alanine.<br>Batch size: 1.29 mmol.<br>Yield: 61% of theory |

TABLE 1-continued

Dipeptide esters

| Ex. No. | Structure Name | Analytical data Preparation method |
|---|---|---|
| 52A | 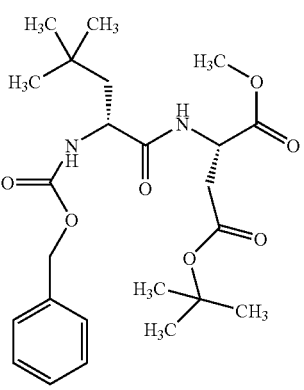<br>Methyl (2S)-2-[(2-{[(benzyloxy)-carbonyl]amino}-3-tert-butyl-D-alanyl)amino]-4-tert-butoxy-4-oxobutanoate | HPLC/UV-Vis (method 36): $R_t$ = 4.94 min.<br>LC-MS (method 26): $R_t$ = 2.69 min,<br>MS (ESIpos.): m/z (%) = 465.3 (70) [M + H]$^+$.<br>$^1$H NMR (400 MHz, d$_6$-DMSO): δ 0.89 (s, 9H), 1.38 (s, 9H), 1.50 (m, 2H), 2.58 (dd, 2H), 2.68 (dd, 2H), 3.61 (s, 3H), 4.10 (m, 1H), 4.58 (m, 1H), 5.00 (d, 1H), 5.06 (d, 1H), 7.25-7.38 (m, 5H), 7.42 (d, 1H), 8.27 (d, 1H).<br>General procedure 14 from O$^4$-tert-butyl O$^1$-methyl L-aspartate and N-[(benzyloxy)carbonyl]-3-tert-butyl-D-alanine. Batch size: 1.3 mmol.<br>Yield: 69% of theory |
| 53A | 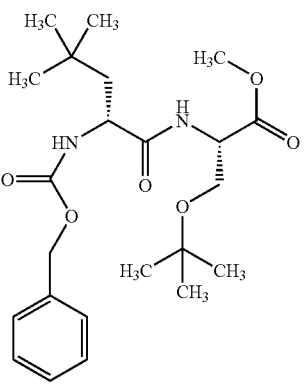<br>N-[(Benzyloxy)carbonyl]-3-tert-butyl-D-alanyl-O-(tert-butyl)-L-serine methyl ester | HPLC/UV-Vis (method 36): $R_t$ = 4.84 min.<br>LC-MS (method 26): $R_t$ = 2.70 min,<br>MS (ESIpos.): m/z (%) = 437.3 (70) [M + H]$^+$.<br>General procedure 15, no HPLC, crude product reacted further. From methyl O-(tert-butyl)-L-serinate and N-[(benzyloxy)carbonyl]-3-tert-butyl-D-alanine. Batch size: 0.43 mmol.<br>Yield: 24% of theory |
| 54A | 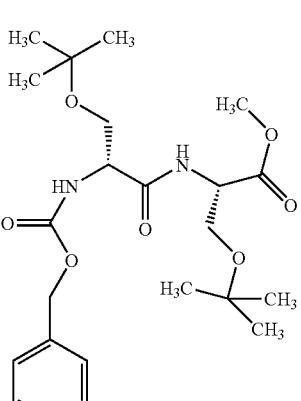<br>N-[(Benzyloxy)carbonyl]-O-(tert-butyl)-D-seryl-O-(tert-butyl)-L-serine methyl ester | HPLC/UV-Vis (method 36): $R_t$ = 4.89 min.<br>General procedure 14 from methyl O-(tert-butyl)-L-serinate and N-[(benzyloxy)carbonyl]-O-(tert-butyl)-D-serine. Batch size: 2.85 mmol.<br>Yield: 32% of theory |

TABLE 1-continued

Dipeptide esters

| Ex. No. | Structure Name | Analytical data Preparation method |
|---|---|---|
| 55A | Methyl 1-{[N-[(benzyloxy)carbonyl]-O-(tert-butyl)-D-seryl]amino}cyclohexanecarboxylate | HPLC (method 36): $R_t$ = 4.92 min.<br>LC-MS (method 26): $R_t$ = 2.87 min,<br>MS (ESIpos.): m/z (%) = 435.4 (100) [M + H]$^+$.<br>$^1$H NMR(300 MHz, d$_6$-DMSO): δ = 1.10 (s, 9H), 1.39-1.68 (m, 8H), 1.89 (d, 1H), 2.00 (d, 1H), 3.39-3.49 (m, 2H), 3.55 (s, 3H), 4.19 (m, 1H), 5.01 (d, 1H), 5.05 (d, 1H), 7.08 (d, 1H), 7.30-7.38 (m, 5H), 7.71 (s, 1H).<br>General procedure 14 from methyl 1-aminocyclohexanecarboxylate and N-[(benzyloxy)carbonyl]-O-(tert-butyl)-D-serine. Batch size: 2.03 mmol. Yield: 86% of theory |
| 56A | Benzyl N-({1-[(tert-butoxycarbonyl)-amino]cyclohexyl]carbonyl)-4-methyl-L-leucinate | HPLC/UV-Vis (method 36) $R_t$ = 5.39 min.<br>LC-MS (method 26): $R_t$ = 3.05 min,<br>MS (ESIpos.): m/z (%) = 461.4 (80) [M + H]$^+$.<br>General procedure 16 from 1-[(tert-butoxycarbonyl)amino]cyclohexanecarboxylic acid and benzyl-L-leucinate. Instead of the RP-HPLC flash chromatography on a C$_{18}$ phase, an ethyl acetate solution is washed with sodium bicarbonate and then 5% citric acid, dried and concentrated.<br>Batch size: 0.82 mmol.<br>Yield: 90% of theory |
| 57A | Methyl N-(tert-butoxycarbonyl)-3-(trimethylsilyl)-D-alanyl-3-(trimethylsilyl)-L-alaninate | HPLC/UV-Vis (method 36): $R_t$ = 5.33 min.<br>LC-MS (method 26): $R_t$ = 2.82 min,<br>MS (ESIpos.): m/z (%) = 419 (100) [M + H]$^+$.<br>General procedure 14 from 25A and 3-trimethylsilyl)-L-alanine methyl ester. Batch size: 1.63 mmol.<br>Yield: 35% of theory |

TABLE 1-continued

Dipeptide esters

| Ex. No. | Structure Name | Analytical data Preparation method |
|---|---|---|
| 58A | 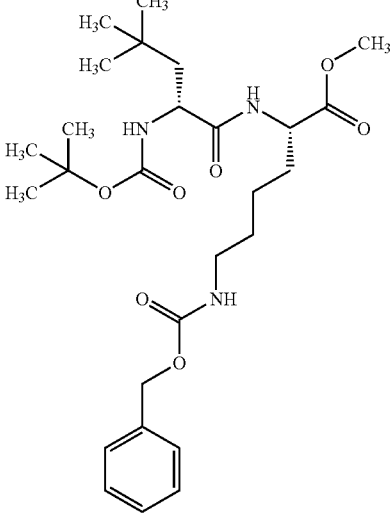  N-(tert-Butoxycarbonyl)-3-tert-butyl-D-alanyl-N⁶-[(benzyloxy)-carbonyl]-L-lysine methyl ester | HPLC/UV-Vis (method 36): $R_t$ = 4.86 min. <br> LC-MS (method 26): $R_t$ = 2.49 min, <br> MS (ESIpos.): m/z (%) = 522 (20) [M + H]⁺. <br> ¹H NMR (300 MHz, $d_6$-DMSO): δ = 0.89 (s, 9H), 1.20-1.35 (m, 2H), 1.40-2.77 (m, 4H), 2.95 (dd, 2H), 3.60 (s, 3H), 4.06 (m, 1H), 4.18 (m, 1H), 5.00 (s, 2H), 6.79 (d, 1H), 7.18 (m, 1H), 7.29-7.40 (m, 5H), 7.96 (d, 1H). <br> General procedure 16 from N⁶-[(benzyloxy)carbonyl]-L-lysine methyl ester and N-(tert-butoxycarbonyl)-3-tert-butyl-D-alanine. <br> Batch size: 0.99 mmol. <br> Yield: 61% of theory |

Dipeptide Acids

Example 59A

N-(tert-Butoxycarbonyl)-3-tert-butyl-D-alanyl-3-tert-butyl-L-alanine

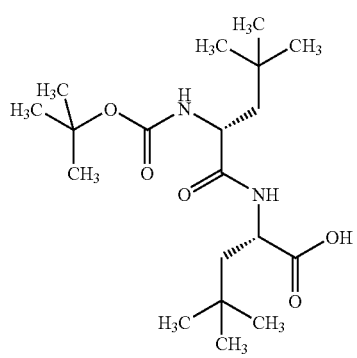

N-(tert-Butoxycarbonyl)-3-tert-butyl-D-alanyl-3-tert-butyl-L-alanine benzyl ester (Example 33A, 285 mg, 0.62 mmol) is reacted by general procedure 8. 225 mg (98% of theory) of product are obtained.

¹H NMR (400 MHz, $d_6$-DMSO): δ=0.83 (s, br, 18H, tBu), 1.31 (s, 9H, OtBu), 1.40 (d, J=6.1 Hz, 2H, β-CH₂), 1.48 (dd, J=14.1, 9.4 Hz, 1H, β-CH), 1.59 (dd, J=14.1, 2.7 Hz, 1H, β-CH'), 3.98 (m, 1H, α-CH), 4.12 (m, 1H, α-CH), 6.73 (d, J=9.1 Hz, 1H, NH), 7.72 (d, J=7.9 Hz, 1H, NH), 12.42 (s, br, 1H, CO₂H).

¹³C NMR (125 MHz, $d_6$-DMSO): δ=28.49 (3C), 29.66 (3C), 29.78 (3C), 30.52, 30.58, 44.63 (β-CH₂), 45.24 (β-CH₂), 49.67 (α-CH), 52.40 (α-CH), 78.29, 155.05, 172.97, 174.61.

$[α]^{20}_{Na}$=+25° (c=0.1 in chloroform).

HPLC/UV-Vis (method 13): $R_t$=7.95 min.

LC-MS (method 22): $R_f$=2.26 min;

MS (ESIpos.): m/z (%)=373 (100) [M+H]⁺.

HR-TOF-MS (method 21): $C_{19}H_{37}N_2O_5$ calc. 373.2702, found 373.2717 [M+H]⁺.

Example 60A

N-tert-Butoxycarbonyl-3-tert-butyl-D-alanyl-3-(3-pyridyl)-L-alanine

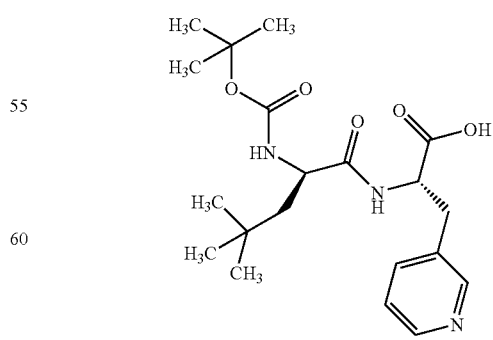

A solution of lithium hydroxide hydrate (2.5 equivalents, 31.9 mmol) in water (1.2 ml) is added to a solution of 34A (1.0 equivalent, 12.8 mmol) in tetrahydrofuran (104 ml) and water (6.2 ml) at −20° C. The reaction mixture warms (approx 1.5 h) to +15° C., with complete reaction being observed by means of HPLC/UV-Vis (method 36). For workup, potassium hydrogenphosphate (10 equivalents, 127 mmol) is added (pH 7). The reaction mixture is filtered and concentrated in vacuo. The crude product (5.5 g) is purified by gel chromatography (method 6, mobile phase methanol/acetone 4/1), resulting in 3.7 g (70% of theory) of product.

$[\alpha]^{20}_{Na}$=+39.3° (c=0.33 in methanol).
HPLC/UV-Vis (method 28): $R_t$=3.8 min.
HPLC/UV-Vis (method 36): $R_t$=3.64 min.
LC-MS (method 26): $R_t$=1.59 min;
MS (ESIpos.): m/z (%)=338 (100), 394 (40) [M+H]$^+$;
MS (ESIneg.): m/z (%)=318 (60), 392 (100) [M−H]$^-$.
HR-TOF-MS (method 21): $C_{20}H_{32}N_3O_5$ [M+H]$^+$ calc. 394.2342, found 394.2322.

TABLE 2

N-protected dipeptide acids

| Ex. No. | Structure Name | Analytical data Preparation method |
|---|---|---|
| 61A | 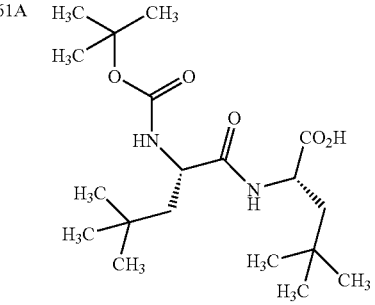<br>N-tert-Butoxycarbonyl-3-tert-butyl-L-alanyl-3-tert-butyl-L-alanine | HPLC/UV-Vis (method 13): $R_t$ = 7.8 min.<br>$^1$H NMR (400 MHz, $d_6$-DMSO, TMS): δ = 0.88 (s, br, 18H, tBu), 1.36 (s, 9H, OtBu), 1.41 (dd, J=13.9, 9.2 Hz, 1H, β-CH), 1.49 (dd, J=13.9, 3.2 Hz, 1H, β-CH'), 1.54 (dd, J=13.9, 9.1 Hz, 1H, β-CH''), 1.65 (dd, J=14.1, 2.5 Hz, 1H, β-CH'''), 4.02 (m, 1H, α-CH), 4.25 (m, 1H, α-CH, 6.87 (d, J=8.9 Hz, 1H, NH), 7.85 (d, J= 8.2 Hz, 1H, NH), 12.48 (s, br, 1H, $CO_2H$).<br>HR-TOF-MS (method 21): $C_{19}H_{37}N_2O_5$ [M + H]$^+$ calc. 373.2702, found 373.2680.<br>General procedure 8 from Example 35A (0.6 mmol).<br>Yield: 98% of theory |
| 62A | 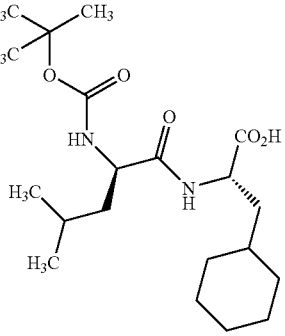<br>N-tert-Butoxycarbonyl-D-leucyl-3-cylcohexyl-L-alanine | HPLC/UV-Vis (method 13): $R_t$ = 8.2 min.<br>HR-TOF-MS (method 21): $C_{20}H_{37}N_2O_5$ [M + H]$^+$ calc. 385.2702, found 385.2693.<br>General procedure 8 from Example 36A (0.65 mmol).<br>Yield: 99% of theory |
| 63A | 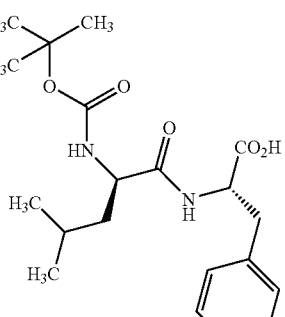<br>N-tert-Butoxycarbonyl-D-leucyl-L-phenylalanine | $[\alpha]^{20}_{Na}$ = +43° (c = 0.1 in methylene chloride).<br>HPLC/UV-Vis (method 13): $R_t$ = 7.52 min.<br>LC-MS (method 22): $R_t$ = 2.12 min;<br>MS (ESIpos.): m/z (%) = 279 (100) [M − Boc + H]$^+$, 379 (60) [M + H]$^+$.<br>HR-TOF-MS (method 21): $C_{20}H_{31}N_2O_5$ [M + H]$^+$ calc. 379.2233, found 379.2227.<br>General procedure 8 from Example 37A (1.49 mmol).<br>Yield: 94% of theory |

TABLE 2-continued

N-protected dipeptide acids

| Ex. No. | Structure Name | Analytical data Preparation method |
|---|---|---|
| 64A | 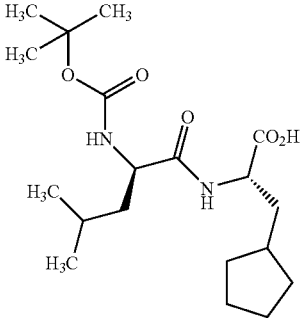<br>N-tert-Butoxycarbonyl-D-leucyl-3-cyclopentyl-L-alanine | $[\alpha]^{20}_{Na}$ = +3° (c = 0.1 in methylene chloride).<br>HPLC/UV-Vis (method 28): $R_t$ = 4.7 min.<br>HR-TOF-MS (method 21): $C_{19}H_{35}N_2O_5$ [M + H]$^+$ calc. 371.2546, found 371.2537.<br>General procedure 8 from Example 38A (0.24 mmol).<br>Yield: 86% of theory |
| 65A | 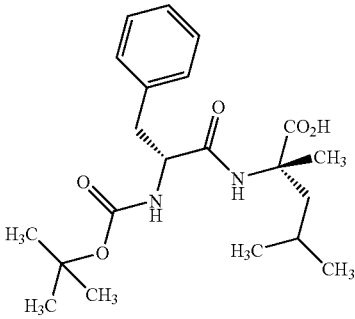<br>N-tert-Butoxycarbonyl-D-phenylalanyl-2-methyl-L-leucine | HPLC/UV-Vis (method 18): $R_t$ = 4.6 min.<br>HR-TOF-MS (method 21): $C_{21}H_{33}N_2O_5$ [M + H]$^+$ calc. 393.2389, found 393.2370.<br>General procedure 8 from Example 39A (0.11 mmol).<br>Yield: 95% of theory |
| 66A | 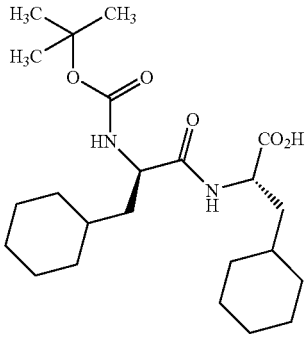<br>N-tert-Butoxycarbonyl-3-cyclohexyl-D-alanyl-3-cyclohexyl-L-alanine | HPLC/UV-Vis (method 18): $R_t$ = 5.1 min.<br>HR-TOF-MS (method 21): $C_{23}H_{41}N_2O_5$ [M + H]$^+$ calc. 425.3015, found 425.3018.<br>General procedure 8 from Example 40A (0.96 mmol).<br>Yield: 88% of theory |
| 67A | 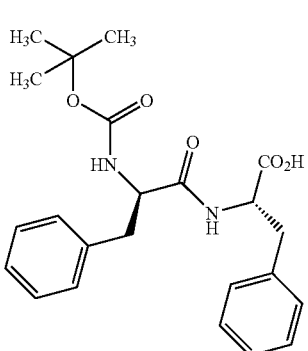<br>N-tert-Butoxycarbonyl-D-phenylalanyl-L-phenylalanine | $[\alpha]^{20}_{Na}$ = +33° (c = 0.6 in methylene chloride).<br>HPLC/UV-Vis (method 13): $R_t$ = 6.64 min.<br>HPLC/UV-Vis (method 28): $R_t$ = 4.4 min.<br>HR-TOF-MS (method 21): $C_{23}H_{29}N_2O_5$ [M + H]$^+$ calc. 413.2076, found 413.2082.<br>General procedure 8 from Example 41A (1.12 mmol).<br>Yield: 98% of theory |

TABLE 2-continued

N-protected dipeptide acids

| Ex. No. | Structure Name | Analytical data Preparation method |
|---|---|---|
| 68A | 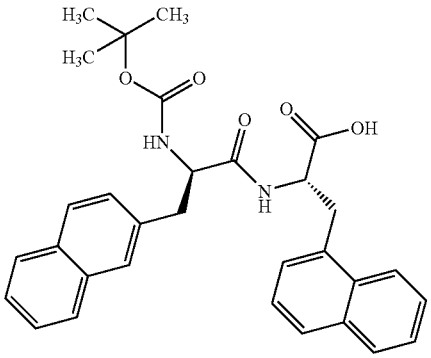<br>N-tert-Butoxycarbonyl-3-(2-naphthyl)-D-alanyl-3-(1-naphthyl)-L-alanine | HPLC/UV-Vis (method 13): $R_t$ = 8.66 min.<br>HPLC/UV-Vis (method 28): $R_t$ = 5.0 min.<br>LC-MS (method 29): $R_t$ = 6.6 min;<br>MS (ESIpos.): m/z (%) = 413 (100) [M − Boc + H]$^+$, 513 (80) [M + H]$^+$.<br>HR-TOF-MS (method 21): $C_{31}H_{33}N_2O_5$ [M + H]$^+$ calc. 513.2389, found 513.2388.<br>General procedure 7 from Example 42A (0.49 mmol).<br>Yield: 67% of theory |
| 69A | 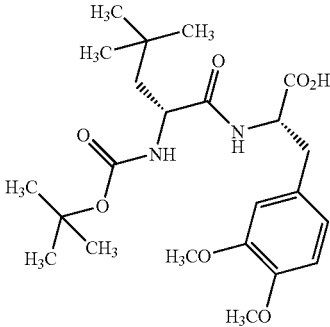<br>N-tert-Butoxycarbonyl-3-tert-butyl-D-alanyl-3-(3,4-dimethoxyphenyl)-L-alanine. | $[\alpha]^{20}_{Na}$ = +31.6° (c = 0.6 in methylene chloride).<br>HPLC/UV-Vis (method 18): $R_t$ = 4.3 min.<br>HPLC/UV-Vis (method 13): $R_t$ = 7.7 min.<br>HR-TOF-MS (method 21): $C_{23}H_{37}N_2O_7$ [M + H]$^+$ calc. 453.2601, found 453.2576.<br>General procedure 8 from Example 43A (0.46 mmol).<br>Yield: quant. |
| 70A | 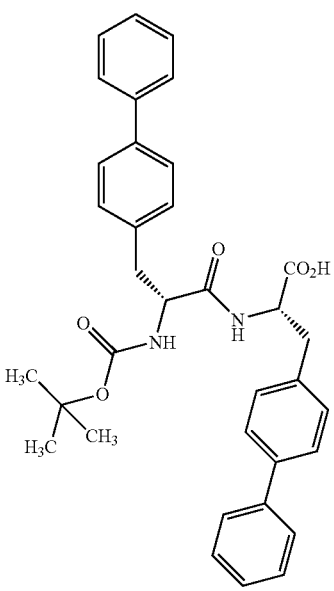<br>N-tert-Butoxycarbonyl-4-phenyl-D-phenylalanyl-4-phenyl-L-phenylalanine | $[\alpha]^{20}_{Na}$ = +31° (c = 0.1 in methanol).<br>HPLC/UV-Vis (method 13): $R_t$ = 9.15 min.<br>HPLC/UV-Vis (method 28): $R_t$ = 5.30 min, $\lambda_{max}$ (qualitative) = 202 nm (s), 254 (m).<br>LC-MS (method 22): $R_t$ = 2.80 min;<br>MS (ESIpos.): m/z (%) = 465 (100) [M − Boc + H]$^+$, 509 (50), 565 (90) [M + H]$^+$, 1129 (30).<br>HR-TOF-MS (method 21): $C_{35}H_{31}N_2O_5$ [M + H]$^+$ calc. 565.2702, found 565.2686.<br>General procedure 8 from Example 44A (0.53 mmol).<br>Yield: 84% of theory |

TABLE 2-continued

N-protected dipeptide acids

| Ex. No. | Structure Name | Analytical data Preparation method |
|---|---|---|
| 71A | N-tert-Butoxycarbonyl-3-tert-butyl-D-alanyl-L-1-amino-4-methoxy-cyclohexanecarboxylic acid | $[\alpha]^{20}_{Na}$ = +47.9° (c = 0.5 in methylene chloride). HPLC/UV-Vis (method 13): $R_t$ = 7.07 min. HPLC/UV-Vis (method 18): $R_t$ = 4.30 min. HR-TOF-MS (method 21): $C_{20}H_{37}N_2O_6$ [M + H]$^+$ calc. 401.2652, found 401.2667. General procedure 7 (here 2 equivalents of lithium hydroxide hydrate) from Example 45A (0.66 mmol). Yield: 48% of theory |
| 72A | N-tert-Butoxycarbonyl-3-tert-butyl-D-alanyl-L-1-amino-4-(trifluoro-methyl)cyclohexane carboxylic acid | $[\alpha]^{20}_{Na}$ = +37.0° (c = 1.05 in CH$_2$Cl$_2$). HPLC/UV-Vis (method 13): $R_t$ = 8.07 min. HPLC/UV-Vis (method 18): $R_t$ = 4.79 min. LC-MS (method 22): $R_t$ = 2.32 min; MS (ESIpos.): m/z (%) = 339 (60) [M − Boc + H]$^+$, 383 (80), 439 (100) [M + H]$^+$. HR-TOF-MS (method 21): $C_{20}H_{34}N_2O_5F_3$ [M + H]$^+$calc. 439.2420, found 439.2398. General procedure 7 (here 2 equivalents of lithium hydroxide hydrate) from Example 46A (1.10 mmol). Yield: 80% of theory |
| 73A | N-tert-Butoxycarbonyl-D-leucyl-4-nitro-L-phenylalanine | The crude product is reacted further directly to Example 178A. General procedure 7 (here 2 equivalents of lithium hydroxide hydrate) from Example 47A (0.50 mmol). Yield: 85% of theory |

TABLE 2-continued

N-protected dipeptide acids

| Ex. No. | Structure Name | Analytical data Preparation method |
|---|---|---|
| 74A | 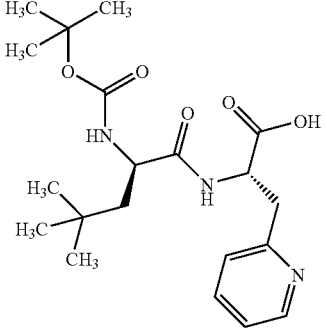<br>N-tert-Butoxycarbonyl-3-tert-butyl-D-alanyl-3-(2-pyridyl)-L-alanine | $[\alpha]^{20}_{Na}$ = +53.8° (c = 1.05 in CHCl$_3$).<br>HPLC/UV-Vis (method 28): R$_t$ = 3.9 min.<br>HPLC/UV-Vis (method 36): R$_t$ = 3.60 min.<br>LC-MS (method 26): R$_t$ = 1.70 min;<br>MS (ESIpos.): m/z (%) 338 (100), 394 (70) [M + H]$^+$;<br>MS (ESIneg.): m/z (%) = 318 (60), 392 (100) [M − H]$^-$.<br>$\nu_{max}$ (NaCl, cm$^{-1}$): 3407, 2957, 1709, 1650, 1522, 1367, 1170.<br>HR-TOF-MS (method 21): C$_{20}$H$_{32}$N$_3$O$_5$ [M + H]$^+$ calc. 394.2342, found 394.2342.<br>From Example 48A (12.8 mmol).<br>Yield: 70% of theory |
| 75A | 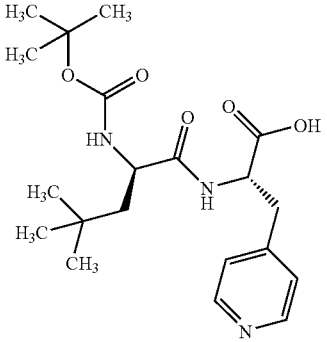<br>N-tert-Butoxycarbonyl-3-tert-butyl-D-alanyl-3-(4-pyridyl)-L-alanine | HPLC/UV-Vis (method 28): R$_t$ = 3.9 min.<br>HPLC/UV-Vis (method 36): R$_t$ = 3.60 min.<br>LC-MS (method 26): R$_t$ = 1.54 min;<br>MS (ESIpos.): m/z (%) = 338 (100), 394 (30) [M + H]$^+$;<br>MS (ESIneg.): m/z (%) = 318 (60), 392 (100) [M − H]$^-$.<br>HR-TOF-MS (method 21): C$_{20}$H$_{32}$N$_3$O$_5$ [M + H]$^+$ calc. 394.2342, found 394.2320.<br>From Example 49A (0.25 mmol).<br>Yield: 87% of theory |
| 76A | 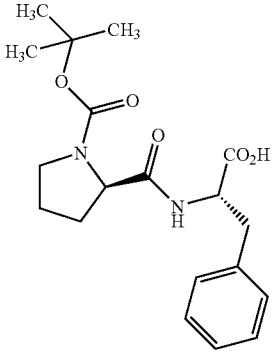<br>N-tert-Butoxycarbonyl-D-prolyl-L-phenylalanine | HPLC/MS (method 26): R$_t$ = 2 min,<br>MS (ESIneg.): m/z (%) = 361 (57) [M − H]$^-$<br>General procedure 12 (1 mmol) from N-(9-fluorenylmethoxycarbonyl)-L-phenylalanine and N-(tert-butoxycarbonyl)-D-proline.<br>Yield: 40% of theory |

TABLE 2-continued

N-protected dipeptide acids

| Ex. No. | Structure Name | Analytical data Preparation method |
|---|---|---|
| 77A | 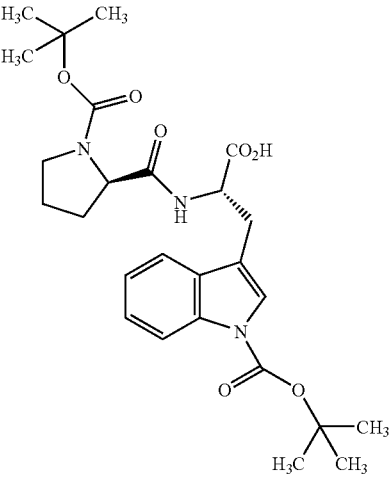<br>N-tert-Butoxycarbonyl-D-prolyl-N-tert-butoxycarbonyl-L-tryptophan | HPLC/MS (method 26): $R_t$ = 2.55 min,<br>MS (ESIneg.): m/z (%) = 500 (66) [M − H]⁻<br>General procedure 12 (1 mmol) from<br>N□-(9-fluorenylmethoxycarbonyl)-N-tert-butoxycarbonyl-L-tryptophan and N-(tert-butoxycarbonyl)-D-proline.<br>Yield: 39% of theory |
| 78A | 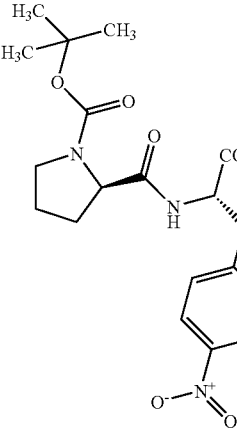<br>N-tert-Butoxycarbonyl-D-prolyl-4-nitro-L-phenylalanine | HPLC/MS (method 26): $R_t$ = 2.02 min,<br>MS (ESIneg.): m/z (%) = 406 (36) [M − H]⁻<br>General procedure 12 (1 mmol) from<br>N-(9-fluorenylmethoxycarbonyl)-4-nitro-L-phenylalanine and N-(tert-butoxycarbonyl)-D-proline.<br>Yield: 44% of theory |
| 79A | 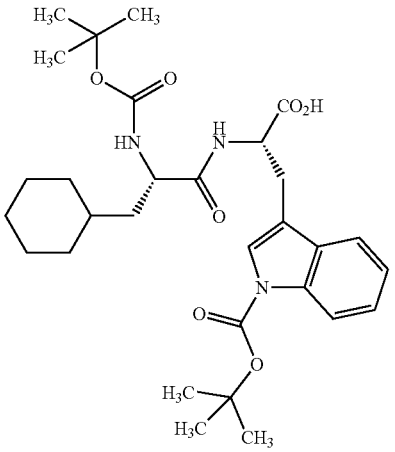<br>N-tert-Butoxycarbonyl-3-cyclohexyl-L-alanyl-N$^{indole}$-tert-butoxycarbonyl-L-tryptophan | HPLC/MS (method 26): $R_t$ = 3.03 min,<br>MS (ESIneg.): m/z (%) = 557 (36) [M − H]⁻<br>General procedure 12 (1 mmol) from<br>N□-(9-fluorenylmethoxycarbonyl)-N-tert-butoxycarbonyl-L-tryptophan and N-(tert-butoxycarbonyl)-3-cyclohexyl-L-alanine.<br>Yield: 29% of theory |

TABLE 2-continued

N-protected dipeptide acids

| Ex. No. | Structure Name | Analytical data Preparation method |
|---|---|---|
| 80A | N-tert-Butoxycarbonyl-3-cyclohexyl-L-alanyl-4-nitro-L-phenylalanine | HPLC/MS (method 26): $R_t$ = 2.54 min, MS (ESIneg.): m/z (%) = 462 (20) [M − H]$^-$ General procedure 12 (1 mmol) from N-(9-fluorenylmethoxycarbonyl)-4-nitro-L-phenylalanine and N-(tert-butoxycarbonyl)-3-cyclohexyl-L-alanine. Yield: 31% of theory |
| 81A | N-tert-Butoxycarbonyl-3-cyclohexyl-L-alanyl-3-benzyl-L-alanine | HPLC/MS (method 26): $R_t$ = 2.65 min, MS (ESIneg.): m/z (%) = 431 (22) [M − H]$^-$ General procedure 12 (1 mmol) from N-(9-fluorenylmethoxycarbonyl)-3-benzyl-L-alanine and N-(tert-butoxycarbonyl)-3-cyclohexyl-L-alanine. Yield: 44% of theory |
| 82A | N-tert-Butoxycarbonyl-D-phenylalanyl-O$^3$-tert-butyl-L-serine | HPLC/MS (method 26): $R_t$ = 2.66 min, MS (ESIneg.): m/z (%) = 521 (54) [M − H]$^-$ General procedure 12 (1 mmol) from N-(9-fluorenylmethoxycarbonyl)-O$^3$-(tert-butyl)-L-serine and N-(tert-butoxycarbonyl)-D-phenylalanine. Yield: 29% of theory |

TABLE 2-continued

N-protected dipeptide acids

| Ex. No. | Structure Name | Analytical data Preparation method |
|---|---|---|
| 83A | 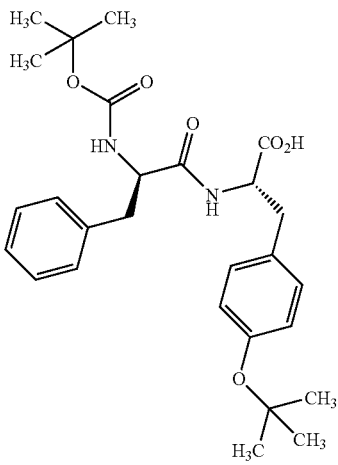 N-tert-Butoxycarbonyl-D-phenylalanyl-O-tert-butyl-L-tyrosine | HPLC/MS (method 26): $R_t$ = 2.8 min, MS (ESIneg.): m/z (%) = 489 (27) [M − H]⁻ General procedure 12 (1 mmol) from N-(9-fluorenylmethoxycarbonyl)-O-tert-butyl-L-tyrosine and N-(tert-butoxycarbonyl)-D-phenylalanine. Yield: 58% of theory |
| 84A | 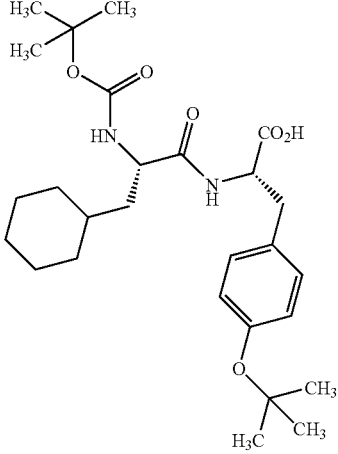 N-tert-Butoxycarbonyl-3-cyclohexyl-L-alanyl-O-tert-butyl-L-tyrosine | HPLC/MS (method 26): $R_t$ = 2.42 min, MS (ESIneg.): m/z (%) = 449 (35) [M − H]⁻ General procedure 12 (1 mmol) from N-(9-fluorenylmethoxycarbonyl)-O-tert-butyl-L-tyrosine and N-(tert-butoxycarbonyl)-3-cyclohexyl-L-alanine. Yield: 27% of theory |
| 85A | 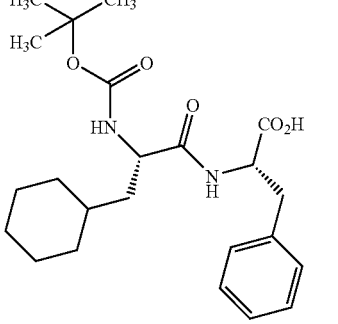 N-tert-Butoxycarbonyl-3-cyclohexylalanyl-L-phenylalanine | HPLC/MS (method 26): $R_t$ = 1.95 min, MS (ESIneg.): m/z (%) = 359 (21) [M − H]⁻ General procedure 12 (1 mmol) from N-(9-fluorenylmethoxycarbonyl)-L-phenylalanine and N-(tert-butoxycarbonyl)-3-cyclohexyl-L-alanine. Yield: 21% of theory |

TABLE 2-continued

N-protected dipeptide acids

| Ex. No. | Structure Name | Analytical data Preparation method |
|---|---|---|
| 86A | N-tert-Butoxycarbonyl-3-cyclohexyl-L-alanyl-L-isoleucine | HPLC/MS (method 26): $R_t$ = 2.89 min, MS (ESIneg.): m/z (%) = 588 (55) $[M - H]^-$. General procedure 12 (1 mmol) from N-(9-fluorenylmethoxycarbonyl)-L-isoleucine and N-(tert-butoxycarbonyl)-3-cyclohexyl-L-alanine. Yield: 41% of theory |
| 87A | N-tert-Butoxycarbonyl-D-phenylalanyl-4-nitro-L-phenylalanine | HPLC/MS (method 26): $R_t$ = 2.37 min, MS (ESIneg.): m/z (%) = 516 (46) $[M - H]^-$. General procedure 12 (1 mmol) from N-(9-fluorenylmethoxycarbonyl)-4-nitro-L-phenylalanine and N-(tert-butoxycarbonyl)-D-phenylalanine. Yield: 45% of theory |
| 88A | N-tert-Butoxycarbonyl-3-tert-butyl-D-alanyl-O-benzyl-L-serine | HPLC/UV-Vis (method 36): $R_t$ = 4.68 min. LC-MS (method 26): $R_t$ = 2.49 min, MS (ESIpos.): m/z (%) = 423 (100) $[M + H]^+$. $^1$H NMR (200 MHz, $d_6$-DMSO): δ = 0.89 (s, 9H), 1.48 (s, 9H), 1.42-1.60 (m, 2H), 3.60 (dd, 1H), 3.75 (dd, 1H), 4.07 (m, 1H), 4.40-4.50 (m, 3H), 7.02 (d, 1H), 7.25-7.40 (m, 5H), 7.80 (d, 1H). General procedure 17 from Example 50A. Batch size: 0.99 mmol. Yield: 76% of theory |

TABLE 2-continued

N-protected dipeptide acids

| Ex. No. | Structure Name | Analytical data Preparation method |
|---|---|---|
| 89A | [Structure of 1-{[N-tert-Butoxycarbonyl)-3-tert-butyl-D-alanyl]amino}cyclohexanecarboxylic acid] | HPLC/UV-Vis (method 36): $R_t$ = 4.99 min. LC-MS (method 26): $R_t$ = 2.17 min, MS (ESIpos.): m/z (%) = 371 (100) [M + H]$^+$. General procedure 17, reaction time: 12 h at room temperature from Example 51A. Batch size: 0.99 mmol. Yield: 46% of theory |
| 90A | [Structure of (2S)-2-[(2-{[(Benzyloxy)carbonyl]-amino}-3-tert-butyl-D-alanyl)amino]-tert-butoxy-4-oxobutyric acid] | HPLC/UV-Vis (method 36): $R_t$ = 4.61 min. LC-MS (method 26): $R_t$ = 2.24 min, MS (ESIpos.): m/z (%) = 451 (100) [M + H]$^+$. $^1$H NMR (300 MHz, $d_6$-DMSO): δ = 0.89 (s, 9H), 1.48 (s, 9H), 1.45-1.60 (m, 2H), 2.56 (dd, 2H), 2.68 (dd, 2H), 4.10 (m, 1H), 4.50 (m, 1H), 4.97 (d, 1H), 5.06 (d, 1H), 7.25-7.38 (m, 5H), 7.42 (d, 1H), 8.00 (d, 1H). General procedure 17 from Example 52A. Batch size: 1.26 mmol. Yield: 78% of theory |
| 91A | [Structure of N-[(Benzyloxy)carbonyl]-3-tert-butyl-D-alanyl-O-(tert-butyl)-L-serine] | HPLC/UV-Vis (method 36): $R_t$ = 4.62 min. LC-MS (method 26): $R_t$ = 2.24 min, MS (ESIpos.): m/z (%) = 423 (100), [M + H]$^+$. $^1$H NMR (300 MHz, $d_6$-DMSO): δ = 0.89 (s, 9H), 1.09 (s, 9H), 1.48-1.60 (m, 2H), 3.48 (dd, 1H), 3.61 (dd, 1H), 4.12 (m, 1H), 4.35 (m, 1H), 5.01 (d, 1H), 5.06 (d, 1H), 7.30-7.40 (m, 5H), 7.53 (d, 1H), 7.65 (d, 1H), 12.65 (br s, 1H). General procedure 17 from Example 53A. Batch size: 0.38 mmol. Yield: 79% of theory |

TABLE 2-continued

N-protected dipeptide acids

| Ex. No. | Structure Name | Analytical data Preparation method |
|---|---|---|
| 92A | 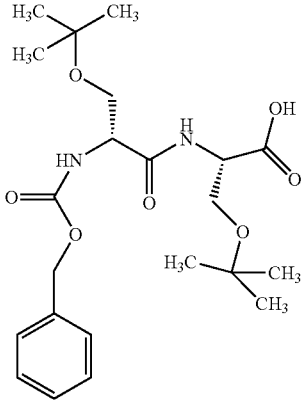<br>N-[(Benzyloxy)carbonyl]-O-(tert-butyl)-D-seryl-O-(tert-butyl)-L-serine | HPLC/UV-Vis (method 36): $R_t$ = 4.55 min.<br>LC-MS (method 26): $R_t$ = 2.57 min,<br>MS (ESIpos.): m/z (%) = 439.4 (100) [M + H]$^+$.<br>General procedure 17 from Example 54A.<br>Batch size: 0.91 mmol.<br>Yield: 54% of theory |
| 93A | 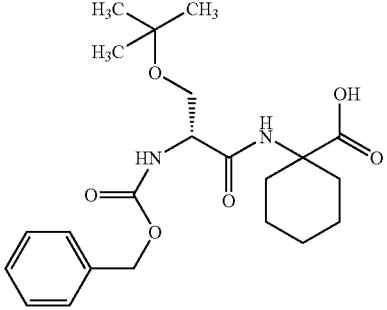<br>1-{[N-[(Benzyloxy)carbonyl]-O-(tert-butyl)-D-seryl]amino}cyclo-hexanecarboxylic acid | HPLC/UV-Vis (method 36): $R_t$ = 4.56 min.<br>LC-MS (method 26): $R_t$ = 2.72 min,<br>MS (ESIpos.): m/z (%) = 435.4 (100) [M + H]$^+$.<br>$^1$H NMR (400 MHz, $d_6$-DMSO): δ = 1.10 (s, 9H),<br>1.39-1.68 (m, 8H), 1.91 (d, 1H), 2.03 (d, 1H),<br>3.39-3.49 (m, 2H), 4.20 (m, 1H), 5.04 (s, 2H),<br>7.28-7.40 (m, 5H), 7.71 (s, 1H), 12.08 (br s, 1H).<br>General procedure 17 from Example 55A.<br>Batch size: 1.69 mmol.<br>Yield: 90% of theory |
| 94A | 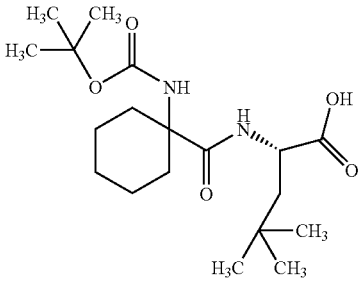<br>N-({1-[(tert-Butoxycarbonyl)-amino]cyclohexyl}carbonyl)-4-methyl-L-leucine | HPLC/UV-Vis (method 36): $R_t$ = 4.56 min.<br>LC-MS (method 26): $R_t$ = 2.36 min,<br>MS (ESIpos.): m/z (%) = 371.3 (100) [M + H]$^+$.<br>$^1$H NMR (300 MHz, $d_6$-DMSO): δ = 0.88 (s, 9H),<br>1.10-1.26 (m, 2H), 1.33 (s, 9H), 1.33-1.68 (m,<br>18H), 1.97 (m, 2H), 4.23 (m, 1H), 6.53 (br s, 1H),<br>7.29 (d, 1H), 12.38 (br s, 1H).<br>General procedure 18 from Example 56A.<br>Batch size: 1.05 mmol.<br>Yield: 90% of theory |

TABLE 2-continued

N-protected dipeptide acids

| Ex. No. | Structure Name | Analytical data Preparation method |
|---|---|---|
| 95A | 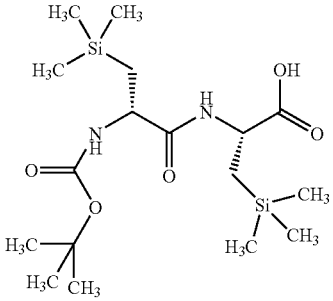<br>N-(tert-Butoxycarbonyl)-<br>3-trimethylsilyl)-D-alanyl-<br>3-(trimethylsilyl)-L-alanine | HPLC/UV-Vis (method 36): $R_t$ = 4.96 min.<br>LC-MS (method 26): $R_t$ = 2.67 min,<br>MS (ESIpos.): m/z (%) = 405.3 (100) [M + H]$^+$.<br>$^1$H NMR (400 MHz, d$_6$-DMSO): δ = 0.00 (s, 8H), 0.85-1.08 (m, 4H), 1.38 (s, 9H), 4.04 (m, 1H), 4.16 (m, 1H), 6.77 (d, 1H), 7.72 (d, 1H), 12.45 (br s, 1H).<br>General procedure 17 from Example 57A.<br>Batch size: 2.13 mmol.<br>Yield: 53% of theory |
| 96A | 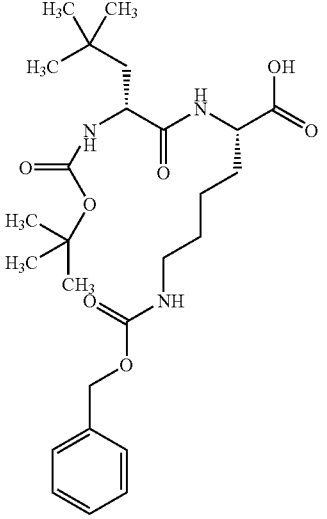<br>N-(tert-Butoxycarbonyl)-3-tert-<br>butyl-D-alanyl-<br>N$^6$-[(benzyloxy)carbonyl]-L-lysine | HPLC/UV-Vis (method 36): $R_t$ = 4.57 min.<br>LC-MS (method 26): $R_t$ = 2.27 min,<br>MS (ESIpos.): m/z (%) = 508 (100) [M + H]$^+$.<br>$^1$H NMR (400 MHz, d$_6$-acetone): δ = 0.95 (s, 9H), 1.40 (s, 9H), 1.40-1.98 (m, 6H), 3.16 (m, 2H), 4.19 (m, 1H), 4.42 (m, 1H), 5.08 (s, 2H), 6.16 (d, 1H), 6.42 (br s, 1H), 7.29-7.40 (m, 5H), 10.80 (br s, 1H).<br>General procedure 17 from Example 58A.<br>Batch size: 0.3 mmol.<br>Yield: 91% of theory |

TABLE 3

N-protected nonadepsipeptides

| Ex. No. | Structure Name | | Analytical data Preparation method |
|---|---|---|---|
| 97A | 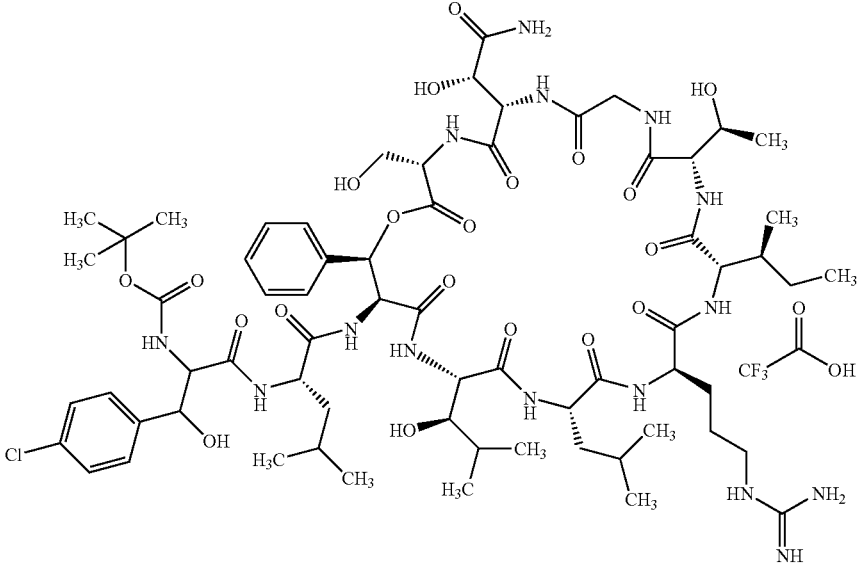 [N-tert-Butoxycarbonyl-3-(4-chlorophenyl)-threo-rac-seryl]-de(1-D-leucyl)lysobactin trifluoroacetate | | HPLC/UV-Vis (method 13): $R_t$ = 7.17 min. LC-MS (method 26): $R_t$ = 2.18 min; MS (ESIpos.): m/z (%) = 681 (100) $[M - Boc + 2H]^{2+}$, 1461 (20) $[M + H]^+$. General procedure 11 from Example 11A (0.04 mmol) and N-tert-butoxy-carbonyl-3-(4-chloro-phenyl)-threo-rac-serine (0.17 mmol). Purification by method 7. Yield 34% of theory (separable mixture of diastereomers) |
| 98A | 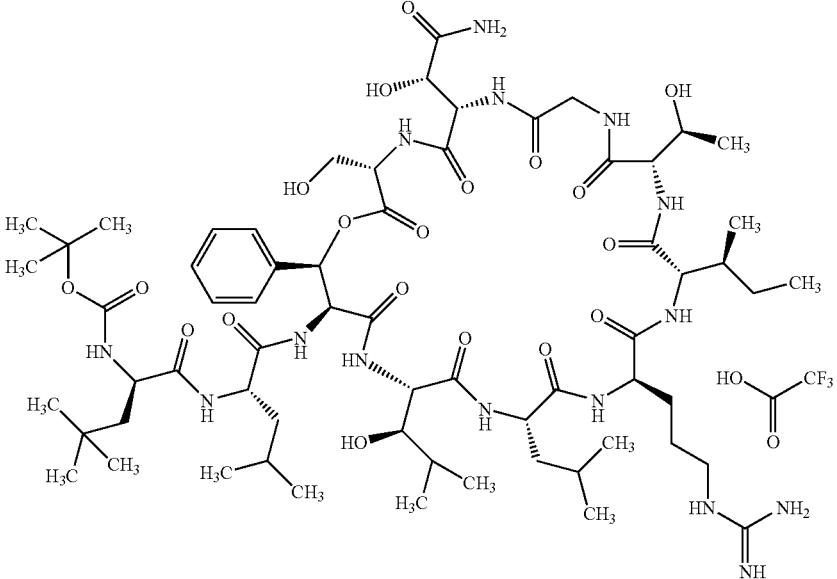 | | HPLC/UV-Vis (method 13): $R_t$ = 7.38 min. LC-MS (method 26): $R_t$ = 2.18 min; MS (ESIpos.): m/z (%) = 646 (90) $[M - Boc + 2H]^{2+}$, 1050 (20), 1391 (100) $[M + H]^+$. |

TABLE 3-continued

N-protected nonadepsipeptides

| Ex. No. | Structure Name | Analytical data Preparation method |
|---|---|---|
| | N-tert-Butoxycarbonyl-3-tert-butyl-D-alanyl-de(1-D-leucyl)lysobactin trifluoroacetate | General procedure 4 from Example 11A (0.01 mmol) and N-tert-butoxycarbonyl-3-tert-butyl-D-alanine (0.04 mmol). Purification by method 7. Yield 65% of theory |
| 99A | 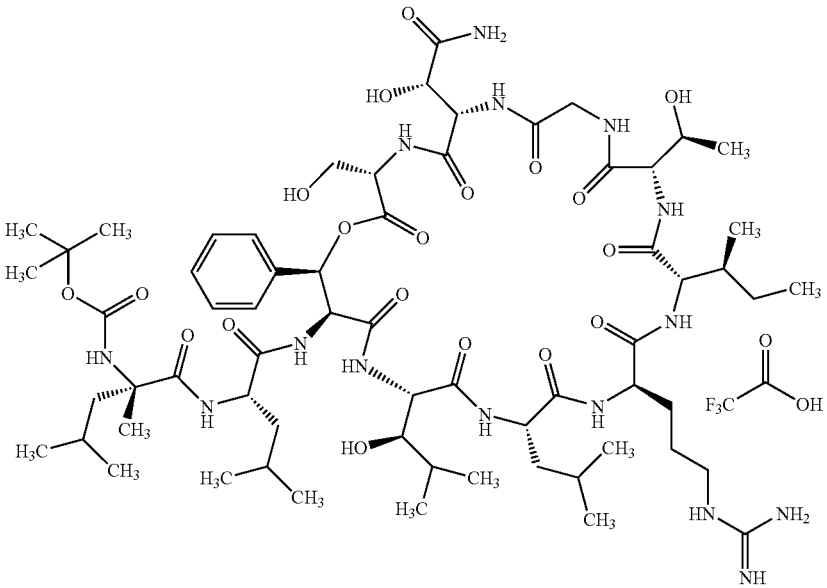 | HPLC/UV-Vis (method 13): $R_t$ = 7.19 min. LC-MS (method 26): $R_t$ = 2.09 min; MS (ESIpos.): m/z (%) = 646 (100) $[M - Boc + 2H]^{2+}$, 1391 (30) $[M + H]^+$. |
| | N-tert-Butoxycarbonyl-2-methyl-L-leucyl-de(1-D-leucyl)lysobactin trifluoroacetate | General procedure 11 from Example 11A (0.11 mmol) and N-(tert-butoxycarbonyl)-2-methyl-L-leucine (0.43 mmol). Purification by method 7. Yield 13% of theory |
| 100A | 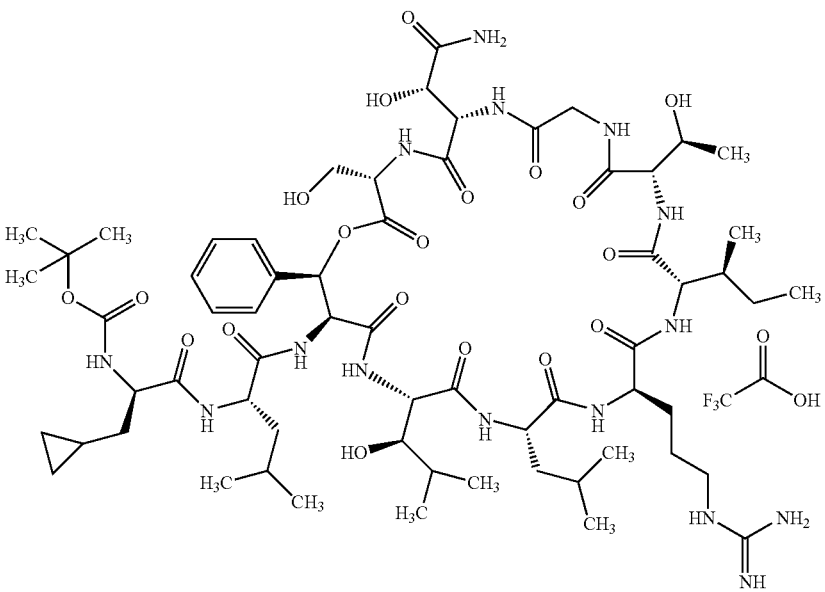 | HPLC/UV-Vis (method 13): $R_t$ = 7.28 min. LC-MS (method 26): $R_t$ = 2.15 min; MS (ESIpos.): m/z (%) = 638 (80) $[M - Boc + 2H]^{2+}$, 688 (100), 1376 (15) $[M + H]^+$. |

TABLE 3-continued

N-protected nonadepsipeptides

| Ex. No. | Structure Name | | Analytical data Prepration method |
|---|---|---|---|
| 101A | N-tert-Butoxycarbonyl-3-cyclopropyl-D-alanyl-de(1-D-leucyl)lysobactin trifluoroacetate 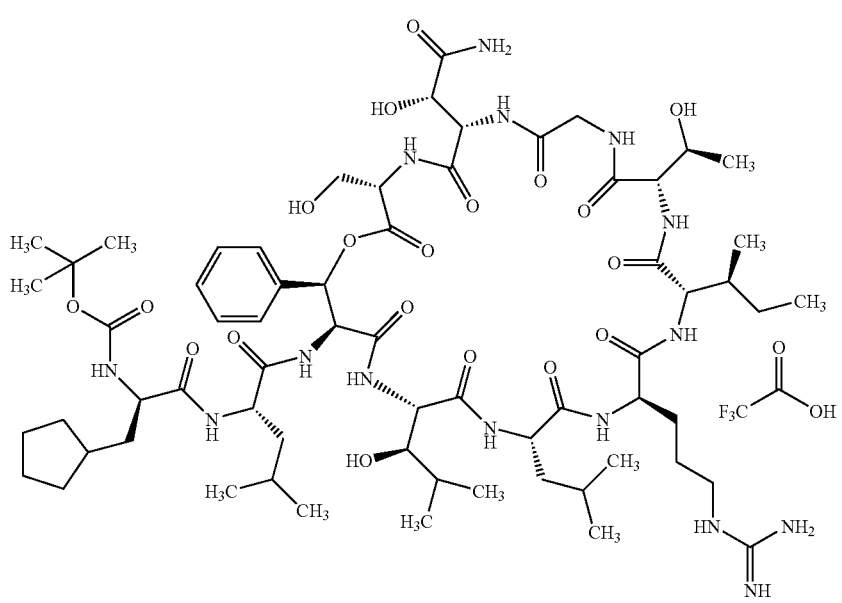 | | General procedure 4 from Example 11A (0.01 mmol) and N-cyclohexyl-cyclohexan-aminium-N-tert-butoxy-carbonyl-3-cyclo-propyl-D-alaninate (0.04 mmol). Purification by method 7. Yield 34% of theory<br><br>HPLC/UV-Vis (method 13): $R_t$ = 7.41 min. LC-MS (method 26): $R_t$ = 2.29 min; MS (ESIpos.): m/z (%) = 652 (70) [M − Boc + 2H]$^{2+}$, 702 (100), 1404 (30) [M + H]$^+$. |
| 102A | N-tert-Butoxycarbonyl-3-cyclopentyl-D-alanyl-de(1-D-leucyl)lysobactin trifluoroacetate 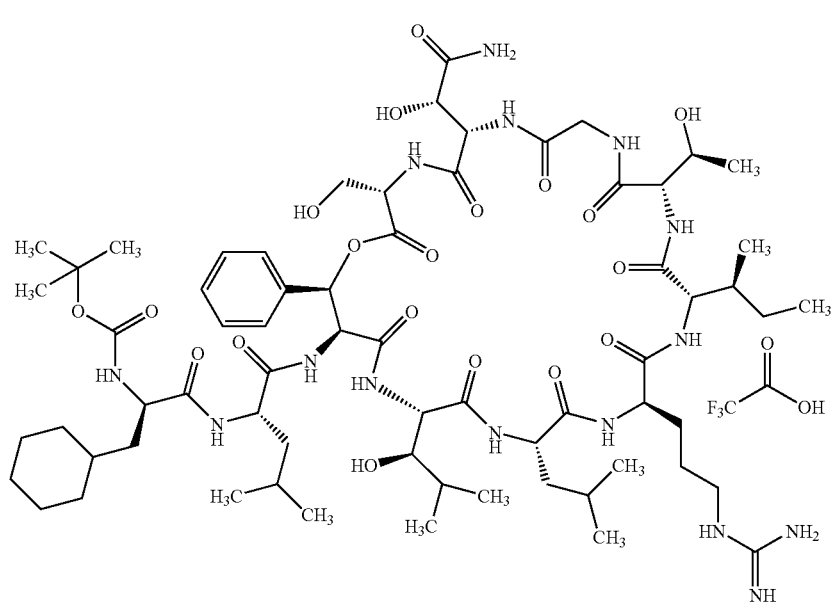 | | General procedure 4 from Example 11A (0.01 mmol) and N-tert-butoxy-carbonyl-3-cyclo-pentyl-D-alanine (0.04 mmol). Purification by method 7. Yield 57% of theory<br><br>HPLC/UV-Vis (method 13): $R_t$ = 7.85 min. LC-MS (method 26): $R_t$ = 2.35 min; MS (ESIpos.): m/z (%) = 709 (100) [M + 2H]$^{2+}$, 718 (20) [M + H]$^+$. |

TABLE 3-continued

N-protected nonadepsipeptides

| Ex. No. | Structure Name | | Analytical data Prepration method |
|---|---|---|---|
| 103A | N-tert-Botoxycarbonyl-3-cyclohexyl-D-alanyl-de(1-D-leucyl)lysobactin trifluoroacetate 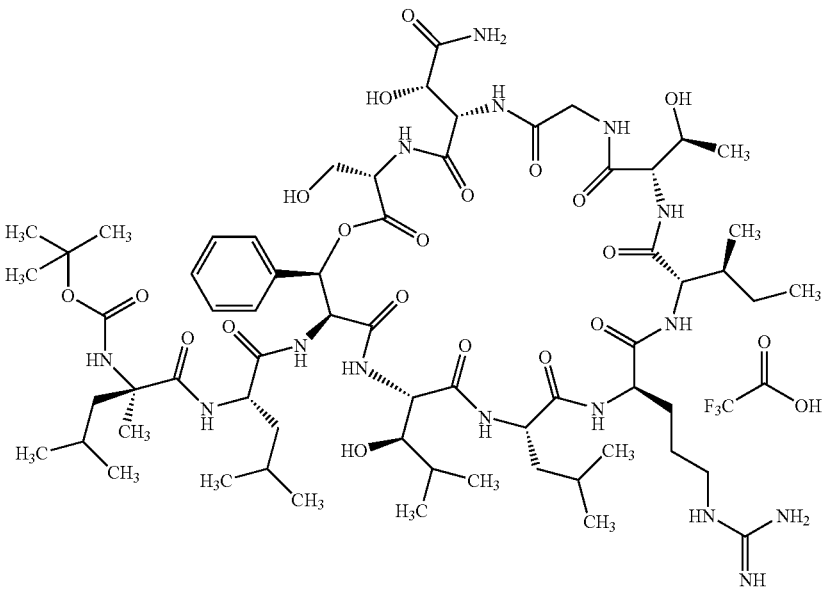 | | General procedure 4 from Example 11A (0.01 mmol) and N-tert-butoxy-carbonyl-3-cyclo-hexyl-D-alanine (0.04 mmol). Purification by method 7. Yield 50% of theory<br><br>HPLC/UV-Vis (method 13): $R_t$ = 7.23 min.<br>LC-MS (method 26): $R_t$ = 2.30 min;<br>MS (ESIpos.): m/z (%) = 646 (100) [M − Boc + 2H]$^{2+}$, 1391 (30) [M + H]$^+$. |
| 104A | N-tert-Butoxycarbonyl-2-methyl-D-leucyl-de(1-D-leucyl)lysobactin trifluoroacetate 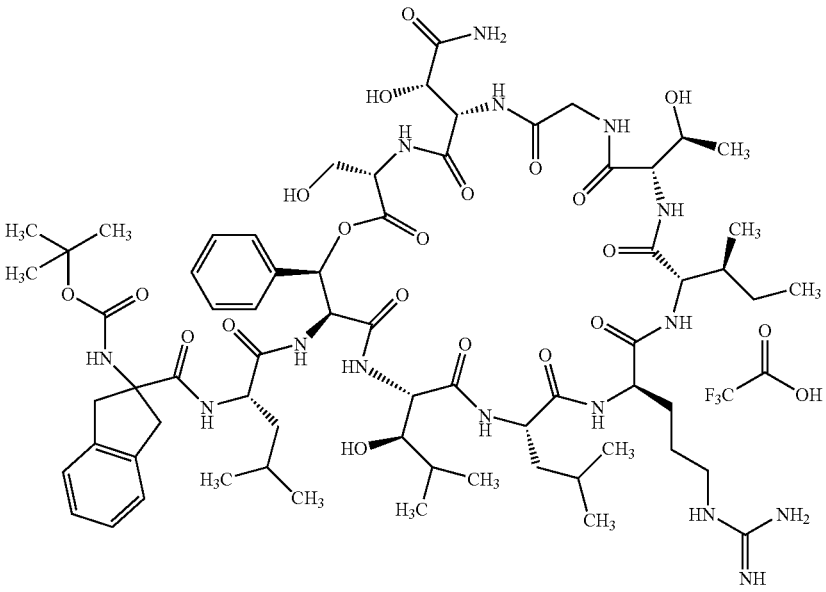 | | General procedure 4 from Example 11A (0.01 mmol) and N-tert-butoxy-carbonyl-2-meth-yl-D-leucine (0.04 mmol). Purification by method 7. Yield 67% of theory<br><br>HPLC/UV-Vis (method 13): $R_t$ = 7.25 min.<br>LC-MS (method 26): $R_t$ = 2.17 min;<br>MS (ESIpos.): m/z (%) = 662 (100) [M − Boc + 2H]$^{2+}$, 1423 (30) [M + H]$^+$.<br>HR-TOF-MS (method 21): $C_{67}H_{104}N_{15}O_{19}$ [M + H]$^+$ calc. 1422.7633, found 1422.7612. |

TABLE 3-continued

N-protected nonadepsipeptides

| Ex. No. | Structure Name | | Analytical data Prepration method |
|---|---|---|---|
| | (N-tert-Butoxycarbonyl-2-amino-2,3-dihydro-1H-indenyl-carbonyl)-de(1-D-leucyl)lysobactin-tri-fluoroacetate | | General procedure 11 from Example 11A (0.07 mmol) and N-tert-butoxycarbonyl-2-a-mino-2,3-dihydro-1H-indenyl-carboxylic acid (0.29 mmol). Purification by method 7. Yield 76% of theory |
| 105A | 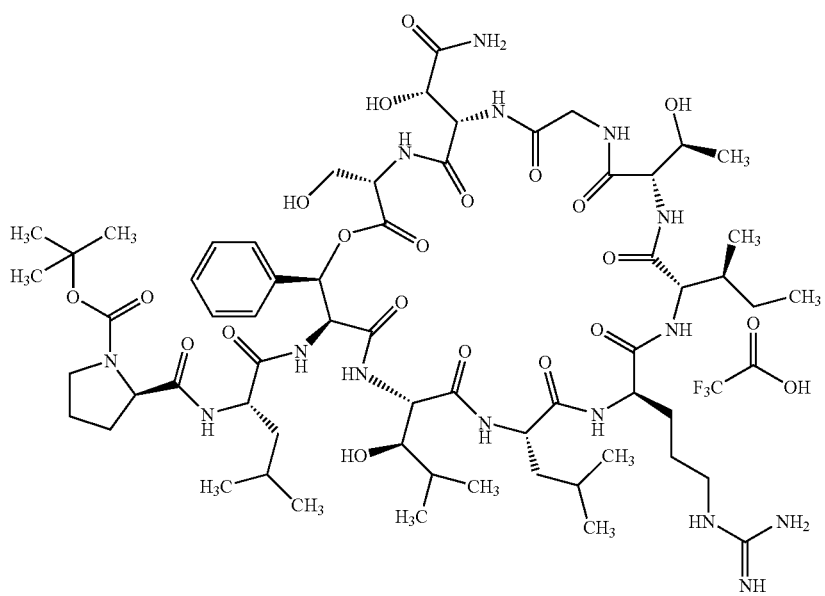 | | HPLC/UV-Vis (method 13): $R_t$ = 7.04 min. LC-MS (method 26): $R_t$ = 2.10 min; MS (ESIpos.): m/z (%) = 631 (90) $[M - Boc + 2H]^{2+}$, 681 (100), 1361 (30) $[M + H]^+$. |
| | N-tert-Butoxycarbonyl-D-prolyl-de(1-D-leu-cyl)lysobactin trifluoroacetate | | General procedure 4 from Example 11A (0.01 mmol) and N-tert-butoxy-carbonyl-D-pro-line (0.04 mmol). Purification by method 7. Yield 55% of theory |
| 106A | 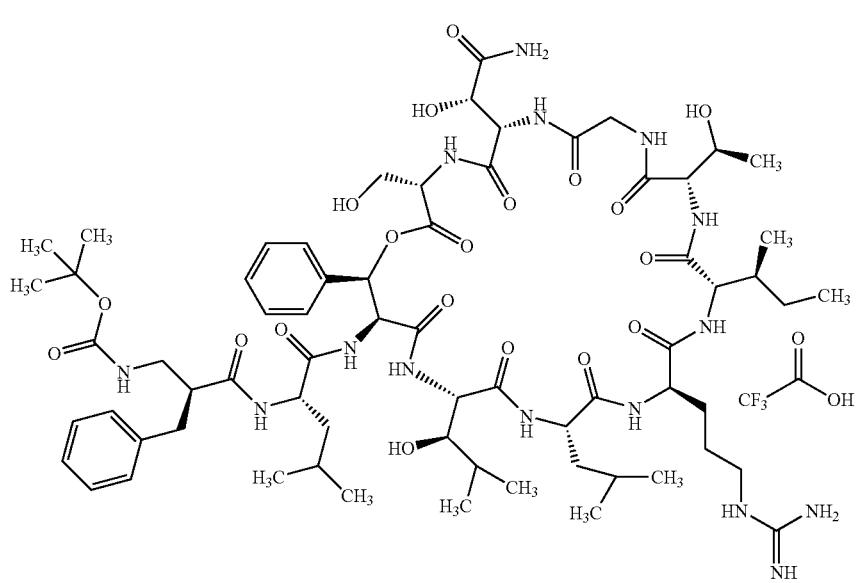 | | LC-MS (method 26): $R_t$ = 2.25 min; MS (ESIpos.): m/z (%) = 1424.9 (15) $[M + H]^+$; MS (ESIneg.): m/z (%) = 711.0 (11) $[M - 2H]^{2-}$, 1469.1 (18) $[M + HCOOH - H]^-$. |

TABLE 3-continued

N-protected nonadepsipeptides

| Ex. No. | Structure Name | | Analytical data Prepration method |
|---|---|---|---|
| 107A | (2S)-2-Benzyl-3-(tert-butoxycarbonylamino)-propanoyl-de(1-D-leucyl)lysobactin trifluoroacetate 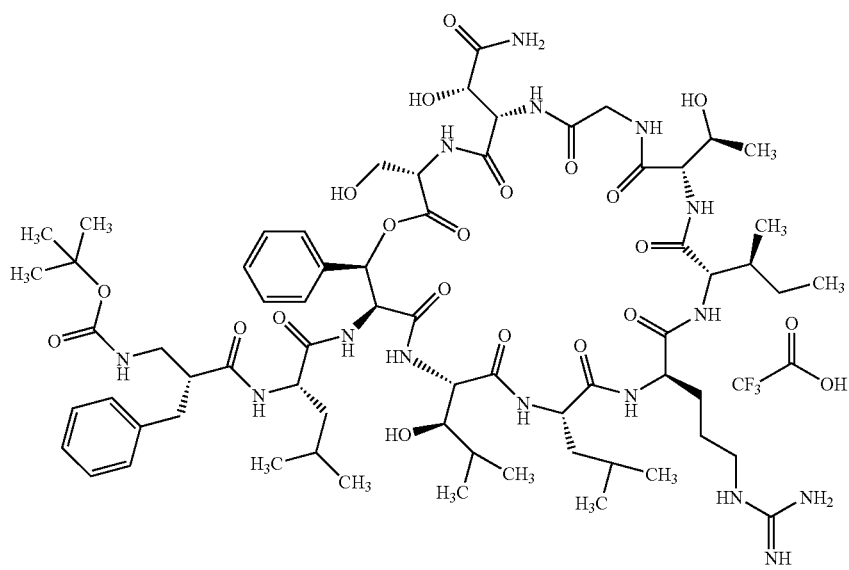 | | From 50 mg of Example 11A and (2S)-2-benzyl-3-(tert-butoxycarbonylamino)-propionic acid (2 equivalents) by general procedure 4 (2 equivalents of HATU and 4.5 equivalents of N-methylmorpholine) in dimethylformamide at room temperature and chromatography (method 8). LC-MS (method 26): $R_t$ = 2.22 min (100%); MS (ESIpos.): m/z (%) = 1424.7(15) [M + H]$^+$; MS (ESIneg.): m/z (%) = 711.1 (100) [M − 2H]$^{2-}$, 1468.9 (28) [M + HCOOH − H]$^-$. |
| 108A | (2R)-2-Benzyl-3-(tert-butoxycarbonylamino)-propanoyl-de(1-D-leucyl)lysobactin trifluoroacetate 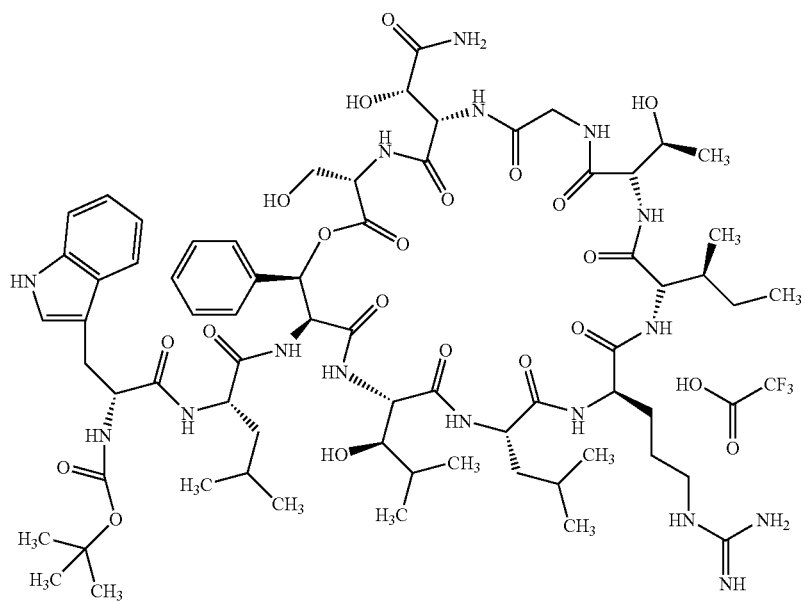 | | In analogy to Example 106A From Example 11A and (2R)-2-benzyl-3-(tert-butoxy-carbonylamino)propionic acid. HPLC/UV-Vis (method 36): $R_t$ = 4.13 min. LC-MS (method 26): $R_t$ = 2.12 min, MS (ESIpos.): m/z (%) = 725.9 (100) [M + 2H]$^{2+}$. |

TABLE 3-continued

N-protected nonadepsipeptides

| Ex. No. | Structure Name | | Analytical data Prepration method |
|---|---|---|---|
| | N-(tert-Butoxycarbonyl)-D-tryptophyl-de(1-D-leucyl)-lyso-bactin trifluoroacetate | | General procedure 19 from Example 11A (36 µmol) and N-(tert-butoxy-carbonyl)-D-trypto-phan (36 µmol). Yield: 84% of theory |
| 109A | | 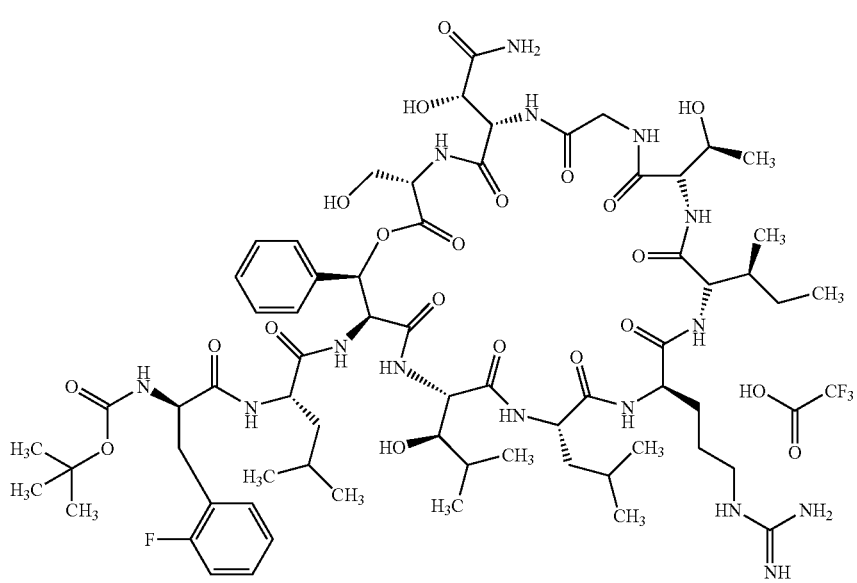 | HPLC/UV-Vis (method 36): $R_t$ = 4.26 min. LC-MS (method 26): $R_t$ = 2.23 min, MS (ESIpos.): m/z (%) = 1430.2 $[M + H]^+$. |
| | N-(tert-Butoxycarbonyl)-2-fluoro-D-phenylalanyl-de(1-D-leu-cyl)lysobactin trifluoroacetate | | General procedure 19 from Example 11A (40 µmol) and N-tert-butoxy-carbonyl-2-fluoro-D-phe-nyl-alanine. Yield 76% of theory |
| 110A | | 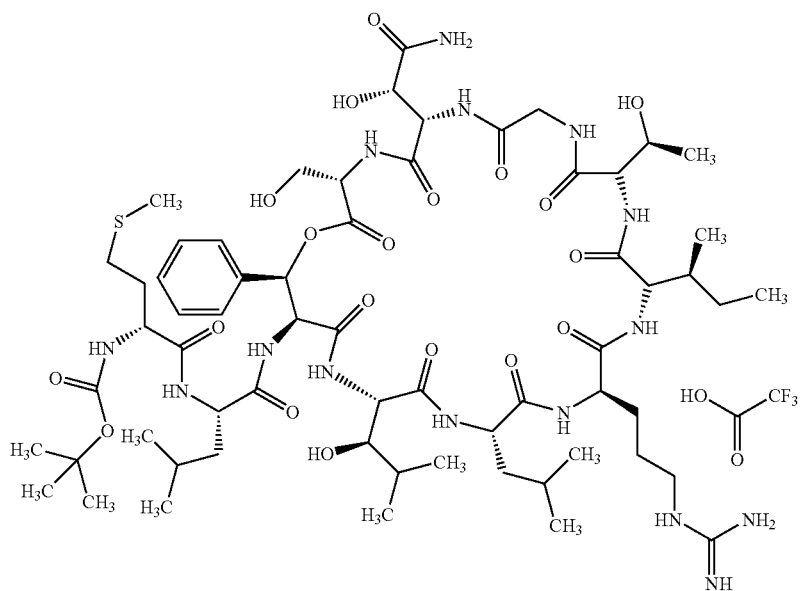 | HPLC/UV-Vis (method 36): $R_t$ = 4.12 min. LC-MS (method 26): $R_t$ = 2.13 min, MS (ESIpos.): m/z (%) = 698.3 $[M + 2H]^{2+}$. |

TABLE 3-continued

N-protected nonadepsipeptides

| Ex. No. | Structure Name | Analytical data Preparation method |
|---|---|---|
| 111A | N-(tert-Butoxycarbonyl)-D-methionyl-de(1-D-leucyl)-lysobactin bistrifluoroacetate 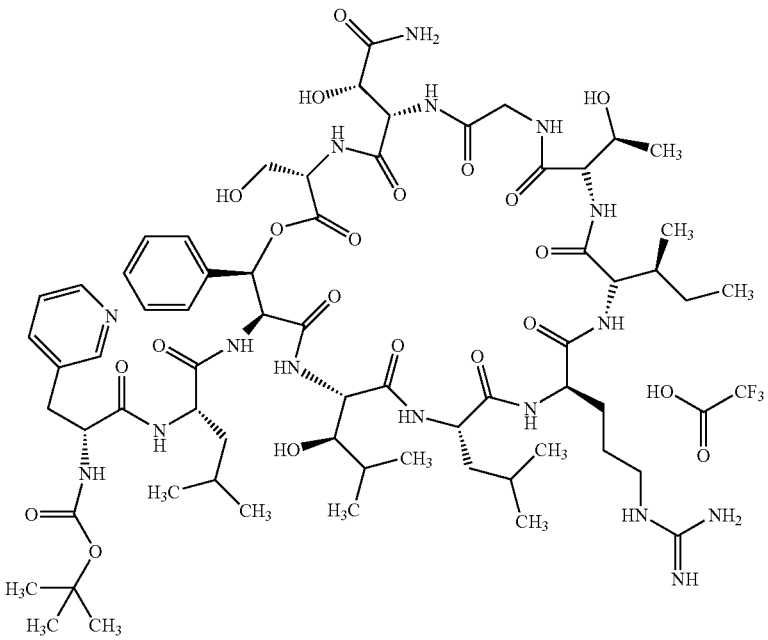 [N-(tert-Butoxycarbonyl)-3-pyrid-3-yl-D-alanyl]-de(1-D-leucyl)lysobactin trifluoroacetate | General procedure 19 from Example 11A (140 μmol) and N-tert-butoxycarbonyl-D-methionine. Yield: 64% of theory<br><br>HPLC/UV-Vis (method 36): $R_t$ = 3.58 min.<br>LC-MS (method 26): $R_t$ = 1.85 min,<br>MS (ESIpos.): m/z (%) = 706.9 (100) $[M + 2H]^{2+}$.<br><br>General procedure 19 from Example 11A (36 μmol) and (N-tert-butoxycarbonyl-3-(3-pyridyl)-D-alanine. Yield: 68% of theory |
| 112A | 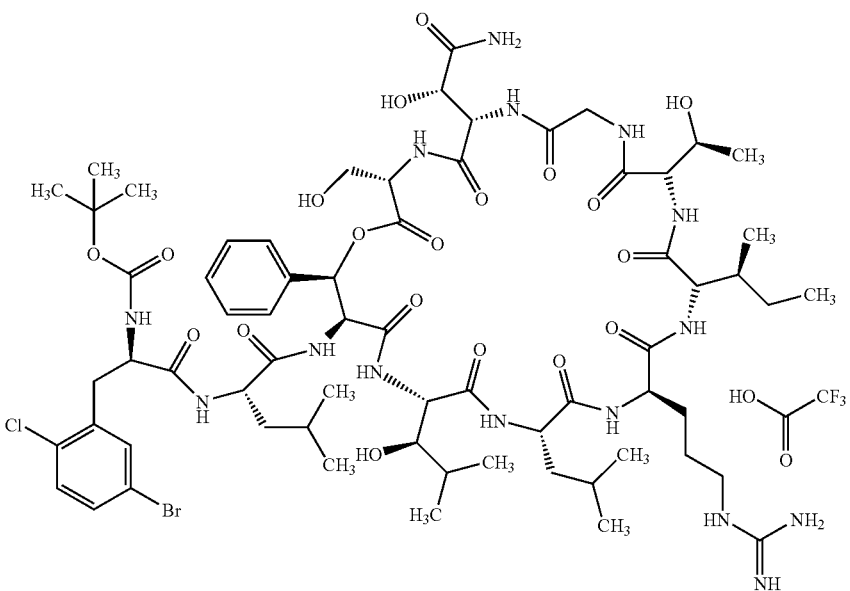 | HPLC/UV-Vis (method 36): $R_t$ = 4.46 min.<br>LC-MS (method 26): $R_t$ = 2.38 min,<br>MS (ESIpos.): m/z (%) = 1522.9 $[M + H]^+$.<br>HR-TOF-MS (method 21): calc. 1522.6348, found 1522.6373 $[M + H]^+$. |

TABLE 3-continued

N-protected nonadepsipeptides

| Ex. No. | Structure Name | Analytical data Preparation method |
|---|---|---|
| | [3-Bromo-N-(tert-butoxycarbonyl)-6-chloro-D-phenyl-alanyl]-de(1-D-leucyl)lysobactin-trifluoroacetate | General procedure 19 from Example 11A (36 μmol) and 3-bromo-N-(tert-butoxy-carbonyl)-6-chloro-D-phenyl-alanine. Yield: 85% of theory |
| 113A | 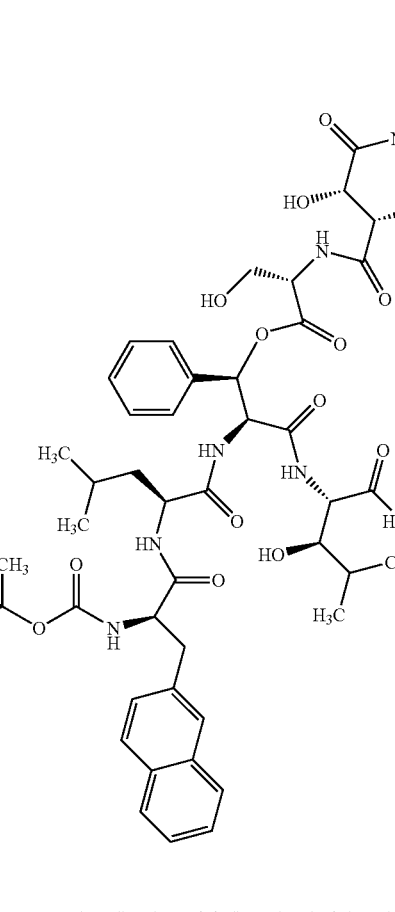 N-[(tert-Butoxycarbonyl)-3-(2-naphthyl)-D-alanyl]-de(1-D-leucyl)lysobactin trifluoroacetate | HPLC/UV-Vis (method 36): $R_t$ = 4.39 min. LC-MS (method 26): $R_t$ = 2.40 min, MS (ESIpos.): m/z (%) = 1461.2 (10) $[M + H]^+$. General procedure 19 from Example 11A (36 μmol) and N-(tert-butoxy-carbonyl)-3-(2-naphthyl)-D-alanine. Yield: 72% of theory |

TABLE 3-continued

N-protected nonadepsipeptides

| Ex. No. | Structure Name | | Analytical data Prepration method |
|---|---|---|---|
| 114A | 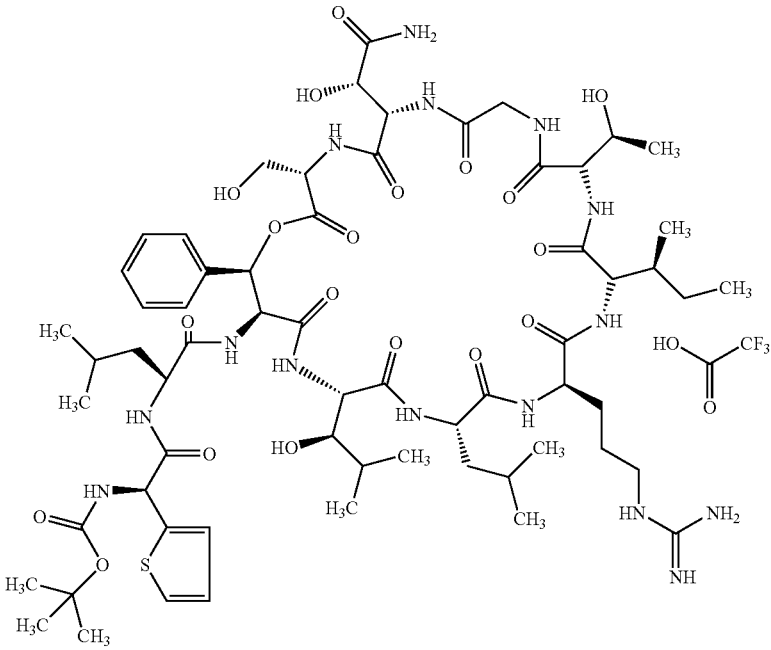 (2R)-[(tert-Butoxycarbonyl)amino]-(2-thienyl)acetyl-de(1-D-leucyl)lysobactin trifluoroacetate | | HPLC/UV-Vis (method 36): $R_t$ = 4.03 min. LC-MS (method 26): $R_t$ = 2.11 min, MS (ESIpos.): m/z (%) = 1402.1 (1) [M + H]$^+$. General procedure 19 from Example 11A (36 µmol) and (2R)-butoxycarbonyl-amino-(2-thienyl)acetic acid. Yield: 20% of theory |
| 115A | 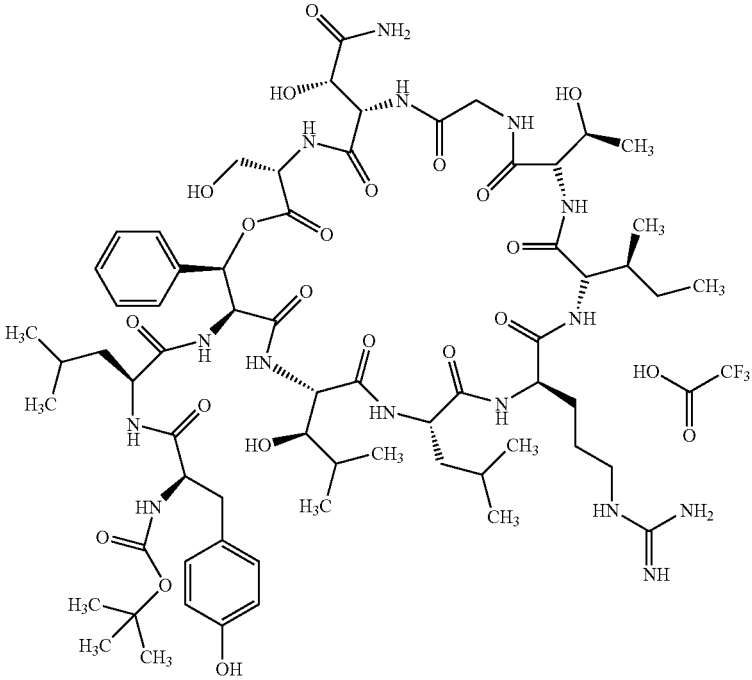 N-(tert-Butoxycarbonyl)-D-tyrosyl-de(1-D-leucyl)-lysobactin trifluoroacetate | | HPLC/UV-Vis (method 36): $R_t$ = 4.43 min. LC-MS (method 26): $R_t$ = 2.35 min, MS (ESIpos.): m/z (%) = 1482.8 (10) [M + H]$^+$. General procedure 19 from Example 11A (36 µmol) and N-(tert-butoxycarbonyl)-D-tyrosine. Yield: 70% of theory |

TABLE 3-continued

N-protected nonadepsipeptides

| Ex. No. | Structure Name | Analytical data Preparation method |
|---|---|---|
| 116A | 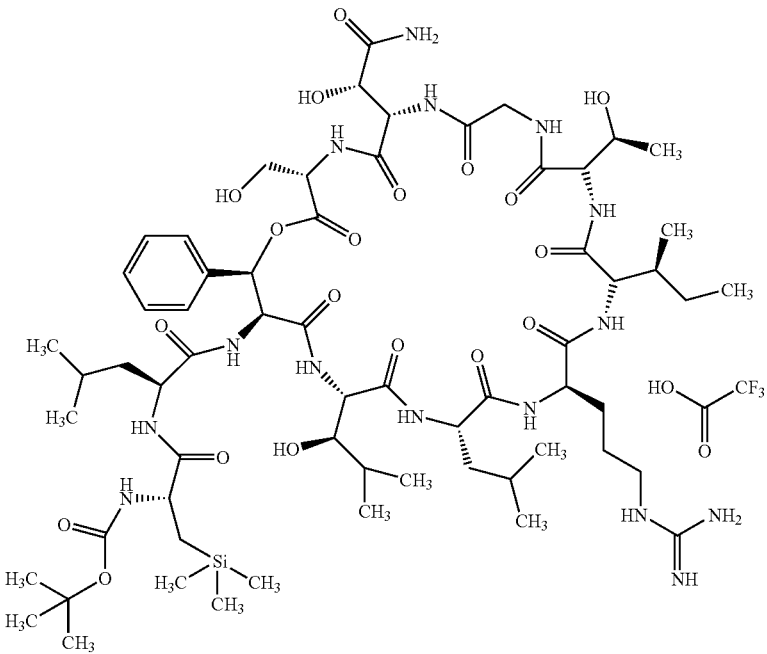<br>N-(tert-Butoxycarbonyl)-3-(trimethylsilyl)-L-alanyl-de(1-D-leu-cyl)lysobactin trifluoroacetate | HPLC/UV-Vis (method 36): $R_t$ = 4.41 min.<br>LC-MS (method 26): $R_t$ = 2.28 min,<br>MS (ESIpos.): m/z (%) = 1407 (15) $[M + H]^+$.<br><br>General procedure 19 from Example 11A (287 μmol) and Example 26A<br>Yield 75% of theory |
| 117A | 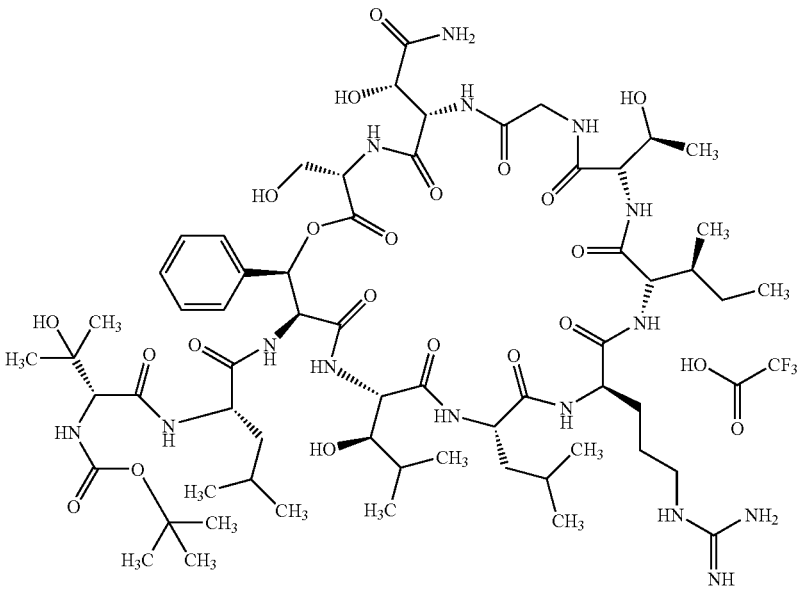<br>N-(tert-Butoxycarbonyl)-(3-hydroxy)-D-valyl-de(1-D-leu-cyl)lysobactin trifluoroacetate | HPLC/UV-Vis (method 36): $R_t$ = 3.91 min.<br>LC-MS (method 26): $R_t$ = 1.92 min,<br>MS (ESIpos.): m/z (%) = 1379.1 (20) $[M + H]^+$.<br><br>General procedure 19 from Example 11A (36 μmol) and N-(tert-butoxycarbonyl)-(3-hydroxy)-D-valine.<br>Yield: 54% of theory |

TABLE 3-continued

N-protected nonadepsipeptides

| Ex. No. | Structure Name | Analytical data Preparation method |
|---|---|---|
| 118A | 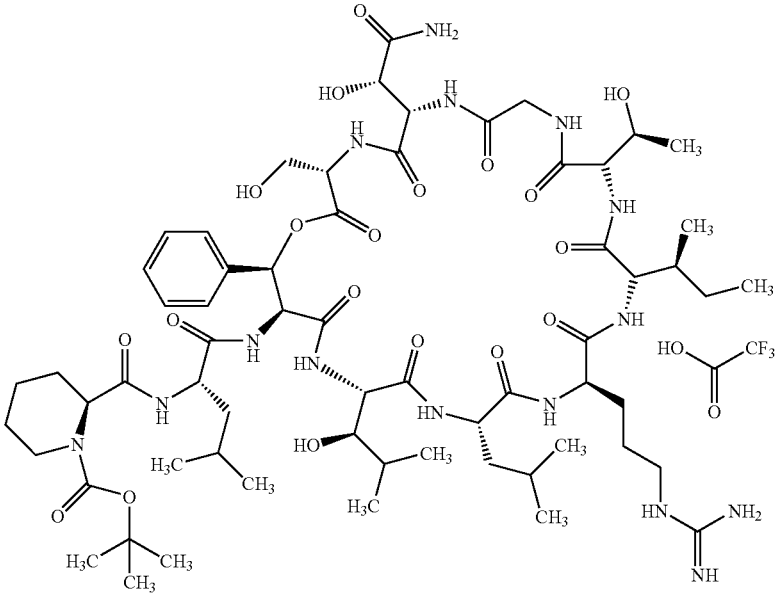<br>N-(tert-Butoxycarbonyl)-L-pipecolyl-de(1-D-leucyl)-lyso-bactin trifluoroacetate | HPLC/UV-Vis (method 36): $R_t$ = 4.38 min. LC-MS (method 26): $R_t$ = 2.26 min, MS (ESIpos.): m/z (%) = 1375.0 (10) [M + H]$^+$.<br><br>General procedure 19 from Example 11A (36 µmol) and N-(tert-butoxycarbonyl)-L-pipecolic acid.<br>Yield: 62% of theory |
| 119A | 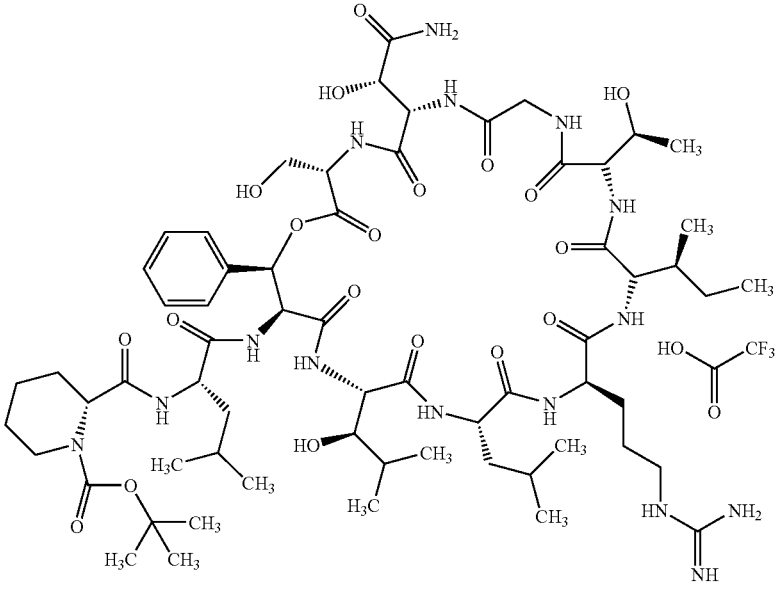<br>N-(tert-Butoxycarbonyl)-D-pipecolyl-de(1-D-leucyl)-lyso-bactin trifluoroacetate | HPLC/UV-Vis (method 36): $R_t$ = 4.3 min. LC-MS (method 26): $R_t$ = 2.21 min, MS (ESIpos.): m/z (%) = 1375.0 (10) [M + H]$^+$.<br><br>General procedure 19 from Example 11A (36 µmol) and N-(tert-butoxycarbonyl)-D-pipecolic acid.<br>Yield: 64% of theory |

TABLE 3-continued

N-protected nonadepsipeptides

| Ex. No. | Structure Name | Analytical data Preparation method |
|---|---|---|
| 120A | 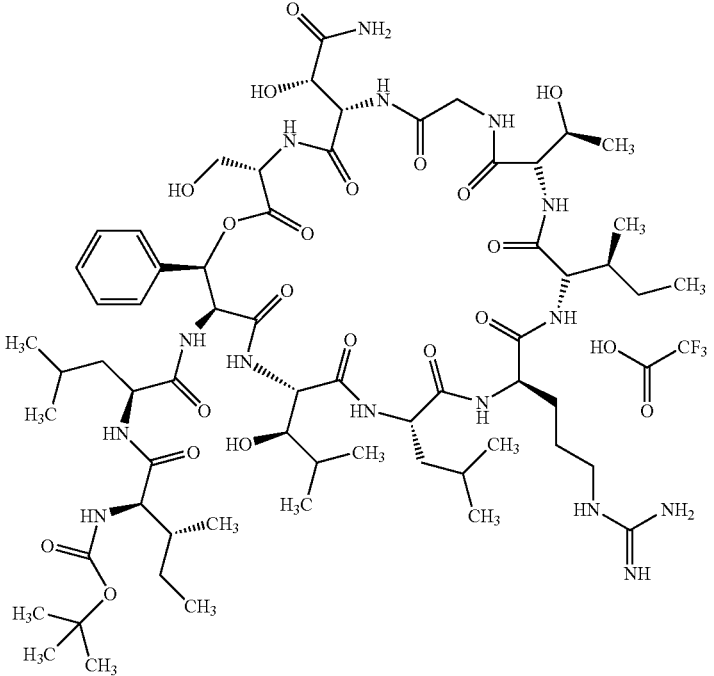<br>N-(tert-Butoxycarbonyl)-D-isoleucyl-de(1-D-leucyl)-lyso-bactin trifluoroacetate | LC-MS (method 26): $R_t$ = 2.23 min,<br>MS (ESIneg.): m/z (%) = 1375.3 (20) [M − H]⁻.<br><br>General procedure 19 from Example 11A (36 μmol) and N-(tert-butoxycarbonyl)-D-iso-leucine.<br>Yield: 58% of theory |
| 121A | 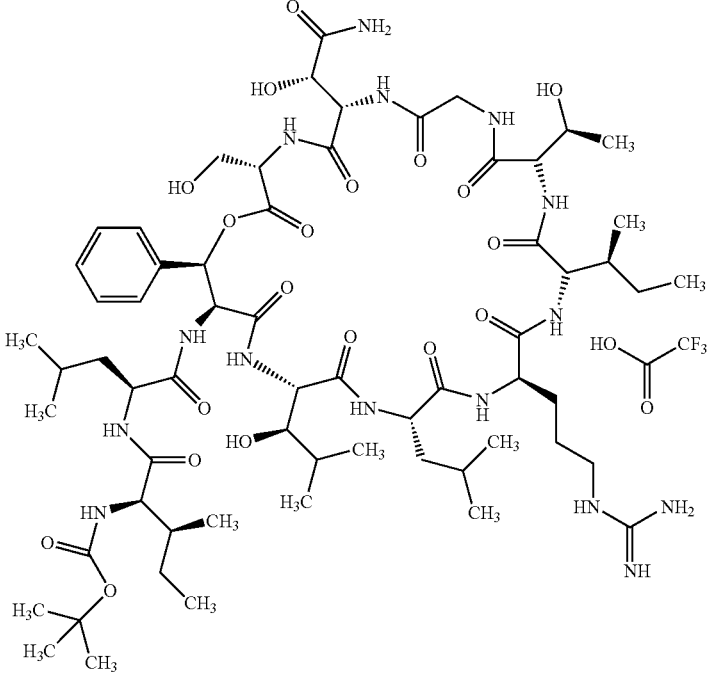 | LC-MS (method 26): $R_t$ = 2.15 min,<br>MS (ESIpos.): m/z (%) = 1377.2 (20) [M + H]⁺. |

TABLE 3-continued

N-protected nonadepsipeptides

| Ex. No. | Structure Name | | Analytical data Preparation method |
|---|---|---|---|
| | N-(tert-Butoxycarbonyl)-D-alloisoleucyl-de(1-D-leu-cyl)lysobactin trifluoroacetate | | General procedure 19 from Example 11A (36 μmol) and N-(tert-butoxycarbonyl)-D-allo-isoleucine.<br>Yield: 49% of theory |
| 122A | 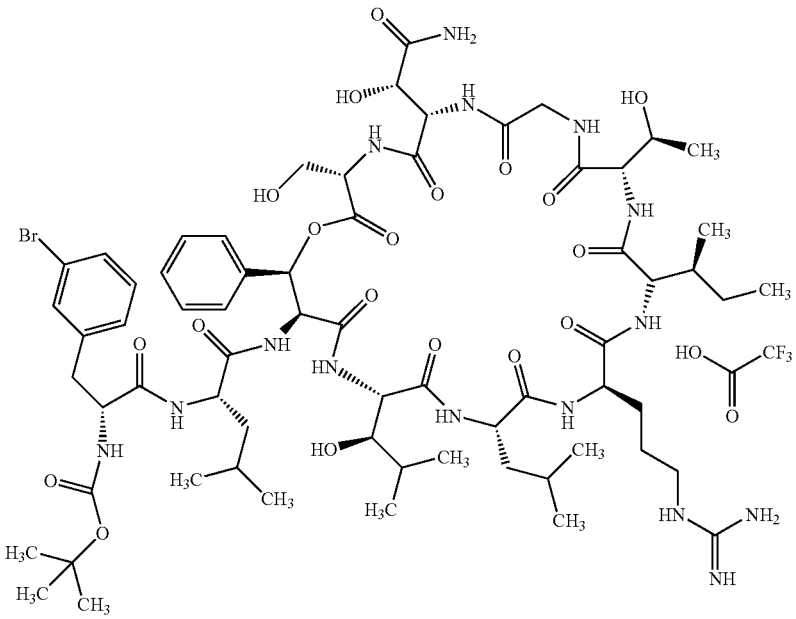 | | HPLC/UV-Vis (method 36): $R_t$ = 4.4 min.<br>LC-MS (method 26): $R_t$ = 2.32 min,<br>MS (ESIpos.): m/z (%) = 1488.9 (1) [M + H]$^+$. |
| | 3-Bromo-N-(tert-butoxycarbonyl)-D-phenylalanyl-de(1-D-leu-cyl)lysobactin trifluoroacetate | | General procedure 19 from Example 11A (36 μmol) and 3-bromo-N-(tert-butoxy-carbo-nyl)-D-phenylalanine.<br>Yield: 44% of theory |
| 123A | 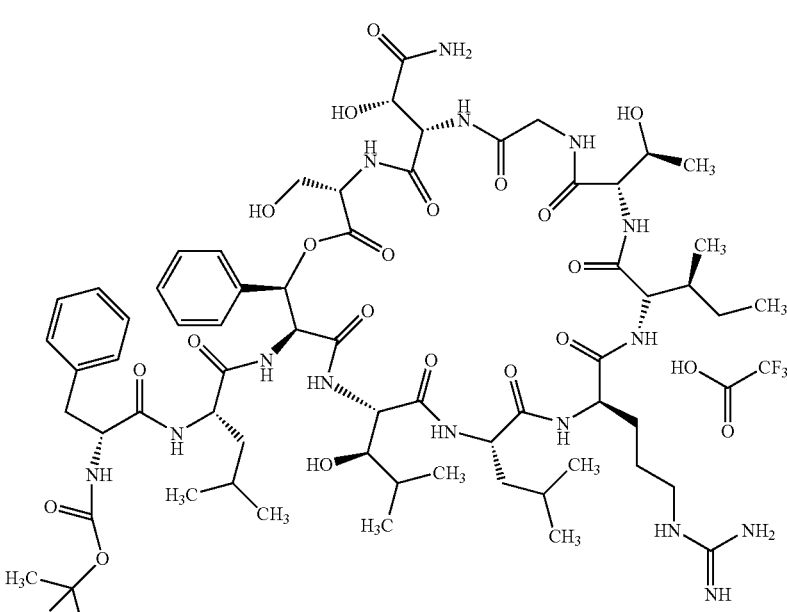 | | HPLC/UV-Vis (method 36): $R_t$ = min.<br>LC-MS (method 26): $R_t$ = 2.18 min,<br>MS (ESIpos.): m/z (%) = 1411.2 [M + H]$^+$. |

US 7,368,424 B2

139                                                                                             140

TABLE 3-continued

N-protected nonadepsipeptides

| Ex. No. | Structure Name | Analytical data Prepration method |
|---|---|---|
| 124A | N-(tert-Butoxycarbonyl)-D-phenylalanyl-de(1-D-leucyl)lysobactin trifluoroacetate<br/>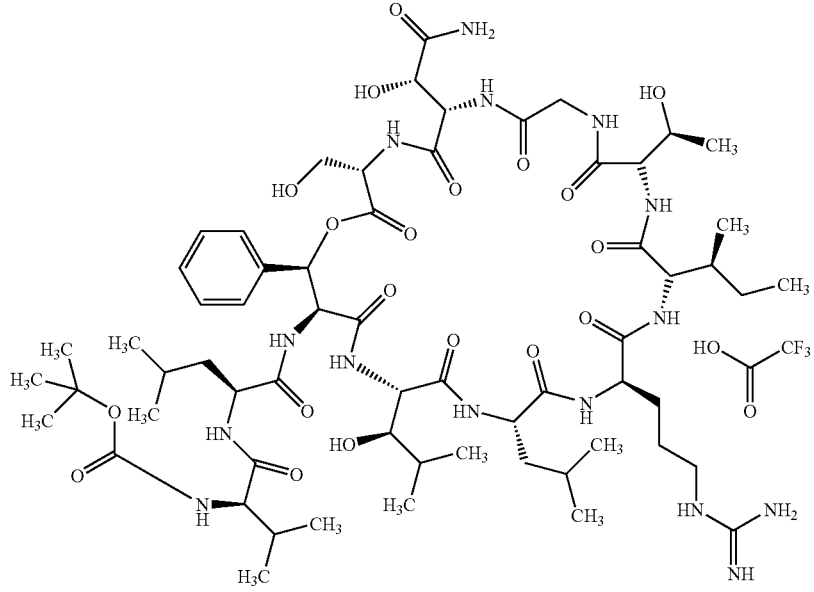 | General procedure 19 from Example 11A (80 µmol) and N-(tert-butoxycarbonyl)-D-phenylalanine.<br/>Yield: 55% of theory<br/><br/>HPLC/UV-Vis (method 36): $R_t$ = 4.16 min.<br/>LC-MS (method 26): $R_t$ = 2.16 min,<br/>MS (ESIpos.): m/z (%) = 1361.7/20) [M + H]$^+$. |
| 125A | N-(tert-Butoxycarbonyl)-D-valyl-de(1-D-leucyl)-lysobactine trifluoroacetate<br/>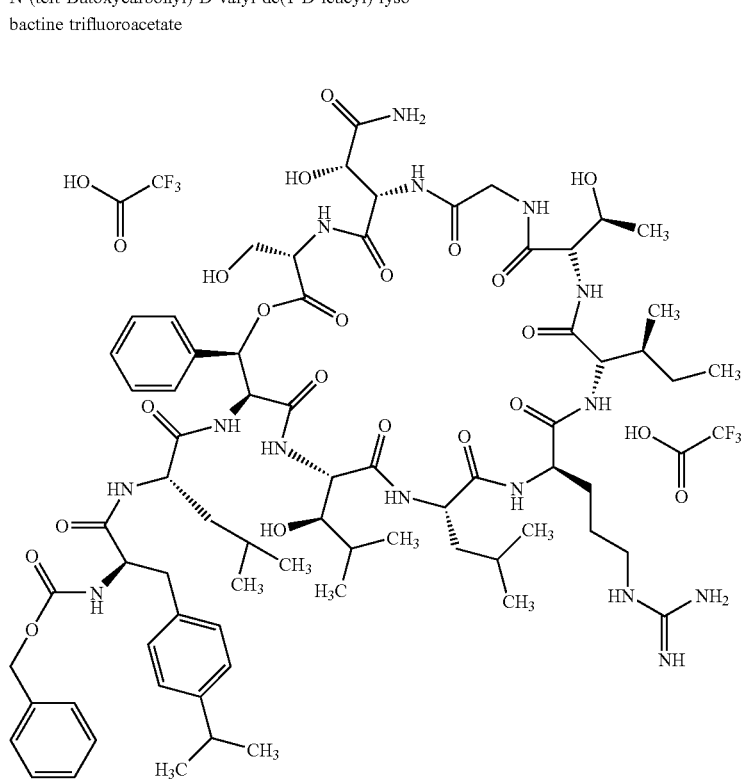 | General procedure 19 from Example 11A (50 µmol) and N-(tert-butoxycarbonyl)-D-valine.<br/>Yield: 58% of theory<br/><br/>HPLC/UV-Vis (method 36): $R_t$ = 4.48 min.<br/>LC-MS (method 26): $R_t$ = 2.42 min,<br/>MS (ESIpos.): m/z (%) = 1487.3 (20) [M + H]$^+$. |

TABLE 3-continued

N-protected nonadepsipeptides

| Ex. No. | Structure Name | Analytical data Preparation method |
|---|---|---|
| 126A | N-(Benzyloxycarbonyl)-(4-isopropyl-D-phenylalanyl)-de(1-D-leu-cyl)lysobactin trifluoroacetate | General procedure 19 from Example 11A (36 µmol) and Example 32A. Yield: 68% of theory<br><br>HPLC/UV-Vis (method 36): R$_t$ = 4.42 min.<br>LC-MS (method 26): R$_t$ = 2.09 min,<br>MS (ESIpos.): m/z (%) = 1487.1 (10) [M + H]$^+$. |
| 127A | N-(tert-Butoxycarbonyl)-3-biphenyl-L-alanyl-de(1-D-leu-cyl)lysobactin trifluoroacetate | General procedure 19 from Example 11A (110 µmol) and N-(tert-butoxycarbonyl)-2-a-mino-3-biphenyl-L-alanine. Yield: 66% of theory<br><br>HPLC/UV-Vis (method 36): R$_t$ = 4.43 min.<br>LC-MS (method 26): R$_t$ = 2.16 min,<br>MS (ESIpos.): m/z (%) = 1487.1 (10) [M + H]$^+$.<br>HR-TOF-MS (method 21): calc. 1486.7946, found 1486.8008 [M + H]$^+$. |

TABLE 3-continued

N-protected nonadepsipeptides

| Ex. No. | Structure Name | Analytical data Prepration method |
|---|---|---|
| | N-(tert-Butoxycarbonyl)-3-biphenyl-D-alanyl-de(1-D-leu-cyl)lysobactin trifluoroacetate | General procedure 19 from Example 11A (110 µmol) and N-(tert-butoxycarbonyl)-2-a-mino-3-biphenyl-D-alanine. Yield: 62% of theory |
| 128A | 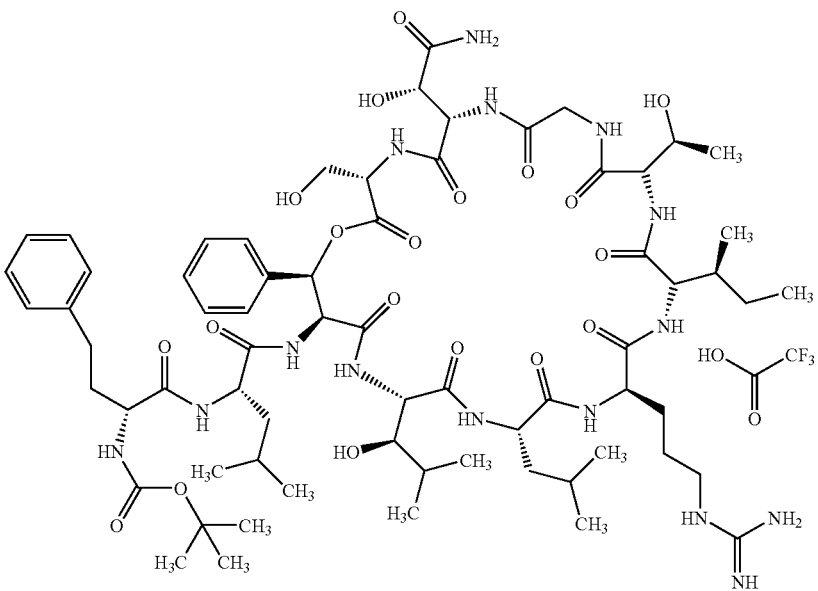 | HPLC/UV-Vis (method 36): $R_t$ = 4.32 min. LC-MS (method 26): $R_t$ = 2.01 min, MS (ESIpos.): m/z (%) = 1425.2 (20) [M + H]$^+$. |
| | N-(tert-Butoxycarbonyl)-(2R)-2-amino-4-phenyl-butanoyl-de(1-D-leucyl)lysobactin trifluoroacetate | General procedure 19 from Example 11A (50 µmol) and N-(tert-butoxy-carbonyl)-(2R)-2-a-mino-4-phenylbutyric acid. Yield: 79% of theory |
| 129A | 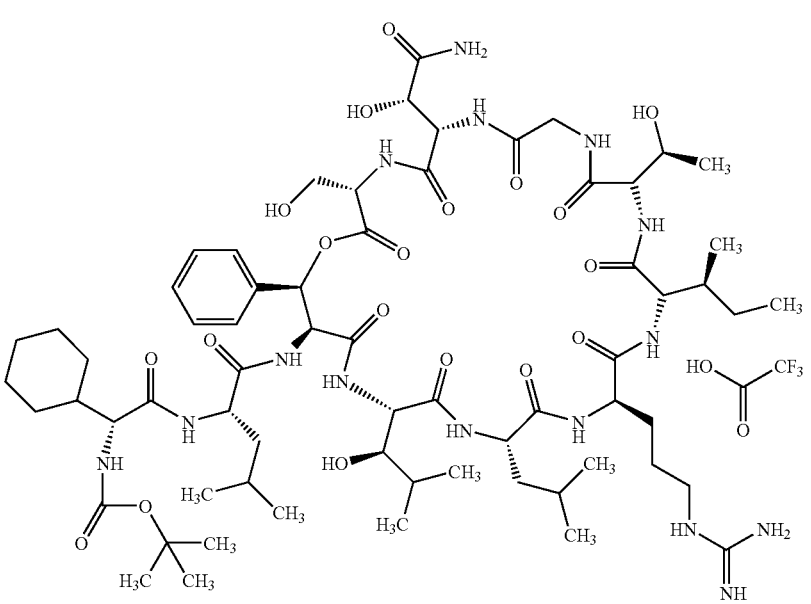 | HPLC/UV-Vis (method 36): $R_t$ = 4.45 min. LC-MS (method 26): $R_t$ = 2.05 min, MS (ESIpos.): m/z (%) = 1402.3 (10) [M + H]$^+$. |

145 146

TABLE 3-continued

N-protected nonadepsipeptides

| Ex. No. | Structure Name | Analytical data Preparation method |
|---|---|---|
| 130A | N-(tert-Butoxycarbonyl)-(2R)-amino(cyclohexyl)acetyl-de(1-D-leucyl)lysobactin trifluoroacetate<br />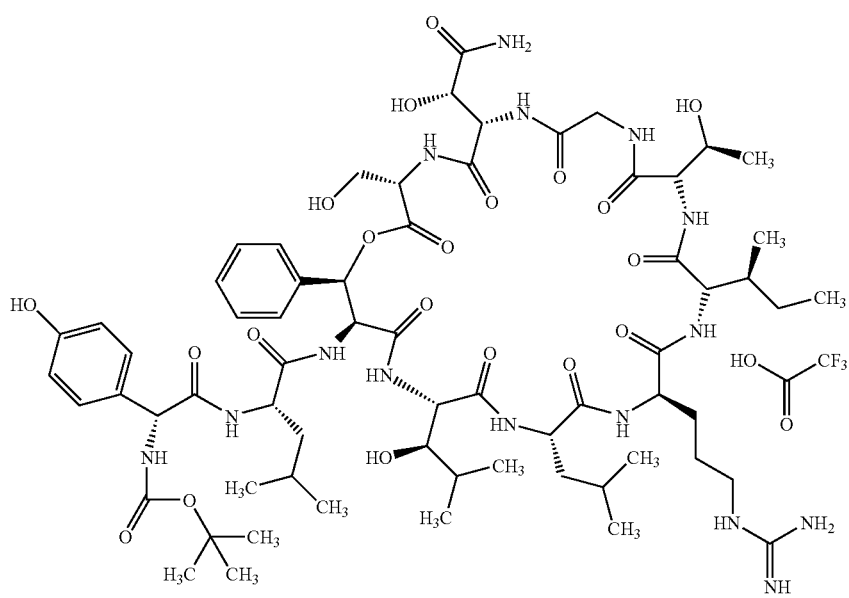 | General procedure 19 from Example 11A (100 μmol) and N-(tert-butoxycarbonyl)-(2R)-amino(cyclohexyl)acetic acid.<br />Yield: 28% of theory.<br />HPLC/UV-Vis (method 36): $R_t$ = 3.81 min.<br />LC-MS (method 26): $R_t$ = 1.71 min,<br />MS (ESIpos.): m/z (%) = 1413.2 (10) $[M + H]^+$. |
| 131A | N-(tert-Butoxycarbonyl)-(2R)-amino(4-hydroxyphenyl)acetyl-de(1-D-leucyl)lysobactin trifluoroacetate<br />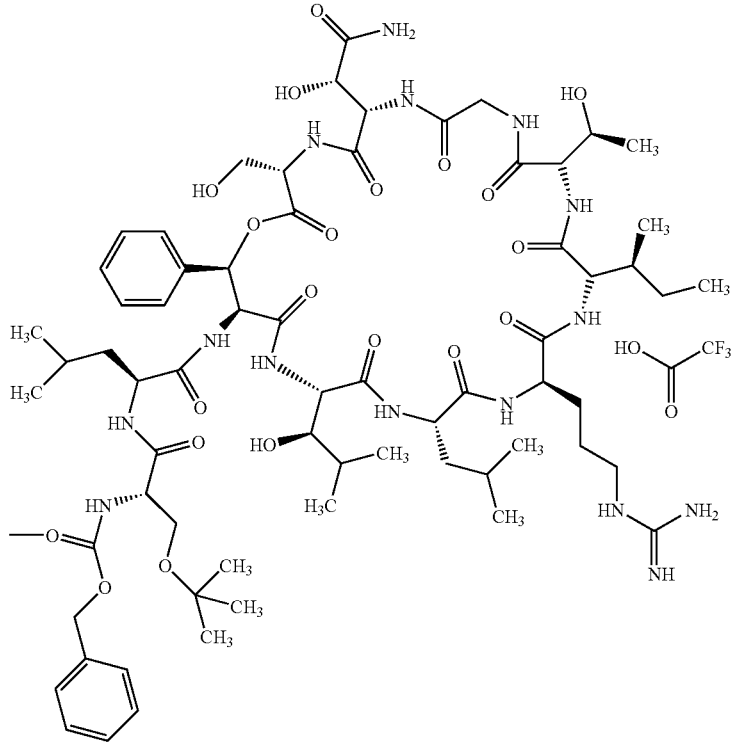 | General procedure 19 from Example 11A (100 μmol) and N-(tert-butoxycarbonyl)-(2R)-amino(4-hydroxyphenyl)-acetic acid.<br />Yield: 18% of theory<br />HPLC/UV-Vis (method 36): $R_t$ = 4.25 min.<br />LC-MS (method 26): $R_t$ = 2.06 min,<br />MS (ESIpos.): m/z (%) = 1441.1 (30) $[M + H]^+$. |

TABLE 3-continued

N-protected nonadepsipeptides

| Ex. No. | Structure Name | Analytical data Preparation method |
|---|---|---|
| 132A | N-(Benzyloxycarbonyl)-O-(tert-butyl)-L-seryl-de(1-D-leucyl)lysobactin trifluoroacetate<br>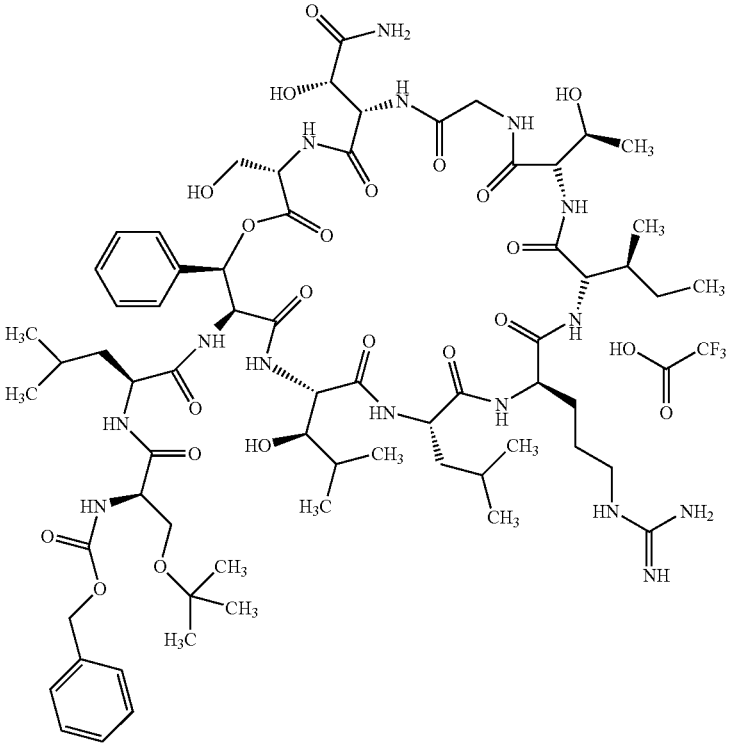 | General procedure 19 from Example 11A (110 µmol) and N-(tert-butoxycarbonyl)-O-(tert-butyl)-L-serine.<br>Yield: 70%.<br>HPLC/UV-Vis (method 36): $R_t$ = 4.11 min.<br>LC-MS (method 26): $R_t$ = 2.08 min,<br>MS (ESIpos.): m/z (%) = 1441.0 (80) $[M + H]^+$. |
| 133A | N-(Benzyloxycarbonyl)-O-(tert-butyl)-D-seryl-de(1-D-leucyl)lysobactin trifluoroacetate<br>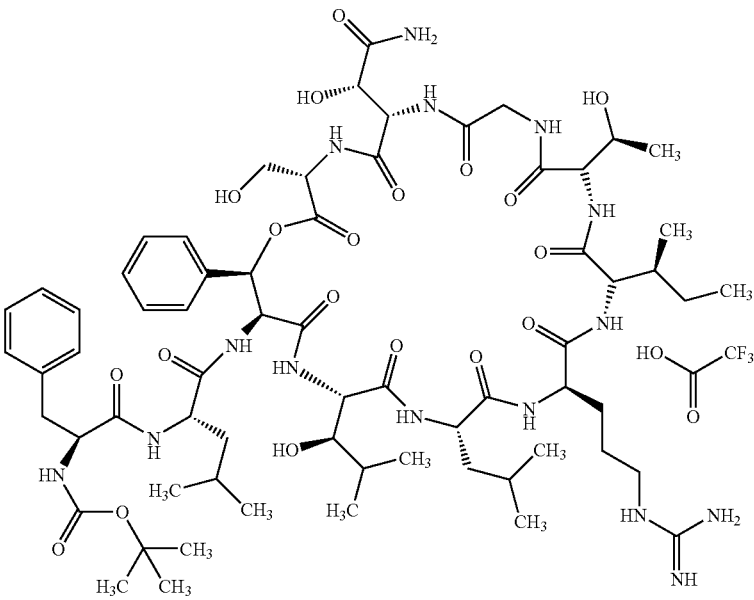 | General procedure 19 from Example 11A (310 µmol) and N-(tert-butoxycarbonyl)-O-(tert-butyl)-D-serine.<br>Yield: 47% of theory<br>HPLC/UV-Vis (method 36): $R_t$ = 4.23 min.<br>LC-MS (method 26): $R_t$ = 2.30 min,<br>MS (ESIpos.): m/z (%) = 1411.0 (30) $[M + H]^+$. |

TABLE 3-continued

N-protected nonadepsipeptides

| Ex. No. | Structure Name | Analytical data Prepration method |
|---|---|---|
| | N-(tert-Butoxycarobnyl)-L-phenylalanyl-de(1-D-leu-cyl)lysobactin trifluoroacetate | General procedure 19 from Example 11A (110 μmol) and N-(tert-butoxy-carbonyl)-L-phenyl-alanine.<br>Yield: 72% of theory |
| 134A | | HPLC/UV-Vis (method 36): R$_t$ = 4.18 min.<br>LC-MS (method 26): R$_t$ = 1.96 min,<br>MS (ESIpos.): m/z (%) = 1361.1 (10) [M + H]$^+$. |
| | N-(tert-Butoxycarbonyl)-L-prolyl-de(1-D-leucyl)-lyso-bactine trifluoroacetate | General procedure 19 from Example 11A (70 μmol) and N-(tert-butoxycarbonyl)-L-pro-line.<br>Yield: 73% of theory |
| 135A | | HPLC/UV-Vis (method 36): R$_t$ = 4.54 min.<br>LC-MS (method 26): R$_t$ = 2.15 min,<br>MS (ESIpos.): m/z (%) = 1465.2 (40) [M + H]$^+$. |

TABLE 3-continued

N-protected nonadepsipeptides

| Ex. No. | Structure Name | | Analytical data Prepration method |
|---|---|---|---|
| | 3-(1-Methylcyclohexyl)-D-alanyl-de(1-D-leucyl)-lyso-bactin trifluoroacetate | | General procedure 19 from Example 11A (90 µmol) and Example 29A. Yield: 66% of theory |
| 136A | 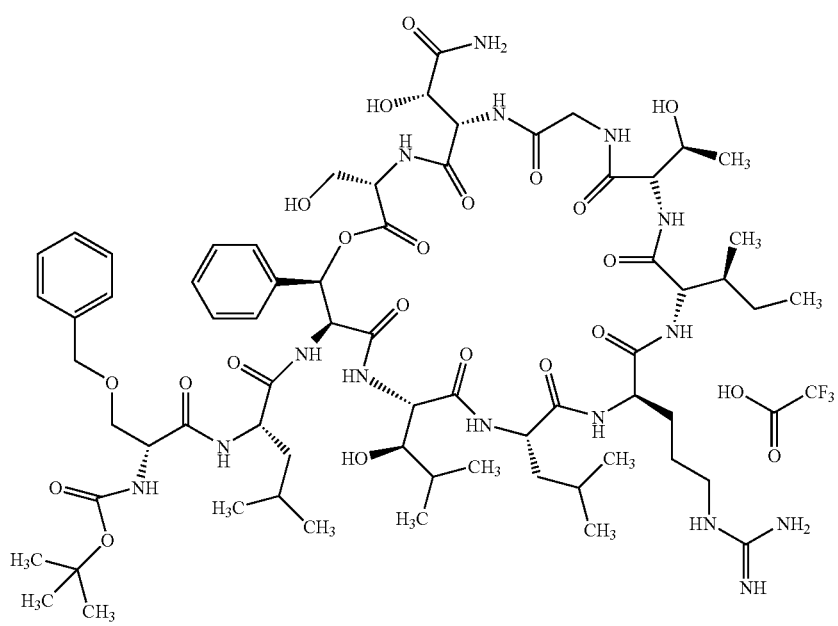 | | HPLC/UV-Vis (method 36): $R_t$ = 4.25 min. LC-MS (method 26): $R_t$ = 2.07 min, MS (ESIpos.): m/z (%) = 1440.9 (30) $[M + H]^+$. |
| | N-(tert-Butoxycarbonyl)-O-benzyl-D-seryl-de(1-D-leu-cyl)lysobactin trifluoroacetate | | General procedure 19 from Example 11A (110 µmol) and N-(tert-butoxycarbonyl)-O-ben-zyl-D-serine. Yield: 56% of theory |
| 137A | 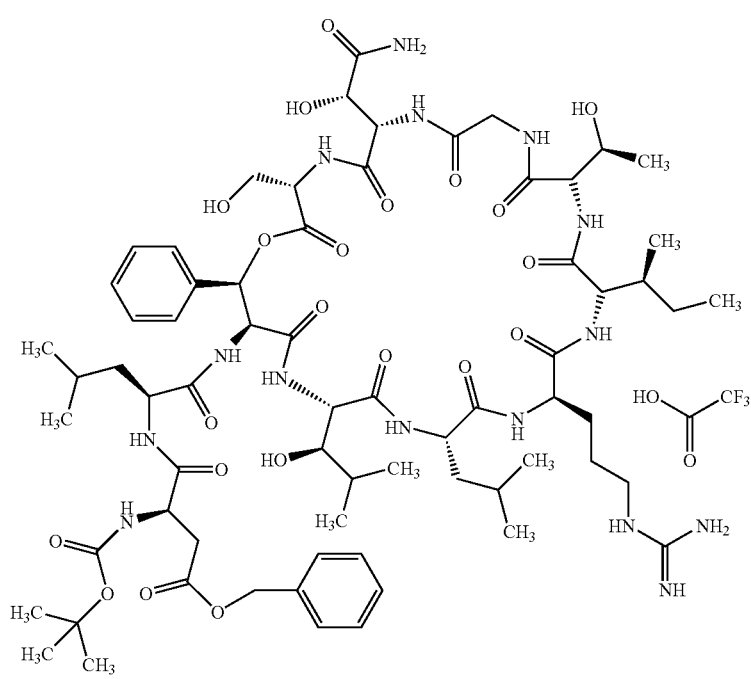 | | HPLC/UV-Vis (method 36): $R_t$ = 4.25 min. LC-MS (method 26): $R_t$ = 2.21 min, MS (ESIpos.): m/z (%) = 1569.2 (10) $[M + H]^+$. |

TABLE 3-continued

N-protected nonadepsipeptides

| Ex. No. | Structure Name | Analytical data Preparation method |
|---|---|---|
| 138A | (2R)-4-(Benzyloxy)-2-[(tert-butoxycarbonyl)amino]-4-oxo-butanoyl-de(1-D-leucyl)lysobactin trifluoroacetate | General procedure 19 from Example 11A (180 μmol) and (2R)-4-(benzyloxy)-2-[(tert-butoxycarbonyl)amino]-4-oxo-butyric acid.<br>Yield: 65% of theory<br><br>HPLC/UV-Vis (method 36): R$_t$ = 4.33 min.<br>LC-MS (method 26): R$_t$ = 2.07 min,<br>MS (ESIpos.): m/z (%) = 1391.4 (5) [M + H]$^+$. |
| 139A | N-(tert-Butoxycarbonyl)-3-(tert-butyl)-L-alanyl-de(1-D-leucyl)lysobactin trifluoroacetate | General procedure 19 from Example 11A (110 μmol) and N-(tert-butoxycarbonyl)-3-(tert-butyl)-L-alanine.<br>Yield: 70% of theory<br><br>HPLC/UV-Vis (method 36): R$_t$ = 4.21 min.<br>LC-MS (method 26): R$_t$ = 1.99 min,<br>MS (ESIpos.): m/z (%) = 1377.6 (1) [M + H]$^+$.<br>HR-TOF-MS (method 21): calc. 1376.7789, found 1376.7765 [M + H]$^+$. |

TABLE 3-continued

N-protected nonadepsipeptides

| Ex. No. | Structure Name | Analytical data Prepration method |
|---|---|---|
| | N-(tert-Butoxycarbonyl)-L-isoleucyl-de(1-D-leucyl)-lysobactin trifluoroacetate | General procedure 19 from Example 11A (110 μmol) and N-(tert-butoxycarobnyl)-L-isoleucine.<br>Yield: 80% of theory |
| 140A | 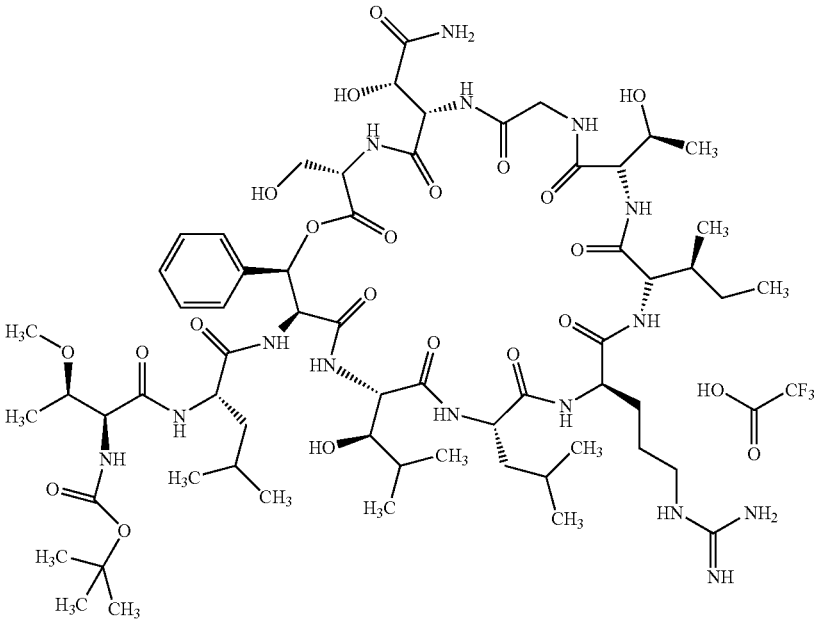 | HPLC/UV-Vis (method 36): $R_t$ = 4.05 min.<br>LC-MS (method 26): $R_t$ = 1.85 min,<br>MS (ESIpos.): m/z (%) = 1379.3 (80) $[M + H]^+$.<br>HR-TOF-MS (method 21): calc. 1378.7582, found 1378.7576 $[M + H]^+$ |
| | N-(tert-Butoxycarbonyl)-O-methyl-L-threonyl-de(1-D-leucyl)lysobactin trifluoroacetate | General procedure 19 from Example 11A (110 μmol) and N-(tert-butoxycarbonyl)-O-methyl-L-threonine.<br>Yield: 47% of theory |
| 141A | 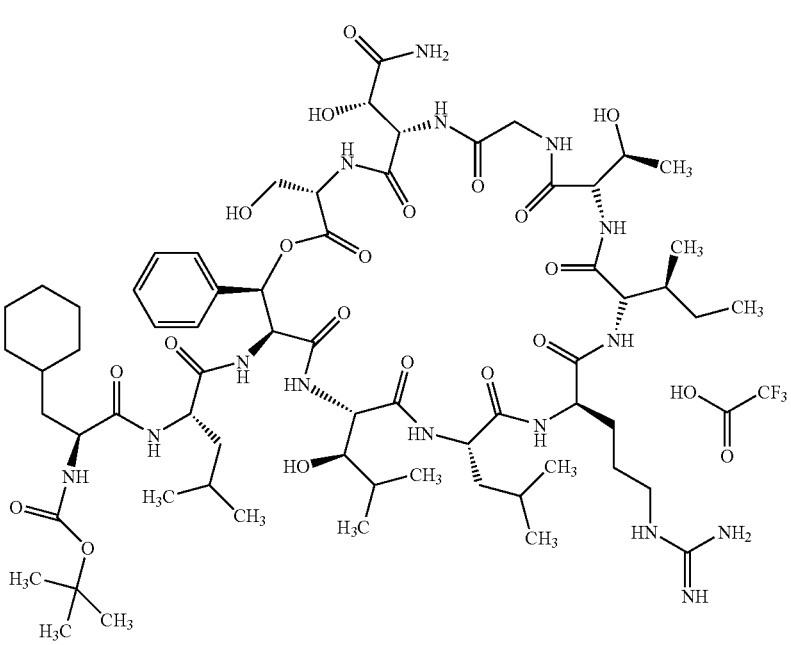 | HPLC/UV-Vis (method 36): $R_t$ = 4.45 min.<br>LC-MS (method 26): $R_t$ = 2.11 min,<br>MS (ESIpos.): m/z (%) = 1417.3 (10) $[M + H]^+$.<br>HR-TOF-MS (method 21): calc. 1416.8102, found 1416.8116 $[M + H]^+$. |

TABLE 3-continued

N-protected nonadepsipeptides

| Ex. No. | Structure Name | Analytical data Preparation method |
|---|---|---|
| | N-(tert-Butoxycarbonyl)-3-cyclohexyl-L-alanyl-de(1-D-leu-cyl)lysobactin trifluoroacetate | General procedure 19 from Example 11A (110 μmol) and N-(tert-butoxycarbonyl)-3-cyclo-hexyl-L-alanine. Yield: 80% of theory |
| 142A | *[chemical structure]* N-(tert-Butoxycarbonyl)-(4S)-4-phenyl-L-prolyl-de(1-D-leu-cyl)lysobactin trifluoroacetate | HPLC/UV-Vis (method 36): $R_t$ = 4.44 min. LC-MS (method 26): $R_t$ = 2.13 min, MS (ESIpos.): m/z (%) = 1437 (20) [M + H]$^+$. General procedure 19 from Example 11A (110 μmol) and N-(tert-butoxy-carbonyl)-(4S)-4-phe-nyl-L-proline. Yield: 63% of theory |
| 143A | *[chemical structure]* | HPLC/UV-Vis (method 36): $R_t$ = 4.28 min. LC-MS (method 26): $R_t$ = 2.06 min, MS (ESIpos.): m/z (%) = 1388.9 (10) [M + H]$^+$. |

TABLE 3-continued

N-protected nonadepsipeptides

| Ex. No. | Structure Name | Analytical data Prepration method |
|---|---|---|
| 144A | N-(tert-Butoxycarbonyl)-(1-aminocyclohexyl)carbonyl-de(1-D-leucyl)lysobactin trifluoroacetate | General procedure 19 from Example 11A (110 µmol) and N-(tert-butoxycarbonyl)-1-aminocyclohexane-carboxylic acid.<br>Yield: 27% of theory<br><br>HPLC/UV-Vis (method 36):<br>$R_t$ = 4.17 min.<br>LC-MS (method 26):<br>$R_t$ = 2.00 min,<br>MS (ESIpos.): m/z (%) = 1441.0 (20) [M + H]$^+$. |
| 145A | N-(tert-Butoxycarbonyl)-(O-benzyl)-L-seryl-de(1-D-leucyl)lysobactin trifluoroacetate | General procedure 19 from Example 11A (110 µmol) and N-(tert-butoxycarbonyl)-(O-benzyl)-L-serine.<br>Yield: 53% of theory<br><br>HPLC/UV-Vis (method 36):<br>$R_t$ = 4.5 min.<br>LC-MS (method 26): $R_t$ = 2.13 min,<br>S (ESIpos.): m/z (%) = 1407.0 (20) [M + H]$^+$. |
| | N-(tert-Butoxycarbonyl)-3-(trimethylsilyl)-D-alanyl-de(1-D-leucyl)lysobactin trifluoroacetate | General procedure 19 from Example 11A (143 µmol) and Example 25A.<br>Yield: 40% of theory |

TABLE 3-continued

N-protected nonadepsipeptides

| Ex. No. | Structure Name | Analytical data Preparation method |
|---|---|---|
| 146A | 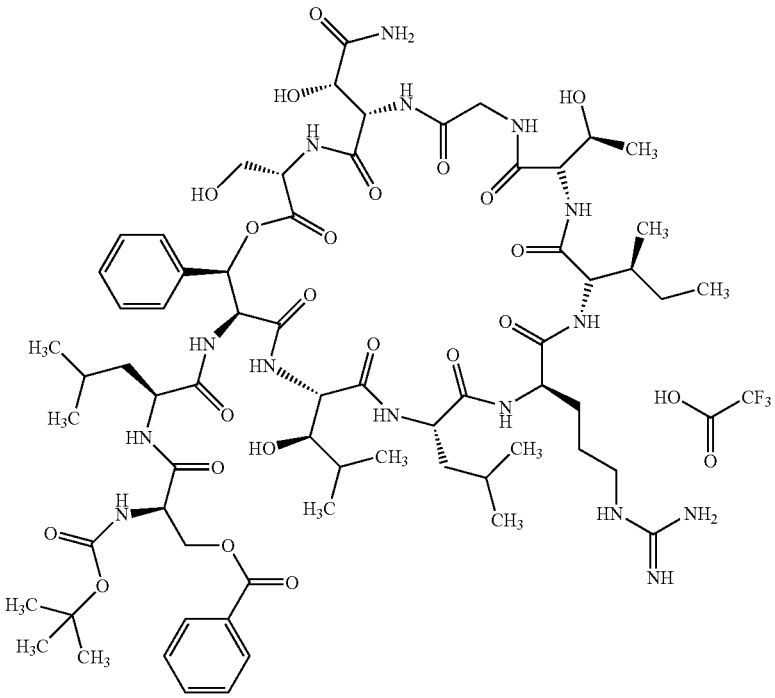<br>N-(tert-Butoxycarbonyl)-(O-benzoyl)-D-seryl-de(1-D-leucyl)lysobactin trifluoroacetate | HPLC/UV-Vis (method 36): $R_t$ = 4.17 min.<br>LC-MS (method 26): $R_t$ = 2.01 min,<br>MS (ESIpos.): m/z (%) = 1455.0 (20) [M + H]$^+$.<br><br>General procedure 19 from Example 11A (110 μmol) and N-(tert-butoxycarbonyl)-O-benzoyl)-D-serine.<br>Yield: 41% of theory |
| 147A | 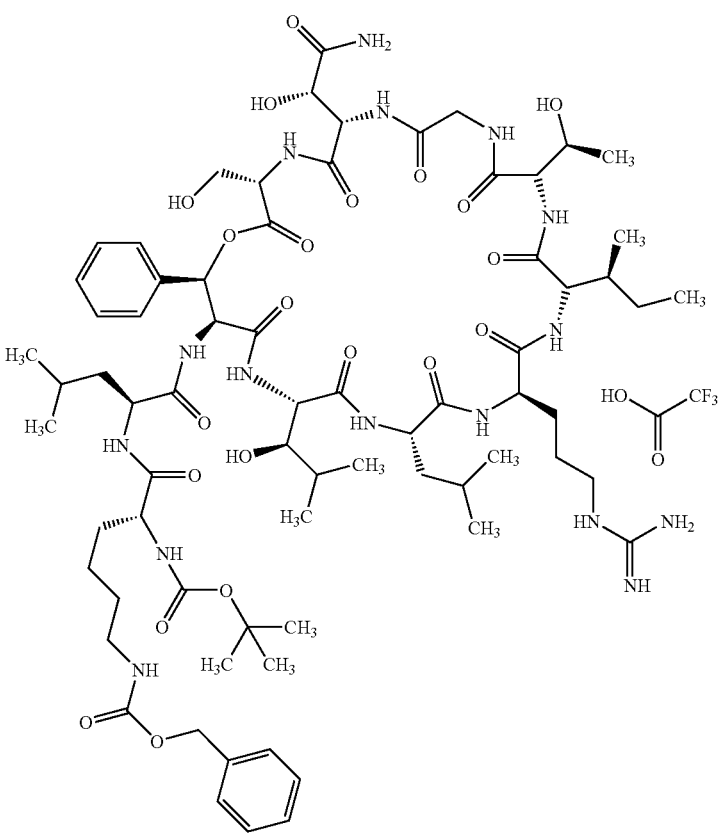 | HPLC/UV-Vis (method 36): $R_t$ = 4.13 min.<br>LC-MS (method 26): $R_t$ = 1.96 min,<br>MS (ESIpos.): m/z (%) = 1526.1 (50) [M + H]$^+$. |

TABLE 3-continued

N-protected nonadepsipeptides

| Ex. No. | Structure Name | Analytical data Prepration method |
|---|---|---|
| | N⁶-[(Benzyloxy)carbonyl]-N²-(tert-butoxycarbonyl)-D-lysyl-de(1-D-leucyl)lysobactin trifluoroacetate | General procedure 19 from Example 11A (110 μmol) and N⁶-[(benzyloxy)carbonyl]-N²-(tert-butoxycarbonyl)-D-lysine. Yield: 50% of theory |
| 148A | | LC-MS (method 26): R$_t$ = 1.93 min, MS (ESIpos.): m/z (%) = 1511.9 (30) [M + H]⁺. |
| | N⁵-[(Benzyloxy)carbonyl]-N²-[(butoxy)carbonyl]-D-ornithyl-de(1-D-leucyl)lysobactin trifluoroacetate | General procedure 19 from Example 11A (110 μmol) and N⁵-[(benzyloxy)carbonyl]-N²-[(butoxy)carbonyl]-D-ornithine. Yield: 48% of theory |

TABLE 3-continued

N-protected nonadepsipeptides

| Ex. No. | Structure Name | Analytical data Prepration method |
|---|---|---|
| 149A | (2S)-4-{[(Benzyloxy)carbonyl]amino}-2-[(tert-butoxycarbonyl)amino]butanoyl-de(1-D-leucyl)-lysobactin trifluoroacetate | HPLC/UV-Vis (method 36): $R_t$ = 4.08 min. LC-MS (method 26): $R_t$ = 1.94 min, MS (ESIpos.): m/z (%) = 1498.0 (20) $[M + H]^+$. General procedure 19 from Example 11A (110 μmol) and (2S)-4-{[(benzyloxy)-carbonyl]amino}-2-[(tert-butoxycarbonyl)amino]butyric acid. Yield: 49% of theory |
| 150A | | HPLC/UV-Vis (method 36): $R_t$ = 4.41 min. LC-MS (method 26): $R_t$ = 2.13 min, MS (ESIpos.): m/z (%) = 1455.0 (30) $[M + H]^+$. |

TABLE 3-continued

N-protected nonadepsipeptides

| Ex. No. | Structure Name | | Analytical data Prepration method |
|---|---|---|---|
| 151A | N-(tert-Butoxycarbonyl)-O-benzyl-D-threonyl-de(1-D-leucyl)lysobactin trifluoroacetate 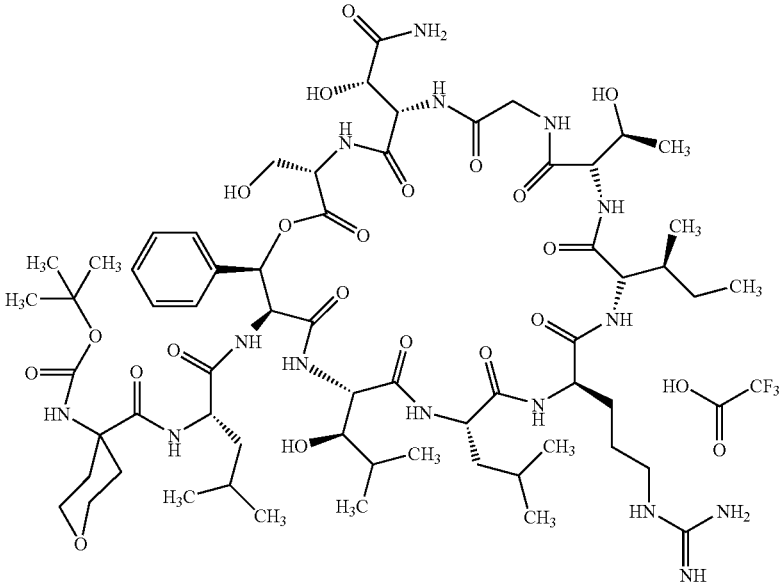 | | General procedure 19 from Example 11A (110 µmol) and N-(tert-butoxycarbonyl)-O-benzyl-D-threonine. Yield: 46% of theory<br><br>HPLC/UV-Vis (method 36): $R_t$ = 3.60 min.<br>LC-MS (method 26): $R_t$ = 1.78 min,<br>MS (ESIneg.): m/z (%) = 1390.8 [M − H]⁻. |
| 152A | 4-[(tert-Butoxycarbonyl)amino]tetrahydro-2H-pyran-4-carbonyl]-de(1-D-leucyl)lysobactin trifluoroacetate 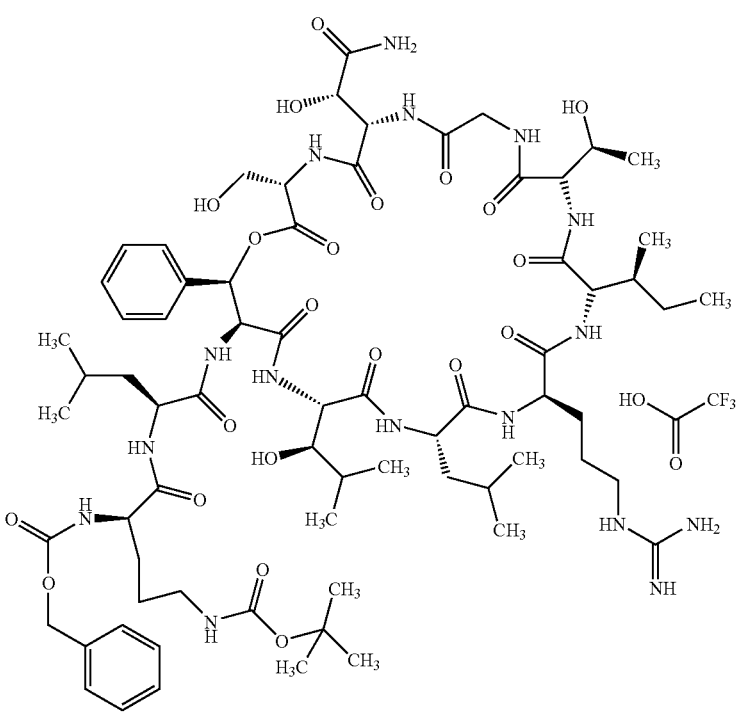 | | General procedure 19 from Example 11A (110 µmol) and 4-[(tert-butoxycarbonyl)-amino]tetrahydro-2H-pyran-4-carboxylic acid. Yield: 26% of theory<br><br>HPLC/UV-Vis (method 36): $R_t$ = 4.08 min.<br>LC-MS (method 26): $R_t$ = 1.99 min,<br>MS(ESIpos.): m/z (%) = 1512.7 (10) [M + H]⁺. |

TABLE 3-continued

N-protected nonadepsipeptides

| Ex. No. | Structure Name | Analytical data Preparation method |
|---|---|---|
| | $N^2$-(Benzyloxycarbonyl)-$N^5$-(tert-butoxycarbonyl)-D-ornithyl-de(1-D-leucyl)lysobactin trifluoroacetate | General procedure 19 from Example 11A (110 μmol) and $N^2$-(benzyloxycarbonyl)-$N^5$-(tert-butoxycarbonyl)-D-ornithine. Yield: 60% of theory |
| 153A | | HPLC/UV-Vis (method 36): $R_t$ = 4.13 min. LC-MS (method 26): $R_t$ = 1.99 min, MS (ESIpos.): m/z (%) = 1525.8 (20) $[M + H]^+$. |
| | $N^2$-(Benzyloxycarbonyl)-$N^6$-(tert-butoxycarbonyl)-D-lysyl-de(1-D-leucyl)lysobactin trifluoroacetate | General procedure 19 from Example 11A (110 μmol) and $N^2$-(benzyloxycarbonyl)-$N^6$-(tert-butoxycarbonyl)-D-lysine. Yield: 82% of theory |

TABLE 3-continued

N-protected nonadepsipeptides

| Ex. No. | Structure Name | Analytical data Prepration method |
|---|---|---|
| 154A | N²,N⁷,N⁸-tris-(Benzyloxycarbonyl)-D-arginyl-de(1-D-leu-cyl)lysobactin trifluoroacetate | HPLC/UV-Vis (method 36): $R_t$ = 4.4 min. LC-MS (method 26): $R_t$ = 2.49 min, MS (ESIpos.): m/z (%) = 1721.0 (10) [M + H]⁺. General procedure 19 from Example 11A (110 µmol) and N²,N⁷,N⁸-tris-(benzyloxy-carbo-nyl)-D-artinine. Yield: 60% of theory |

Example 155A

N-(tert-Butoxycarbonyl)-3-tert-butyl-D-alanyl-N$^1$-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-3-tert-butyl-L-alaninamide trifluoroacetate {N-tert-Butoxycarbonyl-3-tert-butyl-D-alanyl-3-tert-butyl-L-alanyl-de(1-D-leucyl-2-L-leucyl)-lysobactin trifluoroacetate}

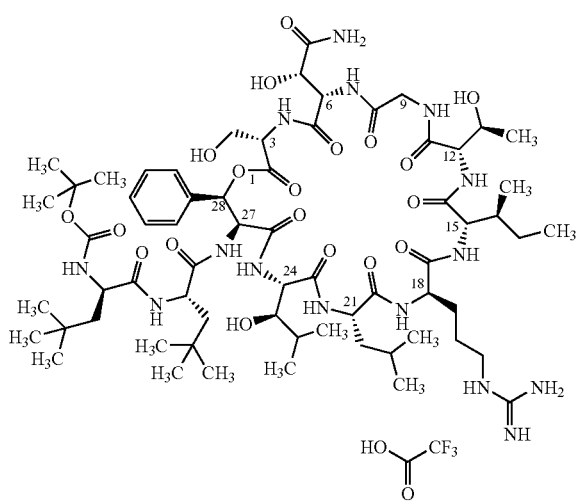

De(1-D-leucyl-2-L-leucyl)lysobactin bistrifluoroacetate (Example 13A, 500 mg, 0.39 mmol) and N-(tert-butoxycarbonyl)-3-tert-butyl-D-alanyl-3-tert-butyl-L-alanine (Example 59A, 583 mg, 1.56 mmol) are reacted by general procedure 4. The crude product is finally purified by preparative HPLC (method 24). 445 mg (95% of theory) of product are obtained.

HPLC/UV-Vis (method 13): $R_t$=7.9 min.

$\lambda_{max}$ (qualitative)=220 nm (s), 255-270 (w).

LC-MS (method 26): $R_t$=2.16 min;

MS (ESIpos.): m/z (%)=653 (100) [M−Boc+2H]$^{2+}$, 1404 (30) [M+H]$^+$.

MS (ESIneg.): m/z (%)=701 (100), 1403 (20) [M−H]$^-$, 1449 [M−H+HCO$_2$H]$^-$

LC-MS (method 29): $R_t$=5.5 min;

MS (ESIpos.): m/z (%)=653 (100) [M−Boc+2H]$^{2+}$, 1405 (90) [M+H]$^+$.

HR-TOF-MS (method 21): C$_{65}$H$_{110}$N$_{15}$O$_{19}$ calc. 1404.8102, found 1404.8057 [M+H]$^+$.

Example 156A

N-tert-Butoxycarbonyl-3-tert-butyl-D-alanyl-3-(3-pyridyl)-L-alanyl-de(1-D-leucyl-2-L-leucyl)lysobactin bistrifluoroacetate N-Methylmorpholine (4 equivalents, 0.13 mmol) and HATU (2.6 equivalents, 0.08 mmol) are slowly added at −78° C. to a solution of Example 13A (1.0 equivalent, 0.03 mmol) and Example 60A (2.5 equivalents, 0.08 mmol) in dry dimethylformamide (2 ml). The reaction mixture is slowly (approx. 2 h) warmed to 0° C., with complete conversion being observed by means of HPLC/UV-Vis (method 36). The reaction is stopped with potassium dihydrogenphosphate (5.0 equivalents, 0.16 mmol). The reaction mixture is purified by gel chromatography (method 6, mobile phase methanol/acetone 4/1), resulting in 53.6 mg (80% of theory) of product.

HPLC/UV-Vis (method 36): $R_t$=3.83 min.

LC-MS (method 26): $R_t$=2.08 min;

MS (ESIpos.): m/z (%)=713 (100) [M+2H]$^{2+}$, 1425 (15) [M+H]$^+$;

MS (ESIneg.): m/z (%)=711 (100) [M−2H]$^{2-}$, 1423 (30) [M−H]$^-$.

HR-TOF-MS (method 21): C$_{66}$H$_{105}$N$_{16}$O$_{19}$ [M+H]$^+$calc. 1425.7742, found 1425.7722.

TABLE 4

N-Protected nonadepsipeptides

| Ex. No. | Structure Name | Analytical data Preparation method |
|---|---|---|
| 157A | 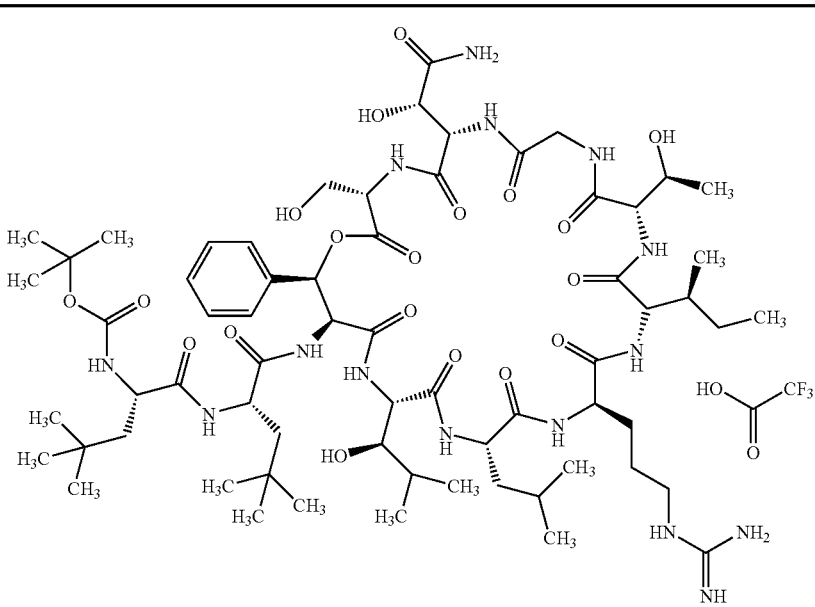<br>N-tert-Butoxycarbonyl-3-tert-butyl-L-alanyl-3-tert-butyl-L-alanyl-de(1-D-leucyl-2-L-leucyl)lysobactin trifluoroacetate | HPLC/UV-Vis (method 13): $R_t$ = 7.3 min. LC-MS (method 27): $R_t$ = 2.45 min; MS (ESIpos.): m/z (%) = 653 (100) $[M - Boc + 2H]^{2+}$, 1405 (30) $[M + H]^+$.<br><br>General procedure 4 from Example 13A (0.05 mmol) and Example 61A (0.2 mmol). Purification by method 7. Yield 51% of theory. |
| 158A | 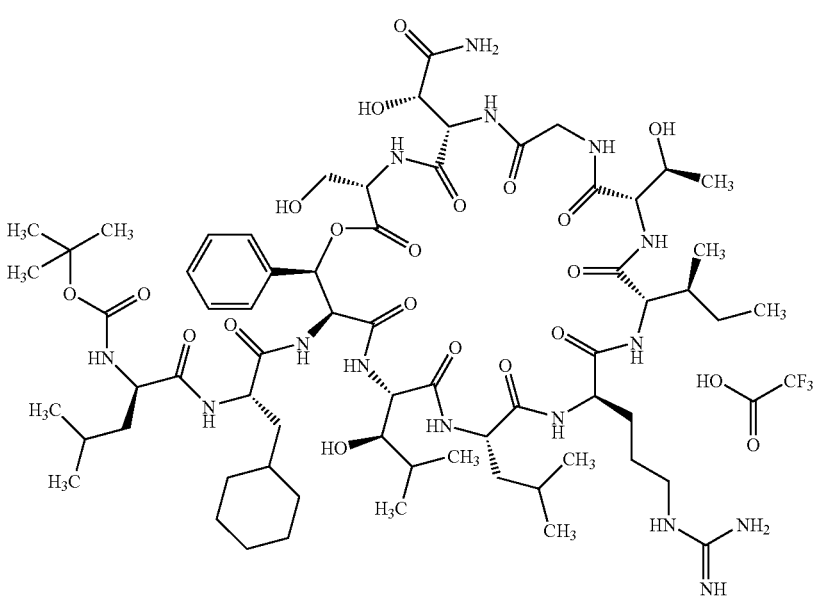<br>N-tert-Butoxycarbonyl-D-leucyl-3-cyclohexyl-L-alanyl de(1-leucyl-2-L-leucyl)lysobactin trifluoroacetate | HPLC/UV-Vis (method 13): $R_t$ = 7.54 min, $\lambda_{max}$ (qualitative) = 220 nm (s), 255-270 (m). LC-MS (method 29): $R_t$ = 5.41 min; MS (ESIpos.): m/z (%) = 659 (100) $[M - Boc + 2H]^{2+}$, 1417 (80) $[M + H]^+$.<br><br>General procedure 4 from Example 13A (0.02 mmol) and Example 62A (0.06 mmol). Purification by method 7. Yield 75% of theory |

TABLE 4-continued

N-Protected nonadepsipeptides

| Ex. No. | Structure Name | Analytical data Preparation method |
|---|---|---|
| 159A | 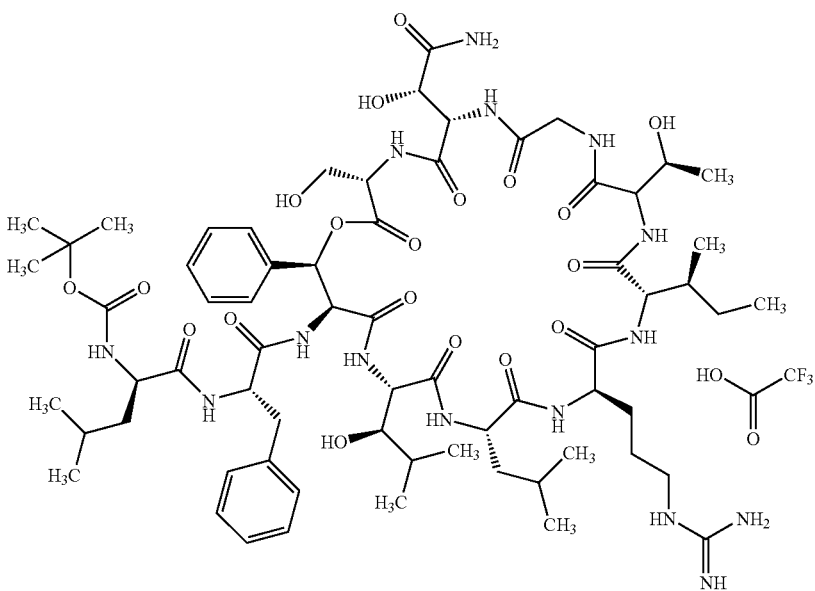<br>N-tert-Butoxycarbonyl-D-leucyl-L-phenylalanyl-de(1-D-leucyl-2-L-leucyl)lysobactin trifluoroacetate | HPLC/UV-Vis (method 13):<br>$R_t$ = 7.32 min,<br>$\lambda_{max}$ (qualitative) = 220 nm (s), 255-270 (m).<br>LC-MS (method 12):<br>$R_t$ = 5.42 min;<br>MS (ESIpos.): m/z (%) = 656 (80) [M − Boc + 2H]$^{2+}$, 1411 (100) [M + H]$^+$.<br><br>General procedure 4 from Example 13A (0.02 mmol) and Example 63A (0.06 mmol). Purification by method 7.<br>Yield 57% of theory |
| 160A | 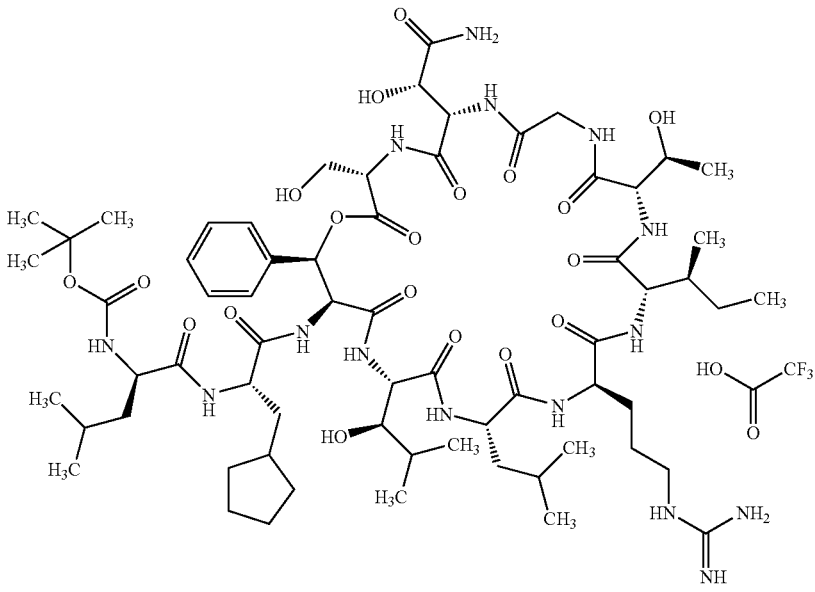<br>N-tert-Butoxycarbonyl-D-leucyl-3-cyclopentyl-L-alanyl-de(1-D-leucyl-2-L-leucyl)lysobactin trifluoroacetate | HPLC/UV-Vis (method 13):<br>$R_t$ = 7.46 min,<br>$\lambda_{max}$ (qualitative) = 220 nm (s), 255-270 (m).<br>LC-MS (method 12):<br>$R_t$ = 5.46 min;<br>MS (ESIpos.): m/z (%) = 652 (100) [M − Boc + 2H]$^{2+}$, 1403 (90) [M + H]$^+$.<br><br>General procedure 4 from Example 13A (0.01 mmol) and Example 64A (0.05 mmol). Purification by method 7.<br>Yield 55% of theory |

TABLE 4-continued

N-Protected nonadepsipeptides

| Ex. No. | Structure Name | Analytical data Preparation method |
|---|---|---|
| 161A | 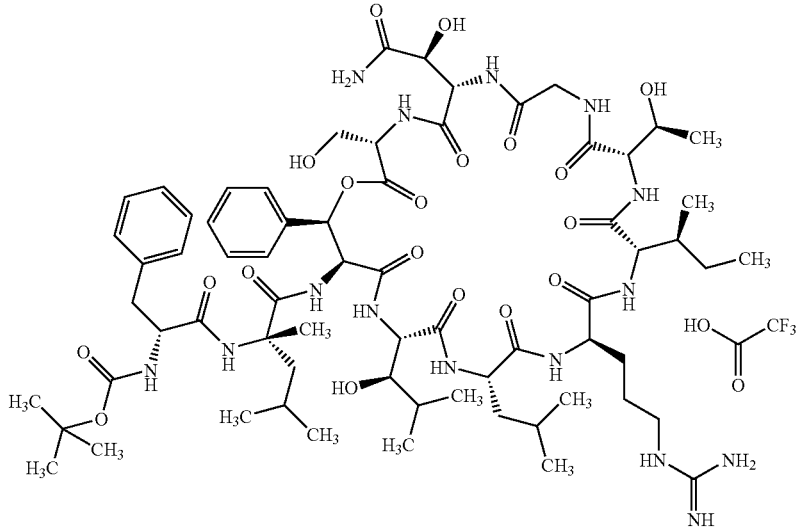<br>N-tert-Butoxycarbonyl-D-phenylalanyl-2-methyl-L-leucyl-de(1-D-leucyl-2-leucyl)lysobactin trifluoroacetate | HPLC/UV-Vis (method 13):<br>$R_t$ = 7.20 min,<br>$\lambda_{max}$ (qualitative) = 220 nm (s), 255-270 (m).<br>LC-MS (method 29):<br>$R_t$ = 5.33 min;<br>MS (ESIpos.): m/z (%) = 663 (100) $[M - Boc + 2H]^{2+}$, 1425 (90) $[M + H]^+$.<br><br>General procedure 4 from Example 13A (0.01 mmol) and Example 65A (0.05 mmol). Purification by method 7.<br>Yield 8% of theory |
| 162A | 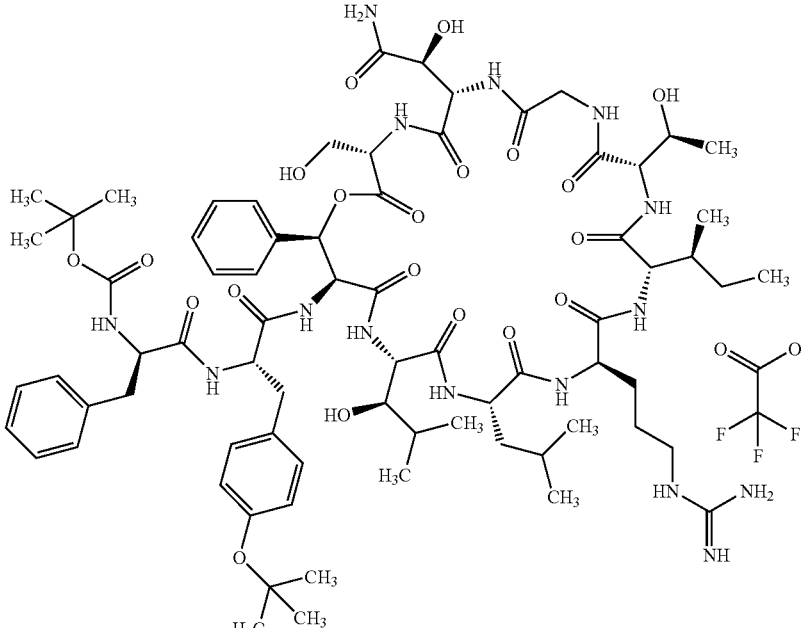<br>N-tert-Butoxycarbonyl-D-phenylalanyl-O-tert-butyl-L-tyrosyl-de(1-D-leucyl-2-L-leucyl)lysobactin trifluoroacetate | HPLC/UV-Vis (method 13):<br>$R_t$ = 7.51 min.<br>LC-MS (method 29):<br>$R_t$ = 5.5 min;<br>MS (ESIneg.):m/z (%) = 1515 (100) $[M - H]^-$.<br><br>General procedure 4 from Example 13A (0.02 mmol) and Example 83A (0.06 mmol). Purification by method 7.<br>Yield 58% of theory |

TABLE 4-continued

N-Protected nonadepsipeptides

| Ex. No. | Structure Name | Analytical data Preparation method |
|---|---|---|
| 163A | 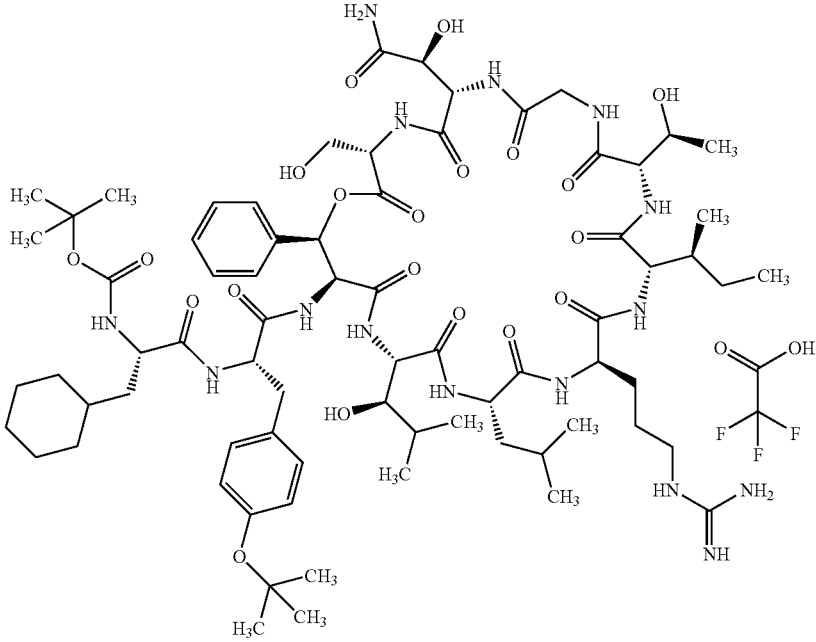<br>N-tert-Butoxycarbonyl-3-cyclohexyl-L-alanyl-O-tert-butyl-L- tyroyl-de(1-D-leucyl-2-L-leucyl)lysobactin trifluoroacetate | HPLC/UV-Vis (method 13): $R_t$ = 7.83 min. LC-MS (method 29): $R_t$ = 5.6 min; MS (ESIpos.): m/z (%) = 734 (100) [M − Boc + 2H]$^{2+}$, 1523 (100) [M + H]$^+$.<br><br>General procedure 4 from Example 13A (0.02 mmol) and Example 84A (0.06 mmol). Purification by method 7.<br>Yield 44% of theory |
| 164A | 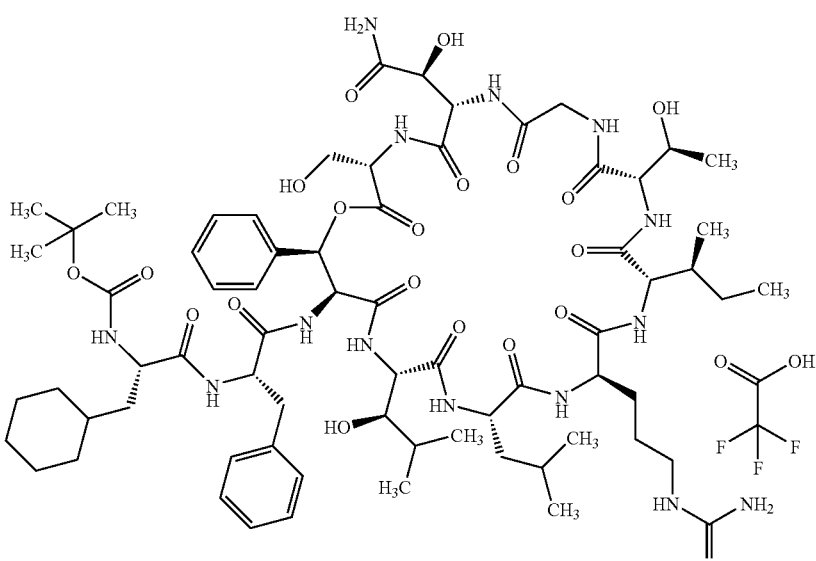<br>N-tert-Butoxycarbonyl-3-cyclohexyl-L-alanyl-L-phenylalanyl-de(1-D-leucyl-2-L-leucyl)lysobactin trifluoroacetate | HPLC/UV-Vis (method 13): $R_t$ = 7.83 min. LC-MS (method 29): $R_t$ = 5.4 min; MS (ESIpos.): m/z (%) = 676 (100) [M − Boc + 2H]$^{2+}$, 698 (60), 1451 (60) [M + H]$^+$.<br><br>General procedure 4 from Example 13A (0.02 mmol) and Example 85A (0.06 mmol). Purification by method 7.<br>Yield 55% of theory |

TABLE 4-continued

N-Protected nonadepsipeptides

| Ex. No. | Structure Name | Analytical data Preparation method |
|---|---|---|
| 165A | 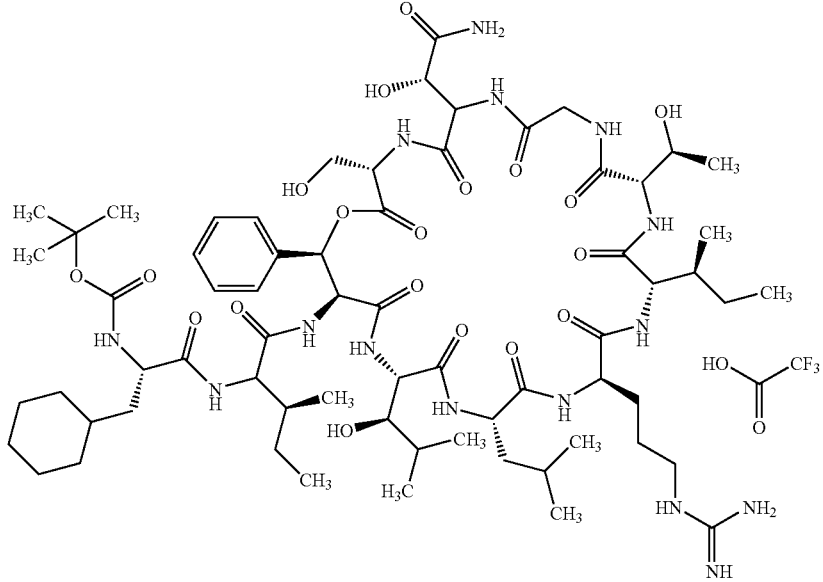<br>N-tert-Butoxycarbonyl-3-cyclohexyl-L-alanyl-L-isoleucyl-de(1-D-leucyl-2-L-leucyl)lysobactin trifluoroacetate | HPLC/UV-Vis (method 13):<br>$R_t$ = 7.37 min.<br>LC-MS (method 26):<br>$R_t$ = 2.09 min;<br>MS (ESIpos.): m/z (%) = 659 (100) $[M - Boc + 2H]^{2+}$, 1417 (30) $[M + H]^+$.<br><br>General procedure 4 from Example 13A (0.02 mmol) and Example 86A (0.06 mmol). Purification by method 7.<br>Yield 41% of theory |
| 166A | 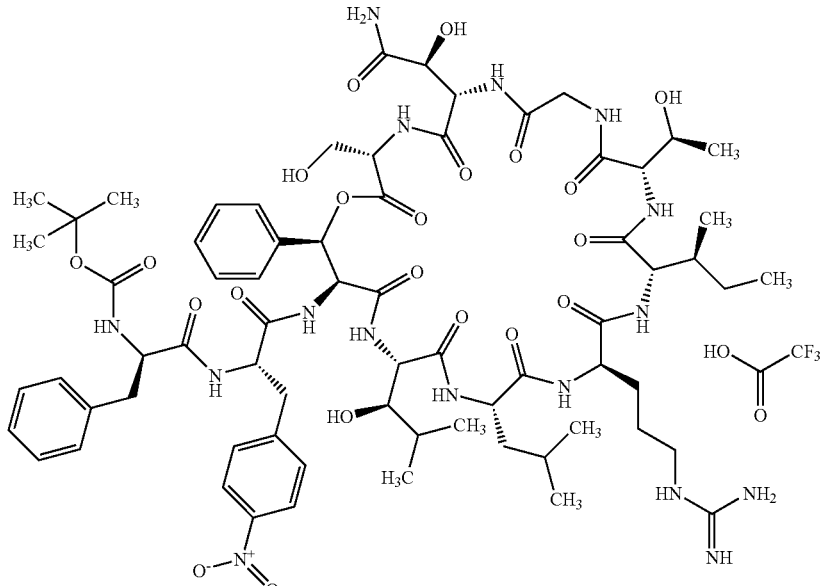<br>N-tert-Butoxycarbonyl-D-phenylalanyl-4-nitro-L-phenylalanyl-de(1-D-leucyl-2-L-leucyl)lysobactin trifluoroacetate | HPLC/UV-Vis (method 13):<br>$R_t$ = 7.18 min.<br>LC-MS (method 29):<br>$R_t$ = 5.3 min;<br>MS (ESIpos.): m/z (%) = 696 (100) $[M - Boc + 2H]^{2+}$, 1490 (80) $[M + H]^+$.<br><br>General procedure 4 from Example 13A (0.02 mmol) and Example 87A (0.06 mmol). Purification by method 7.<br>Yield 49% of theory |

TABLE 4-continued

N-Protected nonadepsipeptides

| Ex. No. | Structure Name | Analytical data Preparation method |
|---|---|---|
| 167A | 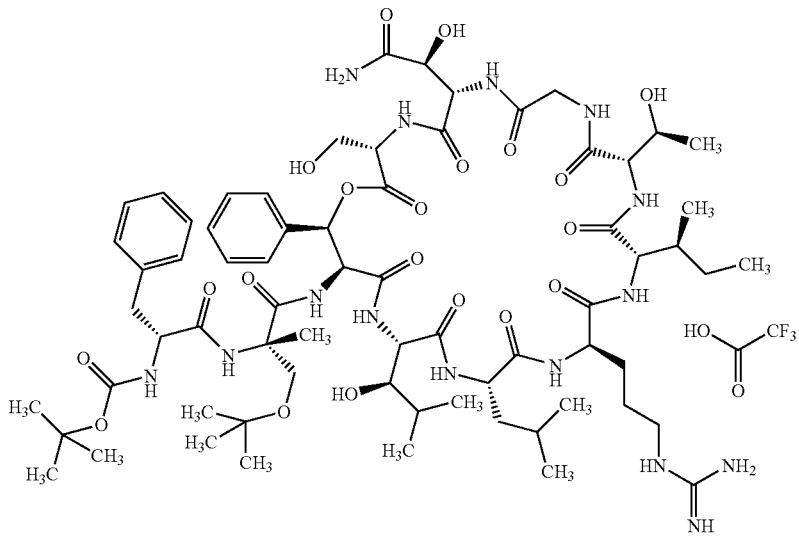<br>N-tert-Butoxycarbonyl-D-phenylalanyl-O³-tert-butyl-L-seryl-de(1-D-leucyl-2-L-leucyl)lysobactin trifluoroacetate | HPLC/UV-Vis (method 13):<br>$R_t$ = 7.19 min.<br>LC-MS (method 29):<br>$R_t$ = 5.3 min;<br>MS (ESIpos.): m/z (%) = 671<br>(60) [M − Boc + 2H]$^{2+}$, 1441<br>(100) [M + H]$^+$.<br><br>General procedure 4 from Example 13A (0.03 mmol) and Example 82A (0.13 mmol). Purification by method 7.<br>Yield 50% of theory |
| 168A | 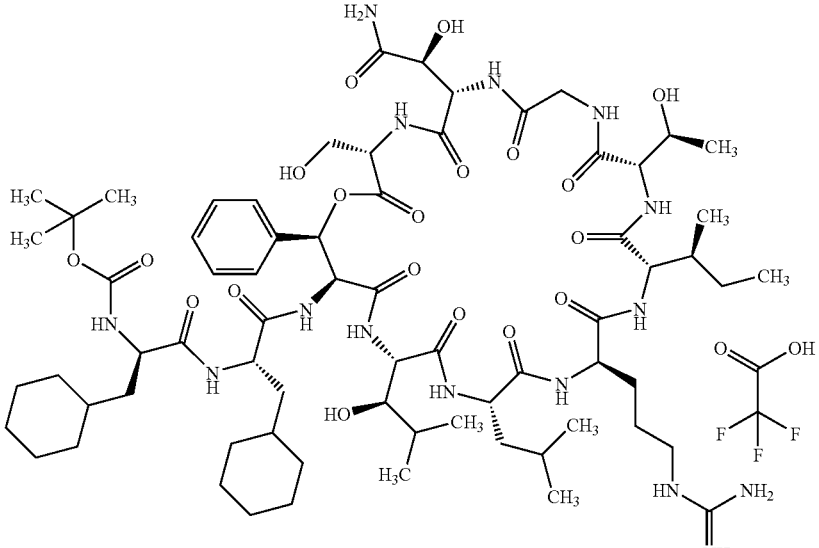<br>N-tert-Butoxycarbonyl-3-cyclohexyl-D-alanyl-3-cyclohexyl-L-alanyl-de(1-D-leucyl-2-L-leucyl)lysobactin trifluoroacetate | HPLC/UV-Vis (method 13):<br>$R_t$ = 7.75 min.<br>LC-MS (method 29):<br>$R_t$ = 5.7 min;<br>MS (ESIpos.): m/z (%) = 679<br>(100) [M − Boc + 2H]$^{2+}$, 1457<br>(100) [M + H]$^+$.<br><br>General procedure 4 from Example 13A (0.02 mmol) and Example 66A (0.06 mmol). Purification by method 7.<br>Yield 16% of theory |

TABLE 4-continued

N-Protected nonadepsipeptides

| Ex. No. | Structure Name | Analytical data Preparation method |
|---|---|---|
| 169A | 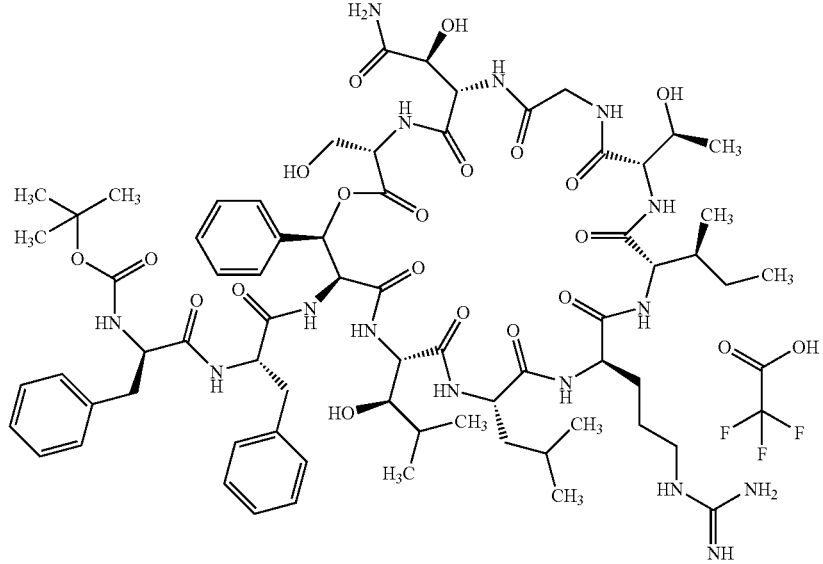<br>N-tert-Butoxycarbonyl-D-phenylalanyl-L-phenylalanyl-de(1-D-leucyl-2-L-leucyl)lysobactin trifluoroacetate | HPLC/UV-Vis (method 13):<br>$R_t$ = 7.18 min.<br>LC-MS (method 29):<br>$R_t$ = 5.31 min;<br>MS (ESIpos.): m/z (%) = 673<br>(50) $[M - Boc + 2H]^{2+}$, 1445<br>(100) $[M + H]^+$.<br><br>General procedure 4 from Example 13A (0.02 mmol) and Example 67A (0.06 mmol). Purification by method 7.<br>Yield 74% of theory |
| 170A | 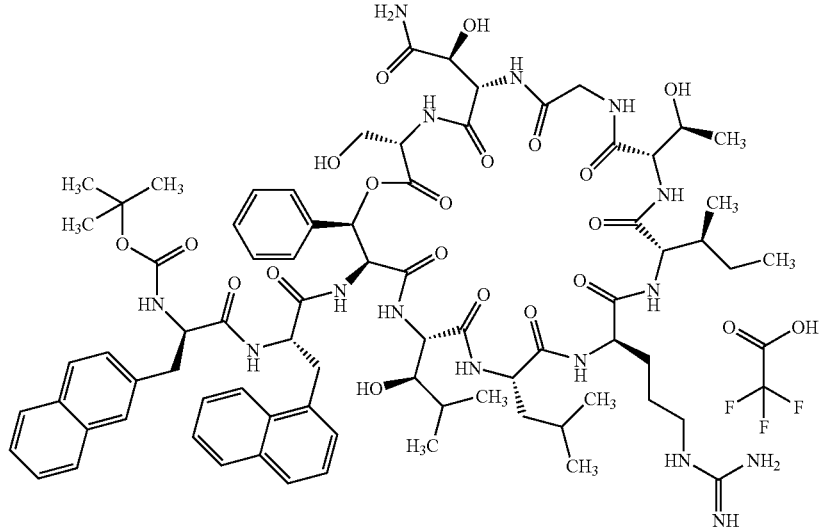<br>N-tert-Butoxycarbonyl-3-(2-naphthyl)-D-alanyl-3-(1-naphthyl)-L-phenylalanyl-de(1-D-leucyl-2-L-leucyl)lysobactin trifluoroacetate | HPLC/UV-Vis (method 13):<br>$R_t$ = 7.53 min,<br>$\lambda_{max}$ (qualitative) = 220 nm (s), 280 (m).<br>LC-MS (method 29):<br>$R_t$ = 5.52 min;<br>MS (ESIpos.): m/z (%) = 723<br>(100) $[M - Boc + 2H]^{2+}$, 1545<br>(10) $[M + H]^+$.<br><br>General procedure 4 from Example 13A (0.02 mmol) and Example 68A (0.06 mmol). Purification by method 7.<br>Yield 33% of theory |

TABLE 4-continued

N-Protected nonadepsipeptides

| Ex. No. | Structure Name | Analytical data Preparation method |
|---|---|---|
| 171A | 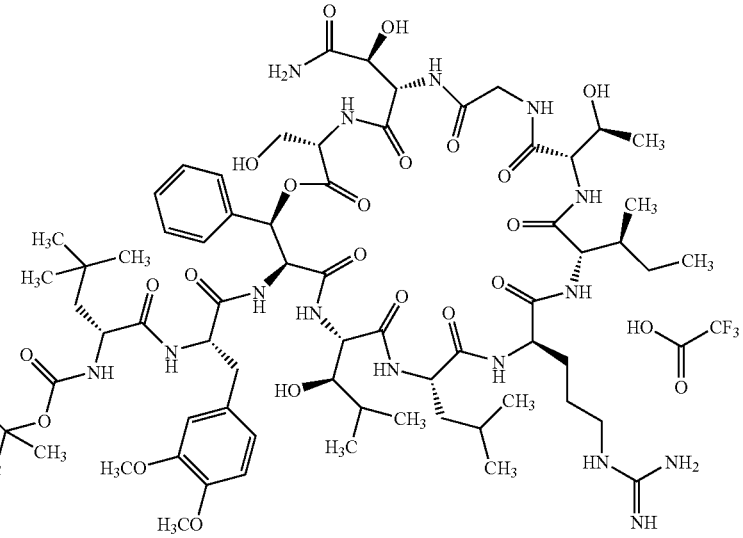<br>N-tert-Butoxycarbonyl-3-tert-butyl-D-alanyl-<br>3-(3,4-dimethoxyphenyl)-L-alanyl-de(1-D-leucyl-<br>2-L-leucyl)lysobactin trifluoroacetate | HPLC/UV-Vis (method 13):<br>$R_t$ = 7.05 min.<br>LC-MS (method 29):<br>$R_t$ = 5.2 min;<br>MS (ESIpos.): m/z (%) = 693<br>(100) $[M - Boc + 2H]^{2+}$, 1485<br>(60) $[M + H]^+$.<br><br>General procedure 11 from<br>Example 13A (0.03 mmol)<br>and Example 69A<br>(0.13 mmol). Purification by<br>method 7.<br>Yield 23% of theory |
| 172A | 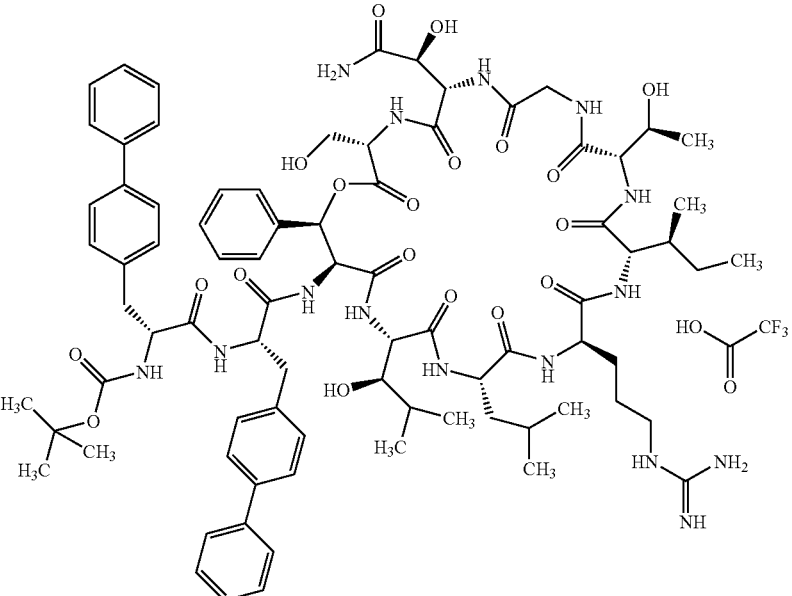<br>N-tert-Butoxycarbonyl-4-phenyl-D-phenylalanyl-4-<br>phenyl-L-phenylalanyl-de(1-D-leucyl-<br>2-L-leucyl)lysobactin trifluoroacetate | HPLC/UV-Vis (method 13):<br>$R_t$ = 7.91 min.<br>LC-MS (method 29):<br>$R_t$ = 5.8 min;<br>MS (ESIpos.): m/z (%) = 749<br>(100) $[M - Boc + 2H]^{2+}$, 1597<br>(30) $[M + H]^+$.<br><br>General procedure 4 from<br>Example 13A (0.03 mmol)<br>and Example 70A<br>(0.13 mmol). Purification by<br>method 7.<br>Yield 56% of theory |

TABLE 4-continued

N-Protected nonadepsipeptides

| Ex. No. | Structure Name | Analytical data Preparation method |
|---|---|---|
| 173A | 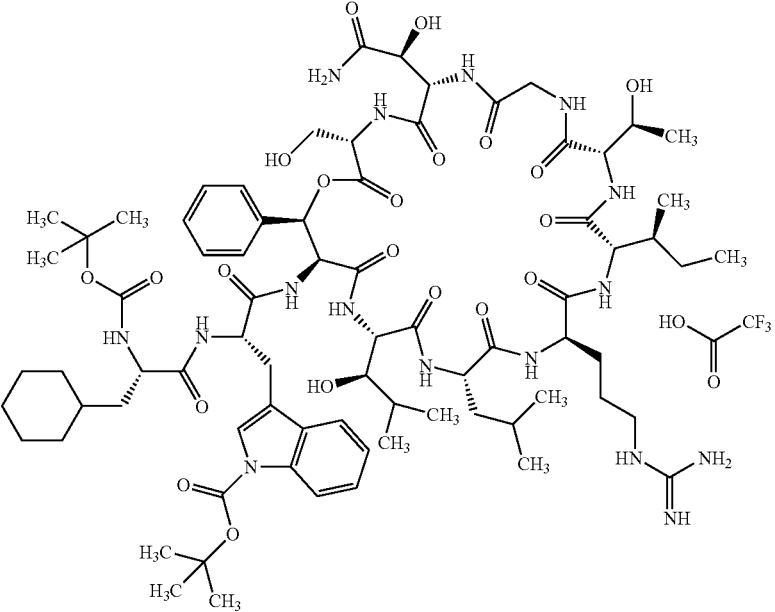  N-tert-Butoxycarbonyl-3-cyclohexyl-L-alanyl-N$^{indole}$-tert-butoxycarbonyl-L-tryptophyl-de(1-D-leucyl-2-L-luecyl)lysobactin trifluoroacetate | HPLC/UV-Vis (method 13): $R_t$ = 7.98 min. LC-MS (method 29): $R_t$ = 5.7 min; MS (ESIpos.): m/z (%) = 746 (60) [M − Boc + 2H]$^{2+}$, 1590 (100) [M + H]$^+$.  General procedure 4 from Example 13A (0.02 mmol) and Example 79A (0.06 mmol). Purification by method 7. Yield 29% of theory |
| 174A | 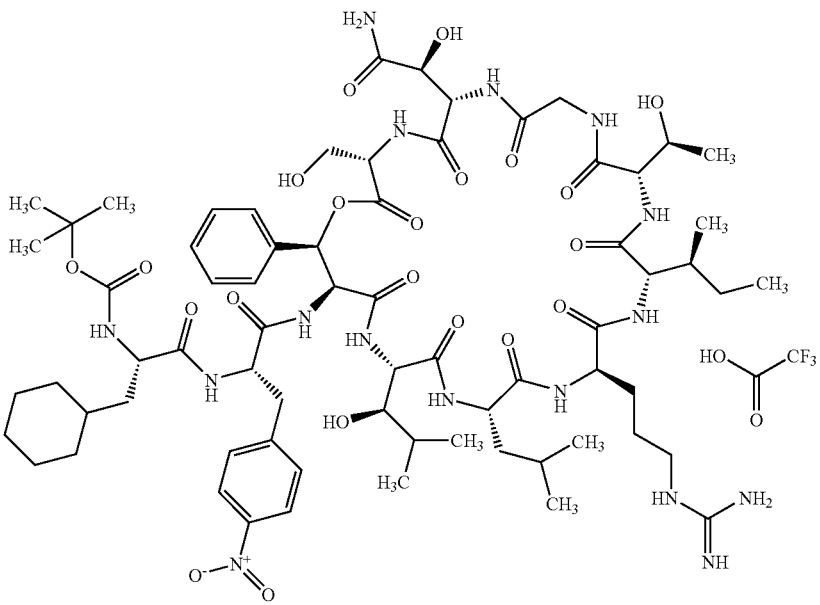  N-tert-Butoxycarbonyl-3-cyclohexyl-L-alanyl-4-nitro-L-phenylalanyl-de(1-D-leucyl-2-L-leucyl)lysobactin trifluoroacetate | HPLC/UV-Vis (method 13): $R_t$ = 7.52 min, $\lambda_{max}$ (qualitative) = 210 nm (s), 272 (m). LC-MS (method 29): $R_t$ = 5.5 min; MS (ESIpos.): m/z (%) = 699 (100) [M − Boc + 2H]$^{2+}$, 1496 (90) [M + H]$^+$.  General procedure 4 from Example 13A (0.02 mmol) and Example 80A (0.06 mmol). Purification by method 7. Yield 17% of theory |

TABLE 4-continued

N-Protected nonadepsipeptides

| Ex. No. | Structure Name | Analytical data Preparation method |
|---|---|---|
| 175A | 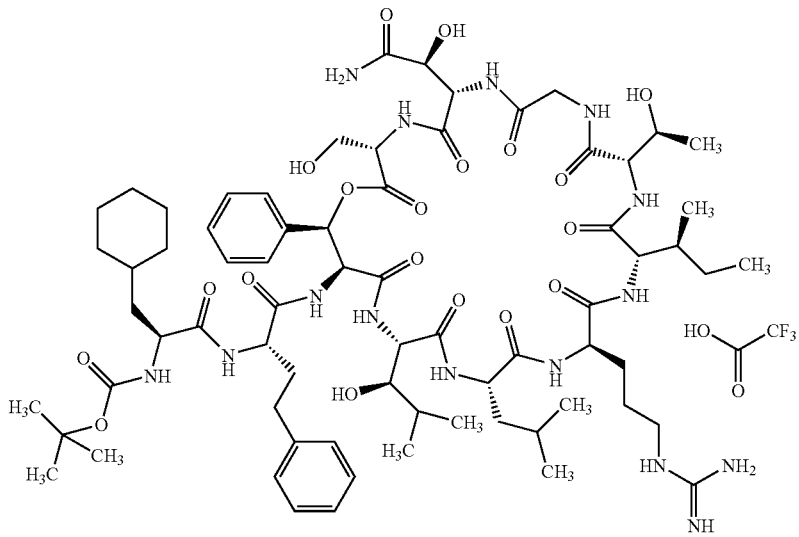<br>N-tert-Butoxycarbonyl-3-cyclohexyl-L-alanyl-3-benzyl-L-alanyl-de(1-D-leucyl-2-L-leucyl)lysobactin trifluoroacetate | HPLC/UV-Vis (method 13):<br>$R_t$ = 7.64 min.<br>LC-MS (method 29):<br>$R_t$ = 5.5 min;<br>MS (ESIpos.): m/z (%) = 683 (100) [M − Boc + 2H]$^{2+}$, 1465 (50) [M + H]$^+$.<br><br>General procedure 4 from Example 13A (0.02 mmol) and Example 81A (0.09 mmol). Purification by method 7.<br>Yield 52% of theory |
| 176A | 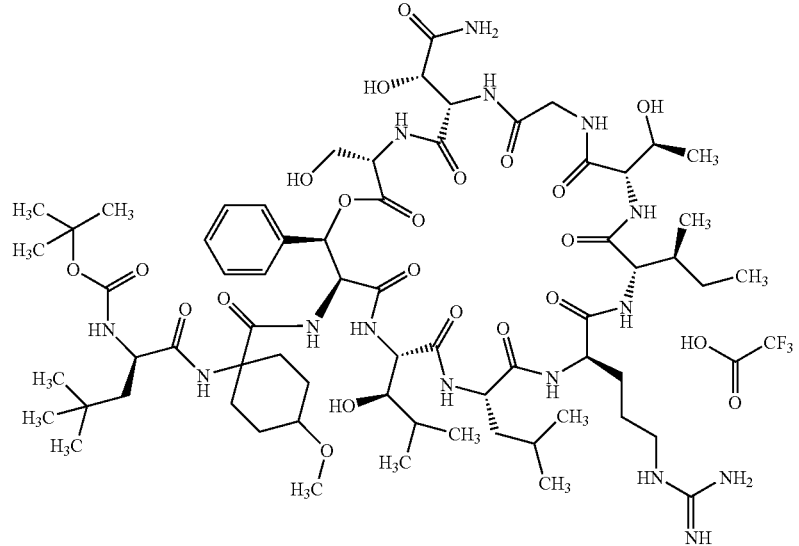<br>N-tert-Butoxycarbonyl-3-tert-butyl-D-alanyl-(1-amino-4-methoxycyclohexylcarbonyl)-de(1-D-leucyl-2-L-leucyl)lysobactin trifluoroacetate | HPLC/UV-Vis (method 13):<br>$R_t$ = 7.18 min.<br>LC-MS (method 26):<br>$R_t$ = 2.23 min;<br>MS (ESIpos.): m/z (%) = 667 (100) [M − Boc + 2H]$^{2+}$, 1050 (10), 1433 (20) [M + H]$^+$.<br><br>General procedure 11 from Example 13A (0.05 mmol) and Example 71A (0.09 mmol). Purification by method 7.<br>Yield 42% of theory |

TABLE 4-continued

N-Protected nonadepsipeptides

| Ex. No. | Structure Name | Analytical data Preparation method |
|---|---|---|
| 177A | 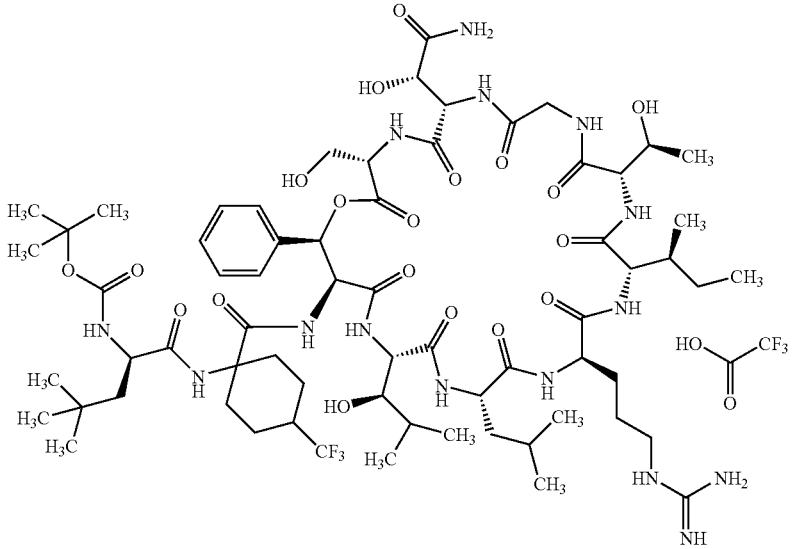<br>N-tert-Butoxycarbonyl-3-tert-butyl-D-alanyl-(1-amino-4-(trifluoromethyl)cyclohexylcarbonyl)-de(1-D-leucyl-2-L-leucyl)lysobactin trifluoroacetate | HPLC/UV-Vis (method 13):<br>$R_t$ = 7.69 min.<br>LC-MS (method 26):<br>$R_t$ = 2.37 min;<br>MS (ESIpos.): m/z (%) = 686 (100) $[M - Boc + 2H]^{2+}$, 1472 (30) $[M + H]^+$.<br><br>General procedure 11 from Example 13A (0.05 mmol) and Example 72A (0.19 mmol). Purification by method 7.<br>Yield 33% of theory |
| 178A | 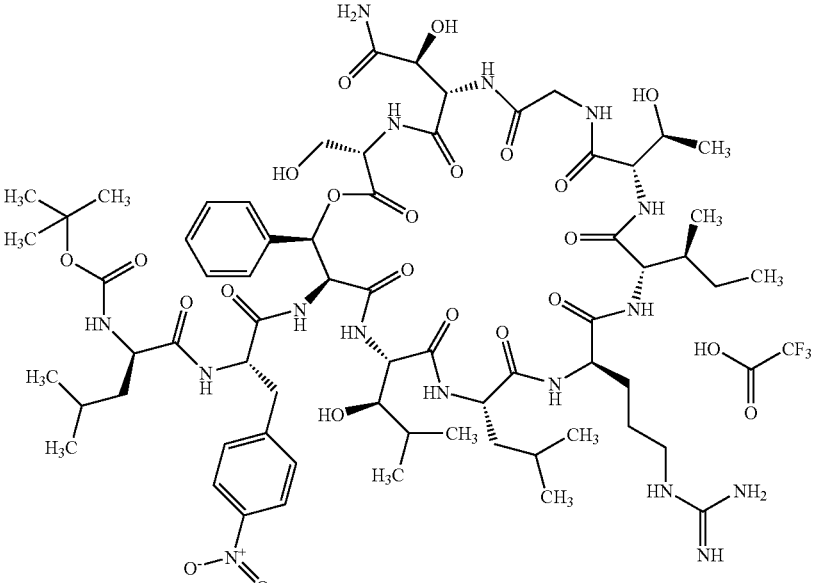<br>N-tert-Butoxycarbonyl-D-leucyl-4-nitro-L-phenylalanyl-de(1-D-leucyl-2-L-leucyl)lysobactin trifluoroacetate | HPLC/UV-Vis (method 13):<br>$R_t$ = 7.37 min.<br>LC-MS (method 26):<br>$R_t$ = 2.24 min;<br>MS (ESIpos.): m/z (%) = 679 (100) $[M - Boc + 2H]^{2+}$, 1456 (30) $[M + H]^+$.<br><br>General procedure 11 from Example 13A (0.08 mmol) and Example 73A (0.31 mmol). Purification by method 7.<br>Yield 30% of theory |

TABLE 4-continued

N-Protected nonadepsipeptides

| Ex. No. | Structure Name | Analytical data Preparation method |
|---|---|---|
| 179A | 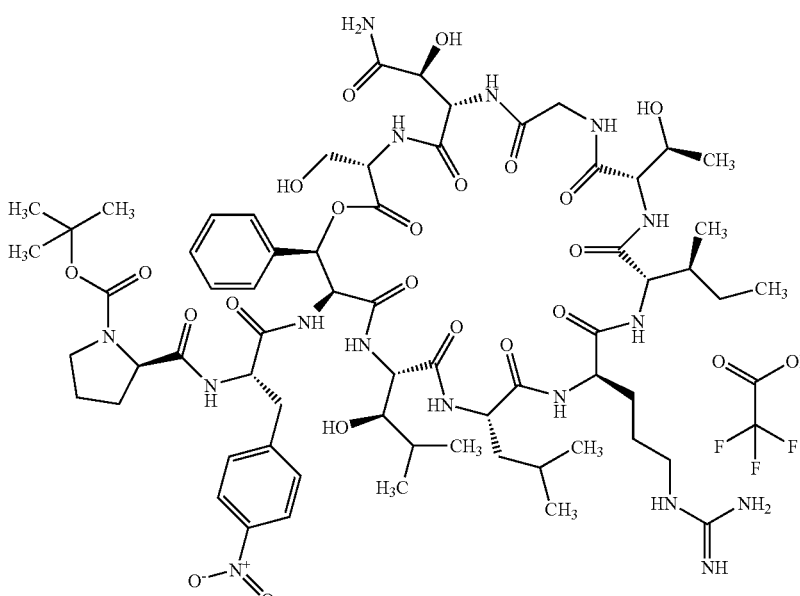<br>N-tert-Butoxycarbonyl-D-prolyl-4-nitro-L-phenylalanyl-de(1-D-leucyl-2-L-leucyl)lysobactin trifluoroacetate | HPLC/UV-Vis (method 13):<br>$R_t$ = 6.94 min,<br>$\lambda_{max}$ (qualitative) = 220 nm (s), 272 (m).<br>LC-MS (method 29):<br>$R_t$ = 5.2 min;<br>MS (ESIpos.): m/z (%) = 671 (100) $[M - Boc + 2H]^{2+}$, 1440 (70) $[M + H]^+$.<br><br>General procedure 4 from Example 13A (0.02 mmol) and Example 78A (0.06 mmol). Purification by method 7.<br>Yield 55% of theory |
| 180A | 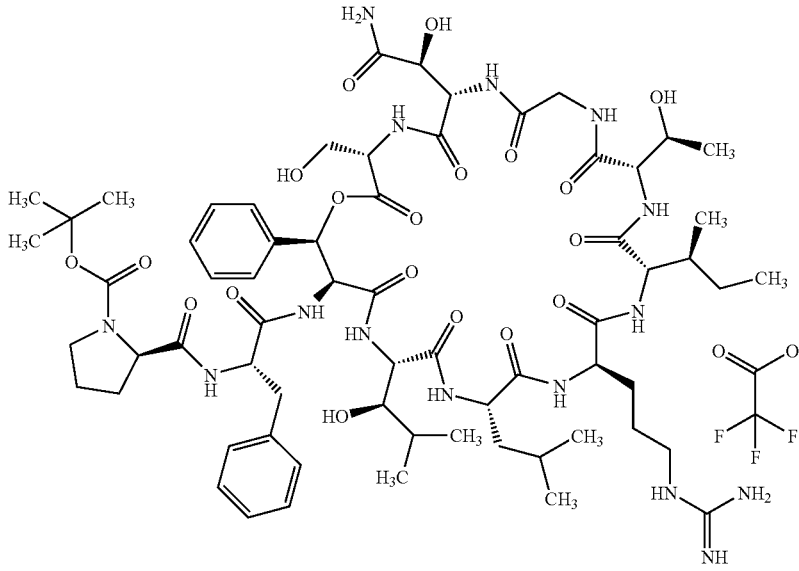<br>N-tert-Butoxycarbonyl-D-prolyl-L-phenylalanyl-de(1-D-leucyl-2-L-leucyl)lysobactin trifluoroacetate | HPLC/UV-Vis (method 13):<br>$R_t$ = 6.39 min.<br>LC-MS (method 29):<br>$R_t$ = 5.2 min;<br>MS (ESIpos.): m/z (%) = 648 (35) $[M - Boc + 2H]^{2+}$, 1395 (100) $[M + H]^+$.<br><br>General procedure 4 from Example 13A (0.016 mmol) and Example 76A (0.063 mmol). Purification by method 7.<br>Yield 40% of theory |

TABLE 4-continued

N-Protected nonadepsipeptides

| Ex. No. | Structure Name | Analytical data Preparation method |
|---|---|---|
| 181A | 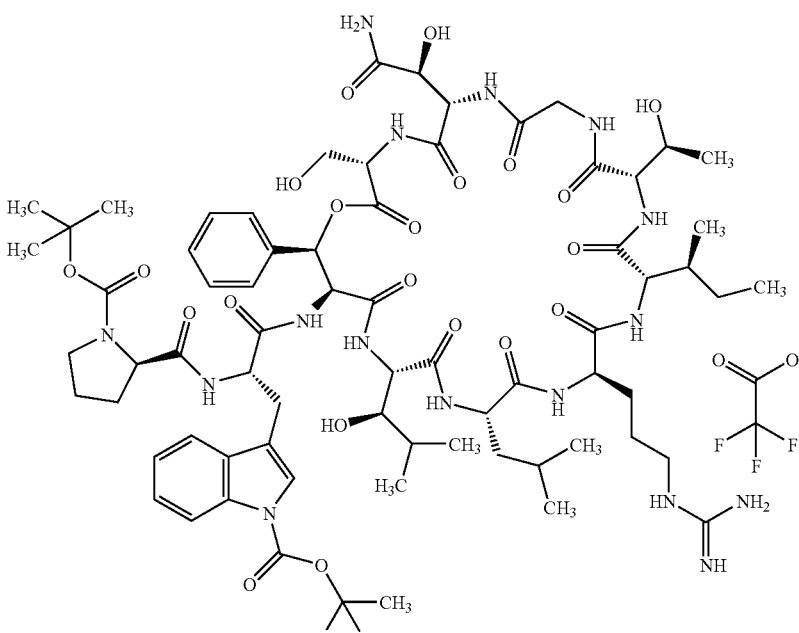<br>N-tert-Butoxycarbonyl-D-prolyl-N-tert-butoxycarbonyl tryptophyl-de(1-D-leucyl-2-L-leucyl)lysobactin trifluoroacetate | HPLC/UV-Vis (method 13):<br>$R_t$ = 7.53 min,<br>$\lambda_{max}$ (qualitative) = 220 nm (s), 265 (m), 290 (sh).<br>LC-MS (method 26):<br>$R_t$ = 2.16 min;<br>MS (ESIpos.): m/z (%) = 718 (100) [M − Boc + 2H]$^{2+}$, 1534 (30) [M + H]$^+$.<br><br>General procedure 4 from Example 13A (0.02 mmol) and Example 77A (0.06 mmol). Purification by method 7.<br>Yield 42% of theory |
| 182A | 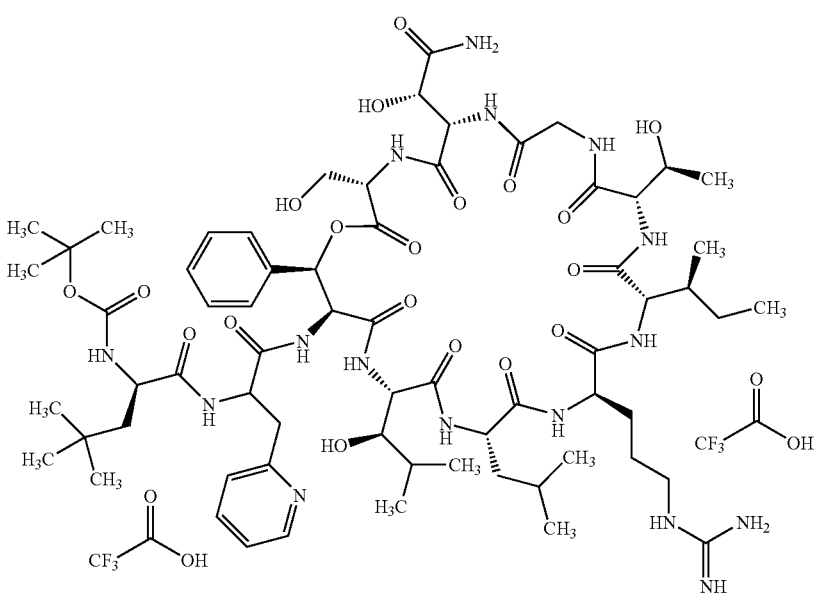<br>N-tert-Butoxycarbonyl-3-tert-butyl-D-alanyl-3-(2-pyridyl)-L-alanyl-de(1-D-leucyl-2-L-leucyl)lysobactin bistrifluoroacetate | HPLC/UV-Vis (method 36):<br>$R_t$ = 3.80 min.<br>LC-MS (method 22):<br>$R_t$ = 1.99 min;<br>MS (ESIpos.): m/z (%) = 713 (100) [M + 2H]$^{2+}$, 1425 (80) [M + H]$^+$;<br>MS (ESIneg.): m/z (%) = 711 (100) [M − 2H]$^{2-}$, 1423 (20) [M − H]$^-$.<br>HR-TOF-MS (method 21):<br>$C_{66}H_{105}N_{16}O_{19}$ [M + H]$^+$ calc. 1425.7742, found 1425.7742.<br>General procedure 4 from Example 74A (0.23 mmol) and Example 13A (0.09 mmol).<br>Yield: 42% of theory |

TABLE 4-continued

N-Protected nonadepsipeptides

| Ex. No. | Structure Name | Analytical data Preparation method |
|---|---|---|
| 183A | 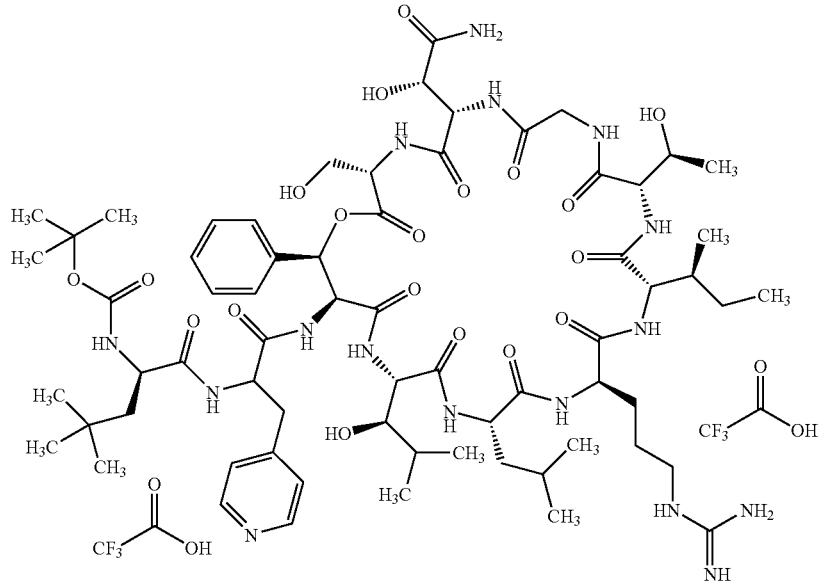<br>N-tert-Butoxycarbonyl-3-tert-butyl-D-alanyl-3-<br>(4-pyridyl)-L-alanyl-de(1-D-leucyl-<br>2-L-leucyl)lysobactin bistrifluoroacetate | HPLC/UV-Vis (method 36):<br>$R_t$ = 3.78 min.<br>LC-MS (method 22):<br>$R_t$ = 2.03 min;<br>MS (ESIpos.): m/z (%) = 713<br>(100) $[M + 2H]^{2+}$, 1425 (10)<br>$[M + H]^+$;<br>MS (ESIneg.): m/z (%) = 711<br>(100) $[M - 2H]^{2-}$, 1423 (20)<br>$[M - H]^-$.<br>HR-TOF-MS (method 21):<br>$C_{66}H_{105}N_{16}O_{19}$ $[M + H]^+$ calc.<br>1425.7742, found 1425.7773.<br>General procedure 4 from<br>N-tert-butoxycarbonyl-3-tert-<br>butyl-D-alanyl-3-(4-pyridyl)-<br>L-alanine (0.15 mmol) and<br>Example 13A (0.06 mmol).<br>Yield: 100% of theory |
| 184A | 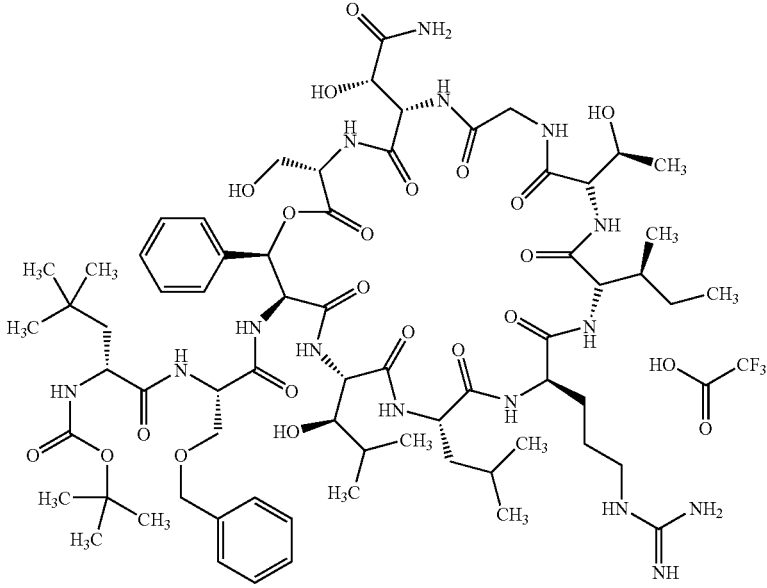<br>[N-(tert-Butoxycarbonyl)-3-tert-butyl-D-alanyl]-(O-<br>benzyl)-L-seryl-de(1-D-leucyl-2-leucyl)lysobactin<br>trifluoroacetate | HPLC/UV-Vis (method 36):<br>$R_t$ = 4.33 min.<br>LC-MS (method 26): $R_t$ =<br>2.12 min;<br>MS (ESIpos.): m/z (%) =<br>1454.9 (10) $[M + H]^+$.<br><br>General procedure 19 from<br>Example 13A (100 µmol) and<br>Example 88A<br>Yield: 29% of theory |

TABLE 4-continued

N-Protected nonadepsipeptides

| Ex. No. | Structure Name | Analytical data Preparation method |
|---|---|---|
| 185A | 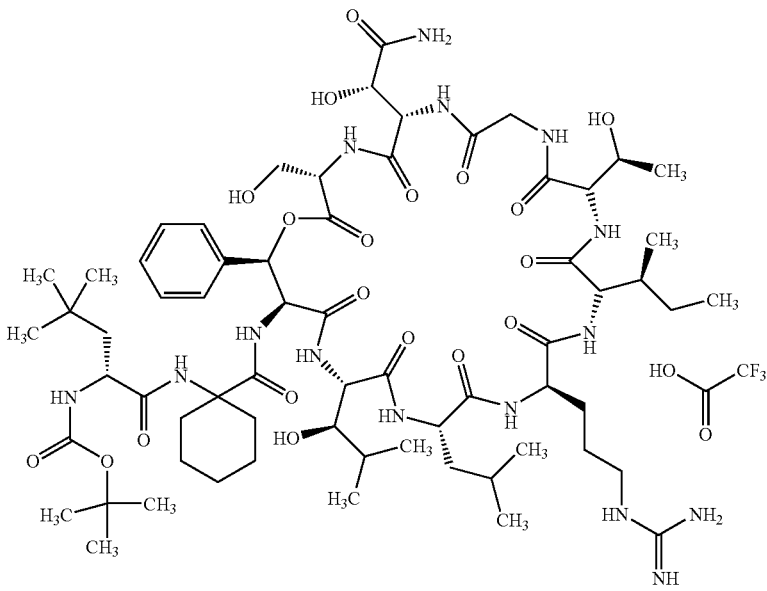 1-{[N-(tert-Butoxycarbonyl)-3-tert-butyl-D-alanyl]amino}cyclohexanecarbonyl-de(1-D-leucyl-2-L-leucyl)lysobactin trifluoroacetate | HPLC/UV-Vis (method 36): $R_t$ = 4.42 min.<br><br>General procedure 19 from Example 13A (80 µmol) and Example 89A.<br>Yield: 46% of theory |
| 186A | 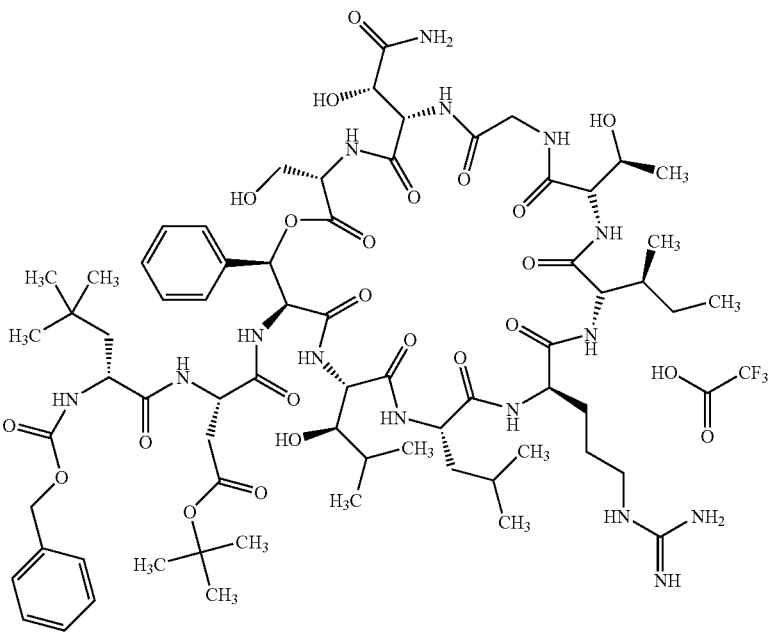 (2S)-2-[((2R)-2-{[(Benzyloxy)carbonyl]amino}-3-tert-butyl-D-alanyl)amino]-4-tert-butoxy-4-oxobutanoyl-de(1-D-leucyl-2-L-leucyl)lysobactin trifluoroacetate | HPLC/UV-Vis (method 36): $R_t$ = 4.37 min.<br>LC-MS (method 26): $R_t$ = 2.25 min,<br>MS (ESIpos.): m/z (%) = 1483.1 (20) $[M + H]^+$.<br><br>General procedure 19 from Example 13A (120 µmol) and Example 90A.<br>Yield: 72% of theory |

TABLE 4-continued

N-Protected nonadepsipeptides

| Ex. No. | Structure Name | Analytical data Preparation method |
|---|---|---|
| 187A | [N-(Benzyloxycarbonyl)-3-tert-butyl-D-alanyl]-(O-(tert-butyl)-L-seryl-de(1-D-leucyl-2-L-leucyl)lysobactin trifluoroacetate | HPLC/UV-Vis (method 36): $R_t$ = 4.41 min. LC-MS (method 26): $R_t$ = 2.47 min, MS (ESIpos.): m/z (%) = 1455.1 (30) [M + H]$^+$. General procedure 19 from Example 13A (90 µmol) and Example 91A. Yield: 90% of theory |
| 188A | [N-(Benzyloxycarbonyl)-O-(tert-butyl)-D-seryl]-O-(tert-butyl)-L-seryl-de(1-D-leucyl-2-L-leucyl)lysobactin trifluoroacetate | HPLC/UV-Vis (method 36): $R_t$ = 4.3 min. LC-MS (method 26): $R_t$ = 1471.1 (30) min, MS (ESIpos.): m/z (%) = 1471.1 (30) [M + H]$^+$. General procedure 19 from Example 13A (120 µmol) and Example 92A. Yield: 70% of theory |

TABLE 4-continued

N-Protected nonadepsipeptides

| Ex. No. | Structure Name | Analytical data Preparation method |
|---|---|---|
| 189A | 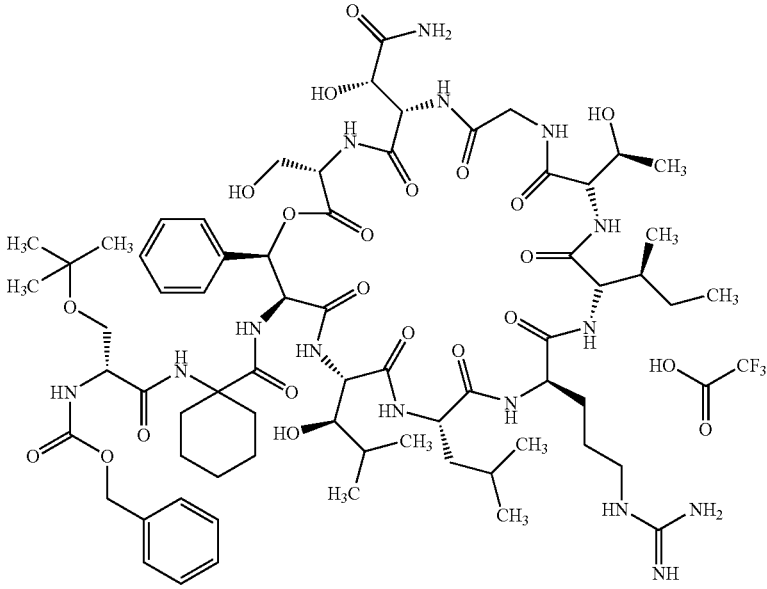<br>N-[(1-{[[(Benzyloxy)carbonyl]-O-(tert-butyl)-D-seryl]amino}cyclohexyl)carbonyl]-de(1-D-leucyl-2-L-leucyl)lysobactin trifluoroacetate | HPLC/UV-Vis (method 36): $R_t$ = 4.23 min.<br>LC-MS (method 26): $R_t$ = 2.15 min,<br>MS (ESIpos.): m/z (%) = 1452.8 (40) [M + H]$^+$.<br><br>General procedure 19 from Example 13A (120 µmol) and Example 93A.<br>Yield: 18% of theory |
| 190A | 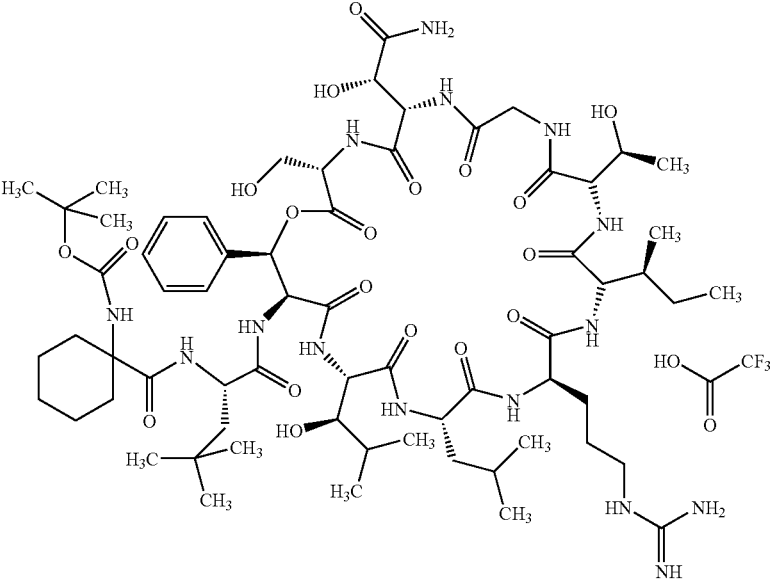<br>N-({1-[(tert-Butoxycarbonyl)amino]-cyclohexyl}carbonyl)-3-tert-butyl-D-alanyl-de(1-D-leucyl-2-L-leucyl)lysobactin trifluoroacetate | HPLC/UV-Vis (method 36): $R_t$ = 4.37 min.<br>LC-MS (method 26): $R_t$ = 2.21 min,<br>MS (ESIpos.): m/z (%) = 1403.1 (60) [M + H]$^+$.<br><br>General procedure 19 from Example 13A (110 µmol) and Example 94A.<br>Yield: 76% of theory |

TABLE 4-continued

N-Protected nonadepsipeptides

| Ex. No. | Structure Name | Analytical data Preparation method |
|---|---|---|
| 191A | 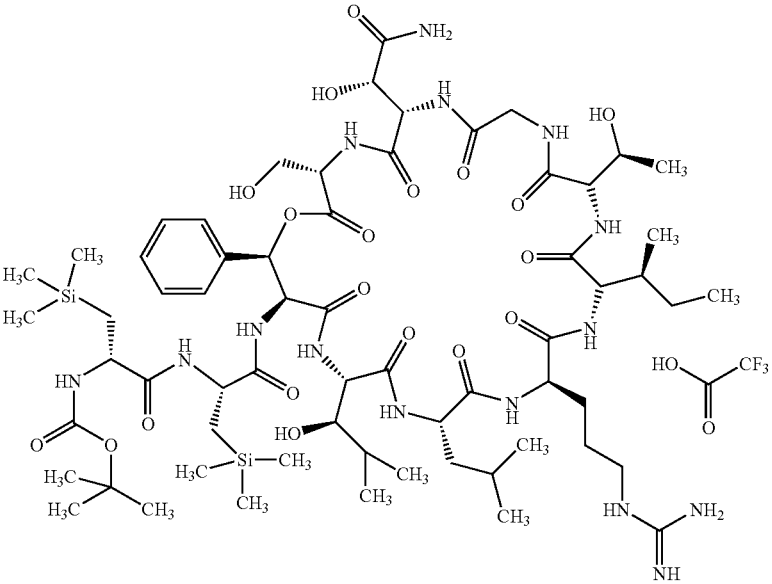<br>N-[(tert-Butoxycarbonyl)-3-(trimethylsily)-D-alanyl-3-(trimethylsilyl)-L-alanyl]-de(1-D-leucyl-2-L-leucyl)-lysobactin trifluoroacetate | HPLC/UV-Vis (method 36): $R_t$ = 4.62 min.<br>LC-MS (method 26): $R_t$ = 2.41 min,<br>MS (ESIpos.): m/z (%) = 1437.1 (30) [M + H]$^+$.<br><br>General procedure 19 from Example 13A (120 µmol) and Example 95A.<br>Yield: 86% of theory |
| 192A | 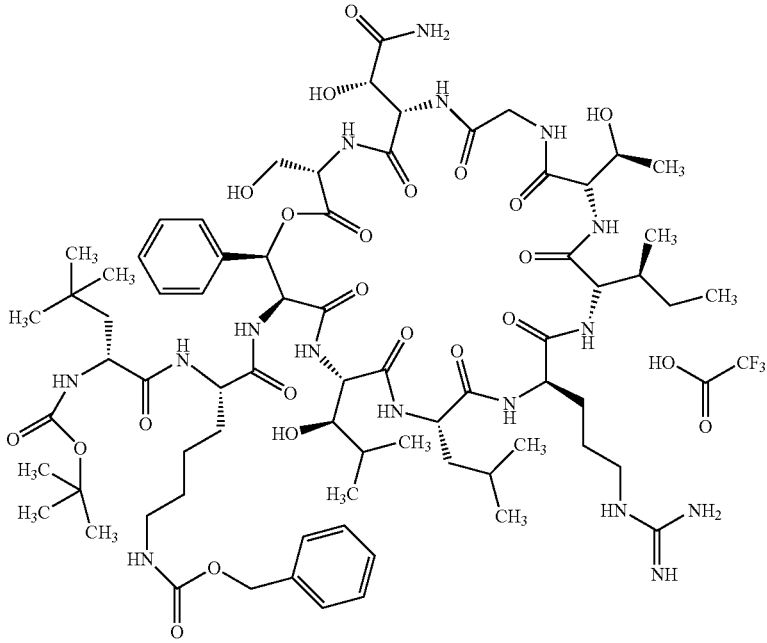<br>N-[(tert-Butoxycarbonyl)-4-methyl-D-leucyl]-$N^6$-[(benzyloxy)carbonyl]-L-lysyl-de(1-D-leucyl-2-L-leucyl)lysobactin trifluoroacetate | HPLC/UV-Vis (method 36): $R_t$ = 4.41 min.<br>LC-MS (method 26): $R_t$ = 2.14 min,<br>MS (ESIpos.): m/z (%) = 1539.8 (20) [M + H]$^+$.<br><br>General procedure 19 from Example 13A (110 µmol) and Example 96A.<br>Yield: 32% of theory |

EXEMPLARY EMBODIMENTS

Example 1

D-Leucyl-N$^1$-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-3-cyclopropyl-L-alaninamide bistrifluoroacetate

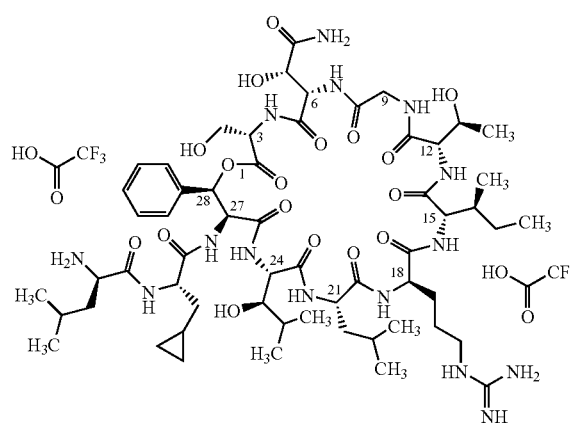

The N-(tert-butoxycarbonyl)-depsipeptide (Example 14A, 40 mg, 30 μmol) is reacted by general procedure 5. Chromatographic purification by preparative HPLC (method 8; or method 7 followed by subsequent metathesis of the chromatography product by adding TFA (300 μmol)) results after freeze drying in 36 mg (89% of theory) of product.

HPLC/UV-Vis (method 13): R$_t$=5.64 min, $\lambda_{max}$ (qualitative)=220 nm (s), 255-270 (w).

LC-MS (method 11): R$_t$=2.0 min;

MS (ESIpos.): m/z (%)=638 (100) [M+2H]$^{2+}$, 1275 (8) [M+H]$^+$.

FT-ICR-HR-MS (method 23):

C$_{58}$H$_{97}$N$_{15}$O$_{17}$ [M+2H]$^{2+}$ calc. 637.85880, found 637.85878;

C$_{58}$H$_9$N$_{15}$NaO$_{17}$ [M+H+Na]$^{2+}$ calc. 648.84977, found 648.84990.

To determine the amino acid sequence, an analytical sample of the product is hydrolysed by general procedure 10.

MALDI-MS (method 20): m/z (%)=1292.5 (100) [M+H]$^+$.

Example 2

D-Leucyl-N$^1$-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-3-cyclopropyl-L-norvalinamide bistrifluoroacetate

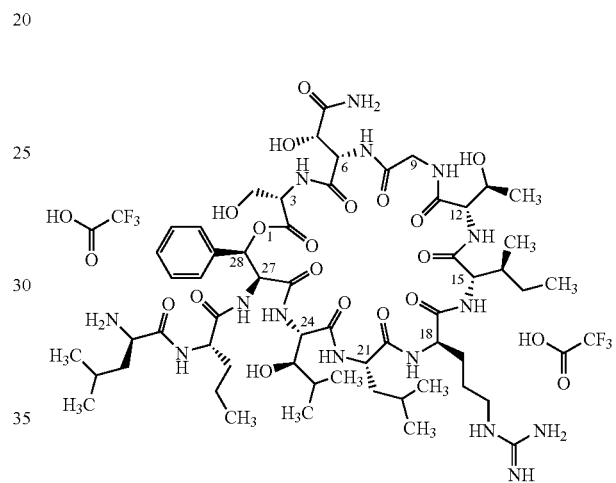

The N-(tert-butoxycarbonyl)-depsipeptide (Example 15A, 3.1 mg, 2 μmol) is reacted by general procedure 5. Chromatographic purification by preparative HPLC (method 10; or method 9 followed by subsequent metathesis of the chromatography product by adding TFA (30 μmol)) results after freeze drying in 3 mg (quant.) of product.

HPLC/UV-Vis (method 13): R$_t$=5.59 min, $\lambda_{max}$ (qualitative)=220 nm (s), 255-270 (w).

LC-MS (method 11): R$_t$=2.01 min;

MS (ESIpos.): m/z (%)=632 (100) [M+2H]$^{2+}$, 1263 (10) [M+H]$^+$;

LC-MS (method 12): R$_t$=4.05 min;

MS (ESIpos.): m/z (%)=632 (100) [M+2H]$^{2+}$, 1263 (10) [M+H]$^+$.

FT-ICR-HR-MS (method 23):

C$_{57}$H$_{97}$N$_{15}$O$_{17}$ [M+2H]$^{2+}$ calc. 631.85879, found 631.85913.

To determine the amino acid sequence, an analytical sample of the product is hydrolysed by general procedure 10.

MALDI-MS (method 20): m/z (%)=1280.5 (100) [M+H]$^+$.

Example 3

D-Leucyl-N¹-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-3-tert-butyl-L-alaninamide bistrifluoroacetate

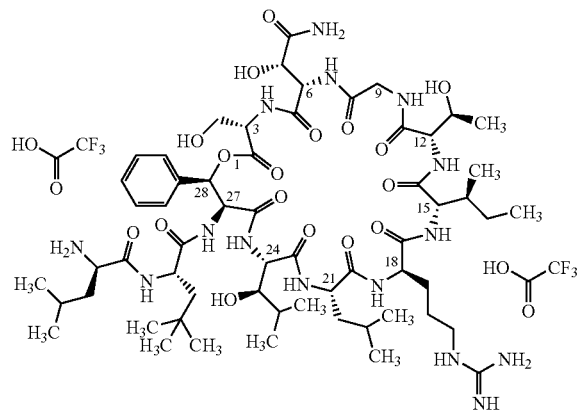

The N-(tert-butoxycarbonyl)-depsipeptide (Example 16A, 17 mg, 113 μmol) is reacted by general procedure 5. Chromatographic purification by preparative HPLC (method 15) results after freeze drying in 15 mg (quant.) of product.

HPLC/UV-Vis (method 13): $R_t$=5.87 min, $\lambda_{max}$ (qualitative)=220 nm (s), 255-270 (w).

LC-MS (method 11): $R_t$=1.95 min;

MS (ESIpos.): m/z (%)=646 (100) [M+2H]²⁺, 1291 (10) [M+H]⁺;

MS (ESIneg.): m/z (%)=644 (100) [M−2H]²⁻, 1289 (10) [M−H]⁻.

Example 4

L-Leucyl-N¹-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide bistrifluoroacetate {epi-Lysobactin bistrifluoroacetate}

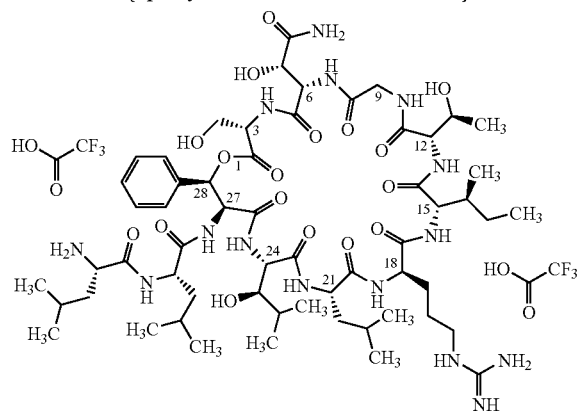

N-(tert-Butoxycarbonyl)-epi-lysobactin monotrifluoroacetate (Example 17A, 1.3 mg, 1 μmol) is reacted in analogy to general procedure 5. The crude product is purified by preparative HPLC (method 15). Freeze drying of the product fractions results in 1.0 mg (42% of theory) of product.

HPLC/UV-Vis (method 13): $R_t$=5.68 min, $\lambda_{max}$ (qualitative)=220 nm (s), 255-270 (w).

LC-MS (method 12): $R_t$=4.35 min;

MS (ESIpos.): m/z (%)=639 (100) [M+2H]²⁺, 1277 (5) [M+H]⁺;

MS (ESIneg.): m/z (%)=1275 (100) [M−H]⁻.

HR-TOF-MS (method 21): calc. 1276.7265, found 1276.7261 [M+H]+.

Example 5

N²-(4-Aminobutanoyl)-N¹-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide bistrifluoroacetate {4-Aminobutanoyl-de(leucyl)lysobactin bistrifluoroacetate}

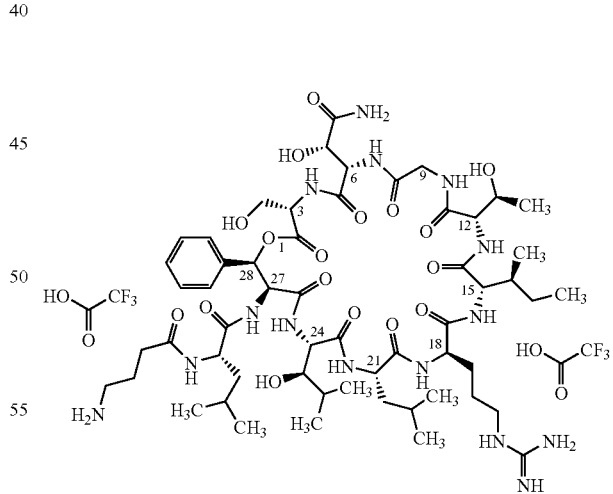

{4-[(tert-Butoxycarbonyl)amino]butanoyl}de(leucyl)lysobactin trifluoroacetate (Example 18A, 2.3 mg, 2 μmol) is reacted in analogy to general procedure 5. The crude product is purified by preparative HPLC (method 15). Freeze drying of the product fractions results in 1.5 mg (35% of theory) of product.

LC-MS (method 12): $R_t$=3.93 min;
MS (ESIpos.): m/z (%)=625 (100) [M+2H]$^{2+}$, 1248 (15) [M+H]$^+$;
MS (ESIneg.): m/z (%)=1247 (100) [M−H]$^−$.

Example 6

N-Methyl-D-leucyl-N$^1$-{(3S,6S,12S,15S,18R,21S, 24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide bistrifluoroacetate {N-Methyllysobactin bistrifluoroacetate}

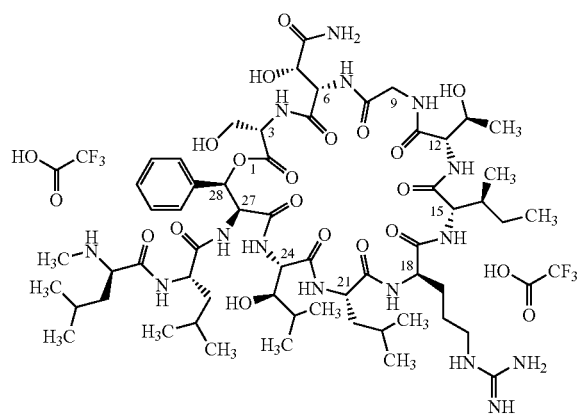

N-(tert-Butoxycarbonyl)-N-methyl-lysobactin monotrifluoroacetate (Example 19A, 1.9 mg, 1 μmol) is reacted in analogy to general procedure 5. The crude product is purified by preparative HPLC (method 15). Freeze drying of the product fractions results in 1.8 mg (quant.) of product.

LC-MS (method 12): $R_t$=4.27 min;
MS (ESIpos.): m/z (%)=646 (100) [M+2H]$^{2+}$, 1291 (15) [M+H]$^+$;
MS (ESIneg.): m/z (%)=1289 (100) [M−H]$^−$.
HR-TOF-MS (method 21): $C_{59}H_{100}N_{15}O_{17}$ [M+H]$^+$ calc. 1290.7422, found 1290.7415.

Example 7

N$^2$-(6-Aminohexanoyl)-N$^1$-{(3S,6S,12S,15S,18R, 21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide bistrifluoroacetate {N-(6-Aminohexanoyl)-de(leucyl)lysobactin bistrifluoroacetate}

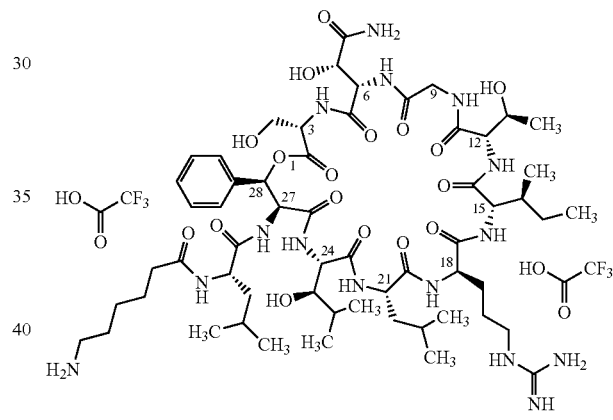

{6-[(tert-Butoxycarbonyl)amino]hexanoyl}-de(leucyl)lysobactin monotrifluoroacetate (Example 20A, 350 μg, 1 μmol) is reacted in analogy to general procedure 5. The crude product is purified by preparative HPLC (method 15). Freeze drying of the product fractions results in 300 μg (quant.) of product.

HPLC/UV-Vis (method 13): $R_t$=5.28 min,
$\lambda_{max}$ (qualitative)=220 nm (s), 255-270 (w).
LC-MS (method 12): $R_t$=4.00 min;
MS (ESIpos.): m/z (%)=639 (100) [M+2H]$^{2+}$, 1277 (10) [M+H]$^+$;
MS (ESIneg.): m/z (%)=1275 (100) [M−H]$^−$.

Example 8

N²-(3-Aminopropionyl)-N¹-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide bistrifluoroacetate {N-(3-Aminopropionyl)-de(leucyl)lysobactin bistrifluoroacetate}

Example 9

N²-({1-Aminocyclopropyl}carbonyl)-N¹-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide bistrifluoroacetate

[N-({1-Aminocyclopropyl}carbonyl)-de(leucyl)lysobactin bistrifluoroacetate]

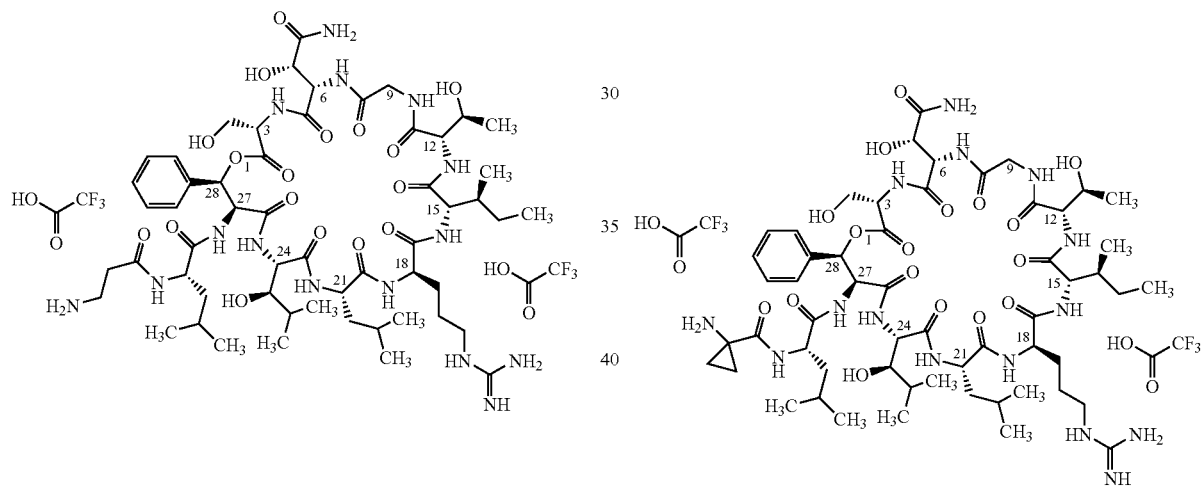

{6-[(tert-Butoxycarbonyl)amino]propionyl}-de(leucyl)lysobactin monotrifluoroacetate (Example 21A, 2.2 mg, 1.5 µmol) is reacted in analogy to general procedure 5. The crude product is purified by preparative HPLC (method 15). Freeze drying of the product fractions results in 200 µg (11% of theory) of product.

HPLC/UV-Vis (method 13): R$_t$=4.96 min,
λ$_{max}$ (qualitative)=220 nm (s), 255-270 (w).
LC-MS (method 12): R$_t$=3.86 min;
MS (ESIpos.): m/z (%)=618 (100) [M+2H]⁺, 1235 (15) [M+H]⁺;
MS (ESIneg.): m/z (%)=1233 (100) [M−H]⁻.

To determine the amino acid sequence, an analytical sample of the product is hydrolysed by general procedure 10.

MALDI-MS (method 20): m/z (%)=1252.8 (100) [M+H]⁺.

N-({1-[(tert-Butoxycarbonyl)amino]cyclopropyl}carbonyl)-de(leucyl)lysobactin monotrifluoroacetate (Example 22A, 400 µg, 0.3 µmol) is reacted in analogy to general procedure 5. The crude product is purified by preparative HPLC (method 15). Freeze drying of the product fractions results in 200 µg (50% of theory) of product.

HPLC/UV-Vis (method 13): R$_t$=5.29 min,
λ$_{max}$ (qualitative)=220 nm (s), 255-270 (w).
LC-MS (method 12): R$_t$=4.08 min;
MS (ESIpos.): m/z (%)=1247 (100) [M+H]⁺;
MS (ESIneg.): m/z (%)=1245 (100) [M−H]⁻.

Example 10

3-Amino-N-[(benzyloxy)carbonyl]-L-alanyl-N¹-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide bistrifluoroacetate

[3-Amino-N-[(benzyloxy)carbonyl]-L-alanyl]-de(leucyl)lysobactin bistrifluoroacetate]

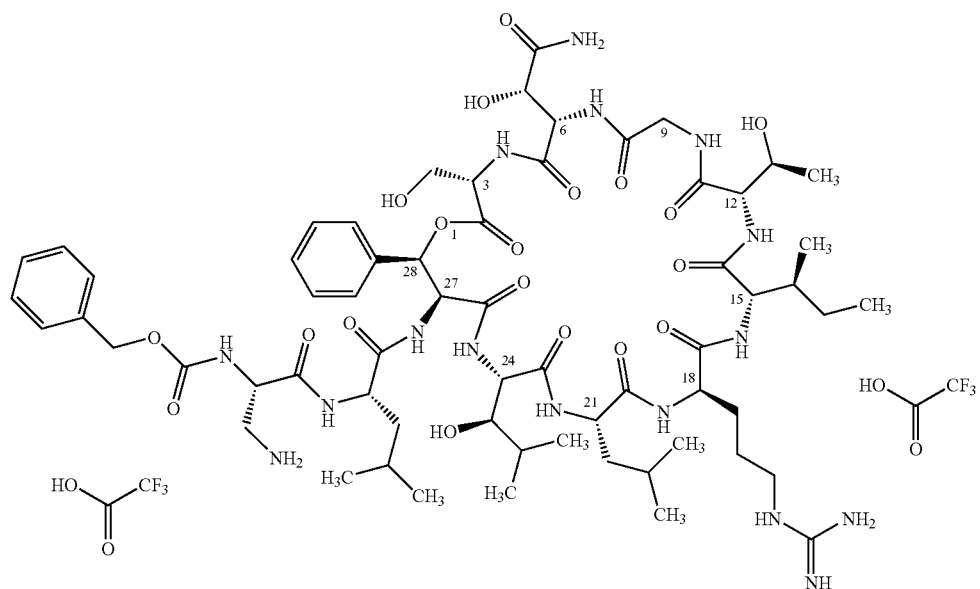

{N-[(Benzyloxy)carbonyl]-3-[(tert-butoxycarbonyl)amino]-L-alanyl}-de(leucyl)lysobactin monotrifluoroacetate (Example 23A, 300 µg, 0.2 µmol) is reacted in analogy to general procedure 5. The crude product is purified by preparative HPLC (method 15). Freeze drying of the product fractions results in 200 µg (65% of theory) of product.

LC-MS (method 12): $R_t$=4.20 min;

MS (ESIpos.): m/z (%)=692.5 (100) $[M+2H]^{2+}$, 1384 (5) $[M+H]^+$;

MS (ESIneg.): m/z (%)=1382 (100) $[M-H]^-$.

TABLE 5

Edman[1.0] route

| Ex. No. | Structure Name | Analytical data Preparation method |
|---|---|---|
| 11 | 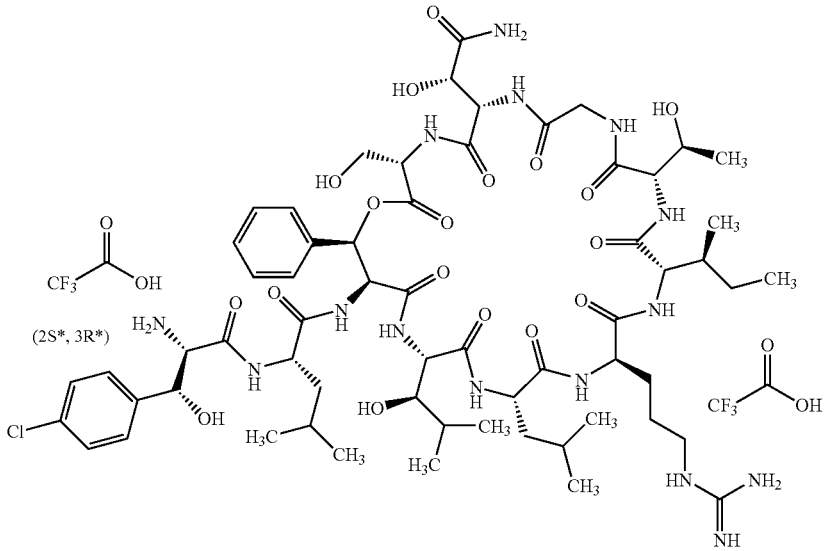<br>[3-(4-Chlorophenyl)-threo-rac-seryl]-de(1-D-leucyl)lysobactin bistrifluoroacetate | HR-TOF-MS (method 21): $C_{61}H_{95}N_{15}O_{18}Cl$ $[M + H]^+$ calc. 1360.6668, found 1360.6697.<br><br>General procedure 5 from Example 97A (0.01 mmol). Purification by method 8 or method 25.<br>Yield: 35% of theory |
| 12 | 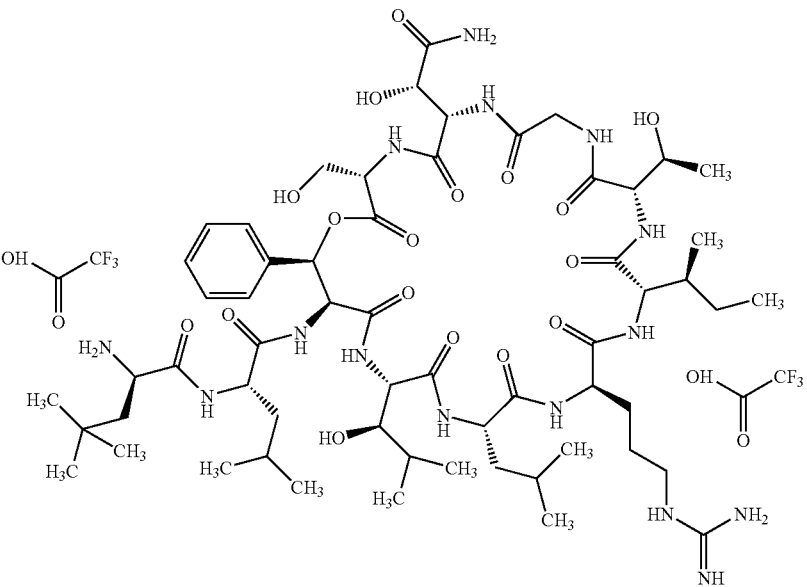<br>3-tert-Butyl-D-alanyl-de(1-D-leucyl)lysobactin bistrifluoroacetate | HPLC/UV-Vis (method 13): $R_t$ = 6.01 min.<br>LC-MS (method 26):<br>$R_t$ = 1.61 min;<br>MS (ESIpos.): m/z (%) = 646 (100) $[M + 2H]^{2+}$, 1291 (30) $[M + H]^+$.<br><br>General procedure 5 from Example 98A (0.01 mmol). Purification by method 8 or method 25.<br>Yield: 34% of theory |

TABLE 5-continued

Edman[1.0] route

| Ex. No. | Structure Name | Analytical data Preparation method |
|---|---|---|
| 13 | 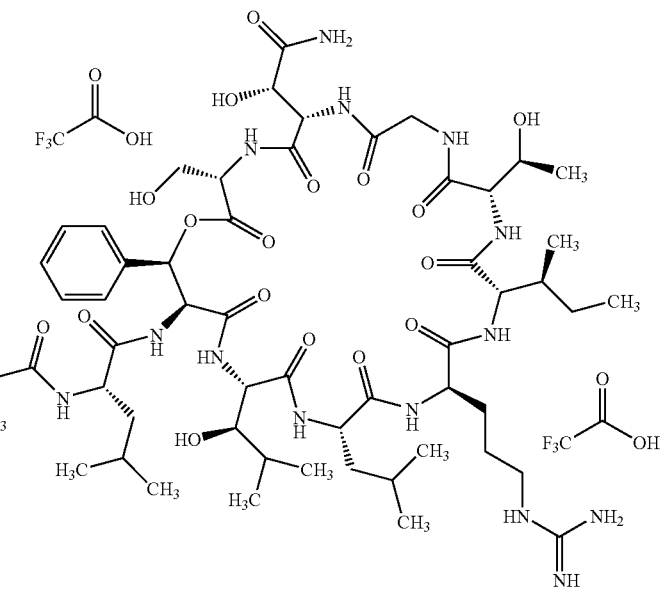<br>2-Methyl-L-leucyl-de(1-D-leucyl)lysobactin bistri-fluoroacetate | HPLC/UV-Vis (method 13):$R_t$ = 5.82 min.<br>LC-MS (method 26):<br>$R_t$ = 1.55 min;<br>MS (ESIpos.): m/z (%) = 646 (100) $[M + 2H]^{2+}$, 1291 (30) $[M + H]^+$.<br><br>General procedure 5 from Example 99A (0.01 mmol). Purification by method 8 or method 25.<br>Yield: 47% of theory |
| 14 | 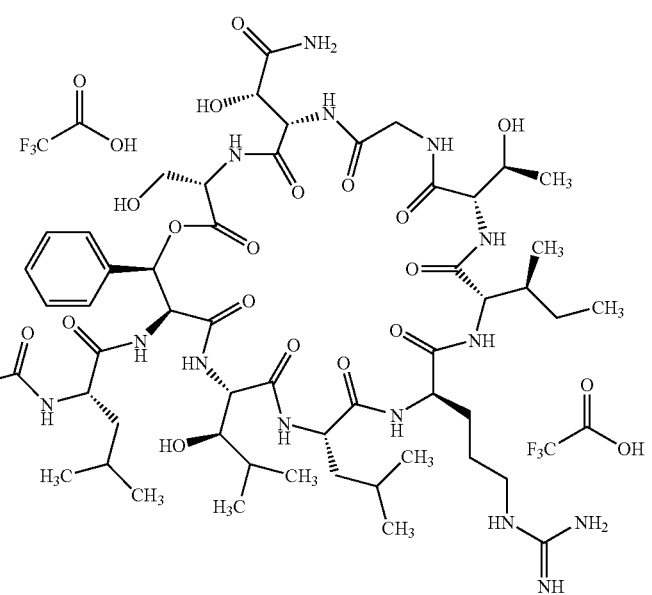<br>3-Cyclopropyl-D-alanyl-de(1-D-leucyl)lysobactin bistri-fluoroacetate | HPLC/UV-Vis (method 36):$R_t$ = 3.5 min.<br>LC-MS (method 29):<br>$R_t$ = 4.29 min;<br>MS (ESIpos.): m/z (%) = 638 (100) $[M + 2H]^{2+}$, 1275 (30) $[M + H]^+$.<br><br>General procedure 5 from Example 100A (0.004 mmol). Purification by method 8 or method 25.<br>Yield: 70% of theory |

TABLE 5-continued

Edman[1.0] route

| Ex. No. | Structure Name | Analytical data Preparation method |
|---|---|---|
| 15 | 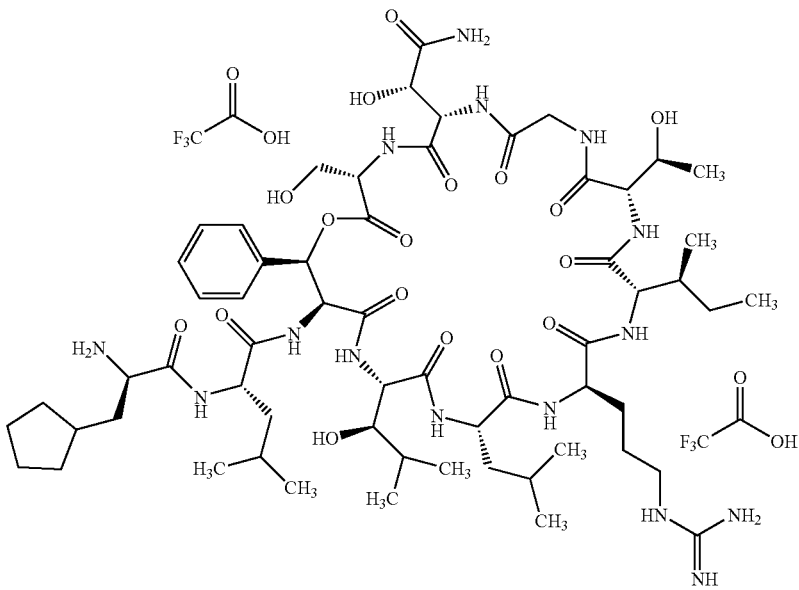<br>Cyclopentyl-D-alanyl-de(1-D-leucyl)lysobactin bistrifluoroacetate | HPLC/UV-Vis (method 13):$R_t$ = 6.19 min.<br>LC-MS (method 26):<br>$R_t$ = 1.66 min;<br>MS (ESIpos.): m/z (%) = 652 (100) [M + 2H]$^{2+}$, 1303 (30) [M + H]$^+$.<br><br>General procedure 5 from Example 101A (0.002 mmol). Purification by method 8 or method 25.<br>Yield: quant. |
| 16 | 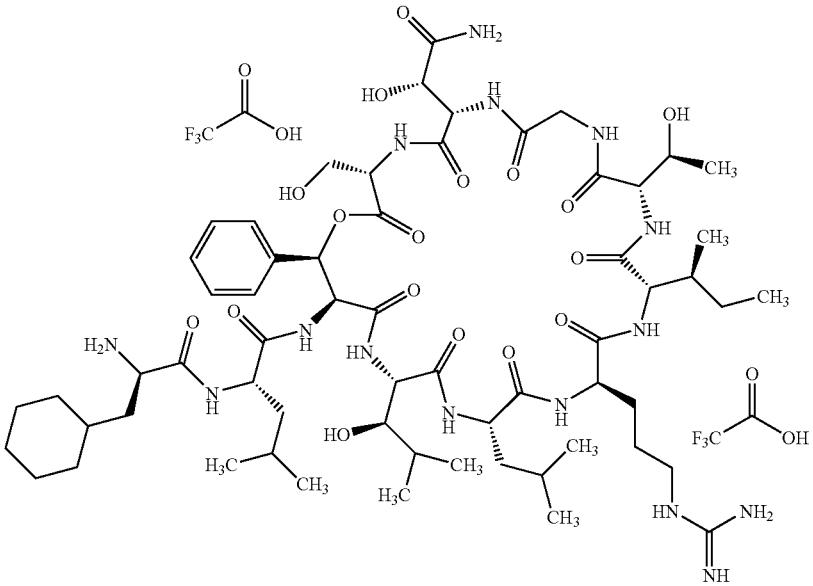<br>3-Cyclohexyl-D-alanyl-de(1-D-leucyl)lysobactin bistrifluoroacetate | HPLC/UV-Vis (method 13):$R_t$ = 6.17 min.<br>LC-MS (method 26):<br>$R_t$ = 1.73 min;<br>MS (ESIpos.): m/z (%) = 659 (100) [M + 2H]$^{2+}$.<br><br>General procedure 5 from Example 102A (0.01 mmol). Purification by method 8 or method 25.<br>Yield: 51% of theory |

TABLE 5-continued

Edman[1.0] route

| Ex. No. | Structure Name | Analytical data Preparation method |
|---|---|---|
| 17 | 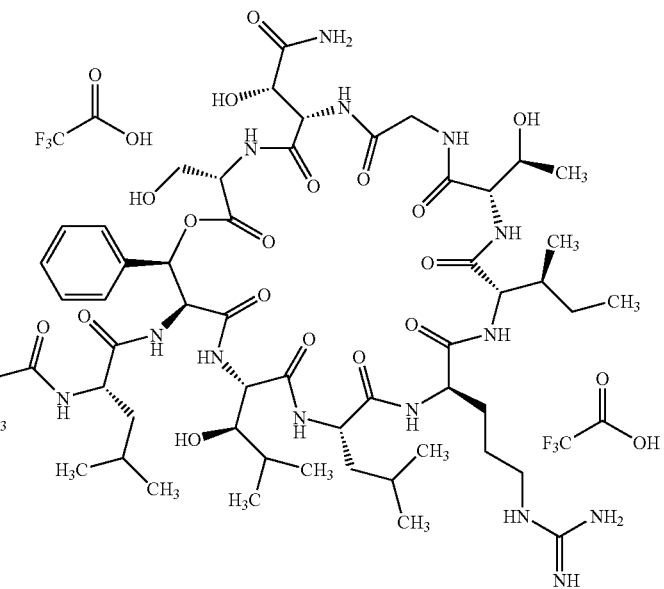  2-Methyl-D-leucyl-de(1-D-leucyl)lysobactin bistrifluoroacetate | HPLC/UV-Vis (method 13):$R_t$ = 5.76 min. LC-MS (method 26): $R_t$ = 1.60 min; MS (ESIpos.): m/z (%) = 646 (100) $[M + 2H]^{2+}$, 1291 (30) $[M + H]^+$.  General procedure 5 from Example 103A (0.01 mmol). Purification by method 8 or method 25. Yield: 68% of theory |
| 18 | 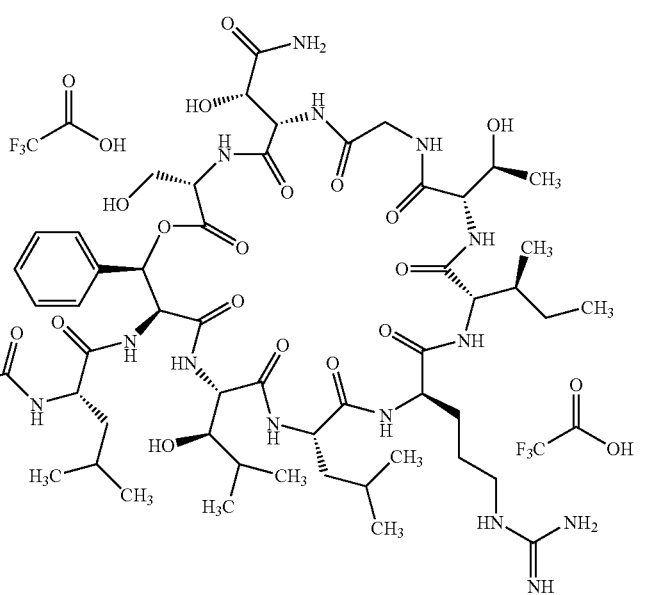  (2-Amino-2,3-dihydro-1H-indenylcarbonyl)-de(1-D-leucyl)lysobactin bistrifluoroacetate | HPLC/UV-Vis (method 13):$R_t$ = 5.96 min. HR-TOF-MS (method 21): $C_{62}H_{96}N_{15}O_{17}Cl$ $[M + H]^+$ calc. 1322.7109, found 1322.7076.  General procedure 5 from Example 104A (0.06 mmol). Purification by method 8 or method 25. Yield: 54% of theory |

TABLE 5-continued

Edman[1.0] route

| Ex. No. | Structure Name | Analytical data Preparation method |
|---|---|---|
| 19 | D-Prolyl-de(1-D-leucyl)lysobactin bistrifluoroacetate | HPLC/UV-Vis (method 13):$R_t$ = 5.79 min.<br>LC-MS (method 26):<br>$R_t$ = 1.45 min;<br>MS (ESIpos.): m/z (%) = 1261 (100) [M + 2H]$^{2+}$, 631 (30) [M + H]$^+$.<br><br>General procedure 5 from Example 105A (0.01 mmol). Purification by method 8 or method 25.<br>Yield: 95% of theory |
| 20 | ((2S)-3-Amino-2-benzyl-propanoyl)-de(1-D-leucyl)lysobactin bistrifluoroacetate | LC-MS (method 26):<br>$R_t$ = 1.62 min;<br>MS (ESIpos.): m/z (%) = 663.2 (100) [M + 2H]$^{2+}$, 1324.8 (8) [M + H]$^+$;<br>MS (ESIneg.): m/z (%) = 661.0 (100) [M − 2H]$^{2-}$, 1368.9 (30) [M + HCOOH − H]$^-$.<br>HR-TOF-MS (method 21):<br>$C_{62}H_{98}N_{15}O_{17}$ [M + H]$^+$<br>calc. 1324.7265, found 1324.7230.<br>From Example 106A by general procedure 5 and chromatography (method 8).<br>Yield: 8.3 mg (14%) over 2 stages. |

TABLE 5-continued

Edman[1.0] route

| Ex. No. | Structure Name | Analytical data Preparation method |
|---|---|---|
| 21 | 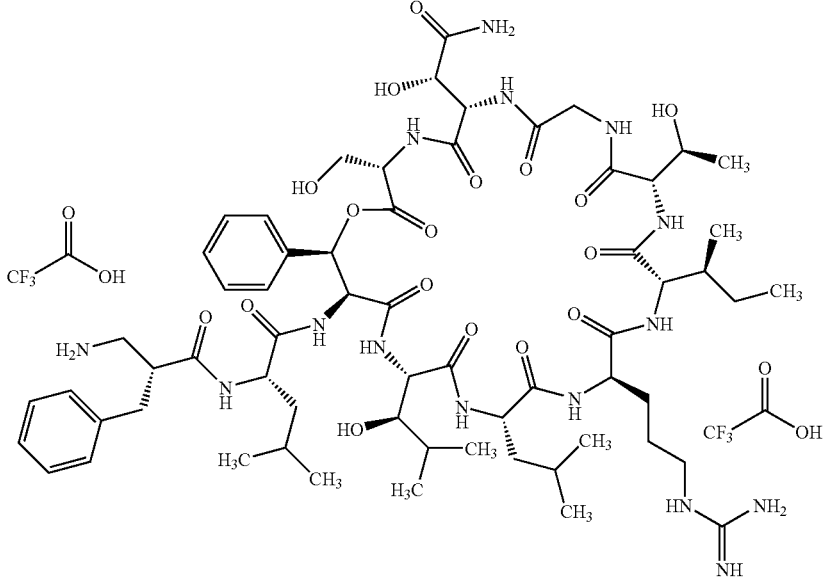<br>[(2R)-3-Amino-2-benzyl-propanoyl]-de(1-D-leucyl)lysobactin bistrifluoroacetate | LC-MS (method 26):<br>$R_t$ = 1.55 min (100);<br>MS (ESIpos.): m/z (%) = 663.2 (100) $[M + 2H]^{2+}$, 1324.8 (8) $[M + H]^+$;<br>MS (ESIneg.): m/z (%) = 661.1 (100) $[M - 2H]^{2-}$, 1322.8 (25) $[M - H]^-$, 1368.9 (36) $[M + HCOOH - H]^-$.<br>HR-TOF-MS (method 21)<br>$C_{62}H_{98}N_{15}O_{17}$ $[M + H]^+$ calc. 1324.7265, found 1324.7230.<br>From Example 107A by general procedure 5 and chromatography (method 8).<br>Yield: 3.1 mg (5%) over 2 stages. |
| 22 | 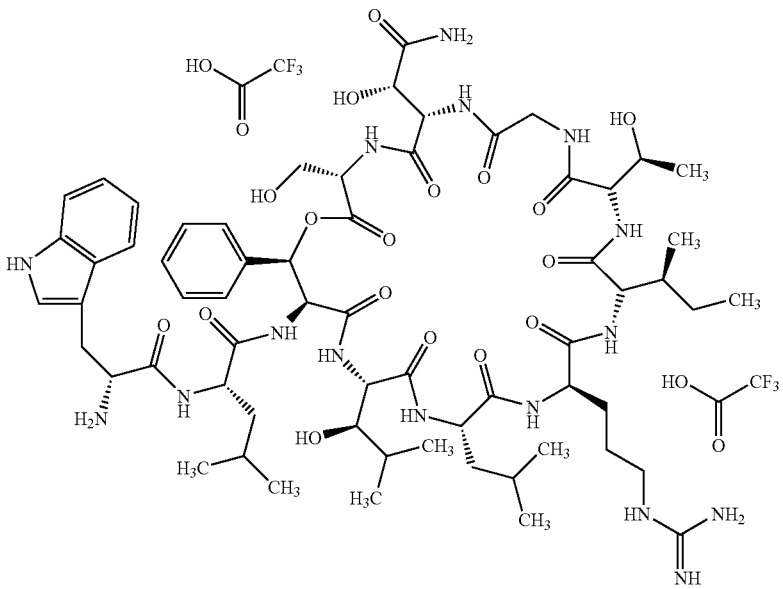<br>D-Tryptophyl-de(1-D-leucyl)lysobactin bistrifluoroacetate | HPLC/UV-Vis (method 36):$R_t$ = 3.55 min.<br>LC-MS (method 26):<br>$R_t$ = 1.56 min,<br>MS (ESIpos.): m/z (%) = 675 (100) $[M + 2H]^{2+}$.<br>HR-TOF-MS (method 21): calc. 1349.7218, found 1349.7202 $[M + H]^+$.<br>General procedure 20 from Example 108A (26 μmol).<br>Yield: 56% |

TABLE 5-continued

Edman[1.0] route

| Ex. No. | Structure Name | Analytical data Preparation method |
|---|---|---|
| 23 | 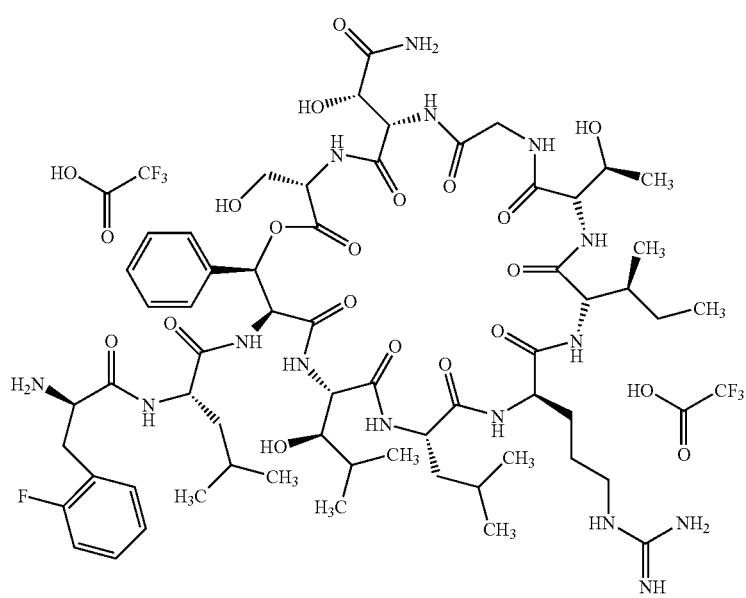<br>(2-Fluoro-D-phenylalanyl)-de(1-D-leucyl)lysobactin bistrifluoroacetate | HPLC/UV-Vis (method 36):$R_t$ = 3.55 min.<br>LC-MS (method 26):<br>$R_t$ = 1.60 min,<br>MS (ESIpos.): m/z (%) = 1327 (35) $[M + H]^+$.<br>HR-TOF-MS (method 21): calc. 1328.7014, found 1328.6971 $[M + H]^+$.<br><br>General procedure 20 from Example 109A (26 μmol).<br>Yield: 44% of theory |
| 24 | 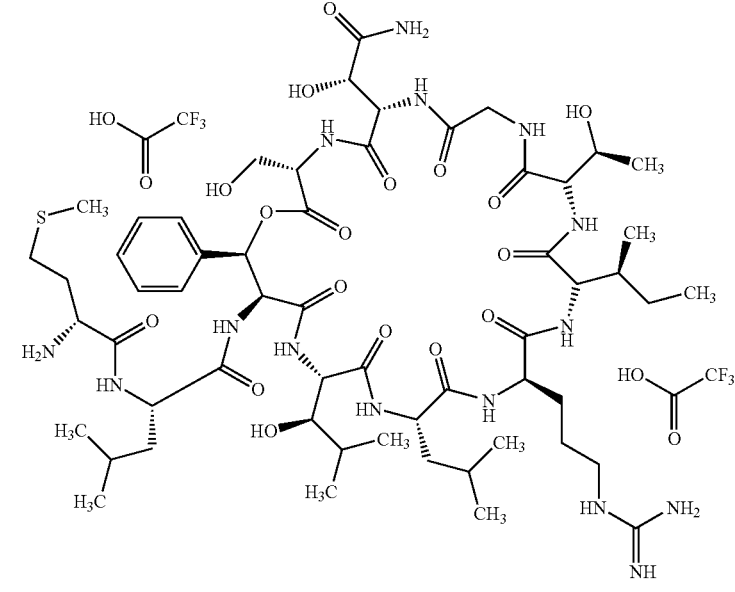<br>D-Methionyl-de(1-D-leucyl)lysobactin bistrifluoroacetate | HPLC/UV-Vis (method 36):$R_t$ = 3.47 min.<br>LC-MS (method 26):<br>$R_t$ = 1.52 min,<br>MS (ESIpos.): m/z (%) = 1293 $[M]^+$.<br>HR-TOF-MS (method 21): calc. 1294.6829, found 1294.6788 $[M + H]^+$.<br><br>General procedure 20 from Example 110A (26 μmol).<br>Yield: 36% of theory |

TABLE 5-continued

Edman[1.0] route

| Ex. No. | Structure Name | Analytical data Preparation method |
|---|---|---|
| 25 | 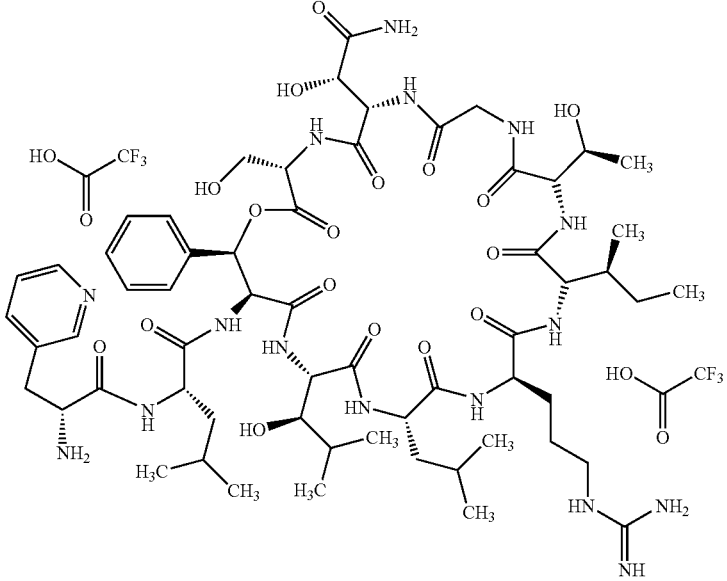<br>(3-Pyrid-3-yl-D-alanyl)-de(1-D-leucyl)lysobactin bistrifluoroacetate | HPLC/UV-Vis (method 36):$R_t$ = 3.28 min.<br>LC-MS (method 26):<br>$R_t$ = 1.45 min,<br>MS (ESIpos.): m/z (%) = 656.8 [M + 2H]$^{2+}$(35).<br><br>General procedure 20 from Example 111A (24 µmol).<br>Yield: 15% of theory |
| 26 | 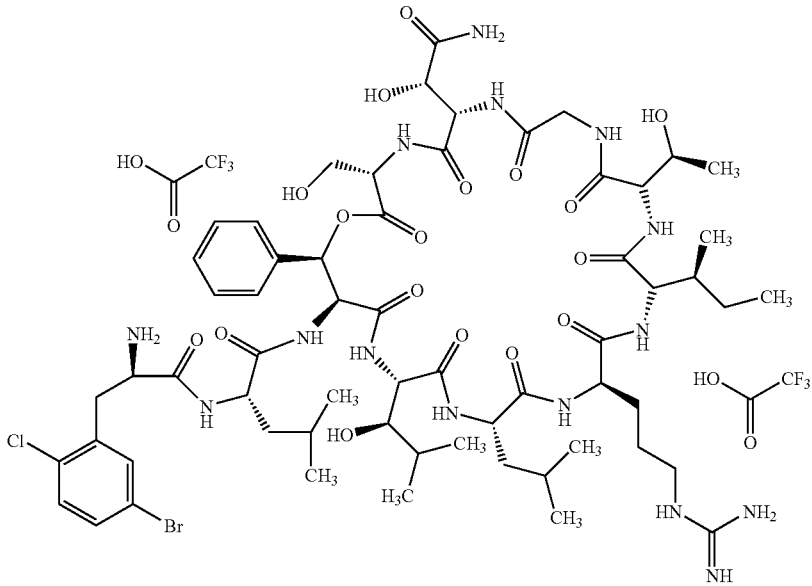<br>(3-Bromo-6-chloro-D-phenylalanyl)-de(1-D-leucyl)lysobactin bistrifluoroacetate | HPLC/UV-Vis (method 36):$R_t$ = 3.65 min.<br>LC-MS (method 26):<br>$R_t$ = 1.75 min,<br>MS (ESIpos.): m/z (%) = 711.5 (100) [M + 2H]$^{2+}$.<br>HR-TOF-MS (method 21): calc. 1422.5824, found 1422.5838 [M + H]$^+$.<br><br>General procedure 20 from Example 112A (79 µmol).<br>Yield: 38% of theory |

TABLE 5-continued

Edman[1.0] route

| Ex. No. | Structure Name | Analytical data Preparation method |
|---|---|---|
| 27 | 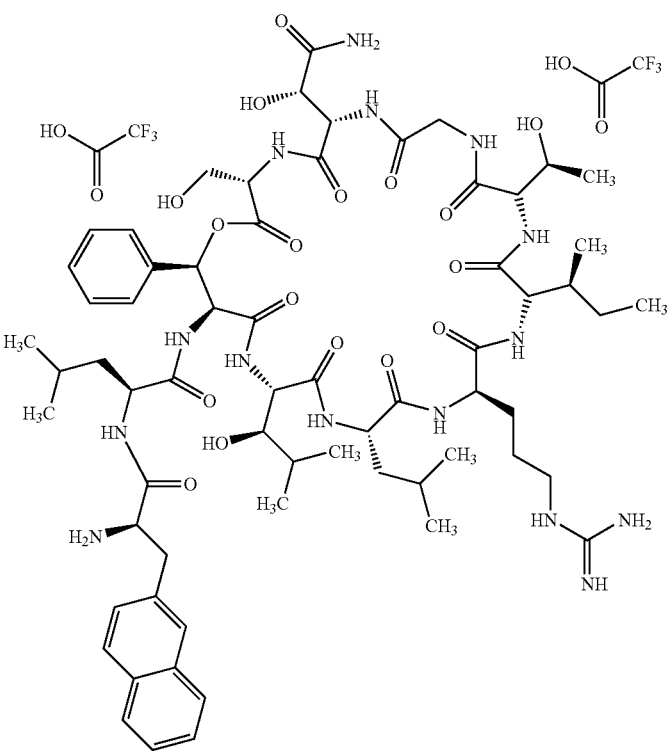<br>[3-(2-Naphthyl)-D-alanyl]-de(1-D-leucyl)lysobactin bistrifluoroacetate | HPLC/UV-Vis (method 36):$R_t$ = 3.68 min.<br>LC-MS (method 26):<br>$R_t$ = 1.82 min,<br>MS (ESIpos.): m/z (%) = 681.3 (100) [M ]$^{2+}$.<br>HR-TOF-MS (method 21): calc. 1360.7265, found 1360.7285 [M + H]$^+$.<br><br>General procedure 20 from Example 113A (25 μmol).<br>Yield: 37% |
| 28 | 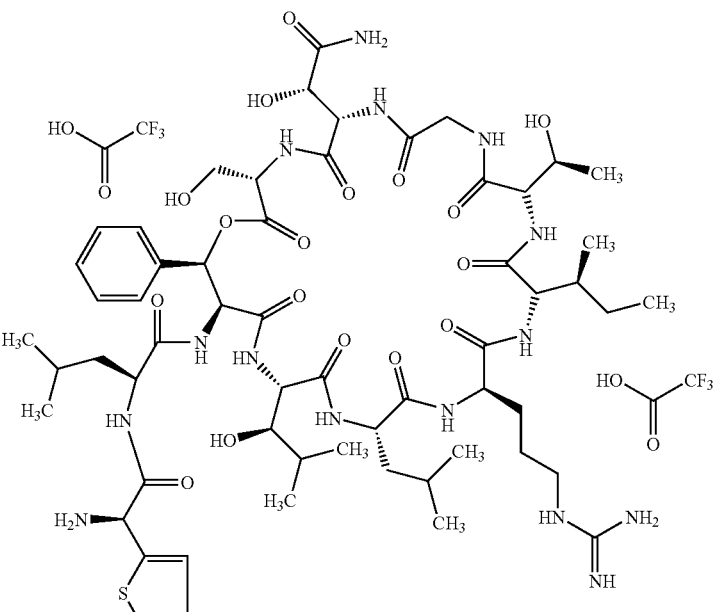<br>[(2R)-Amino(2-thienyl)acetyl]-de(1-D-leucyl)lysobactin bistrifluoroacetate | HPLC/UV-Vis (method 36):$R_t$ = 3.46 min.<br>LC-MS (method 26):<br>$R_t$ = 1.60 min,<br>MS (ESIpos.): m/z (%) = 1303 (5) [M + H]$^+$.<br>HR-TOF-MS (method 21): calc. 1302.6694, found 1302.6698 [M + H]$^+$.<br><br>General procedure 20 from Example 114A (8 μmol).<br>Yield: 45% |

TABLE 5-continued

Edman[1.0] route

| Ex. No. | Structure Name | Analytical data Preparation method |
|---|---|---|
| 29 | 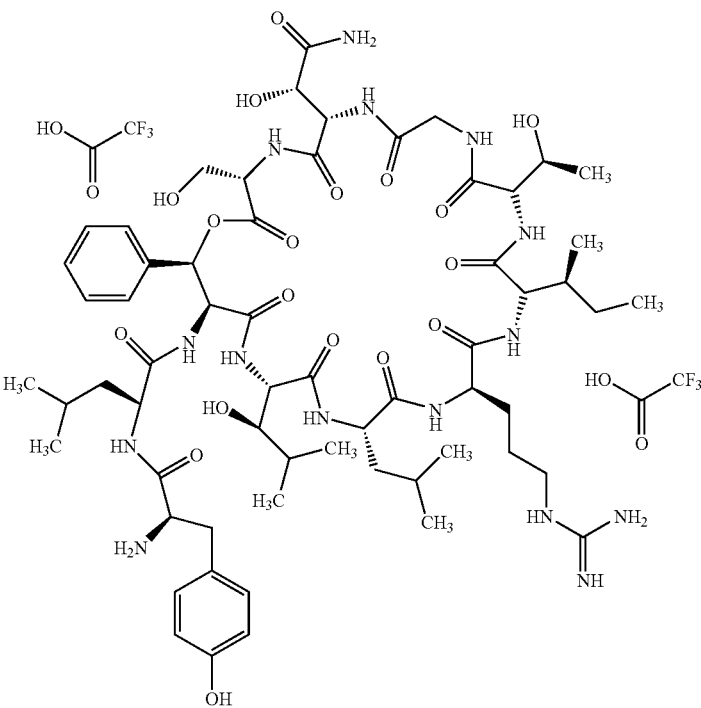<br>D-Tyrosyl-de(1-D-leucyl)lysobactin bistrifluoroacetate | HPLC/UV-Vis (method 36):$R_t$ = 3.39 min.<br>LC-MS (method 26):<br>$R_t$ = 1.43 min,<br>MS (ESIpos.): m/z (%) = 664.3 (100) [M + 2H]$^{2+}$.<br>HR-TOF-MS (method 21): calc. 1326.7058, found 1326.7032 [M + H]$^+$.<br><br>General procedure 20 from Example 115A (25 µmol).<br>Yield: 50% |
| 30 | 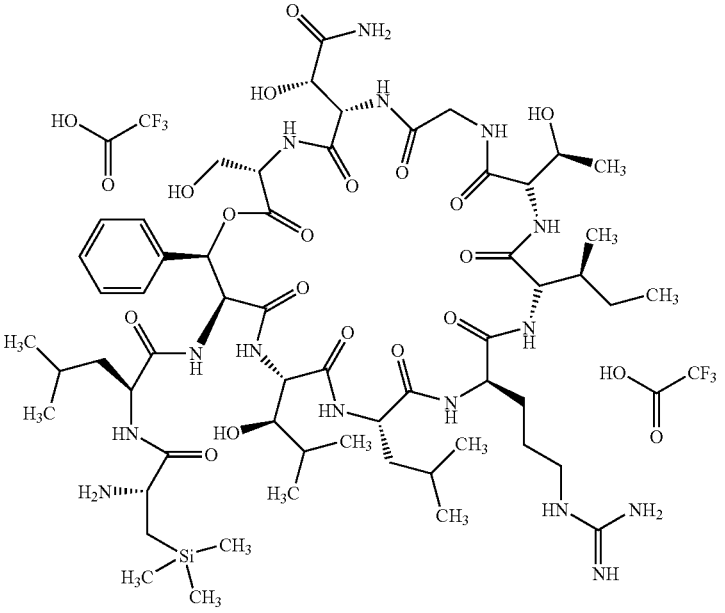<br>[3-(Trimethylsilyl)-L-alanyl]-de(1-D-leucyl)lysobactin bistrifluoroacetate | HPLC/UV-Vis (method 36):$R_t$ = 3.64 min.<br>LC-MS (method 26):<br>$R_t$ = 1.56 min,<br>MS (ESIpos.): m/z (%) = 654.3 (100) [M + 2H]$^{2+}$;1307 (2) [M + H]$^+$.<br>HR-TOF-MS (method 21): calc. 1326.7058, found 1326.7032 [M + H]$^+$.<br><br>General procedure 20 from Example 116A (216 µmol).<br>Yield: 36% |

TABLE 5-continued

Edman[1.0] route

| Ex. No. | Structure Name | Analytical data Preparation method |
|---|---|---|
| 31 | 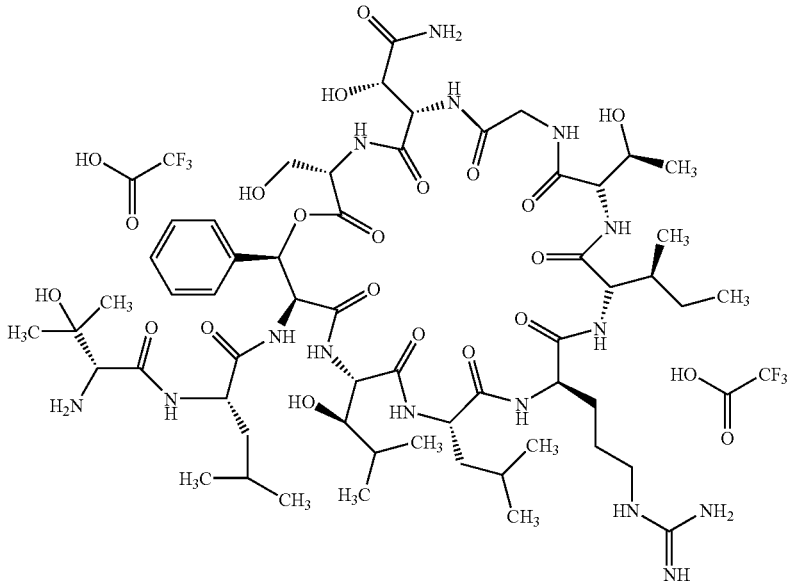<br>(3-Hydroxy-D-valyl)-de(1-D-leucyl)lysobactin bistrifluoroacetate | HPLC/UV-Vis (method 36): $R_t$ = 3.39 min.<br>LC-MS (method 26):<br>$R_t$ = 1.59 min,<br>MS (ESIpos.): m/z (%) = 640.1 (100) $[M + 2H]^{2+}$.<br>HR-TOF-MS (method 21): calc. 1278.7058, found 1728.7039 $[M + H]^+$.<br>General procedure 20 from Example 117A (19 µmol).<br>Yield: 22% of theory |
| 32 | 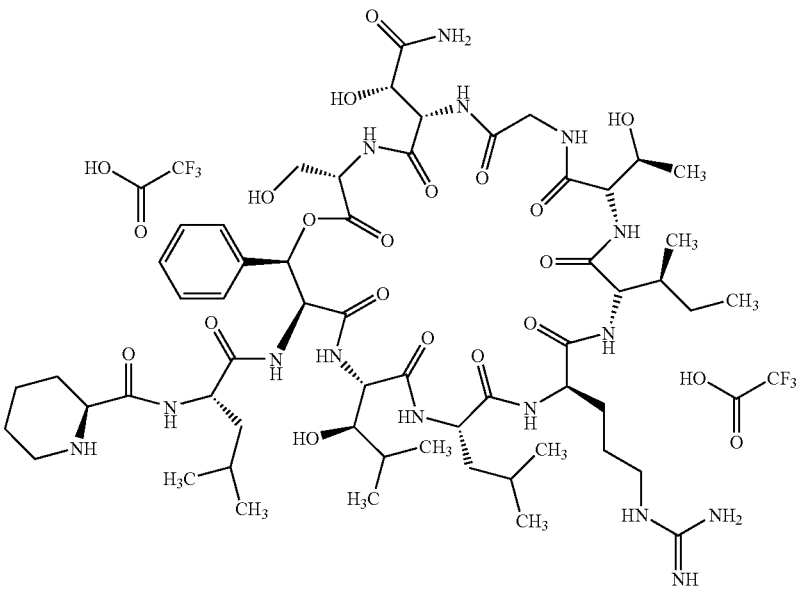<br>L-Pipecolyl-de(1-D-leucyl)lysobactin bistrifluoroacetate | HPLC/UV-Vis (method 36): $R_t$ = 3.39 min.<br>LC-MS (method 26):<br>$R_t$ = 1.35 min,<br>MS (ESIpos.): m/z (%) = 638.3 (100) $[M + 2H]^{2+}$.<br>HR-TOF-MS (method 21): calc. 1274.7109, found 1274.7087 $[M + H]^+$.<br>General procedure 20 from Example 118A (21 µmol).<br>Yield: 40% of theory |

TABLE 5-continued

Edman[1.0] route

| Ex. No. | Structure Name | Analytical data Preparation method |
|---|---|---|
| 33 | D-Pipecolyl-de(1-D-leucyl)lysobactin bistrifluoroacetate | HPLC/UV-Vis (method 36): $R_t$ = 3.42 min.<br>LC-MS (method 26): $R_t$ = 1.38 min,<br>MS (ESIpos.): m/z (%) = 1275 (10) [M + H]$^+$.<br>HR-TOF-MS (method 21): calc. 1274.7109, found 1274.7083 [M + H]$^+$.<br><br>General procedure 20 from Example 119A (22 µmol).<br>Yield: 36% of theory |
| 34 | D-Isoleucyl-de(1-D-leucyl)lysobactin bistrifluoroacetate | HPLC/UV-Vis (method 36): $R_t$ = 3.55 min.<br>LC-MS (method 26): $R_t$ = 1.54 min,<br>MS (ESIpos.): m/z (%) = 639.3 (100) [M + 2H]$^{2+}$.<br><br>General procedure 20 from Example 120A (20 µmol).<br>Yield: 36% of theory |

TABLE 5-continued

Edman[1.0] route

| Ex. No. | Structure Name | Analytical data Preparation method |
|---|---|---|
| 35 | 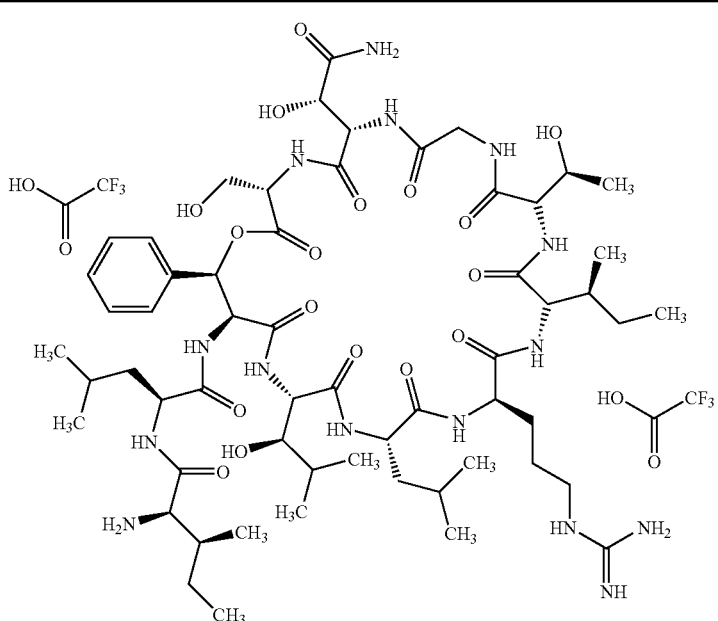<br>D-Alloisoleucyl-de(1-D-leucyl)lysobactin bistrifluoroacetate | HPLC/UV-Vis (method 36):$R_t$ = 3.56 min.<br>LC-MS (method 26):<br>$R_t$ = 1.57 min,<br>MS (ESIpos.): m/z (%) = 639.3 (100) $[M + 2H]^{2+}$.<br><br>General procedure 20 from Example 121A (17 μmol).<br>Yield: 6% of theory |
| 36 | 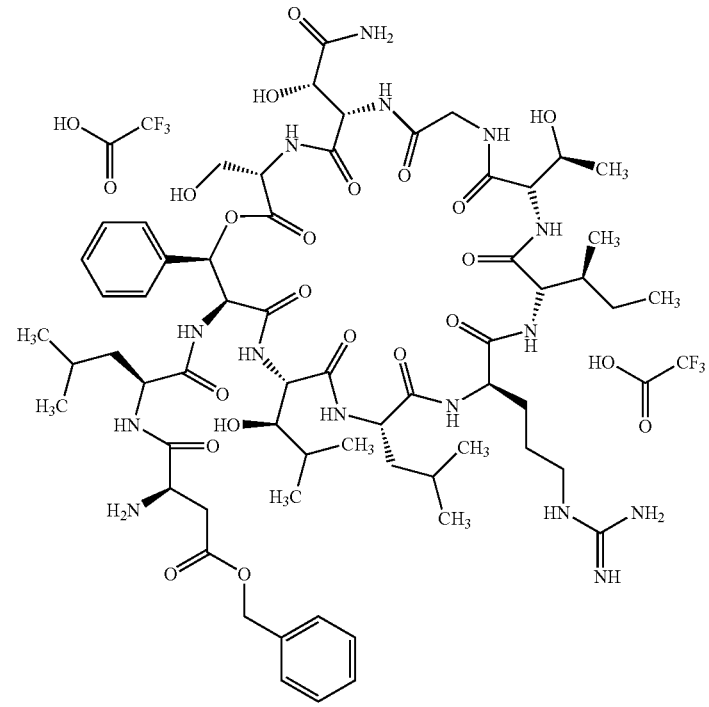<br>[(2R)-2-Amino-4-(benzyloxy)-4-oxobutanoyl]-de(1-D-leucyl)lysobactin bistrifluoroacetate | HPLC/UV-Vis (method 36):$R_t$ = 3.62 min.<br>LC-MS (method 26):<br>$R_t$ = 1.60 min,<br>MS (ESIpos.): m/z (%) = 685 (100) $[M + 2H]^{2+}$.<br>HR-TOF-MS (method 21): calc. 1368.7133, found 1368.7163 $[M + H]^+$.<br><br>General procedure 20 from Example 137A (117 μmol).<br>Yield: 28% of theory |

TABLE 5-continued

Edman[1.0] route

| Ex. No. | Structure Name | Analytical data Preparation method |
|---|---|---|
| 37 | 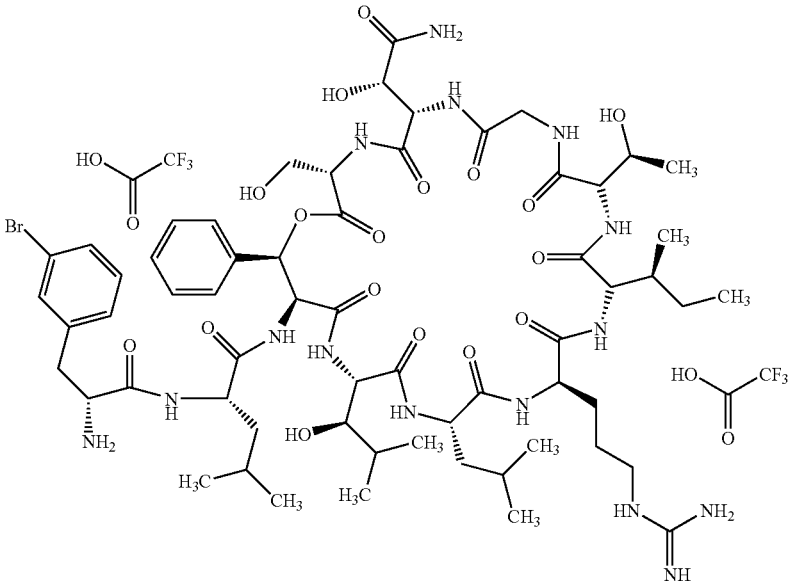<br>(3-Bromo-D-phenylalanyl)-de(1-D-leucyl)lysobactin bistrifluoroacetate | HPLC/UV-Vis (method 36): $R_t$ = 3.64 min.<br>LC-MS (method 26): $R_t$ = 1.70 min,<br>MS (ESIpos.): m/z (%) = 695.1 (100) $[M + 2H]^{2+}$.<br>HR-TOF-MS (method 21): calc. 1388.6214, found 1388.6243 $[M + H]^+$.<br><br>General procedure 20 from Example 122A (22 μmol).<br>Yield: 22% of theory |
| 38 | 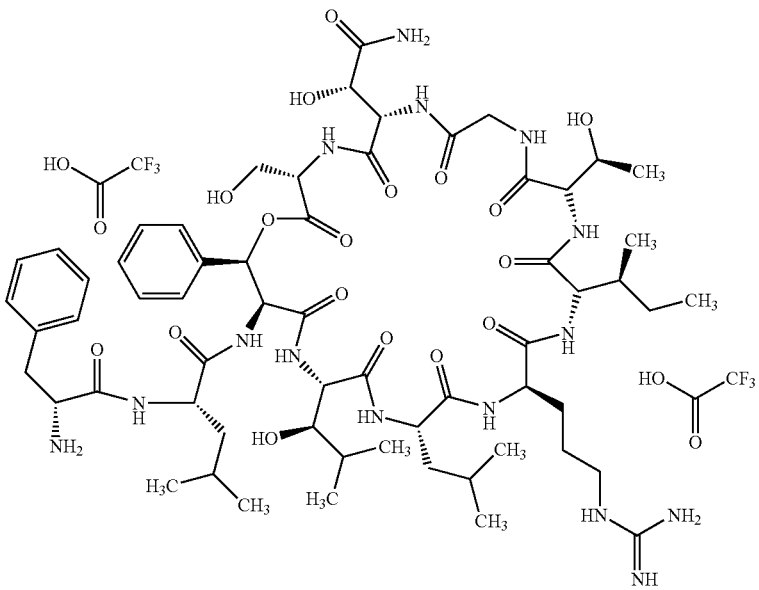<br>D-Phenylalanyl-de(1-D-leucyl)lysobactin bistrifluoracetate | HPLC/UV-Vis (method 36): $R_t$ = 3.56 min.<br>LC-MS (method 26): $R_t$ = 1.59 min,<br>MS (ESIpos.): m/z (%) = 656 (100) $[M + 2H]^{2+}$.<br>HR-TOF-MS (method 21): calc. 1310.7157, found 1310.7109 $[M + H]^+$.<br><br>General procedure 20 from Example 123A (43 μmol).<br>Yield: 33% of theory |

TABLE 5-continued

Edman[1.0] route

| Ex. No. | Structure Name | Analytical data Preparation method |
|---|---|---|
| 39 | 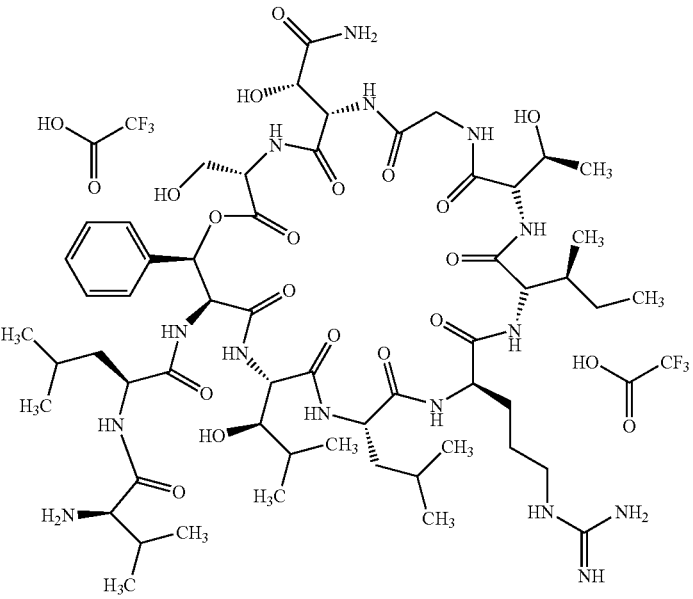<br>D-Valyl-de(1-D-leucyl)lysobactin bistrifluoroacetate | HPLC/UV-Vis (method 36):$R_t$ = 4.49 min.<br>LC-MS (method 26):<br>$R_t$ = 1.47 min,<br>MS (ESIpos.): m/z (%) = 632 (100) $[M + 2H]^{2+}$.<br>HR-TOF-MS (method 21): calc. 1262.7168, found 1262.7109 $[M + H]^+$.<br><br>General procedure 20 from Example 124A (29 μmol).<br>Yield: 39% of theory |
| 40 | 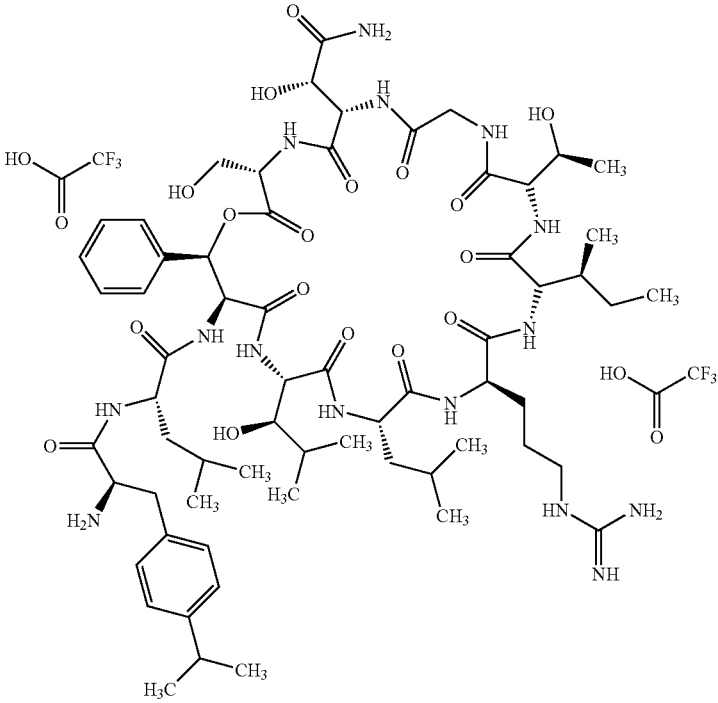<br>(4-Isopropyl-D-phenylalanyl)-de(1-D-leucyl)lysobactin bistrifluoroacetate | HPLC/UV-Vis (method 36):$R_t$ = 3.76 min.<br>LC-MS (method 26):<br>$R_t$ = 1.75 min,<br>MS (ESIpos.): m/z (%) = 677.4 (100) $[M + 2H]^{2+}$.<br>HR-TOF-MS (method 21): calc. 1352.7578, found 1352.7510 $[M + H]^+$.<br><br>General procedure 22 from Example 125A (24 μmol).<br>Yield: 52% of theory |

TABLE 5-continued

Edman[1.0] route

| Ex. No. | Structure Name | Analytical data Preparation method |
|---|---|---|
| 41 | 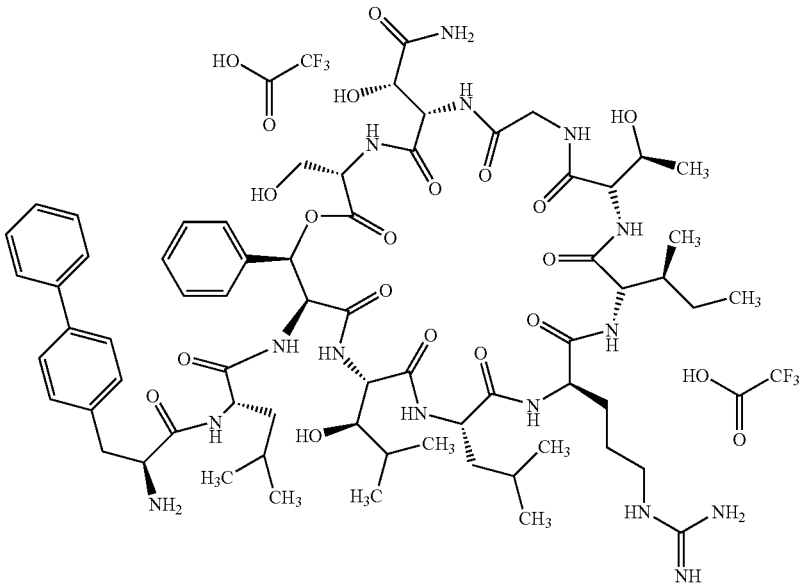<br>(3-Biphenyl-L-alanyl)-de(1-D-leucyl)lysobactin bistrifluoroacetate | HPLC/UV-Vis (method 36):$R_t$ = 3.73 min.<br>LC-MS (method 26):<br>$R_t$ = 1.80 min,<br>MS (ESIpos.): m/z (%) = 694.3 (100) [M + 2H]$^{2+}$.<br>HR-TOF-MS (method 21): calc. 1386.7422, found 1386.7412 [M + H]$^+$.<br><br>General procedure 20 from Example 126A (37 μmol).<br>Yield: 28% of theory |
| 42 | 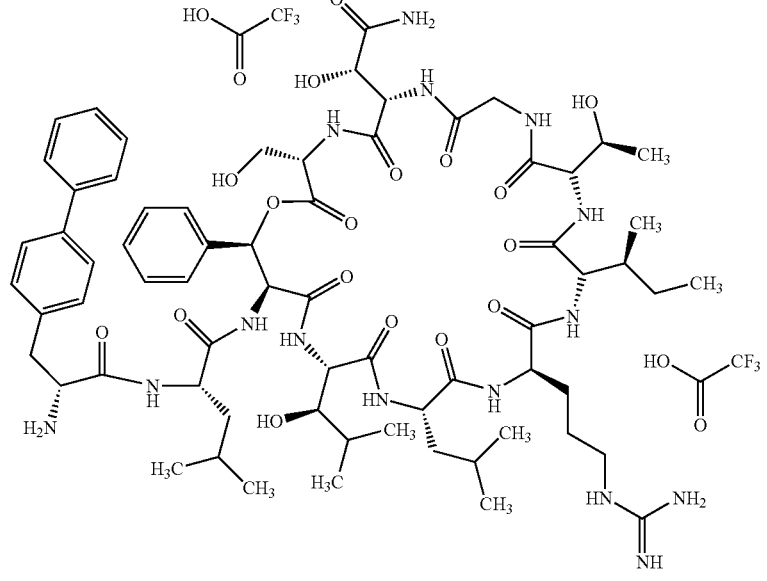<br>(3-Biphenyl-D-alanyl)-de(1-D-leucyl)lysobactin bistrifluoroacetate | HPLC/UV-Vis (method 36):$R_t$ = 3.74 min.<br>LC-MS (method 26):<br>$R_t$ = 1.58 min,<br>MS (ESIpos.): m/z (%) = 694.3 (100) [M + 2H]$^{2+}$.<br>HR-TOF-MS (method 21): calc. 1386.7422, found 1386.7407 [M + H]$^+$.<br><br>General procedure 20 from Example 127A (74 μmol).<br>Yield: 45% of theory |

TABLE 5-continued

Edman[1.0] route

| Ex. No. | Structure Name | Analytical data Preparation method |
|---|---|---|
| 43 | 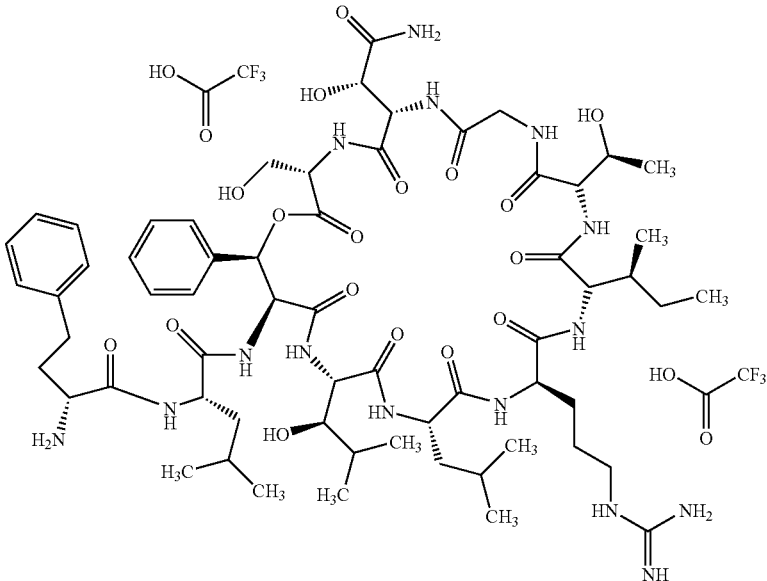<br>((2R)-2-Amino-4-phenylbutanoyl)-de(1-D-leucyl)-lysobactin bistrifluoroacetate | HPLC/UV-Vis (method 36):$R_t$ = 3.64 min.<br>LC-MS (method 26): $R_t$ = 1.47 min,<br>MS (ESIpos.): m/z (%) = 663.3 (100) $[M + 2H]^{2+}$.<br>HR-TOF-MS (method 21): calc. 1324.7265, found 1324.7226 $[M + H]^+$.<br><br>General procedure 21 from Example 128A (37 μmol).<br>Yield: 27% of theory |
| 44 | 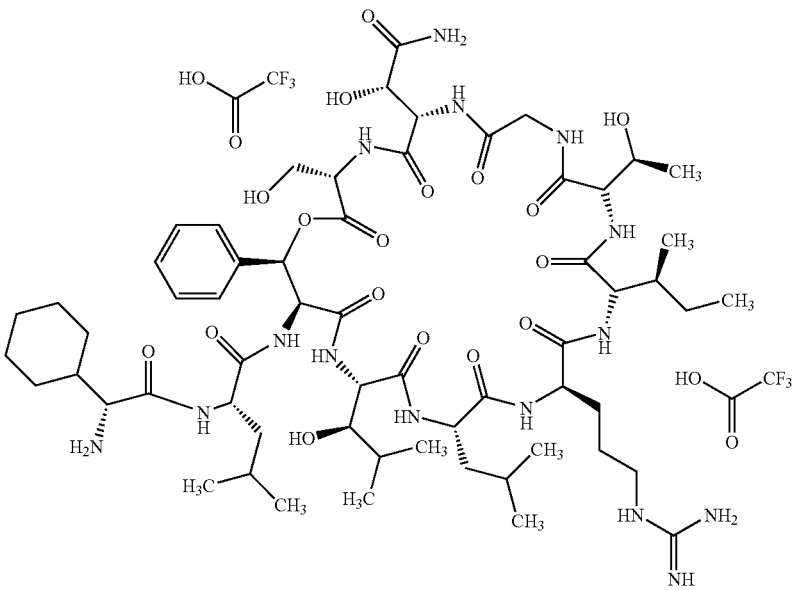<br>[(2R)-Amino(cyclohexyl)acetyl]-de(1-D-leucyl)-lysobactin bistrifluoroacetate | HPLC/UV-Vis (method 36):$R_t$ = 3.6 min.<br>LC-MS (method 26): $R_t$ = 1.44 min,<br>MS (ESIpos.): m/z (%) = 652.3 (100) $[M + 2H]^{2+}$.<br>HR-TOF-MS (method 21): calc. 1302.7422, found 1302.7346 $[M + H]^+$.<br><br>General procedure 21 from Example 129A (36 μmol).<br>Yield: 38% of theory |

TABLE 5-continued

Edman[1.0] route

| Ex. No. | Structure Name | Analytical data Preparation method |
|---|---|---|
| 45 | 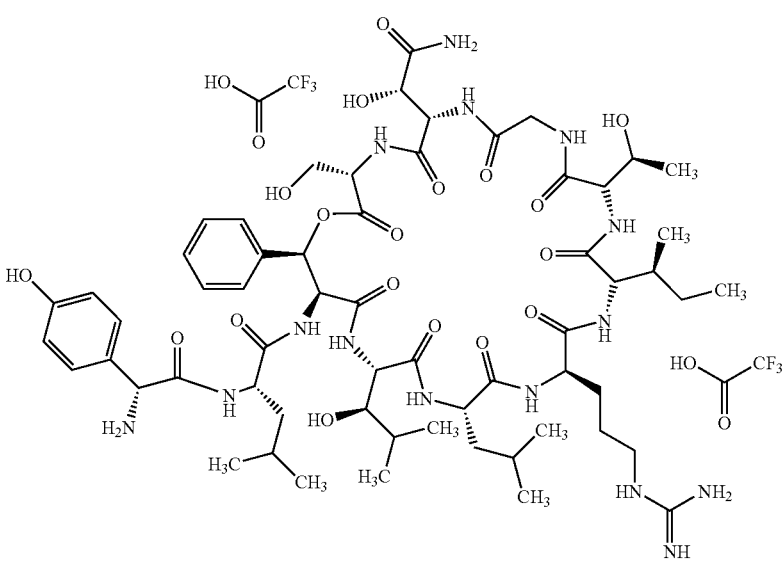<br>[(2R)-Amino(4-hydroxyphenyl)acetyl]-de(1-D-leucyl)-lysobactin bistrifluoroacetate | HPLC/UV-Vis (method 36):$R_t$ = 3.35 min.<br>LC-MS (method 26):<br>$R_t$ = 1.24 min,<br>MS (ESIpos.): m/z (%) = 657.3 (100) $[M + 2H]^{2+}$, 1313.1 (3) $[M + H]^+$.<br>HR-TOF-MS (method 21): calc. 1312.6901, found 1312.6916 $[M + H]^+$.<br><br>General procedure 21 from Example 130A (37 μmol).<br>Yield: 24% of theory |
| 46 | 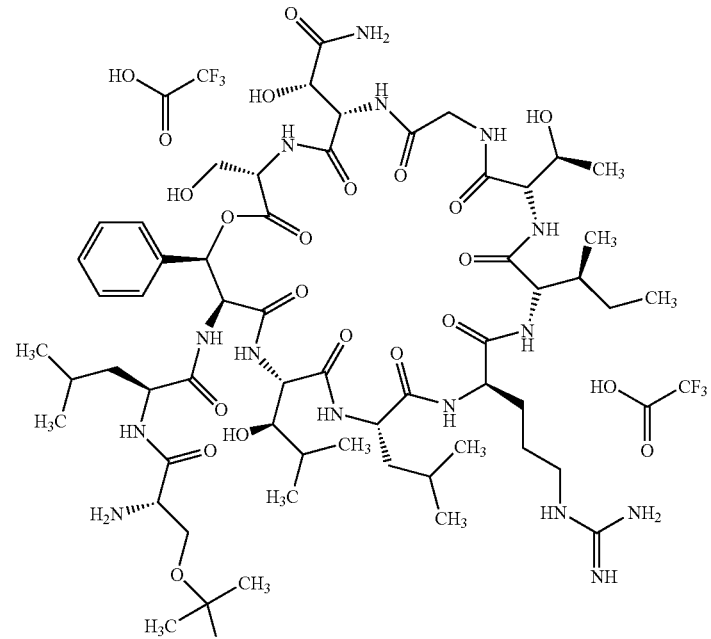<br>[O-(tert-Butyl)-L-seryl]-de(1-D-leucyl)lysobactin bistrifluoroacetate | HPLC/UV-Vis (method 36):$R_t$ = 3.52 min.<br>LC-MS (method 26):<br>$R_t$ = 1.54 min,<br>MS (ESIpos.): m/z (%) = 1307 (3) $[M + H]^+$.<br>HR-TOF-MS (method 21): calc. 1306.7371, found 1306.7307 $[M + H]^+$.<br><br>General procedure 22 from Example 131A (76 μmol).<br>Yield: 48% of theory |

TABLE 5-continued

Edman[1.0] route

| Ex. No. | Structure Name | Analytical data Preparation method |
|---|---|---|
| 47 | 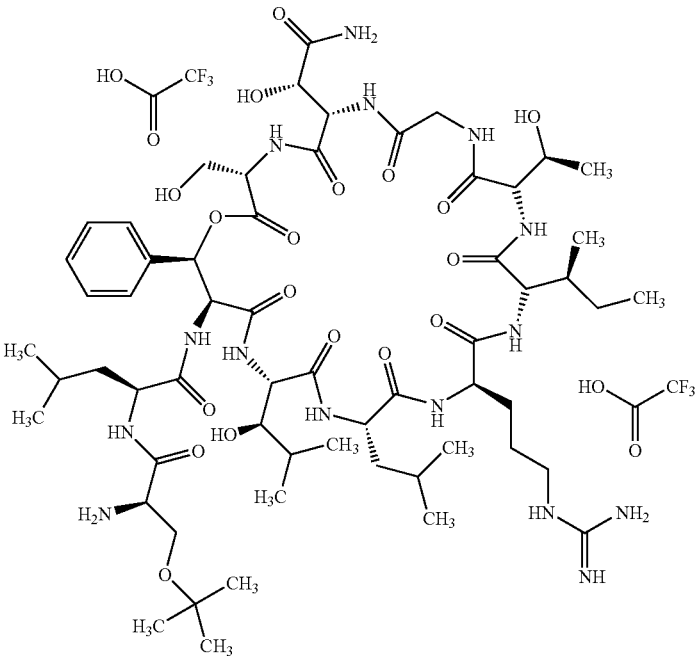<br>[O-(tert-Butyl)-D-seryl]-de(1-D-leucyl)lysobactin bistrifluoroacetate | HPLC/UV-Vis (method 36): $R_t$ = 3.56 min.<br>LC-MS (method 26):<br>$R_t$ = 1.47 min,<br>MS (ESIpos.): m/z (%) = 1306.9 (3) $[M + H]^+$.<br>HR-TOF-MS (method 21): calc. 1306.7371, found 1306.7393 $[M + H]^+$.<br><br>General procedure 22 from Example 132A (37 µmol).<br>Yield: 79% of theory |
| 48 | 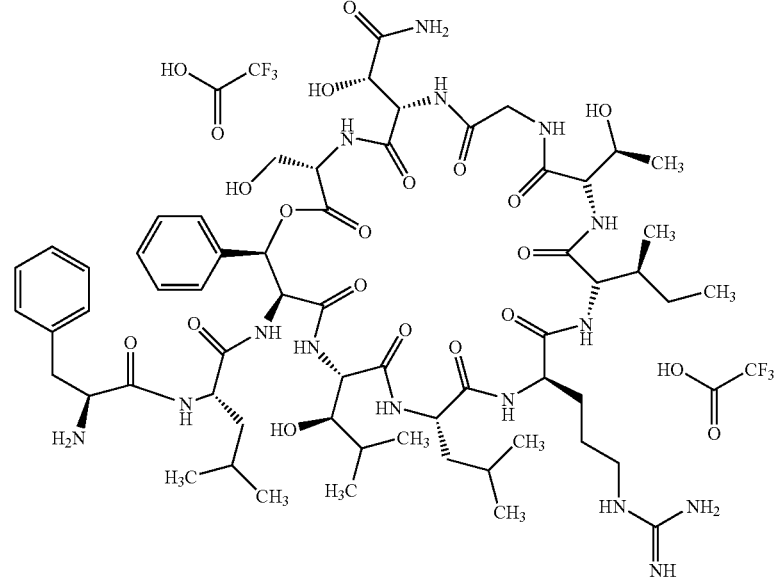<br>L-Phenylalanyl-de(1-D-leucyl)lysobactin bistrifluoroacetate | HPLC/UV-Vis (method 36): $R_t$ = 3.52 min.<br>LC-MS (method 26):<br>$R_t$ = 1.44 min,<br>MS (ESIpos.): m/z (%) = 1311.1 (5) $[M + H]^+$.<br>HR-TOF-MS (method 21): calc. 1310.7109, found 1310.7153 $[M + H]^+$.<br><br>General procedure 22 from Example 133A (77 µmol).<br>Yield: 63% of theory |

TABLE 5-continued

Edman[1.0] route

| Ex. No. | Structure Name | Analytical data Preparation method |
|---|---|---|
| 49 | 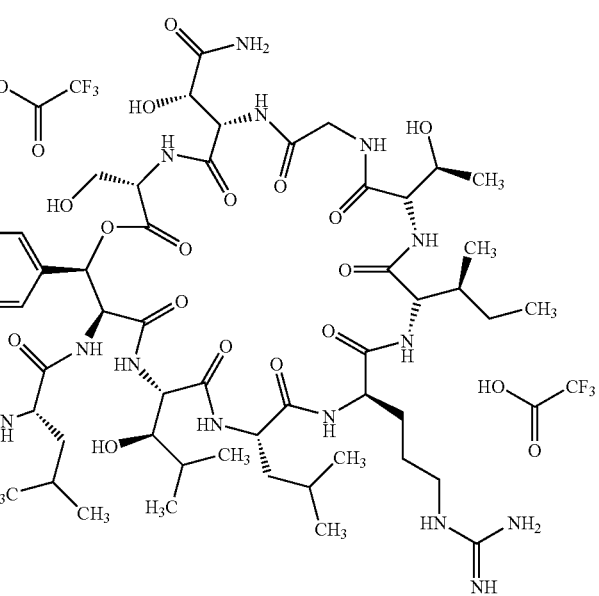<br>L-Prolyl-de(1-D-leucyl)lysobactin bistrifluoroacetate | HPLC/UV-Vis (method 36):$R_t$ = 3.32 min.<br>LC-MS (method 26):<br>$R_t$ = 1.20 min,<br>MS (ESIpos.): m/z (%) = 631.2 (100) $[M + 2H]^{2+}$.<br>HR-TOF-MS (method 21): calc. 1260.6952, found 1260.6962 $[M + H]^+$.<br><br>General procedure 21 from Example 134A (52 μmol).<br>Yield: 64% of theory |
| 50 | 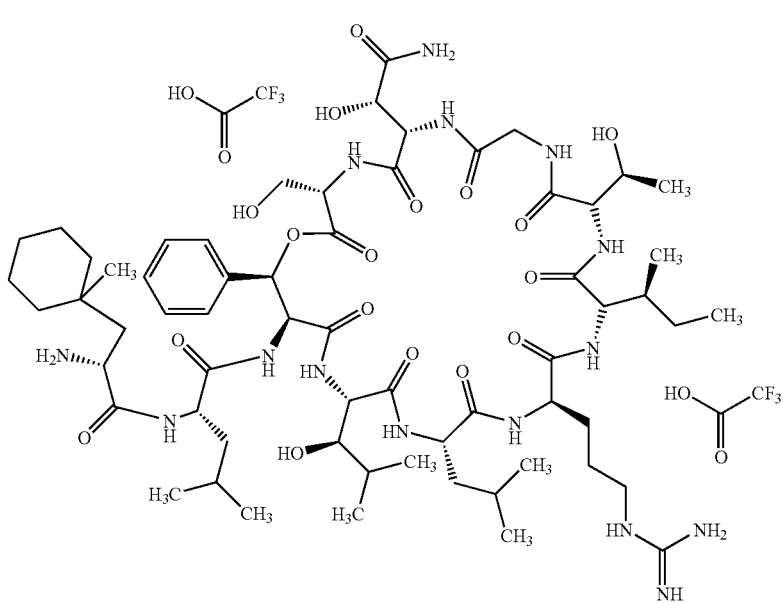<br>[3- (1-Methylcyclohexyl)-D-alanyl]-de(1-D-leucyl)-lysobactin bistrifluoroacetate | HPLC/UV-Vis (method 36):$R_t$ = 3.71 min.<br>LC-MS (method 26):<br>$R_t$ = 1.61 min,<br>MS (ESIpos.): m/z (%) = 666.3 (100) $[M + 2H]^{2+}$.<br>HR-TOF-MS (method 21): calc. 1330.7735, found 1330.7759 $[M + H]^+$.<br><br>General procedure 22(pure acetic acid is used as solvent) from Example 135A (57 μmol).<br>Yield: 30% of theory |

TABLE 5-continued

Edman[1.0] route

| Ex. No. | Structure Name | Analytical data Preparation method |
|---|---|---|
| 51 | 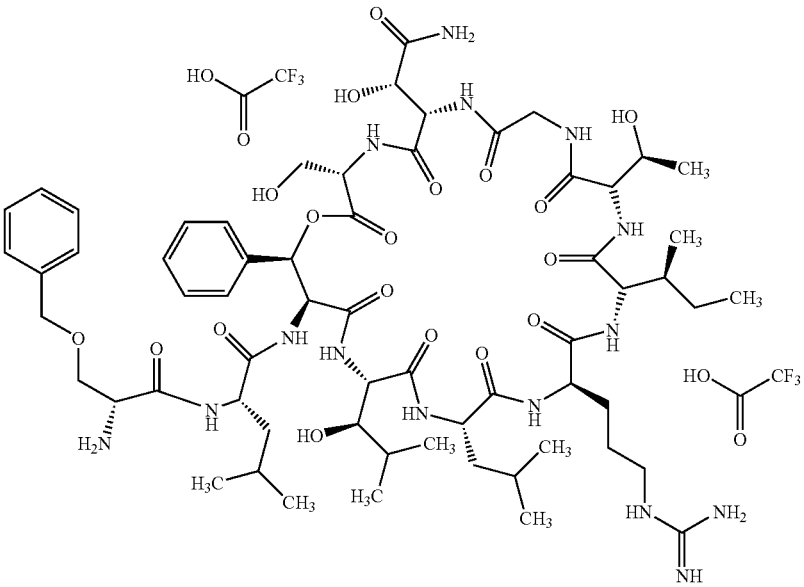<br>(O-Benzyl-D-seryl)-de(1-D-leucyl)lysobactin bistrifluoroacetate | HPLC/UV-Vis (method 36):$R_t$ = 3.57 min.<br>LC-MS (method 26):<br>$R_t$ = 1.51 min,<br>MS (ESIpos.): m/z (%) = 671.3 (100) $[M + 2H]^{2+}$,<br>1340.9 (1) $[M + H]^+$.<br>HR-TOF-MS (method 21): calc. 1340.7214, found 1340.7155 $[M + H]^+$.<br><br>General procedure 21 from Example 136A (67 µmol).<br>Yield: 28% of theory |
| 52 | 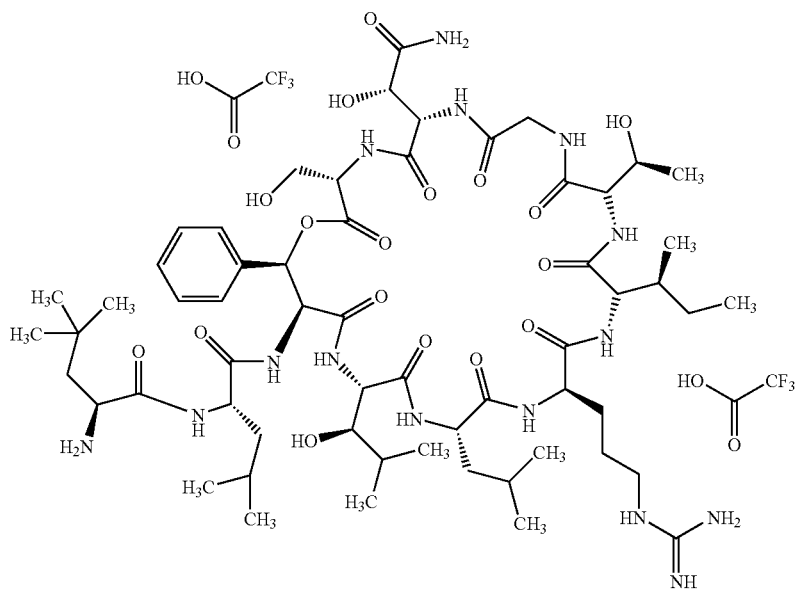<br>[3-(tert-Butyl)-L-alanyl]-de(1-D-leucyl)lysobactin bistrifluoroacetate | HPLC/UV-Vis (method 36):$R_t$ = 3.57 min.<br>LC-MS (method 26):<br>$R_t$ = 1.59 min,<br>MS (ESIpos.): m/z (%) = 646.4 (100) $[M + 2H]^{2+}$.<br>HR-TOF-MS (method 21): calc. 1290.7422, found 1290.7373 $[M + H]^+$.<br><br>General procedure 21 from Example 138A (74 µmol).<br>Yield: 41% of theory |

TABLE 5-continued

Edman[1.0] route

| Ex. No. | Structure Name | Analytical data Preparation method |
|---|---|---|
| 53 | 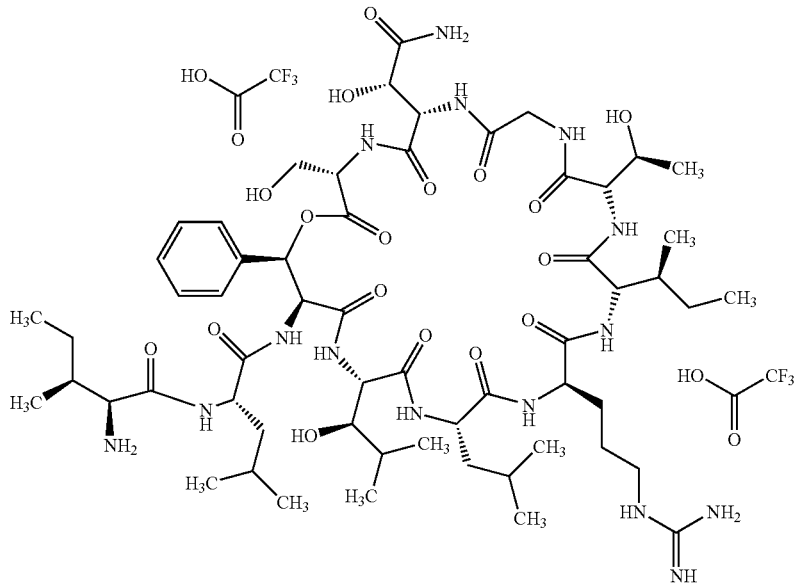<br>L-Isoleucyl-de(1-D-leucyl)lysobactin bistrifluoroacetate | HPLC/UV-Vis (method 36):$R_t$ = 3.46 min.<br>LC-MS (method 26):<br>$R_t$ = 1.50 min,<br>MS (ESIpos.): m/z (%) = 639.4 (100) $[M + 2H]^{2+}$.<br>HR-TOF-MS (method 21): calc. 1276.7265, found 1276.7290 $[M + H]^+$.<br><br>General procedure 21 from Example 139A (95 μmol).<br>Yield: 33% of theory |
| 54 | 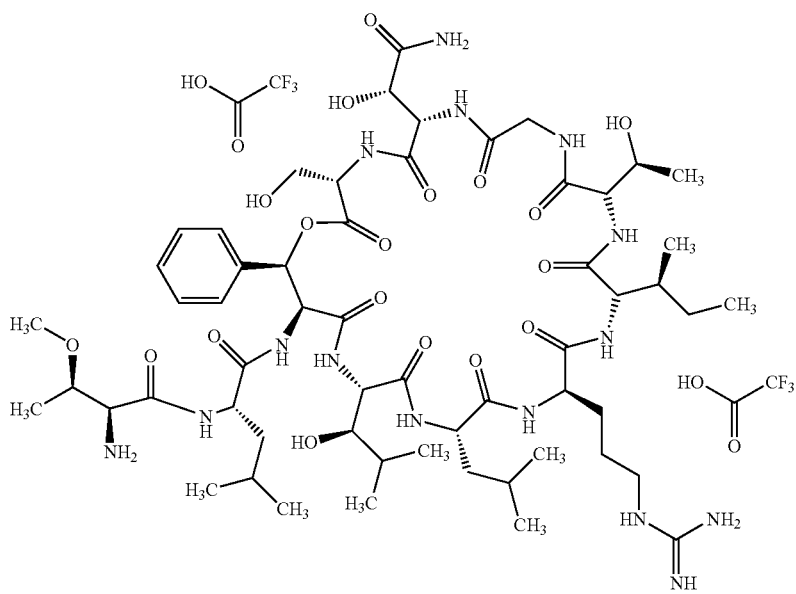<br>(O-Methyl-L-threonly)-de(1-D-leucyl)lysobactin bistrifluoroacetate | HPLC/UV-Vis (method 36):$R_t$ = 3.31 min.<br>LC-MS (method 26):<br>$R_t$ = 1.32 min,<br>MS (ESIpos.): m/z (%) = 640.2 (100) $[M + 2H]^{2+}$.<br>HR-TOF-MS (method 21): calc. 1278.7058, found 1278.7037<br><br>General procedure 21 from Example 140A (50 μmol).<br>Yield: 77% of theory |

TABLE 5-continued

Edman[1.0] route

| Ex. No. | Structure Name | Analytical data Preparation method |
|---|---|---|
| 55 | 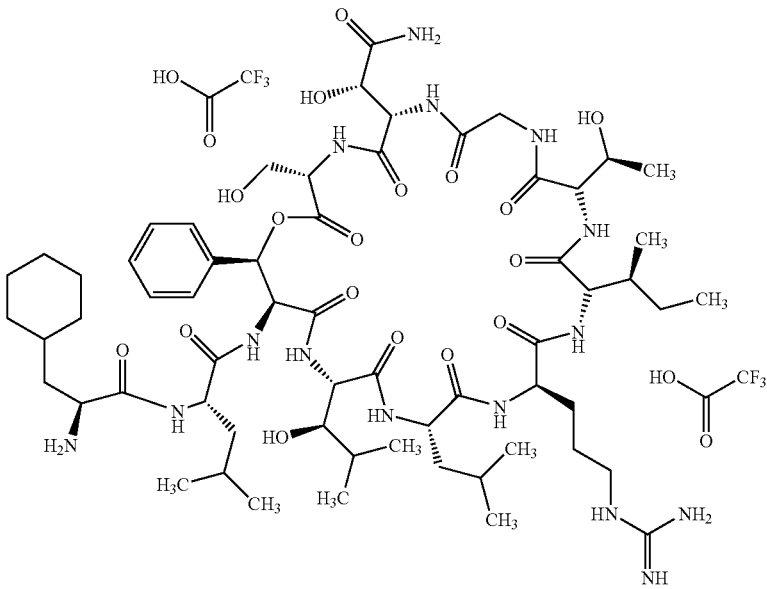<br>3-Cyclohexyl-L-alanyl-de(1-D-leucyl)lysobactin bistrifluoroacetate | HPLC/UV-Vis (method 36):$R_t$ = 3.63 min.<br>LC-MS (method 26): $R_t$ = 1.61 min,<br>MS (ESIpos.): m/z (%) = 659.3 (100) $[M + 2H]^{2+}$.<br>HR-TOF-MS (method 21): calc. 1316.7578, found 1316.7532 $[M + H]^+$.<br><br>General procedure 21 from Example 141A (95 µmol).<br>Yield: 40% of theory |
| 56 | 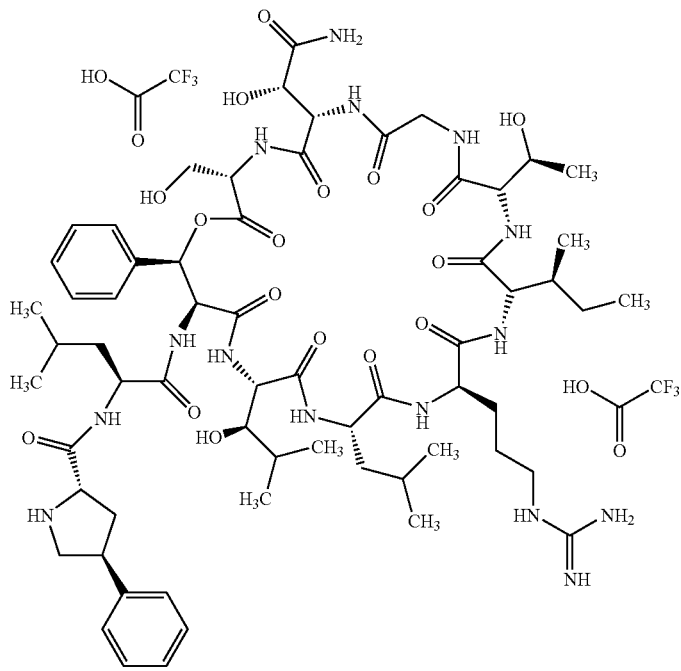<br>(4S)-4-Phenyl-L-prolyl-de(1-D-leucyl)lysobactin bistrifluoroacetate | HPLC/UV-Vis (method 36):$R_t$ = 3.65 min.<br>LC-MS (method 26): $R_t$ = 1.54 min,<br>MS (ESIpos.): m/z (%) = 669.1 (100) $[M + 2H]^{2+}$.<br>HR-TOF-MS (method 21): calc. 1316.7265, found 1316.7242 $[M + H]^+$.<br><br>General procedure 21 from Example 142A (68 µmol).<br>Yield: 58% of theory |

TABLE 5-continued

Edman[1.0] route

| Ex. No. | Structure Name | Analytical data Preparation method |
|---|---|---|
| 57 | 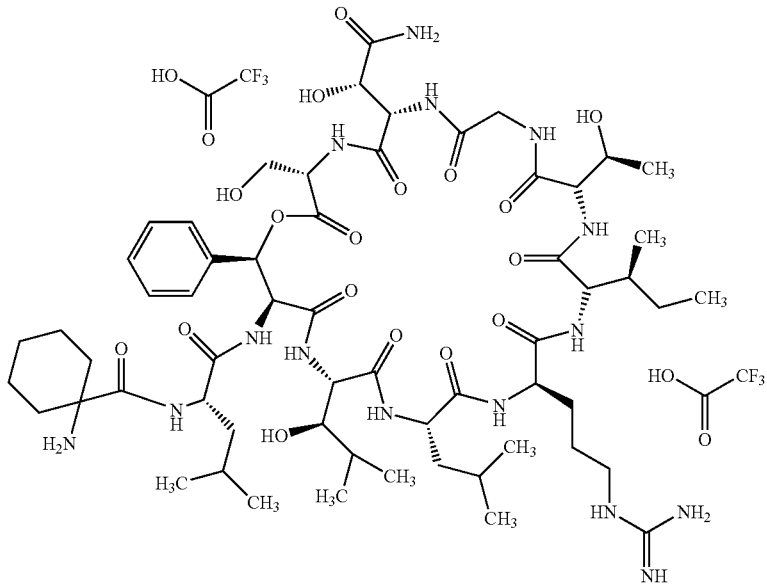<br>N-(1-Aminocyclohexyl)carbonyl-de(1-D-leucyl)-lysobactin bistrifluoroacetate | HPLC/UV-Vis (method 36):$R_t$ = 3.48 min.<br>LC-MS (method 26):<br>$R_t$ = 1.50 min,<br>MS (ESIpos.): m/z (%) = 645.2 (100) [M + 2H]$^{2+}$.<br>HR-TOF-MS (method 21): calc. 1288.7264, found 1288.7291 [M + H]$^+$.<br><br>General procedure 21 from Example 143A (28 µmol).<br>Yield: 92% of theory |
| 58 | 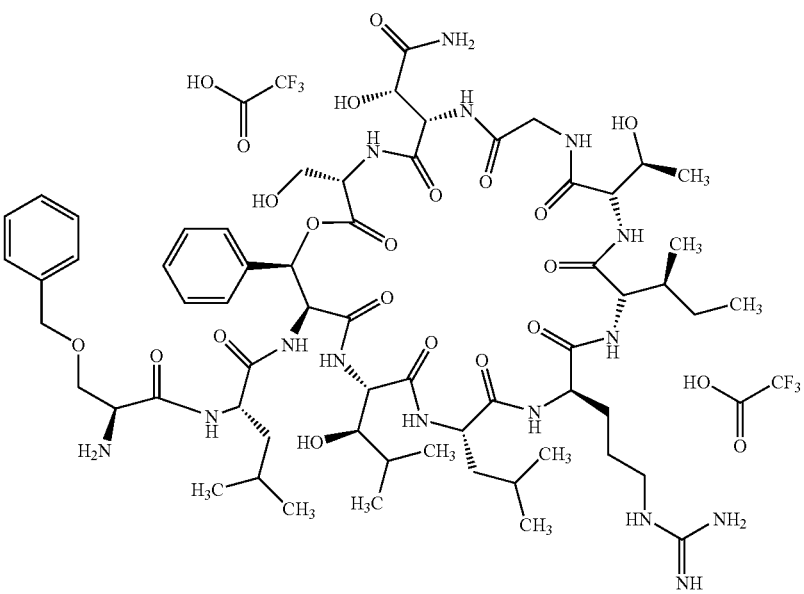<br>(O-Benzyl)-L-seryl-de(1-D-leucyl)lysobactin bistrifluoroacetate | HPLC/UV-Vis (method 36):$R_t$ = 3.45 min.<br>LC-MS (method 26):<br>$R_t$ = 1.55 min,<br>MS (ESIpos.): m/z (%) = 1340.8 (5) [M + H]$^+$.<br>HR-TOF-MS (method 21): calc. 1340.7214, found 1340.7214 [M + H]$^+$.<br><br>General procedure 21 from Example 144A (55 µmol).<br>Yield: 71% of theory |

TABLE 5-continued

Edman[1.0] route

| Ex. No. | Structure Name | Analytical data Preparation method |
|---|---|---|
| 59 | 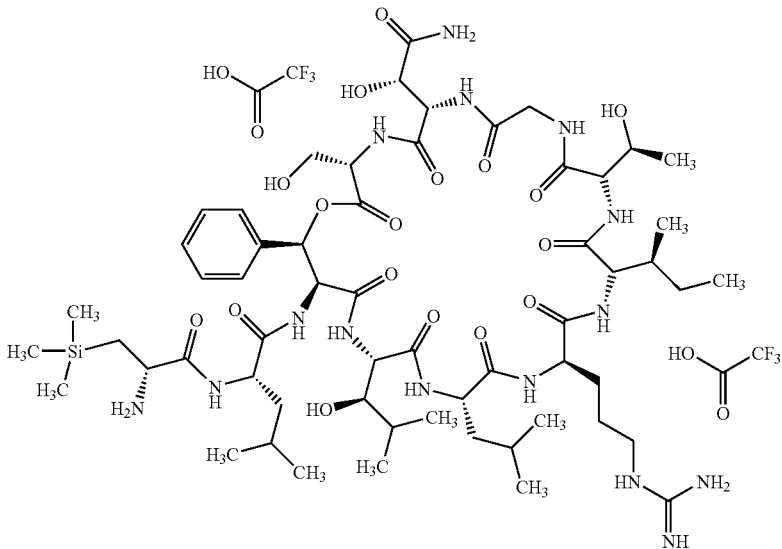<br>3-(Trimethylsilyl-D-alanyl-de(1-D-leucyl)lysobactin bistrifluoroacetate | HPLC/UV-Vis (method 36):$R_t$ = 3.67 min.<br>LC-MS (method 26):<br>$R_t$ = 1.56 min,<br>MS (ESIpos.): m/z (%) = 654.2 (100) $[M + 2H]^{2+}$.<br>HR-TOF-MS (method 21): calc. 1306.7191, found 1306.7228 $[M + H]^+$.<br><br>General procedure 21 from Example 145A (58 µmol).<br>Yield: 40% of theory |
| 60 | 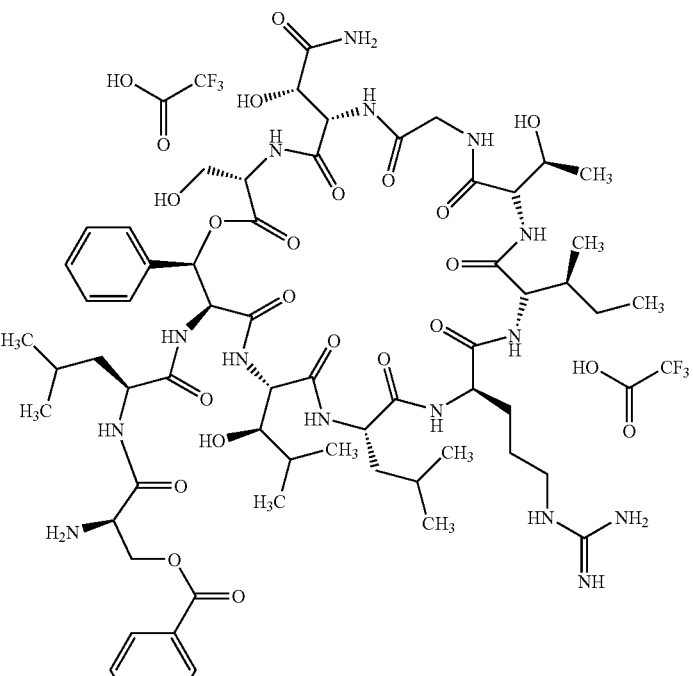<br>($O^3$-Benzoyl)-D-seryl-de(1-D-leucyl)lysobactin bistrifluoroacetate | HPLC/UV-Vis (method 36):$R_t$ = 3.56 min.<br>LC-MS (method 26):<br>$R_t$ = 1.52 min,<br>MS (ESIpos.): m/z (%) = 678.2 (100) $[M + 2H]^{2+}$.<br>HR-TOF-MS (method 21): calc. 1354.7007, found 1354.6946 $[M + H]^+$.<br><br>General procedure 21 from Example 146A (31 µmol).<br>Yield: 58% of theory |

TABLE 5-continued

Edman[1.0] route

| Ex. No. | Structure Name | Analytical data Preparation method |
|---|---|---|
| 61 | 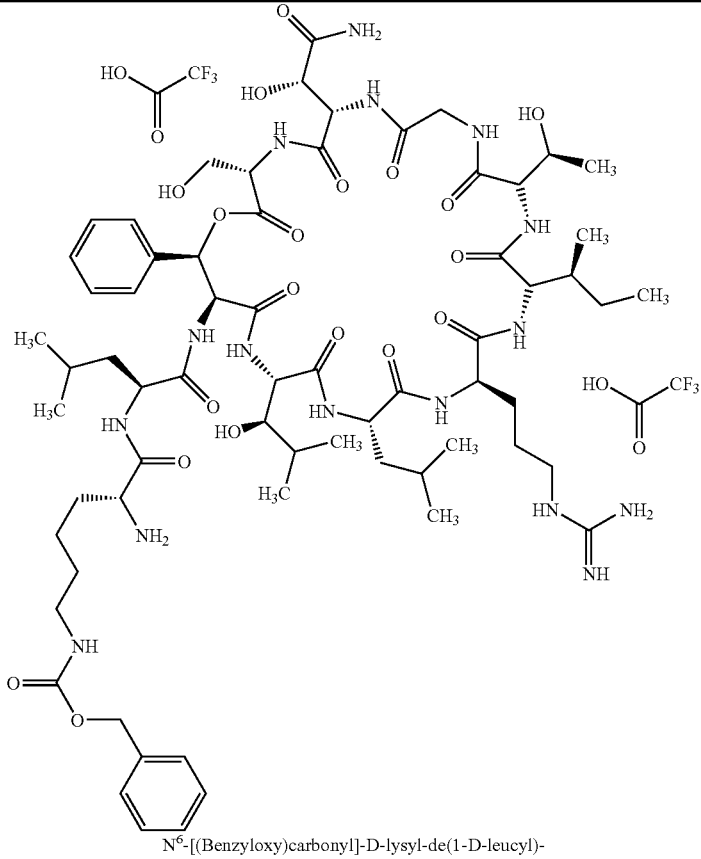<br>N[6]-[(Benzyloxy)carbonyl]-D-lysyl-de(1-D-leucyl)-lysobactin bistrifluoroacetate | HPLC/UV-Vis (method 36):$R_t$ = 3.64 min.<br>LC-MS (method 26):<br>$R_t$ = 1.48 min,<br>MS (ESIpos.): m/z (%) = 713.7 (100) $[M + 2H]^{2+}$.<br>HR-TOF-MS (method 21): calc. 1425.7742, found 1425.7769 $[M + H]^+$.<br><br>General procedure 21 from Example 147A (54 μmol).<br>Yield: 51% of theory |
| 62 | 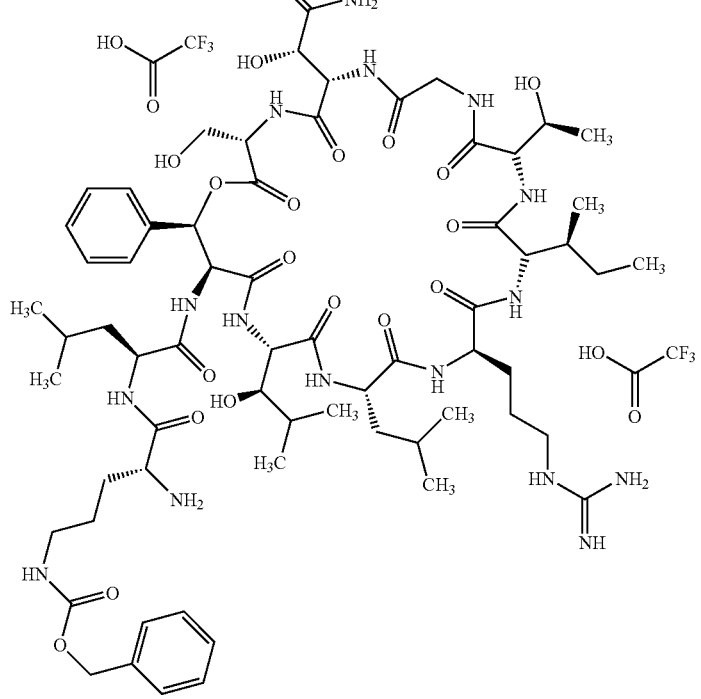 | HPLC/UV-Vis (method 36):$R_t$ = 3.60 min.<br>LC-MS (method 26):<br>$R_t$ = 1.43 min,<br>MS (ESIpos.): m/z (%) = 706.8 (100) $[M + 2H]^{2+}$.<br>HR-TOF-MS (method 21): calc. 1411.7585, found 1411.7596 $[M + H]^+$. |

TABLE 5-continued

Edman[1.0] route

| Ex. No. | Structure Name | Analytical data Preparation method |
|---|---|---|
| 63 | N[6]-[(Benzyloxy)carbonyl]-D-ornithyl-de(1-D-leucyl)-lysobactin bistrifluoroacetate | General procedure 21 from Example 148A (51 μmol). Yield: 63% of theory<br><br>HPLC/UV-Vis (method 36):$R_t$ = 3.55 min.<br>LC-MS (method 26):<br>$R_t$ = 1.48 min,<br>MS (ESIpos.): m/z (%) = 699.7 (100) $[M + 2H]^{2+}$.<br>HR-TOF-MS (method 21): calc. 1397.7429, found 1397.7367 $[M + H]^+$. |
| 64 | (2S)-2-Amino-4-{[(benzyloxy)carbonyl]amino}-butanoyl-de(1-D-leucyl)lysobactin bistrifluoroacetate | General procedure 21 from Example 149A (52 μmol). Yield: 48% of theory<br><br>HPLC/UV-Vis (method 36):$R_t$ = 3.67 min.<br>LC-MS (method 26):<br>$R_t$ = 1.54 min,<br>MS (ESIpos.): m/z (%) = 678.1 (100) $[M + 2H]^{2+}$.<br>HR-TOF-MS (method 21): calc. 1354.7371, found 1354.7358 $[M + H]^+$. |
|  | O[6]-Benzyl-D-threonyl-de(1-D-leucyl)lysobactin bistrifluoroacetate | General procedure 21 from Example 150A (50 μmol). Yield: 46% of theory |

TABLE 5-continued

Edman[1.0] route

| Ex. No. | Structure Name | Analytical data Preparation method |
|---|---|---|
| 65 | N-[(4-Aminotetrahydro-2H-pyran-4-yl)carbonyl]-de(1-D-leucyl)lysobactin bistrifluoroacetate | HPLC/UV-Vis (method 36):$R_t$ = 3.36 min. LC-MS (method 26): $R_t$ = 1.43 min, MS (ESIpos.): m/z (%) = 646.1 (100) [M + 2H]$^{2+}$. HR-TOF-MS (method 21): calc. 1290.7058, found 1290.7075 [M + H]$^+$. General procedure 21 from Example 151A (28 µmol). Yield: 7% of theory |
| 66 | N$^6$-(tert-Butoxycarbonyl)-D-ornithyl-de(1-D-leucyl)-lysobactin bistrifluoroacetate | HPLC/UV-Vis (method 36):$R_t$ = 3.56 min. LC-MS (method 26): $R_t$ = 1.49 min, MS (ESIpos.): m/z (%) = 689.7 (100) [M + 2H]$^{2+}$. HR-TOF-MS (method 21): calc. 1377.7742, found 1377.7769 [M + H]$^+$. General procedure 23 from Example 152A (60 µmol). Yield: 36% of theory |

TABLE 5-continued
Edman[1.0] route
| Ex. No. | Structure Name | Analytical data Preparation method |
|---|---|---|
| 67 | 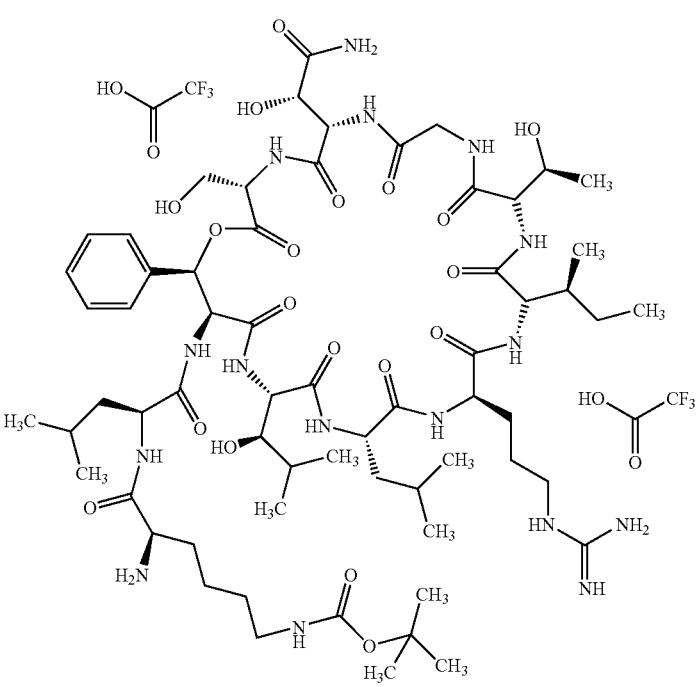<br>N[6]-(tert-Butoxycarbonyl)-D-lysyl-de(1-D-leucyl)-lysobactin bistrifluoroacetate | HPLC/UV-Vis (method 36): $R_t$ = 3.60 min.<br>LC-MS (method 26): $R_t$ = 1.48 min,<br>MS (ESIpos.): m/z (%) = 696.8 (100) $[M + 2H]^{2+}$.<br>HR-TOF-MS (method 21): calc. 1391.7898, found 1391.7869 $[M + H]^+$.<br><br>General procedure 23 from Example 153A (69 μmol).<br>Yield: 46% of theory |

Example 68

3-tert-Butyl-D-alanyl-N¹-{(3S,6S,12S,15S,18R,21S, 24S,27S,28R)-6-[(1S)-2-amino-1-hydroxy-2oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-3-tert-butyl-L-alaninamide bistrifluoroacetate {3-tert-Butyl-D-alanyl-3-tert-butyl-L-alanyl-de(1-D-leucyl-2-L-leucyl)lysobactin bistrifluoroacetate}

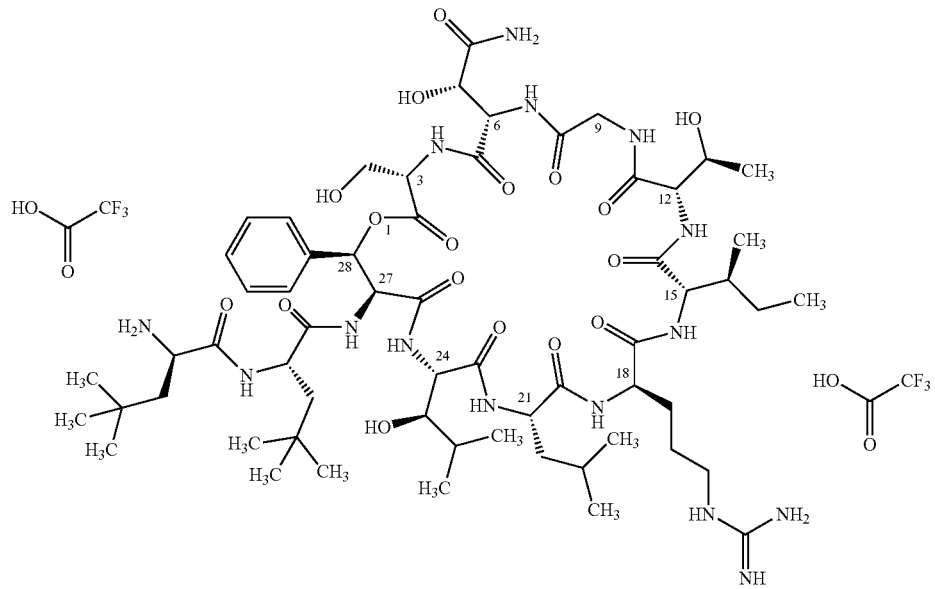

The N-(tert-butoxycarbonyl)depsipeptide (Example 155A, 103 mg, 0.07 mmol) is reacted by general procedure 5. Chromatographic purification by preparative HPLC (method 25) results after freeze drying in 75.5 mg (73% of theory) of product.

HPLC/UV-Vis (method 13): $R_t$=6.09 min,
$\lambda_{max}$ (qualitative)=220 nm (s), 255-270 (w).
LC-MS (method 12): $R_t$=4.62 min;
MS (ESIpos.): m/z (%)=653 (100) [M+2H]$^{2+}$, 1305 (10) [M+H]$^+$;
MS (ESIneg.): m/z (%)=651 (40) [M−2H]$^{2-}$, 1303 (100) [M−H]$^-$.
LC-MS (method 26): $R_t$=1.64 min;
MS (ESIpos.): m/z (%)=653 (100) [M+2H]$^{2+}$, 1305 (5) [M+H]$^+$;
MS (ESIneg.): m/z (%)=651(100) [M−2H]$^{2-}$, 1303 (10) [M−H]$^-$.
HR-TOF-MS (method 21): $C_{60}H_{102}N_{15}O_{17}$ calc. 1304.7578, found 1304.7606 [M+H]$^+$.

Example 69

3-tert-Butyl-D-alanyl-3-(3-pyridyl)-L-alanyl-de(1-D-leucyl-2-L-leucyl)lysobactin tristrifluoroacetate

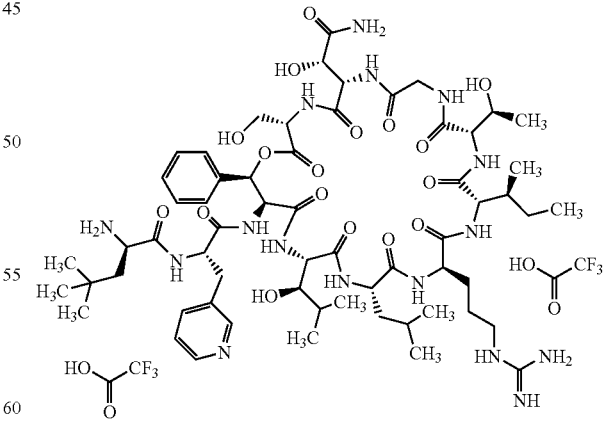

Trifluoroacetic acid (13.0 mmol, 1 ml) is slowly added dropwise to a solution of Example 156A (1.0 equivalent, 0.03 mmol) in dichloromethane (3 ml) at 0° C. The reaction mixture is stirred at 0° C. (50 min), with complete reaction being observed by means of HPLC/UV-Vis (method 36).

The reaction mixture is evaporated in a rotary evaporator and purified by gel chromatography (method 6, mobile phase methanol/acetone 4/1). The crude product is purified by preparative HPLC (method 8), resulting in 34 mg (59% of theory) of product.

$[\alpha]^{20}_{Na}=-36°$ (c=0.24 in water)
HPLC/UV-Vis (method 28): $R_t$=3.6 min.
HPLC/UV-Vis (method 36): $R_t$=3.28 min.
LC-MS (method 26): $R_t$=1.49 min;
MS (ESIpos.): m/z (%)=663 (100) [M+2H]$^{2+}$, 1325 (10) [M+H]$^+$;
MS (ESIneg.): m/z (%)=661 (100) [M−2H]$^{2−}$, 1323 (40) [M−H]$^−$.
HR-MS (method 21): $C_{61}H_{97}N_{16}O_{17}$ [M+H]$^+$ calc. 1325.7218, found 1325.7261.

TABLE 6

Edman$^{2.0}$ route

| Ex. No. | Structure Name | Analytical data Preparation method |
|---|---|---|
| 70 | 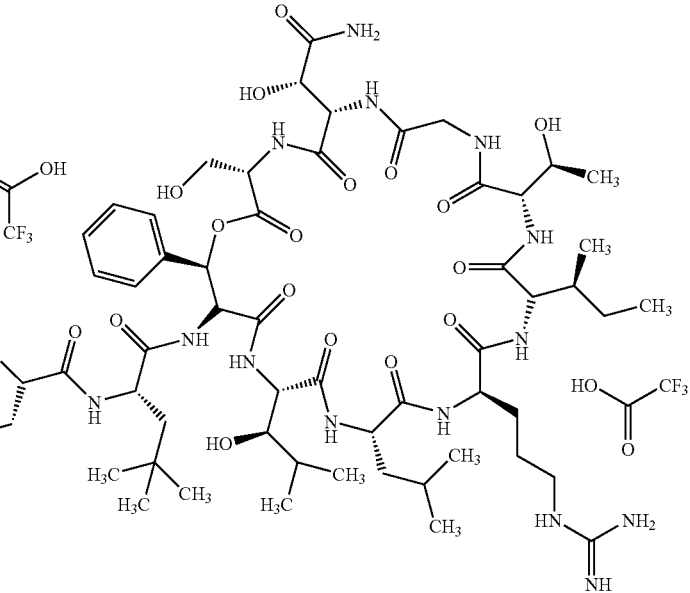<br>3-tert-Butyl-L-alanyl-3-tert-butyl-L-alanyl-de(1-D-leucyl-2-L-leucyl)lysobactin bistrifluoroacetate | HPLC/UV-Vis (method 13): $R_t$ = 5.9 min.<br>LC-MS (method 26): $R_t$ = 1.68 min;<br>MS (ESIpos.): m/z (%) = 653 (100) [M + 2H]$^{2+}$, 1305 (5) [M + H]$^+$.<br>General procedure 5 (short reaction time) from Example 157A (0.023 mmol). Purification by method 8 or method 25.<br>Yield: 57% of theory |
| 71 | 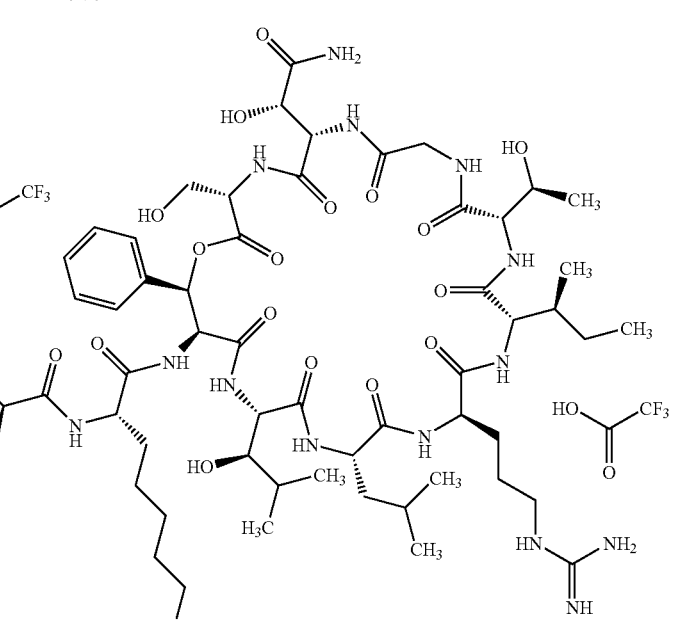<br>D-Leucyl-3-pentyl-L-alanyl-de(1-D-leucyl-2-L-leucyl)lysobactin bistrifluoroacetate | HPLC/UV-Vis (method 13): $R_t$ = 6.12 min,<br>$\lambda_{max}$ (qualitative) = 220 nm (s), 255–270 (m).<br>LC-MS (method 29): $R_t$ = 4.61 min;<br>MS (ESIpos.): m/z (%) = 653 (100) [M + 2H]$^{2+}$, 1305 (5) [M + H]$^+$.<br>HR-TOF-MS (method 21): $C_{60}H_{102}N_{15}O_{17}$ [M + H]$^+$ calc. 1304.7578, found 1304.7610.<br>In analogy to Example 68A from Example 13A (0.016 mmol) and (2S)-2-{[N-(tert-butoxycarbonyl)-D-leucyl]amino} octanoic acid (0.063 mmol). Purification by method 8 or method 25.<br>Yield: 16% of theory (over 2 stages) |

TABLE 6-continued

Edman[2.0] route

| Ex. No. | Structure Name | Analytical data Preparation method |
|---|---|---|
| 72 | D-Phenylalanyl-L-tryptophyl-de(1-D-leucyl-2-L-leucyl)lysobactin bistrifluoroacetate | HPLC/UV-Vis (method 13): $R_t$ = 5.92 min. LC-MS (method 29): $R_t$ = 4.37 min; MS (ESIpos.): m/z (%) = 693 (100) $[M + 2H]^{2+}$, 1384 (5) $[M + H]^+$. HR-TOF-MS (method 21): $C_{66}H_{95}N_{16}O_{17}$ $[M + H]^+$ calc. 1383.7061, found 1383.7098. In analogy to Example 68A from Example 13A (0.016 mmol) and N-tert-butoxycarbonyl-D-phenylala-nyl-L-tryptophan (0.063 mmol). Purification by method 8 or method 25. Yield: 47% of theory (over 2 stages) |
| 73 | D-Leucyl-3-cyclohexyl-L-alanyl-de(1-leucyl-2-L-leucyl)lysobactin bistrifluoroacetate | HPLC/UV-Vis (method 13): $R_t$ = 6.14 min. LC-MS (method 29): $R_t$ = 4.54 min; LC-MS (ESIpos.): m/z (%) = 659 (100) $[M + 2H]^{2+}$, 1317 (15) $[M + H]^+$. HR-TOF-MS (method 21): $C_{61}H_{102}N_{15}O_{17}$ $[M + H]^+$ calc. 1316.7578, found 1316.7616. General procedure 5 from Example 158A (0.01 mmol). Purification by method 8 or method 25. Yield: 49% of theory |

TABLE 6-continued

Edman[2.0] route

| Ex. No. | Structure Name | Analytical data Preparation method |
|---|---|---|
| 74 | D-Leucyl-L-phenylalanyl-de(1-D-leucyl-2-L-leucyl)lysobactin bistrifluoroacetate | HPLC/UV-Vis (method 13): $R_t$ = 6.03 min, $\lambda_{max}$ (qualitative) = 220 nm (s), 255–270 (m). LC-MS (method 12): $R_t$ = 4.51 min; MS (ESIpos.): m/z (%) = 656 (100) $[M + 2H]^{2+}$, 1311 (5) $[M + H]^+$. HR-TOF-MS (method 21): $C_{61}H_{96}N_{15}O_{17}$ $[M + H]^+$ calc. 1310.7109, found 1310.7094. General procedure 5 from Example 159A (0.01 mmol). Purification by method 8 or method 25. Yield: 74% of theory |
| 75 | D-Leucyl-3-cyclopentyl-L-alanyl-de(1-D-leucyl-2-L-leucyl)lysobactin bistrifluoroacetate | HPLC/UV-Vis (method 13): $R_t$ = 6.16 min, $\lambda_{max}$ (qualitative) = 220 nm (s), 255–270 (m). LC-MS (method 12): $R_t$ = 4.55 min; MS (ESIpos.): m/z (%) = 652 (100) $[M + 2H]^{2+}$, 1303 (20) $[M + H]^+$. HR-TOF-MS (method 21): $C_{60}H_{100}N_{15}O_{17}$ $[M + H]^+$ calc. 1302.7422, found 1302.7404. General procedure 5 from Example 160A (0.01 mmol). Purification by method 8 or method 25. Yield: 92% of theory |

TABLE 6-continued

Edman[2.0] route

| Ex. No. | Structure Name | Analytical data Preparation method |
|---|---|---|
| 76 | D-Phenylalanyl-2-methyl-L-leucyl-de(1-D-leucyl-2-L-leucyl)lysobactin bistrifluoroacetate | HPLC/UV-Vis (method 13): $R_t$ = 6.02 min, $\lambda_{max}$ (qualitative) = 220 nm (s), 255–270 (m). LC-MS (method 26): Rt = 2.25 min; MS (ESIpos.): m/z (%) = 663 (100) $[M + 2H]^{2+}$. General procedure 5 from Example 161A (0.012 mmol). Purification by method 8 or method 25. Yield: 8.5% of theory |
| 77 | D-Phenylalanyl-L-tyrosyl-de(1-D-leucyl-2-L-leucyl)lysobactin bistrifluoroacetate | HPLC/UV-Vis (method 13): $R_t$ = 5.39 min. LC-MS (method 29): Rt = 4.2 min; MS (ESIpos.): m/z (%) = 681 (100) $[M + 2H]^{2+}$, 1361 (10) $[M + H]^+$. HR-TOF-MS (method 21): $C_{64}H_{94}N_{15}O_{18}$ $[M + H]^+$ calc. 1360.6901, found 1360.6901. General procedure 5 from Example 162A (0.01 mmol). Yield: 93% of theory. |

TABLE 6-continued

Edman[2.0] route

| Ex. No. | Structure Name | Analytical data Preparation method |
|---|---|---|
| 78 | 3-Cyclohexyl-L-alanyl-L-tyrosyl-de(1-D-leucyl-2-L-leucyl)lysobactine-bistrifluoracetate | HPLC/UV-Vis (method 13): $R_t$ = 5.66 min. LC-MS (method 29): $R_t$ = 4.4 min; MS (ESIpos.): m/z (%) = 684 (100) [M + 2H]$^{2+}$, 1367 (10) [M + H]$^+$. HR-TOF-MS (method 21): $C_{64}H_{100}N_{15}O_{18}$ [M + H]$^+$ calc. 1366.7371, found 1366.7335. General procedure 5 from Example 163A (0.01 mmol). Yield: 97% of theory |
| 79 | 3-Cyclohexyl-L-alanyl-L-phenylalanyl-de(1-D-leucyl-2-L-leucyl)lysobactin bistrifluoroacetate | HPLC/UV-Vis (method 13): $R_t$ = 6.01 min. LC-MS (method 29): $R_t$ = 4.6 min; MS (ESIpos.): m/z (%) = 677 (100) [M + 2H]$^{2+}$, 1352 (10) [M + H]$^+$. HR-TOF-MS (method 21): $C_{64}H_{100}N_{15}O_{17}$ [M + H]$^+$ calc. 1350.7422, found 1350.7393. General procedure 5 from Example 164A (0.01 mmol). Yield: 95% of theory |

TABLE 6-continued

Edman[2.0] route

| Ex. No. | Structure Name | Analytical data Preparation method |
|---|---|---|
| 80 | 3-Cyclohexyl-L-alanyl-L-isoleucyl-de(1-D-leucyl-2-L-leucyl)lysobactin bistrifluoroacetate | LC-MS (method 26): $R_t$ = 1.53 min; MS (ESIpos.): m/z (%) = 659 (100) [M + 2H]$^{2+}$, 1317 (5) [M + H]$^+$. HR-TOF-MS (method 21): $C_{61}H_{102}N_{15}O_{17}$ [M + H]$^+$ calc. 1316.7578, found 1316.7574. General procedure 5 from Example 165A (0.006 mmol). Yield: 99% of theory |
| 81 | D-Phenylalanyl-4-nitro-L-phenylalanyl-de(1-D-leucyl-2-L-leucyl)lysobactine bistrifluoroacetate | HPLC/UV-Vis (method 13): $R_t$ = 5.83 min. LC-MS (method 29): $R_t$ = 4.5 min; MS (ESIpos): m/z (%) = 696 (100) [M +2H]$^{2+}$, 1390 (10) [M + H]$^+$. HR-TOF-MS (method 21): $C_{64}H_{93}N_{16}O_{19}$ [M + H]$^+$ calc. 1389.6803, found 1389.6823. General procedure 5 from Example 166A (0.007 mmol). Purification by method 8 or method 25. Yield: 46% of theory |

TABLE 6-continued

Edman[2.0] route

| Ex. No. | Structure Name | Analytical data Preparation method |
|---|---|---|
| 82 | D-Phenylalanyl-L-phenylalanyl-de(1-D-leucyl-2-L-leucyl)lysobactine bistrifluoroacetate | HPLC/UV-Vis (method 13): $R_t$ = 5.84 min, $\lambda_{max}$ (qualitative) = 220 nm (s), 255–270 (m). LC-MS (method 12): $R_t$ = 4.5 min; MS (ESIpos.): m/z (%) = 674 (100) $[M + 2H]^{2+}$, 1345 (50) $[M + H]^+$. HR-TOF-MS (method 21): $C_{64}H_{94}N_{15}O_{17}$ $[M + H]^+$ calc. 1344.6952, found 1344.6927. General procedure 5 from Example 169A (0.06 mmol). Purification by method 8 or method 25. Yield: 82% of theory |
| 83 | 3-(2-Naphthyl)-D-alanyl-3-(1-naphthyl)-L-alanyl-de(1-D-leucyl-2-L-leucyl)lysobactin bistrifluoroacetate | LC-MS/UV-Vis (method 12): $R_t$ = 4.8 min; $\lambda_{max}$ (qualitative) = 224 nm (s), 280 (m); MS (ESIpos.): m/z (%) = 723 (100) $[M + 2H]^{2+}$, 1445 (10) $[M + H]^+$. HR-TOF-MS (method 21): $C_{72}H_{98}N_{15}O_{17}$ $[M + H]^+$ calc. 1444.7265, found 1444.7290. General procedure 5 from Example 170A (0.005 mmol). Purification by method 8 or method 25. Yield: 86% of theory |

TABLE 6-continued

Edman[2.0] route

| Ex. No. | Structure Name | Analytical data Preparation method |
|---|---|---|
| 84 | D-Phenylalanyl-O[3]-tert-butyl-L-seryl-de(1-D-leucyl-2-L-leucyl)lysobactin bistrifluoroacetate | HR-TOF-MS (method 21): $C_{62}H_{98}N_{15}O_{18}$ calc. 1340.7214, found 1340.7245 [M + H]+. General procedure 5 from Example 167A (0.015 mmol). Yield: 94% of theory |
| 85 | 3-Cyclohexyl-D-alanyl-3-cyclohexyl-L-alanyl-de(1-D-leucyl)lysobactin bistrifluoroacetate | HPLC/UV-Vis (method 13): $R_t$ = 6.57 min. LC-MS/UV-Vis (method 29): $R_t$ = 4.7 min; MS (ESIneg.): m/z (%) = 1355 (100), [M − H]−. HR-TOF-MS (method 21): $C_{64}H_{106}N_{15}O_{17}$ calc. 1356.7891, found 1356.7921 [M + H]+. General procedure 5 from Example 168A (0.003 mmol). Yield: 94% of theory |

TABLE 6-continued

Edman[2.0] route

| Ex. No. | Structure Name | Analytical data Preparation method |
|---|---|---|
| 86 | 3-tert-Butyl-D-alanyl-3-(3,4-dimethoxyphenyl)-L-alanyl-de(1-D-leucyl-2-L-leucyl)lysobactin bistrifluoroacetate | HPLC/UV-Vis (method 13): $R_t$ = 5.86 min. LC-MS (method 29): $R_t$ = 4.3 min; MS (ESIpos.): m/z (%) = 693 (100) $[M + 2H]^{2+}$, 1384 (30) $[M + H]^+$. HR-TOF-MS (method 21): $C_{64}H_{102}N_{15}O_{19}$ calc. 1384.7476, found 1384.7466 $[M + H]^+$. General procedure 5 from Example 171A (0.006 mmol). Purification by method 8 or method 25. Yield: 69% of theory |
| 87 | 4-Phenyl-D-phenylalanyl-4-phenyl-L-phenylalanyl-de(1-D-leucyl-2-L-leucyl)lysobactin bistrifluoroacetate | HPLC/UV-Vis (method 13): $R_t$ = 6.69 min. LC-MS (method 29): $R_t$ = 4.9 min; MS (ESIpos.): m/z (%) = 749 (100) $[M + 2H]^{2+}$, 1497 (10) $[M + H]^+$. HR-TOF-MS (method 21): $C_{76}H_{102}N_{15}O_{17}$ $[M + H]^+$ calc. 1496.7578, found 1496.7604. General procedure 5 from Example 172A (0.011 mmol). Yield: quant. |

TABLE 6-continued

Edman[2.0] route

| Ex. No. | Structure Name | Analytical data Preparation method |
|---|---|---|
| 88 | 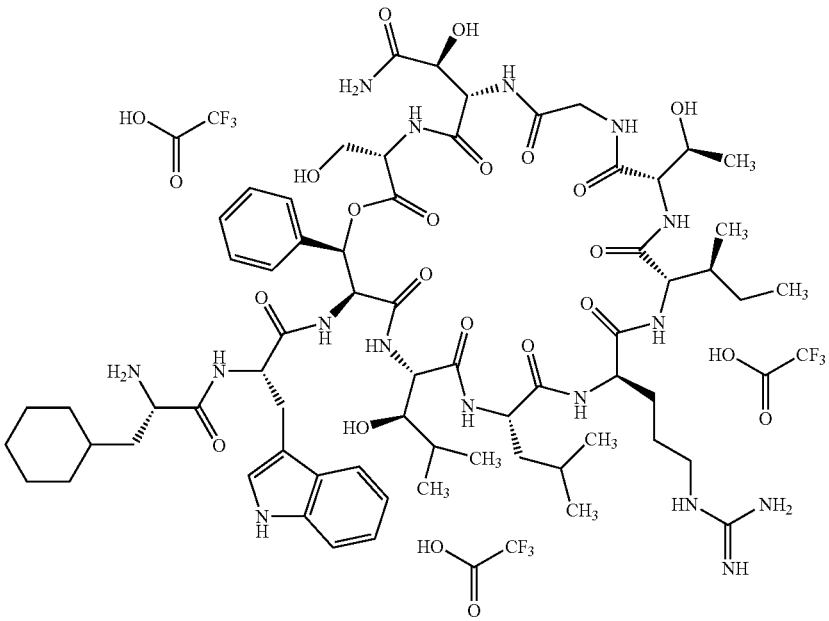<br>3-Cyclohexyl-L-alanyl-L-tryptophyl-de(1-D-leucyl-2-L-leucyl)lysobactin bistrifluoroacetate | HPLC/UV-Vis (method 13): $R_t$ = 6.8 min. LC-MS (method 29): $R_t$ = 4.6 min; MS (ESIneg.): m/z (%) = 1388 (100) $[M - H]^+$. HR-TOF-MS (method 21): $C_{66}H_{101}N_{16}O_{17}$ calc. 1389.7531, found 1389.7559 $[M + H]^+$. General procedure 5 from Example 173A (0.004 mmol). Purification by method 8 or method 25. Yield: 72% of theory |
| 89 | 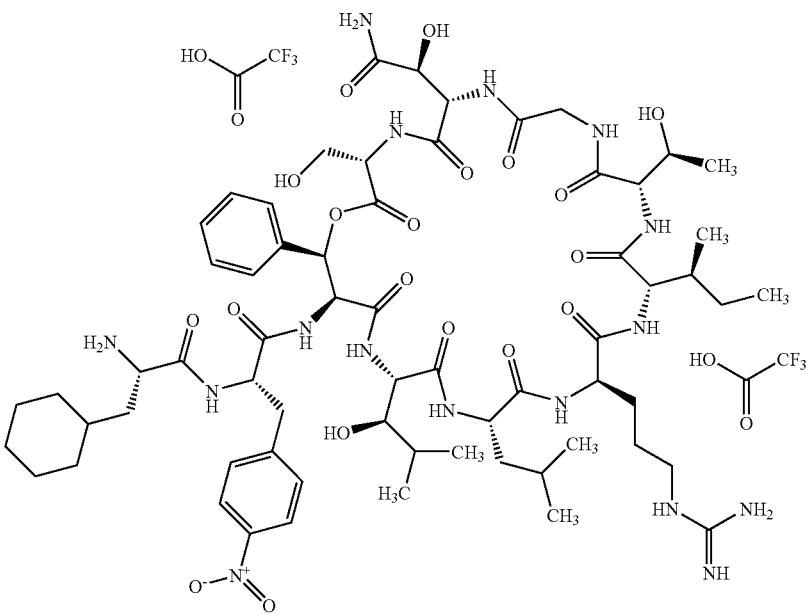<br>3-Cyclohexyl-L-alanyl-4-nitro-L-phenylalanyl-de(1-D-leucyl-2-L-leucyl)lysobactin bistrifluoroacetate | HPLC/UV-Vis (method 13): $R_t$ = 6.06 min. LC-MS (method 29): $R_t$ = 4.5 min; MS (ESIpos.): m/z (%) = 699 (100) $[M + 2H]^{2+}$, 1395 (20) $[M + H]^+$. HR-TOF-MS (method 21): $C_{64}H_{99}N_{16}O_{19}$ $[M + H]^+$ calc. 1395.7272, found 1395.7247. General procedure 5 from Example 174A (0.004 mmol). Purification by method 8 or method 25. Yield: 87% of theory |

TABLE 6-continued

Edman[2.0] route

| Ex. No. | Structure Name | Analytical data Preparation method |
|---|---|---|
| 90 | 3-Cyclohexyl-L-alanyl-3-benzyl-L-alanyl-de(1-D-leucyl-2-L-leucyl)lysobactin bistrifluoroacetate | LC-MS (method 29): $R_t$ = 4.7 min; (ESIpos.): m/z (%) = 683 (100) [M + 2H]$^{2+}$, 1364 (20) [M + H]$^+$. HR-TOF-MS (method 21): $C_{65}H_{102}N_{15}O_{17}$ calc. 1364.7578 found 1364.7626 [M + H]$^+$. General procedure 5 from Example 175A (0.012 mmol). Yield: quant. |
| 91 | 3-tert-Butyl-D-alanyl-(1-amino-4-methoxy-cyclohexylcarbonyl)-de(1-D-leucyl-2-L-leucyl)lysobactin bistrifluoroacetate | HPLC/UV-Vis (method 13): $R_t$ = 5.88 min. LC-MS (method 26): $R_t$ = 1.52 min; MS (ESIpos.): m/z (%) = 667 (100) [M + 2H]$^{2+}$, 1051 (10), 1333 (10) [M + H]$^+$. HR-TOF-MS (method 21): $C_{61}H_{102}N_{15}O_{18}$ [M + H]$^+$ calc. 1332.7527, found 1332.7561. General procedure 5 from Example 176A (0.019 mmol). Purification by method 8 or method 25. Yield: 91% of theory |

TABLE 6-continued

Edman[2.0] route

| Ex. No. | Structure Name | Analytical data Preparation method |
|---|---|---|
| 92 | 3-tert-Butyl-D-alanyl-(1-amino-4-(trifluoromethyl)-cyclohexylcarbonyl)-de(1-D-leucyl-2-L-leucyl)lysobactin bistrifluoroacetate | HPLC/UV-Vis (method 13): $R_t$ = 6.68 min, $\lambda_{max}$ (qualitative) = 220 nm (s), 255–270 (m). HR-TOF-MS (method 21): $C_{61}H_{99}N_{15}O_{17}F_3$ [M + H]$^+$ calc. 1370.7295, found 1370.7263. General procedure 5 from Example 177A (0.02 mmol). Purification by method 8 or method 25. Yield: 81% of theory |
| 93 | D-Leucyl-4-nitro-L-phenylalanyl-de(1-D-leucyl-2-L-leucyl)lysobactin bistrifluoroacetate | HPLC/UV-Vis (method 13): $R_t$ = 5.96 min, $\lambda_{max}$ (qualitative) = 220 nm (s), 255–270 (m). LC-MS (method 26): $R_t$ = 1.60 min; MS (ESIpos.): m/z (%) = 679 (100) [M + 2H]$^{2+}$, 1356 (10) [M + H]$^+$. HR-TOF-MS (method 21): $C_{61}H_{95}N_{16}O_{19}$ [M + H]$^+$ calc. 1355.6959, found 1355.6943. General procedure 5 from Example 178A (0.02 mmol). Purification by method 8 or method 25. Yield: 40% of theory |

TABLE 6-continued

Edman²·⁰ route

| Ex. No. | Structure Name | Analytical data Preparation method |
|---|---|---|
| 94 | D-Propyl-4-nitro-L-phenylalanyl-de(1-D-leucyl-2-L-leucyl)lysobactin bistrifluoroacetate | HR-TOF-MS (method 21): $C_{60}H_{91}N_{16}O_{19}$ calc. 1339.6646, found 1339.6602 $[M + H]^+$. General procedure 5 from Example 179A (0.003 mmol). Purification by method 8 or method 25. Yield: quant. |
| 95 | D-Propyl-L-phenylalanyl-de(1-D-leucyl-2-L-leucyl)lysobactin bistrifluoroacetate | HPLC/UV-Vis (method 13): $R_t$ = 5.40 min. LC-MS (method 29): $R_t$ = 4.2 min; MS (ESIpos.): m/z (%) = 648 (100) $[M + 2H]^{2+}$, 1295 (50) $[M + H]^+$. General procedure 5 from Example 180A (0.01 mmol). Purification by method 8 or method 25. Yield: 90% of theory |

TABLE 6-continued

Edman[2.0] route

| Ex. No. | Structure Name | Analytical data Preparation method |
|---|---|---|
| 96 | 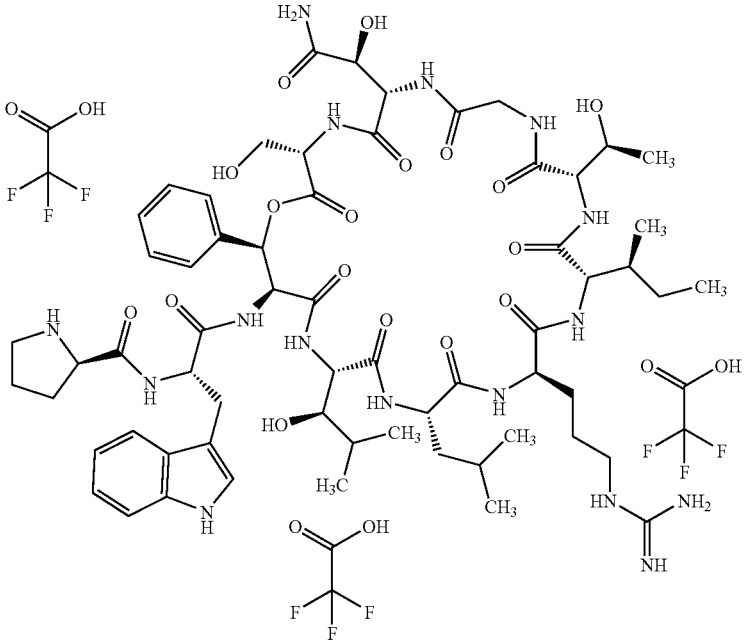<br>D-Propyl-L-tryptophyl-de(1-D-leucyl-2-L-leucyl)lysobactin tristrifluoracetate | HPLC/UV-Vis (method 13): $R_t$ = 5.40 min. LC-MS (method 29): $R_t$ = 4.1 min; MS (ESIpos.): m/z (%) = 668 (100) $[M + 2H]^{2+}$; ms (ESIneg.): m/z (%) = 1332 (100) $[M - H]^+$. HR-TOF-MS (method 21): $C_{62}H_{93}N_{16}O_{17}$ $[M + H]^+$ calc. 1333.6905, found 1333.6885. General procedure 5 from Example 181A (0.003 mmol). Purification by method 8 or method 25. Yield: 55% of theory |
| 97 | 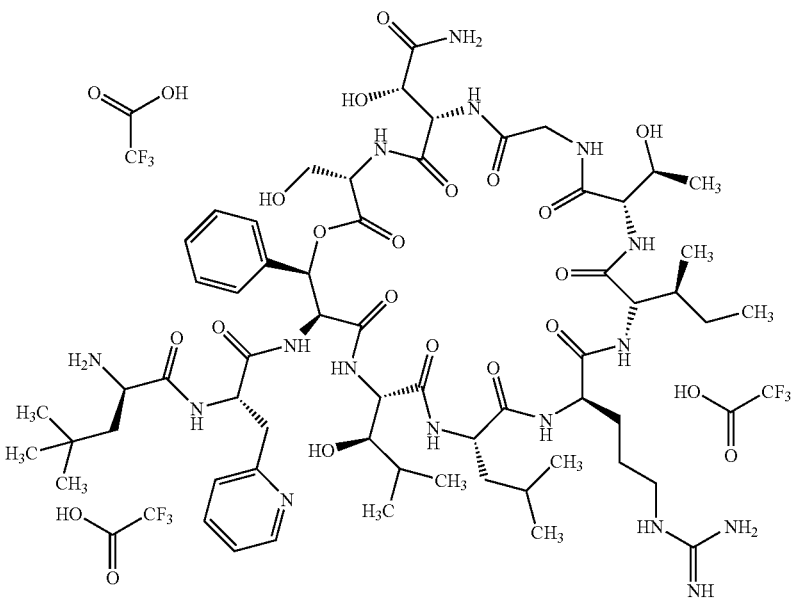<br>3-tert-Butyl-D-alanyl-3-(2-pyridyl)-L-alanyl-de(1-D-leucyl-2-L-leucyl)lysobactin tristrifluoroacetate | HPLC/UV-Vis (method 36): $R_t$ = 3.53 min. LC-MS (method 26): $R_t$ = 1.58 min; MS (ESIpos.): m/z (%) = 663 (100) $[M + 2H]^{2+}$, 1325 (10) $[M + H]^+$; MS (ESIneg): m/z (%) = 661 (100) $[M - 2H]^{2-}$, 1323 (20) $[M - H]^-$. HR-MS (method 21): $C_{61}H_{97}N_{16}O_{17}$ $[M + H]^+$ calc. 1325.7218, found 1325.7178. General procedure 5 from Example 182A (0.03 mmol). Yield: 38% of theory |

TABLE 6-continued

Edman[2.0] route

| Ex. No. | Structure Name | Analytical data Preparation method |
|---|---|---|
| 98 | 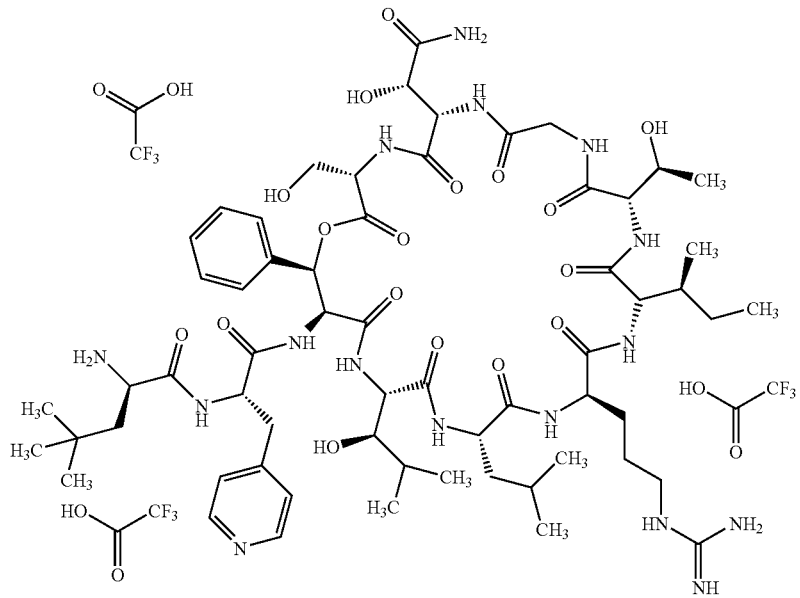<br>3-tert-Butyl-D-alanyl-3-(4-pyridyl)-L-alanyl-de(1-D-leucyl-2-L-leucyl)lysobactin tristrifluoroacetate | HPLC/UV-Vis (method 36): $R_t$ = 3.24 min.<br>LC-MS (method 26): $R_t$ = 1.31 min;<br>MS (ESIpos.): m/z (%) = 663 (100) [M + 2H]$^{2+}$, 1325 (5) [M + H]$^+$;<br>MS (ESIneg.): m/z (%) = 661 (100) [M − 2H]$^{2−}$, 1323 (20) [M − H]$^−$.<br>HR-MS (method 21):<br>$C_{61}H_{97}N_{16}O_{17}$ [M + H]$^+$ calc. 1325.7218, found 1325.7186.<br>General procedure 5 from Example 98A (0.05 mmol).<br>Yield: 8% of theory |
| 99 | 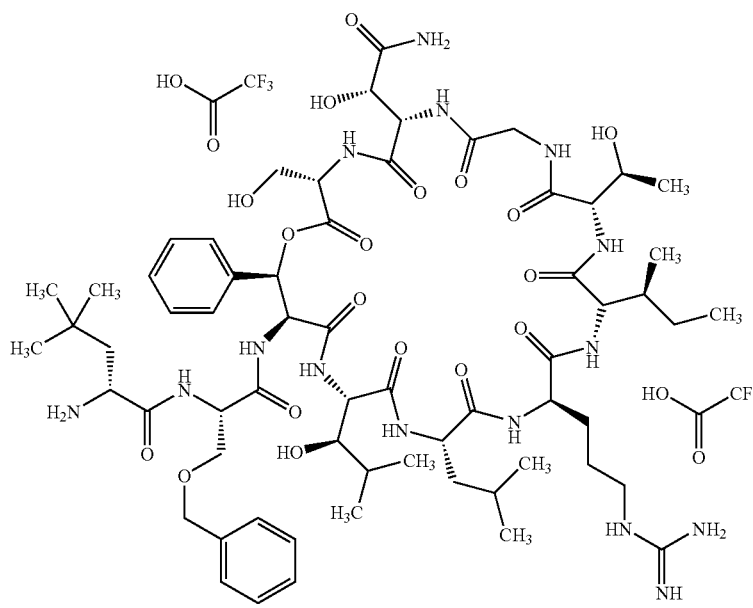<br>(3-tert-Butyl-D-alanyl-O-benzyl-L-seryl)-de(1-D-leucyl-2-L-leucyl)lysobactin bistrifluoroacetate | HPLC/UV-Vis (method 36): $R_t$ = 3.69 min.<br>LC-MS (method 26): $R_t$ = 1.60 min,<br>MS (ESIpos.): m/z (%) = 678.3 (100) [M + 2H]$^{2+}$.<br>HR-TOF-MS (method 21): calc. 1354.7371 found 1354.7323 $C_{63}H_{99}N_{15}O_{18}$ [M + H]$^+$.<br>General procedure 21 from Example 184A (68 μmol).<br>Yield: 47% of theory |

TABLE 6-continued

Edman[2.0] route

| Ex. No. | Structure Name | | Analytical data Preparation method |
|---|---|---|---|
| 100 | 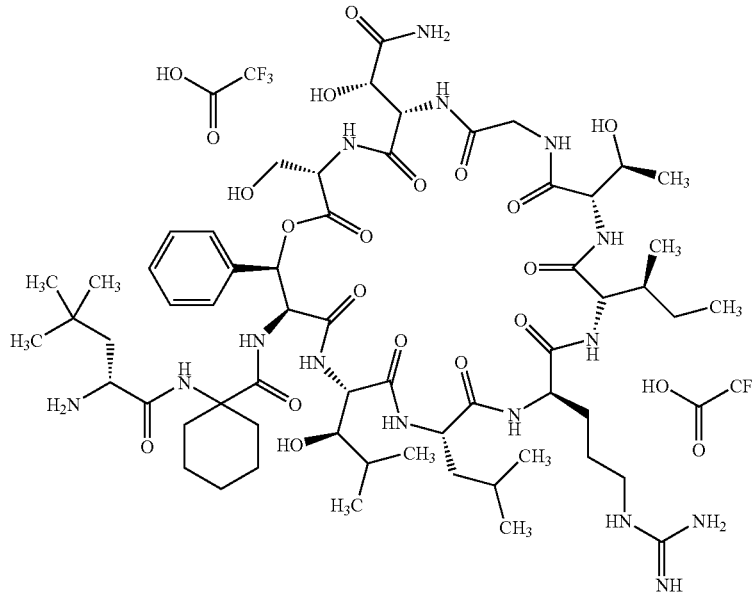 N-({1-[(3-tert-Butyl-D-alanyl)amino]cyclohexyl}carbonyl)-de(1-D-leucyl-2-L-leucyl)lysobactin bistrifluoroacetate | | HPLC/UV-Vis (method 36): $R_t$ = 3.64 min. LC-MS (method 26): $R_t$ = 1.58 min, MS (ESIpos.): m/z (%) = 652.24 (100) [M + 2H]$^{2+}$. HR-TOF-MS (method 21): calc. 1302.7422 found 1302.7471 [M + H]$^+$. General procedure 21 from Example 185A (36 µmol). Yield: 48% of theory |
| 101 | 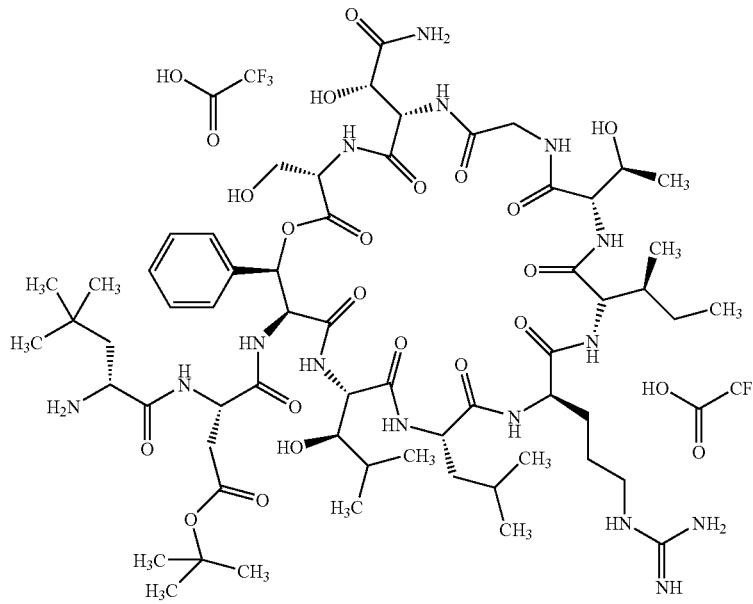 (2S)-2-[(3-tert-Butyl-D-alanyl)amino]-4-tert-butoxy-4-oxobutanoyl-de(1-D-leucyl-2-L-leucyl)lysobactin bistri-fluoroacetate | | HPLC/UV-Vis (method 36): $R_t$ = 3.67 min. LC-MS (method 26): $R_t$ = 1.69 min, MS (ESIpos.): m/z (%) = 675.3 (100) [M + 2H]$^{2+}$. HR-TOF-MS (method 21): calc. 1348.7476 found 1348.7478 [M + H]$^+$. General procedure 22 from Example 186A (85 µmol). Yield: 33% of theory |

TABLE 6-continued

Edman[2.0] route

| Ex. No. | Structure Name | Analytical data Preparation method |
|---|---|---|
| 102 | [3-tert-Butyl-D-alanyl-O-(tert-butyl)-L-seryl]-de(1-D-leucyl-2-L-leucyl)lysobactin bistrifluoroacetate | HPLC/UV-Vis (method 36): $R_t$ = 3.69 min. LC-MS (method 26): $R_t$ = 1.75 min, MS (ESIpos.): m/z (%) = 661.3 (100) [M + 2H]$^{2+}$. HR-TOF-MS (method 21): calc. 1320.7572 found 1320.7477 [M + H]$^+$. General procedure 22 from Example 187A (77 μmol). Yield: 49% of theory |
| 103 | [O-(tert-Butyl)-D-seryl]-O-(tert-butyl)-L-seryl]-de(1-D-leucyl-2-L-leucyl)lysobactin bistrifluoroacetate | HPLC/UV-Vis (method 36): $R_t$ = 3.61 min. LC-MS (method 26): $R_t$ = 1.64 min, MS (ESIpos.): m/z (%) = 669.2 (100) [M + 2H]$^{2+}$. HR-TOF-MS (method 21): calc. 133 6.7476 found 1336.7483 [M + H]$^+$. General procedure 22 from Example 188A (84 μmol). Yield: 16% of theory |

TABLE 6-continued

Edman[2.0] route

| Ex. No. | Structure Name | Analytical data Preparation method |
|---|---|---|
| 104 | 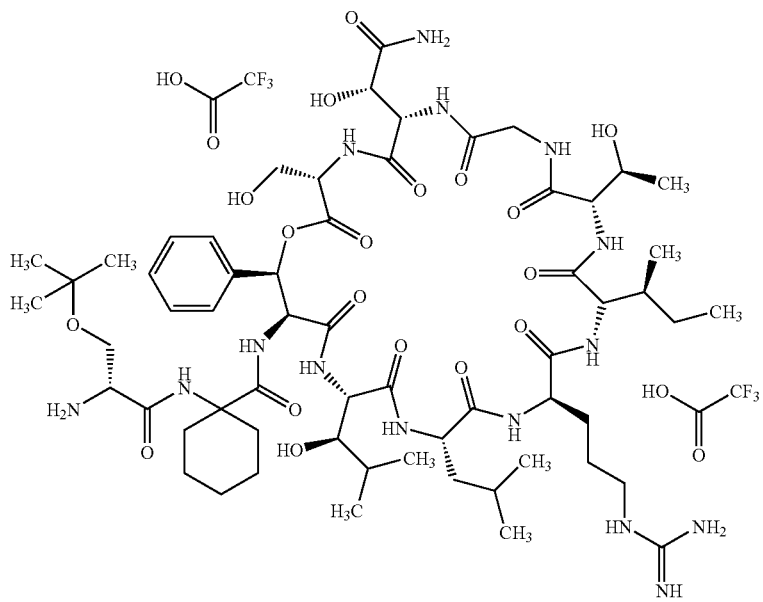<br>N-[(1-{[O-(tert-Butyl)-D-seryl]amino}-cyclohexyl)carbonyl]-de(1-D-leucyl-2-L-leucyl)-lysobactin bistrifluoroacetate | HPLC/UV-Vis (method 36): $R_t$ = 3.61 min.<br>LC-MS (method 26): $R_t$ = 1.62 min,<br>MS (ESIpos.): m/z (%) = 1318.7 (5) [M + H]$^+$.<br>HR-TOF-MS (method 21): calc. 1318.7371 found 1318.7351 [M + H]$^+$.<br>General procedure 22 from Example 189A (24 µmol).<br>Yield: 75% of theory |
| 105 | 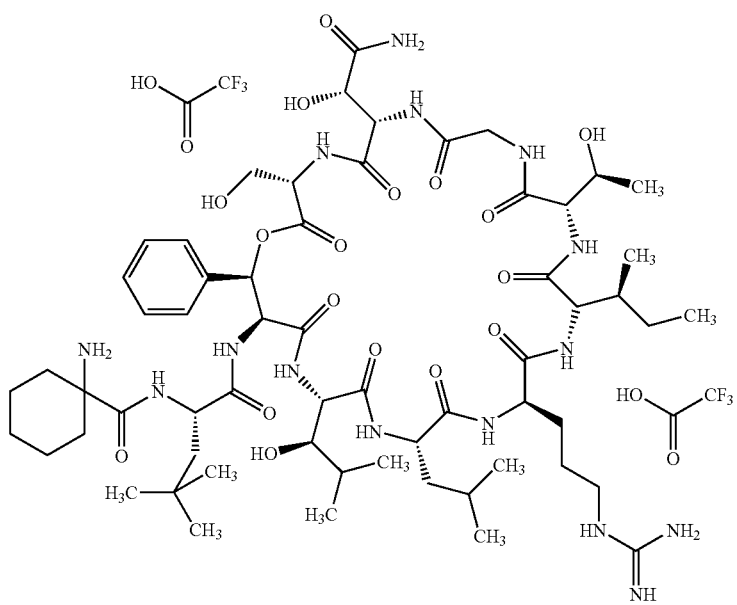<br>N-[(1-Aminocyclohexyl)carbonyl]-(3-tert-butyl-D-alanyl)-de(1-D-leucyl-2-L-leucyl)lysobactin bistrifluoroacetate | HPLC/UV-Vis (method 36): $R_t$ = 3.54 min.<br>LC-MS (method 26): $R_t$ = 1.61 min,<br>MS (ESIpos.): m/z (%) = 1302.9 [M + H]$^+$.<br>HR-TOF-MS (method 21): calc. 1302.7422 found 1302.7373 [M + H]$^+$.<br>General procedure 21 from Example 190A (35 µmol).<br>Yield: 81% of theory |

TABLE 6-continued

Edman[2.0] route

| Ex. No. | Structure Name | Analytical data Preparation method |
|---|---|---|
| 106 | 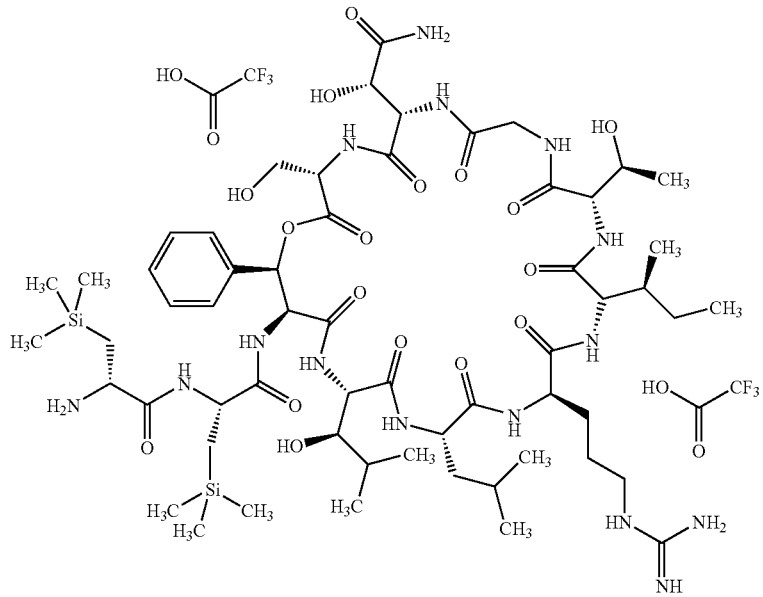<br>3-(Trimethylsilyl)-D-alanyl-3-(trimethylsilyl)-L-alanyl-de(1-D-leucyl-2-L-leucyl)lysobactin bistrifluoroacetate | HPLC/UV-Vis (method 36): $R_t$ = 3.74 min.<br>LC-MS (method 26): $R_t$ = 1.76 min,<br>MS (ESIpos.): m/z (%) = 1336.9 (3) [M + H]+.<br>HR-TOF-MS (method 21): calc. 1336.7117 found 1336.7100 [M + H]+.<br>General procedure 21 from Example 191A (84 μmol).<br>Yield: 63% of theory |
| 107 | 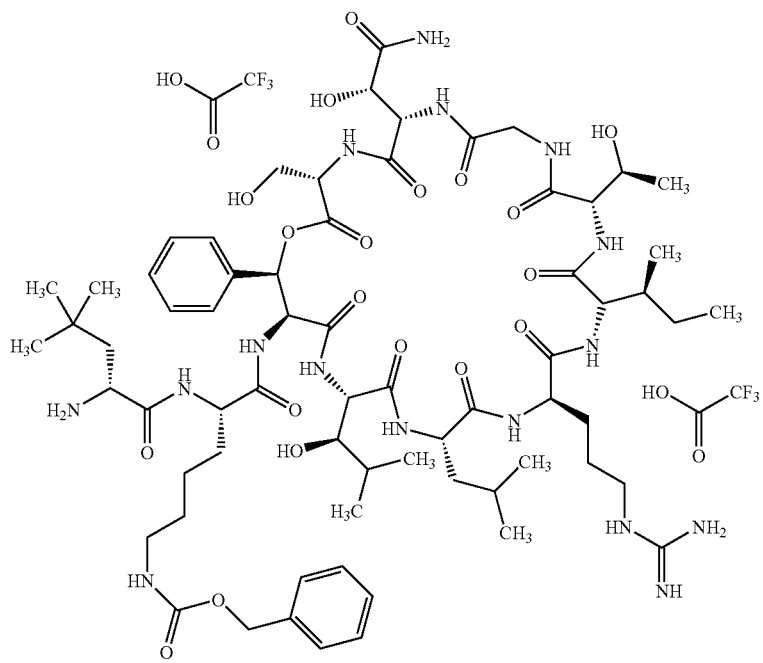<br>{(3-tert-Butylalanyl)-[N[6]-(benzyloxycarbonyl)lysyl]}-de(1-D-leucyl-2-L-leucyl)lysobactin bistrifluoroacetate | HPLC/UV-Vis (method 36): $R_t$ = 3.67 min.<br>LC-MS (method 26): $R_t$ = 1.62 min,<br>MS (ESIpos.): m/z (%) = 720.7 (100) [M + 2H]2+.<br>HR-TOF-MS (method 21): calc. 1439.7898, found 1439.7909 [M + H]+.<br>General procedure 21 from Example 192A (41 μmol).<br>Yield: 69% of theory |

TABLE 7

N-Alkyl derivatives

| Ex. No. | Structure Name | Analytical data Preparation method |
|---|---|---|
| 108 | 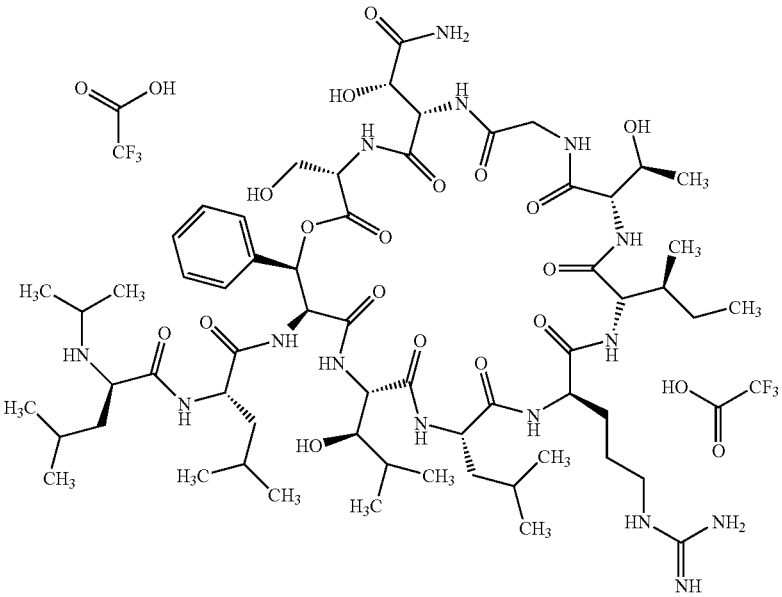<br>N-(iso-Propyl)lysobactin bistrifluoroacetate | LC-MS (method 19):<br>$R_t$ = 2.73 min;<br>MS (ESIpos.): m/z (%) = 660.4 (100) $[M + 2H]^{2+}$.<br>General procedure 13 from Example 1A (0.010 mmol) and acetone.<br>Yield: 21% of theory |
| 109 | 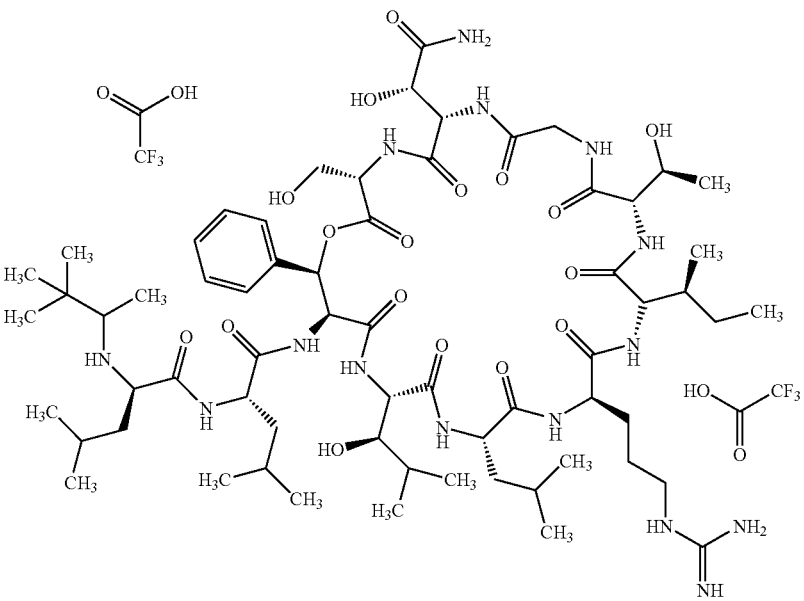<br>N-(2,3,3-Trimethylpropyl)lysobactin bistrifluoroacetate | LC-MS (method 19):<br>$R_t$ = 2.88 min;<br>MS (ESIpos.): m/z (%) = 681.4 (100) $[M + 2H]^{2+}$.<br>General procedure 13 from Example 1A (0.010 mmol) and methyl tert-butyl ketone.<br>Yield: 27% of theory |

B. Assessment of the Physiological Activity

The in vitro effect of the compounds of the invention can be shown in the following assays:

Determination of the Minimum Inhibitory Concentration (MIC):

The MIC is determined in the liquid dilution test in accordance with the NCCLS guidelines. Overnight cultures of *Staphylococcus aureus* 133, *Enterococcus faecalis* 27159, *E. faecium* 4147 and *Streptococcus pneumoniae* G9a are incubated with the desired test substances in a 1:2 dilution series. The MIC determination is carried out with a cell count of $10^5$ microbes per ml in Isosensitest medium (Difco, Irvine/USA), with the exception of *S. pneumoniae* which is tested in BHI broth (Difco, Irvine/USA) with 10% bovine serum with a cell count of $10^6$ microbes per ml. The cultures are incubated at 37° C. for 18-24 hours, *S. pneumoniae* in the presence of 10% $CO_2$.

The MIC is defined as the lowest concentration of each substance at which visible bacterial growth no longer occurs. The MIC values are reported in μg/ml.

Representative in-vitro data on the effect of the compounds of the invention are shown in Table A:

TABLE A

| Example No. | MIC S. aureus 133 | MIC S. pneumoniae | MIC E. faecium L4001 | MIC E. faecalis ICB 27159 |
|---|---|---|---|---|
| 1 | 0.125 | 0.125 | 0.5 | 0.5 |
| 3 | 0.125 | 0.031 | 0.25 | 0.25 |
| 18 | 1 | 2 | 1 | 1 |
| 23 | 0.125 | 0.125 | 0.5 | 1 |
| 24 | 0.25 | 0.5 | 1 | 2 |
| 30 | 0.25 | 0.25 | 0.5 | 1 |
| 38 | 0.125 | 0.063 | 0.5 | 1 |
| 47 | 0.25 | 0.25 | 1 | 2 |
| 48 | 0.125 | 0.125 | 0.25 | 0.5 |
| 57 | 0.5 | 0.25 | 1 | 1 |
| 59 | 0.125 | <0.063 | 0.25 | 0.25 |
| 62 | 0.25 | 0.5 | 0.5 | 1 |
| 68 | 0.125 | 0.031 | 0.5 | 0.5 |
| 69 | 0.5 | 0.5 | 1 | 1 |
| 74 | 0.125 | 0.063 | 0.5 | 1 |
| 81 | 0.5 | 0.25 | 0.25 | 0.25 |
| 82 | 0.125 | 0.125 | 0.5 | 1 |
| 86 | 0.25 | 0.125 | 1 | 0.5 |
| 97 | 1 | 0.125 | 1 | 0.5 |
| 99 | 0.25 | ≦0.063 | 0.063 | 0.063 |
| 101 | 1 | 0.5 | 1 | 1 |
| 105 | 0.5 | 0.063 | 0.5 | 1 |
| 107 | 0.25 | 0.25 | 0.5 | 1 |
| 1A | 0.25 | 0.063 | 0.5 | 1 |

The suitability of the compounds of the invention for the treatment of bacterial infections can be shown in the following animal model:

Systemic Infection with *Staphylococcus aureus* 133:

Cells of *S. aureus* 133 are grown overnight in BHI broth (Oxoid, New York/USA). The overnight culture is diluted 1:100 in fresh BHI broth and incubated for 3 hours. The cells which are then in the logarithmic phase of growth are spun down and washed twice with buffered physiological saline. Then a cell suspension in saline is adjusted photometrically to an extinction of 50 units. After a dilution step (1:15), the suspension is mixed 1:1 with a 10% strength mucin solution. 0.25 ml of this infection solution are administered intraperitoneally to a 20 g mouse (equivalent to $1 \times 10^6$ microbes/mouse). Therapy takes place intraperitoneally or intravenously 30 minutes after the infection. Female CFW1 mice are used for the infection test. The survival of the animals is recorded over 6 days.

The properties of the compounds of the invention in relation to renal tolerability can be shown in the following animal model:

Mouse Model for Determining Nephrotoxic Effects:

Nephrotoxic side effects of the nonadepsipeptides are analysed by histopathological examinations of the kidneys in mice after multiple administration of a particular dosage. For this purpose, 5-6 animals are treated each day either intravenously (i.v.) or intraperitoneally (i.p.) with substances which are dissolved in aqueous solution or with addition of Solutol. Nephrotoxic effects are determined by optical microscopic assessment of haematoxylin and eosin (H&E) stained paraffin sections of the kidneys. A periodic acid shift (PAS) reaction is optionally carried out to visualize glycoproteins better. Nephrotoxic effects are specified semiquantitatively for each animal as severities of the tubular basophilia and degeneration/regeneration occurring (severities: 0=no effect; 1=minimal effect; 2=slight effect; 3=moderate effect; 4=severe lesions). The average severity of the tubular degeneration/regeneration and the incidence (number of affected animals) is calculated for each animal group or derivative. Renal changes going beyond this, such as tubular dilatation and necroses and accumulation of necrotic material, are likewise listed.

C. Exemplary Embodiments of Pharmaceutical Compositions

The compounds of the invention can be converted into pharmaceutical preparations in the following ways:

Tablet:

Composition:

100 mg of the compound of Example 1, 50 mg of lactose (monohydrate), 50 mg of maize starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

A mixture of active ingredient, lactose and starch is granulated with a 5% strength solution (m/m) of PVP in water. The granules are dried and then mixed with the magnesium stearate for 5 min. This mixture is compressed with a conventional tablet press (see above for format of the tablet). A compressive force of 15 kN is used as guideline for the compression.

Suspension Which Can Be Administered Orally:

Composition:

1000 mg of the compound of Example 1, 1000 mg of ethanol (96%), 400 mg of Rhodigel (xanthan gum from FMC, Pennsylvania, USA) and 99 g of water.

10 ml of oral suspension are equivalent to a single dose of 100 mg of the compound of the invention.

Production:

The Rhodigel is suspended in ethanol, and the active ingredient is added to the suspension. The water is added while stirring. The mixture is stirred for about 6 h until the swelling of the Rhodigel is complete.

Solution Which Can Administered Intravenously:

Composition:

100-200 mg of the compound of Example 1, 15 g of polyethylene glycol 400 and 250 g of water for injection.

Production:

The compound of Example 1 is dissolved together with polyethylene glycol 400 in the water with stirring. The solution is sterilized by filtration (pore diameter 0.22 μm) and used to fill heat-sterilized infusion bottles under aseptic conditions. The latter are closed with infusion stoppers and crimped caps.

The invention claimed is:
1. A compound of the formula

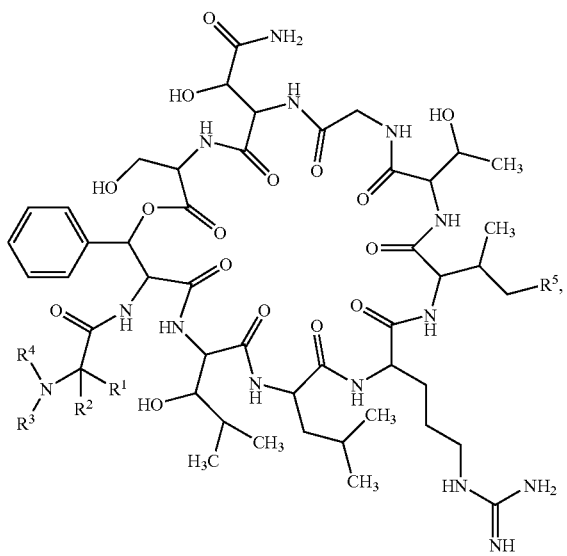

(I)

in which
R¹ is hydrogen, $C_3$-$C_6$-cycloalkyl, $C_5$-$C_6$-cycloalkenyl, $C_3$-$C_6$-cycloalkylmethyl, 5- to 7-membered heterocyclylmethyl, methyl, ethyl, n-propyl, isopropyl, 1-methylprop-1-yl, 2-methylprop-1-yl, 2,2-dimethylprop-1-yl, 1,1-dimethylprop-1-yl, 1-ethyl-prop-1-yl, 1-ethyl-1-methylprop-1-yl, n-butyl, 2-methylbut-1-yl, 3-methylbut-1-yl, 1-ethylbut-1-yl, tert-butyl, 4-methylpent-1-yl, n-hexyl, alkenyl or aryl,
where R¹ may be substituted by 0, 1, 2 or 3 substituents independently of one another selected from the group consisting of halogen, hydroxy, amino, cyano, trimethylsilyl, alkyl, alkoxy, benzyloxy, $C_3$-$C_6$-cycloalkyl, aryl, 5- to 10-membered heteroaryl, alkylamino, arylamino, alkylcarbonylamino, arylcarbonylamino, alkylcarbonyl, alkoxycarbonyl, arylcarbonyl and benzyloxycarbonylamino,
in which aryl and heteroaryl in turn may be substituted by 0, 1, 2 or 3 substituents independently of one another selected from the group consisting of halogen, hydroxy, amino, cyano, nitro, alkyl, alkoxy and phenyl,
R² is hydrogen or $C_1$-$C_4$-alkyl, or
R¹ and R² together with the carbon atom to which they are bonded form a $C_3$-$C_6$-cycloalkyl ring or a 5- to 7-membered heterocyclyl ring, where the cycloalkyl ring and the heterocyclyl ring may be substituted by 0, 1, 2 or 3 substituents independently of one another selected from the group consisting of trifluoromethyl, alkyl, alkoxy and alkylcarbonyl,
R³ is alkyl, $C_3$-$C_6$-cycloalkyl, 5- to 7-membered heterocyclyl, aryl, 5- or 6-membered heteroaryl, alkylcarbonyl, alkoxycarbonyl, $C_3$-$C_6$-cycloalkyl-carbonyl, 5- to 7-membered heterocyclylcarbonyl, arylcarbonyl, 5- or 6-membered heteroarylcarbonyl or alkylaminocarbonyl,
where alkyl, cycloalkyl, heterocyclyl, aryl, heteroaryl, alkoxycarbonyl, cycloalkylcarbonyl, heterocyclylcarbonyl, arylcarbonyl, heteroarylcarbonyl and alkylaminocarbonyl may be substituted by 0, 1, 2 or 3 substituents independently of one another selected from the group consisting of halogen, hydroxy, amino, alkylamino and phenyl, and
where alkylcarbonyl is substituted by one amino or alkylamino substituent, and
where alkylcarbonyl may be substituted by a further 0, 1 or 2 substituents independently of one another selected from the group consisting of halogen, hydroxy, trimethylsilyl, alkoxy, alkylthio, benzyloxy, $C_3$-$C_6$-cycloalkyl, phenyl, naphthyl, 5- to 10-membered heteroaryl, alkylcarbonylamino, alkoxycarbonylamino, arylcarbonylamino, arylcarbonyloxy, benzyloxycarbonyl and benzyloxycarbonylamino,
in which phenyl and heteroaryl in turn may be substituted by 0, 1, 2 or 3 substituents independently of one another selected from the group consisting of halogen, hydroxy, nitro, alkyl, alkoxy and phenyl,
or two substituents on the same carbon atom in the alkylcarbonyl form together with the carbon atom to which they are bonded a $C_3$-$C_6$-cycloalkyl ring or a 5- to 7-membered heterocyclyl ring,
where the cycloalkyl ring and the heterocyclyl ring may be substituted by 0, 1, 2 or 3 substituents independently of one another selected from the group consisting of trifluoromethyl, alkyl and alkoxy, or
where the cycloalkyl ring may be benzo-fused,
R⁴ is hydrogen, $C_1$-$C_4$-alkyl, cyclopropyl or cyclopropylmethyl, or
R³ and R⁴ together with the nitrogen atom to which they are bonded form a 5- to 7-membered heterocyclyl ring, where the heterocyclyl ring may be substituted by 0, 1, 2 or 3 substituents independently of one another selected from the group consisting of halogen, hydroxy, amino, cyano, alkyl, alkoxy and alkylamino, and
R⁵ is hydrogen or methyl,
or one of its salts, its solvates and the solvates of its salts,
with the proviso that in the case where R¹ is hydrogen, R² is 2-methylprop-1-yl, R⁴ is hydrogen and R⁵ is methyl, and the carbon atom to which R¹ and R² are bonded has the (S) configuration, or where R¹ is 2-methylprop-1-yl, R² is hydrogen, R⁴ is hydrogen and R⁵ is methyl, and the carbon atom to which R¹ and R² are bonded has the (S) configuration, R³ is not glycyl, D-alanyl, L-alanyl or D-leucyl, and
with the proviso that in the case where R¹ is hydrogen, R² is 2-methylprop-1-yl, R⁴ is hydrogen and R⁵ is hydrogen, and the carbon atom to which R¹ and R² are bonded has the (S) configuration, or where R¹ is 2-methylprop-1-yl, R² is hydrogen, R⁴ is hydrogen and R⁵ is hydrogen, and the carbon atom to which R¹ and R² are bonded has the (S) configuration, R³ is not D-leucyl.

2. A compound according to claim 1, characterized in that it corresponds to the formula

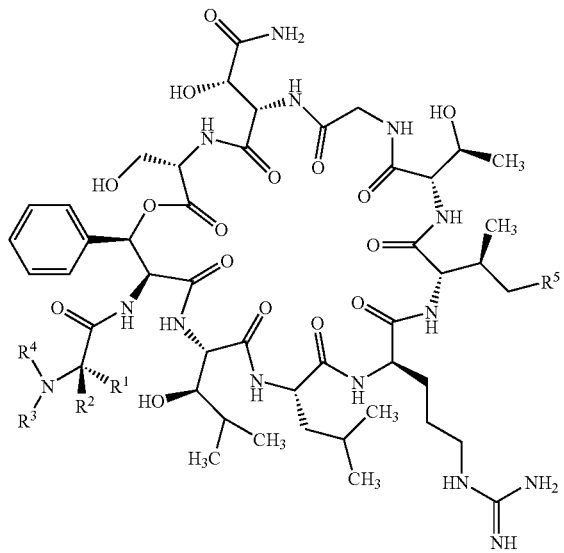

(Ib)

in which
$R^1$, $R^2$, $R^3$, $R^4$ and $R^5$ have the meaning indicated in claim 1,
or one of its salts, its solvates and the solvates of its salts.

3. A compound according to claim 2, characterized in that
$R^1$ is 2-methylprop-1-yl,
$R^2$ is hydrogen or $C_1$-$C_4$-alkyl,
$R^3$ is alkyl, $C_3$-$C_6$-cycloalkyl, 5- to 7-membered heterocyclyl, aryl, 5- or 6-membered heteroaryl, alkylcarbonyl, alkoxycarbonyl, $C_3$-$C_6$-cycloalkylcarbonyl, 5- to 7-membered heterocyclylcarbonyl, arylcarbonyl, 5- or 6-membered heteroarylcarbonyl or alkylaminocarbonyl,
where alkyl, cycloalkyl, heterocyclyl, aryl, heteroaryl, alkoxycarbonyl, cycloalkylcarbonyl, heterocyclylcarbonyl, arylcarbonyl, heteroarylcarbonyl and alkylaminocarbonyl may be substituted by 0, 1, 2 or 3 substituents independently of one another selected from the group consisting of halogen, hydroxy, amino, alkylamino and phenyl, and
where alkycarbonyl is substituted by one amino or alkylamino substituent, and
where alkylcarbonyl may be substituted by a further 0, 1 or 2 substituents independently of one another selected from the group consisting of halogen, hydroxy, trimethylsilyl, alkoxy, alkylthio, benzyloxy, $C_3$-$C_6$-cycloalkyl, phenyl, naphthyl, 5- to 10-membered heteroaryl, alkylcarbonylamino, alkoxycarbonylamino, arylcarbonylamino, arylcarbonyloxy, benzyloxycarbonyl and benzyloxycarbonylamino,
in which phenyl and heteroaryl in turn may be substituted by 0, 1, 2 or 3 substituents independently of one another selected from the group consisting of halogen, hydroxy, nitro, alkyl, alkoxy and phenyl,
or two substituents on the same carbon atom in the alkylcarbonyl form together with the carbon atom to which they are bonded a $C_3$-$C_6$-cycloalkyl ring or a 5- to 7-membered heterocyclyl ring,
where the cycloalkyl ring and the heterocyclyl ring may be substituted by 0, 1, 2 or 3 substituents independently of one another selected from the group consisting of trifluoromethyl, alkyl and alkoxy, or
where the cycloalkyl ring may be benzo-fused,
$R^4$ is hydrogen, $C_1$-$C_4$-alkyl, cyclopropyl or cyclopropylmethyl, or
$R^3$ and $R^4$ together with the nitrogen atom to which they are bonded form a 5- to 7-membered heterocyclyl ring, where the heterocyclyl ring may be substituted by 0, 1, 2 or 3 substituents independently of one another selected from the group consisting of halogen, hydroxy, amino, cyano, alkyl, alkoxy and alkylamino, and
$R^5$ is hydrogen or methyl.

4. A compound according to claim 3, characterized in that
$R^1$ is 2-methylprop-1-yl,
$R^2$ is hydrogen,
$R^3$ is $C_1$-$C_6$-alkylcarbonyl,
where alkylcarbonyl is substituted by one amino substituent, and
where alkylcarbonyl may be substituted by a further 0, 1 or 2 substituents independently of one another selected from the group consisting of trimethylsilyl, $C_1$-$C_4$-alkoxy, methylthio, benzyloxy, $C_3$-$C_6$-cycloalkyl, phenyl, naphthyl, thienyl, pyridyl, indolyl, $C_1$-$C_4$-alkoxycarbonylamino, benzyloxycarbonyl and benzyloxycarbonylamino,
in which phenyl in turn may be substituted by 0, 1, 2 or 3 substituents independently of one another selected from the group consisting of halogen, $C_1$-$C_4$-alkyl, $C_1$-$C_4$-alkoxy and phenyl,
or two substituents on the same carbon atom in alkylcarbonyl form together with the carbon atom to which they are bonded a $C_3$-$C_6$-cycloalkyl ring,
where the cycloalkyl ring may be benzo-fused,
$R^4$ is hydrogen, and
$R^5$ methyl.

5. A compound according to claim 2, characterized in that
$R^1$ is hydrogen, $C_3$-$C_6$-cycloalkyl, $C_5$-$C_6$-cycloalkenyl, $C_3$-$C_6$-cycloalkylmethyl, 5- to 7-membered heterocyclylmethyl, methyl, ethyl, n-propyl, isopropyl, 1-methylprop-1-yl, 2,2-dimethylprop-1-yl, 1,1-dimethylprop-1-yl, 1-ethyl-prop-1-yl, 1-ethyl-1-methylprop-1-yl, n-butyl, 2-methylbut-1-yl, 3-methylbut-1-yl, 1-ethylbut-1-yl, tert-butyl, 4-methylpent-1-yl, n-hexyl, alkenyl or aryl,
where $R^1$ may be substituted by 0, 1, 2 or 3 substituents independently of one another selected from the group consisting of halogen, hydroxy, amino, cyano, trimethylsilyl, alkyl, alkoxy, benzyloxy, $C_3$-$C_6$-cycloalkyl, aryl, 5- to 10-membered heteroaryl, alkylamino, arylamino, alkylcarbonylamino, arylcarbonylamino, alkylcarbonyl, alkoxycarbonyl, arylcarbonyl and benzyloxycarbonylamino,
in which aryl and heteroaryl in turn may be substituted by 0, 1, 2 or 3 substituents independently of one another selected from the group consisting of halogen, hydroxy, amino, cyano, nitro, alkyl, alkoxy and phenyl,
$R^2$ is hydrogen or $C_1$-$C_4$-alkyl, or
$R^1$ and $R^2$ together with the carbon atom to which they are bonded form a $C_3$-$C_6$-ycloalkyl ring or a 5- to 7-membered heterocyclyl ring, where the cycloalkyl ring and the heterocyclyl ring may be substituted by 0, 1, 2 or 3 substituents independently of one another selected from the group consisting of trifluoromethyl, alkyl, alkoxy and alkylcarbonyl, $R^3$ is alkyl, $C_3$-$C_6$-cycloalkyl, 5- to 7-membered heterocyclylaryl, 5- or 6-membered heteroaryl, alkylcarbonyl, alkoxycarbonyl, $C_3$-$C_6$-cycloalkylcarbonyl, 5- to 7-membered heterocyclylcarbonyl, arylcarbonyl, 5- or 6-membered heteroarylcarbonyl or alkylaminocarbonyl, where alkyl, cycloalkyl, heterocyclyl, aryl, heteroaryl, alkoxycarbonyl, cycloalkylcarbonyl, heterocyclylcarbonyl, arylcarbonyl, heteroarylcarbonyl and alkylaminocarbonyl may be substituted by 0, 1, 2 or 3 substituents independently of one another selected from the group consisting of halogen, hydroxy, amino, alkylamino and phenyl, and where alkylcarbonyl is substituted by one amino or alkylamino substituent, and where alkylcarbonyl may be substituted by a further 0, 1 or 2 substituents independently of one another selected from the group consisting of halogen, hydroxy, trimethylsilyl, alkoxy, alkylthio, benzyloxy, $C_3$-$C_6$-cycloalkyl, phenyl, naphthyl, 5- to 10-membered heteroaryl, alkylcarbonylamino, alkoxycarbonylamino, arylcarbonylamino, arylcarbonyloxy, benzyloxycarbonyl and benzyloxycarbonylamino, in which phenyl and heteroaryl in turn may be substituted by 0, 1, 2 or 3 substituents independently of one another selected from the group consisting of halogen, hydroxy, nitro, alkyl, alkoxy and phenyl, or two substituents on the same carbon atom the alkyl carbonyl form together with the carbon atom to which they are bonded a $C_3$-$C_6$-cycloalkyl ring or a 5- to 7-membered heterocyclyl ring, where the cycloalkyl ring and the heterocyclyl ring may be substituted by 0, 1, 2 or 3 substituents independently of one another selected from the group consisting of trifluoromethyl, alkyl and alkoxy, or where the cycloalkyl ring may be benzo-fused, $R^4$ is hydrogen, $C_1$-$C_4$-alkyl, cyclopropyl or cyclopropylmethyl, or $R^3$ and $R^4$ together with the nitrogen atom to which they are bonded form a 5- to 7-membered heterocyclyl ring, where the heterocyclyl ring may be substituted by 0, 1, 2 or 3 substituents independently of one another selected from the group consisting of halogen, hydroxy, amino, cyano, alkyl, alkoxy and alkylamino, and $R^5$ is hydrogen or methyl.

6. A compound according to claim 5, characterized in that $R^1$ is methyl, ethyl, n-propyl, isopropyl, 1-methylprop-1-yl, 2,2-dimethylprop-1-yl, 1,1-dimethylprop-1-yl, 1-ethyl-prop-1-yl, 1-ethyl-1-methylprop-1-yl, n-butyl, 2-methylbut-1-yl, 3-methylbut-1-yl, 1-ethylbut-1-yl, tert-butyl, 4-methylpent-1-yl or n-hexyl, where $R^1$ may be substituted by 0 or 1 substituent selected from the group consisting of trimethylsilyl, $C_1$-$C_4$-alkoxy, benzyloxy, $C_3$-$C_6$-cycloalkyl, phenyl, naphthyl, pyridyl, indolyl, $C_1$-$C_4$-alkoxycarbonyl and benzyloxycarbonylamino, in which phenyl and pyridyl in turn may be substituted by 0, 1, 2 or 3 substituents independently of one another selected from the group consisting of halogen, hydroxy, nitro, $C_1$-$C_4$-alkyl, $C_1$-$C_4$-alkoxy and phenyl, $R^2$ is hydrogen, or $R^1$ and $R^2$ together with the carbon atom to which they are bonded form a $C_3$-$C_6$-cycloalkyl ring, where the cycloalkyl ring may be substituted by 0 or 1 substituent selected from the group consisting of trifluoromethyl and $C_1$-$C_4$-alkoxy, $R^3$ is $C_1$-$C_6$-alkylcarbonyl, where alkylcarbonyl is substituted by one amino substituent, and where alkylcarbonyl may be substituted by a further 0, 1 or 2 substituents independently of one another selected from the group consisting of trimethylsilyl, $C_1$-$C_4$-alkoxy, methylthio, benzyloxy, $C_3$-$C_6$-cycloalkyl, phenyl, naphthyl, thienyl, pyridyl, indolyl, $C_1$-$C_4$-alkoxycarbonylamino, benzyloxycarbonyl and benzyloxycarbonylamino, in which phenyl in turn may be substituted by 0, 1, 2 or 3 substituents independently of one another selected from the group consisting of halogen, $C_1$-$C_4$-alkyl, $C_1$-$C_4$-alkoxy and phenyl, or two substituents on the same carbon atom in the alkylcarbonyl form together with the carbon atom to which they are bonded a $C_3$-$C_6$-cycloalkyl ring, where the cycloalkyl ring may be benzo-fused, $R^4$ is hydrogen, and $R^5$ methyl.

7. A process for preparing a compound of the formula (I) according to claim 1, wherein a compound of the formula

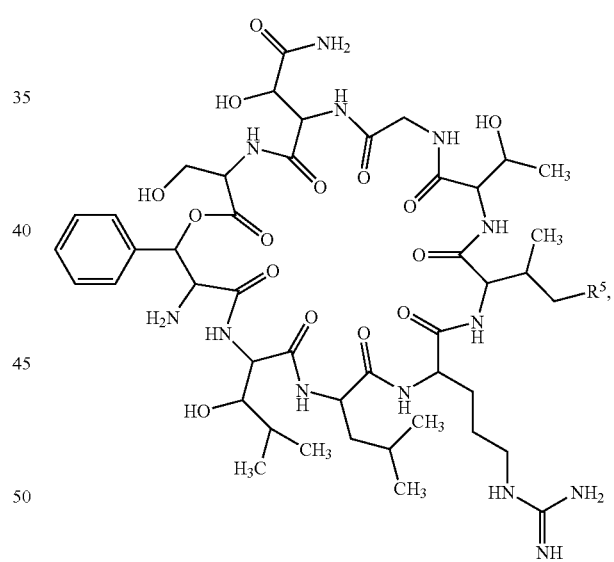

(II), in which $R^5$ the meaning indicated in claim 1, is reacted with a compound of the formula

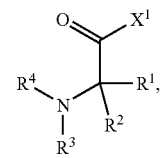

(III)

in which

R¹, R², R³ and R⁴ have the meaning indicated in claim 1, and

X¹ is halogen or hydroxy;

to produce a compound of formula (I):

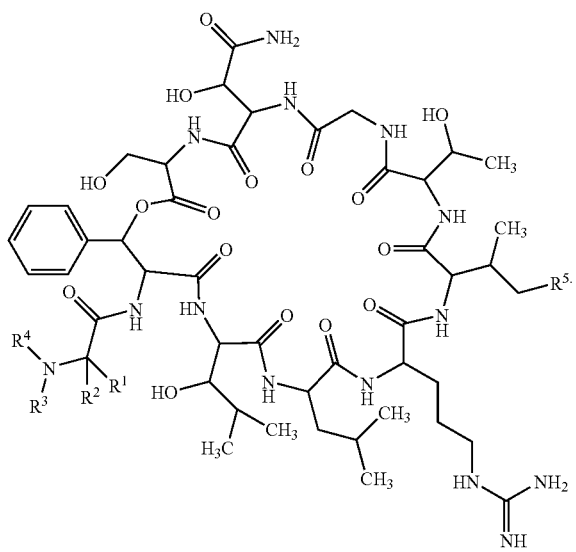

(I)

8. A medicament comprising a compound as claimed in claim 1 in combination with an inert, nontoxic, pharmaceutically suitable excipient.

9. A medicament according to claim 8 for the treatment of bacterial infections caused by Gram-positive bacteria.

10. A method for controlling bacterial infections caused by Gram-positive bacteria in humans and animals by administering an antibacterially effective amount of at least one compound according to claim 1.

11. A method for controlling bacterial infections caused by Gram-positive bacteria in humans and animals by administering a medicament according to claim 8.

12. A method according to claim 10, wherein the bacterial infection is an infection caused by Gram-positive cocci.

13. A method according to claim 12, wherein the Gram-positive cocci are selected from the group consisting of *Staphylococcus aureus, Enterococcus faecalis, Enterococcus faecium* and *Streptococcus pneumoniae*.

14. A method according to claim 11, wherein the bacterial infection is an infection caused by Gram-positive cocci.

15. A method according to claim 14, wherein the Gram-positive cocci are selected from the group consisting of *Staphylococcus aureus, Enterococcus faecalis, Enterococcus faecium* and *Streptococcus pneumoniae*.

\* \* \* \* \*